(12) United States Patent
Stockwell et al.

(10) Patent No.: US 10,233,171 B2
(45) Date of Patent: Mar. 19, 2019

(54) COMPOUNDS, COMPOSITIONS, AND METHODS FOR MODULATING FERROPTOSIS AND TREATING EXCITOTOXIC DISORDERS

(71) Applicant: THE TRUSTEES OF COLUMBIA UNIVERSITY IN THE CITY OF NEW YORK, New York, NY (US)

(72) Inventors: Brent R. Stockwell, New York, NY (US); Scott J. Dixon, New York, NY (US); Rachid Skouta, New York, NY (US)

(*) Notice: Subject to any disclaimer, the term of this patent is extended or adjusted under 35 U.S.C. 154(b) by 0 days.

(21) Appl. No.: 15/442,475

(22) Filed: Feb. 24, 2017

(65) Prior Publication Data

US 2017/0233370 A1   Aug. 17, 2017

Related U.S. Application Data

(62) Division of application No. 14/390,256, filed as application No. PCT/US2013/035021 on Apr. 2, 2013, now Pat. No. 9,580,398.

(Continued)

(51) Int. Cl.
| | | |
|---|---|---|
| C07D 213/74 | (2006.01) |
| A61K 31/47 | (2006.01) |
| C07D 401/12 | (2006.01) |
| C07D 309/14 | (2006.01) |
| C07C 255/58 | (2006.01) |
| C07D 213/80 | (2006.01) |
| C07C 271/16 | (2006.01) |
| C07C 271/24 | (2006.01) |
| C07C 271/28 | (2006.01) |
| C07C 205/57 | (2006.01) |
| C07C 205/58 | (2006.01) |

(Continued)

(52) U.S. Cl.
CPC .......... *C07D 401/12* (2013.01); *A61K 31/245* (2013.01); *A61K 31/27* (2013.01); *A61K 31/325* (2013.01); *A61K 31/351* (2013.01); *A61K 31/44* (2013.01); *A61K 31/444* (2013.01); *A61K 31/4465* (2013.01); *A61K 31/4468* (2013.01); *A61K 31/495* (2013.01); *A61K 31/505* (2013.01); *A61K 31/506* (2013.01); *A61K 31/5375* (2013.01); *A61K 45/06* (2013.01); *C07C 69/78* (2013.01); *C07C 205/57* (2013.01); *C07C 205/58* (2013.01); *C07C 211/50* (2013.01); *C07C 225/22* (2013.01); *C07C 229/60* (2013.01); *C07C 233/54* (2013.01); *C07C 237/30* (2013.01); *C07C 255/58* (2013.01); *C07C 271/16* (2013.01); *C07C 271/24* (2013.01); *C07C 271/28* (2013.01); *C07D 211/58* (2013.01); *C07D 213/36* (2013.01); *C07D 213/74* (2013.01); *C07D 213/80* (2013.01); *C07D 239/26* (2013.01); *C07D 239/42* (2013.01); *C07D 295/088* (2013.01); *C07D 295/192* (2013.01); *C07D 295/30* (2013.01); *C07D 309/14* (2013.01); *C07C 2601/02* (2017.05); *C07C 2601/04* (2017.05); *C07C 2601/08* (2017.05); *C07C 2601/14* (2017.05); *C07C 2601/18* (2017.05); *C07C 2601/20* (2017.05); *C07C 2603/74* (2017.05)

(58) Field of Classification Search
None
See application file for complete search history.

(56) References Cited

U.S. PATENT DOCUMENTS

| 3,959,261 A | 5/1976 | Lerch et al. |
| 2003/0232816 A1 | 12/2003 | Beaulieu et al. |

(Continued)

FOREIGN PATENT DOCUMENTS

| WO | 0609798 A1 | 1/1994 | |
| WO | WO-03026587 A2 * | 4/2003 | ........... C07D 235/18 |

(Continued)

OTHER PUBLICATIONS

Abdel-Magid, A. F, et al. Reductive Amination of Aldehydes and Ketones with Sodium Triacetoxyborohydride. Studies on Direct and Indirect Reductive Amination Procedures(1). J. Org. Chem. 1996, 61, 3849-3862.

(Continued)

*Primary Examiner* — Zinna Northington Davis
(74) *Attorney, Agent, or Firm* — Bryan Cave Leighton Paisner LLP

(57) ABSTRACT

The present invention provides, inter alia, a compound having the structure:

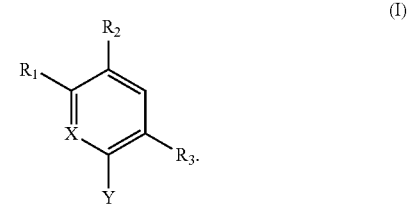

Also provided are compositions containing a pharmaceutically acceptable carrier and a compound according to the present invention. Further provided are methods for treating or ameliorating the effects of an excitotoxic disorder in a subject, methods of modulating ferroptosis in a subject, methods of reducing reactive oxygen species (ROS) in a cell, and methods for treating or ameliorating the effects of a neurodegenerative disease.

26 Claims, 31 Drawing Sheets
Specification includes a Sequence Listing.

Related U.S. Application Data

(60) Provisional application No. 61/619,315, filed on Apr. 2, 2012.

(51) Int. Cl.

| | |
|---|---|
| C07C 211/50 | (2006.01) |
| C07D 239/26 | (2006.01) |
| C07C 229/60 | (2006.01) |
| C07C 233/54 | (2006.01) |
| C07C 237/30 | (2006.01) |
| C07D 295/088 | (2006.01) |
| C07D 211/58 | (2006.01) |
| C07D 295/30 | (2006.01) |
| C07D 213/36 | (2006.01) |
| A61K 31/245 | (2006.01) |
| A61K 31/325 | (2006.01) |
| A61K 31/351 | (2006.01) |
| A61K 31/4465 | (2006.01) |
| A61K 31/495 | (2006.01) |
| A61K 31/5375 | (2006.01) |
| A61K 45/06 | (2006.01) |
| C07C 69/78 | (2006.01) |
| C07D 295/192 | (2006.01) |
| A61K 31/27 | (2006.01) |
| A61K 31/44 | (2006.01) |
| A61K 31/444 | (2006.01) |
| A61K 31/4468 | (2006.01) |
| A61K 31/505 | (2006.01) |
| A61K 31/506 | (2006.01) |
| C07C 225/22 | (2006.01) |
| C07D 239/42 | (2006.01) |

(56) References Cited

U.S. PATENT DOCUMENTS

2007/0049565 A1  3/2007  Gwag et al.
2008/0132559 A1  6/2008  Peleg-Schulman

FOREIGN PATENT DOCUMENTS

WO  WO 2010/100249 A1  9/2010
WO  2013/152039  10/2013

OTHER PUBLICATIONS

Banjac, A., et al. (2008). The cystine/cysteine cycle: a redox cycle regulating susceptibility versus resistance to cell death. Oncogene 27, 1618-1628.
Beaulieu, P. L, et al. A Practical Oxone®-Mediated, High-Throughput, Solution-Phase Synthesis of Benzimidazoles from 1,2-Phenylenediamines and Aldehydes and its Application to Preparative Scale. Synthesis, 2003, 11, 1683-1692.
Bergsbaken, T., et al. (2009). Pyroptosis: host cell death and inflammation. Nat Rev Microbiol, 7, 99-109.
Blois, M.S. (1958). Antioxidant determinations by the use of a stable free radical. Nature, 181, 1199-1200.
Cater, H.L., et al. (2007). Stretch-induced injury in organotypic hippocampal slice cultures reproduces in vivo post-traumatic neurodegeneration: role of glutamate receptors and voltage-dependent calcium channels. J Neurochem, 101 , 434-447.
Cheah, J.H., et al. (2006). NMDA receptor-nitric oxide transmission mediates neuronal iron homeostasis via the GTPase Dexrasl. Neuron, 51(4), 431-440.
Choi, D.W. (1988). Glutamate neurotoxicity and diseases of the nervous system. Neuron, 1, 623-634.
Christofferson, D.E., and Yuan, J. (2010). Necroptosis as an alternative form of programmed cell death. Current Opinion in Cell Biology, 22, 263-268.

Chung, N., et al. (2008). Median absolute deviation to improve hit selection for genome-scale RNAi screens. J Biomol Screen, 13, 149-158.
Dixon, S.J., et al. Ferroptosis: An Iron-Dependent Form of Non-Apoptotic Cell Death. Cell. May 25, 2012; 149(5): 1060-1072.
Dolma, S., et al. (2003). Identification of genotype-selective anti-tumor agents using synthetic lethal chemical screening in engineered human tumor cells. Cancer Cell, 3, 285-296.
Duce, J.A., et al. (2010). Iron-export ferroxidase activity of beta-amyloid precursor protein is inhibited by zinc in Alzheimer's disease. Cell, 142, 857-867.
Fuchs, Y., and Steller, H. (2011). Programmed cell death in animal development and disease. Cell, 147, 742-758.
Gout, P.W., et al. (2001). Sulfasalazine, a potent suppressor of lymphoma growth by inhibition of the x(c)-cystine transporter: a new action for an old drug. Leukemia, 15, 1633-1640.
Guo, W., et al. (2008). Identification of a small molecule with synthetic lethality for K-ras and protein kinase C iota. Cancer Res, 68, 7403-7408.
Ishida, T., et al. (2006). Benzimidazole inhibitors of hepatitis C virus NS5B polymerase: identification of 2-[(4-diarylmethoxy)phenyl]-benzimidazole. Bioorg Med Chem Lett, 16, 1859-1863.
Ishii, T., et al. (1981). Mechanism of growth stimulation of L1210 cells by 2-mercaptoethanol in vitro. Role of the mixed disulfide of 2-mercaptoethanol and cysteine. J Biol Chem. Dec. 10, 1981;256(23):12387-92.
Jacobson, M.D., and Raff, M.C. (1995). Programmed cell death and Bcl-2 protection in very low oxygen. Nature 374, 814-816.
Kamata, T. (2009). Roles of Nox1 and other Nox isoforms in cancer development. Cancer Sci 100, 1382-1388.
Kanai, Y., and Endou, H. (2003). Functional properties of multispecific amino acid transporters and their implications to transporter-mediated toxicity. J Toxicol Sci 28, 1-17.
Kaplan, A., et al. Therapeutic approaches to preventing cell death in Huntington disease. Progress in Neurobiology 99 (2012) 262-280.
Laleu, B., et al. (2010). First in class, potent, and orally bioavailable NADPH oxidase isoform 4 (Nox4) inhibitors for the treatment of idiopathic pulmonary fibrosis. Journal of medicinal chemistry 53, 7715-7730.
Lei, P., et al. (2012). Tau deficiency induces parkinsonism with dementia by impairing APP-mediated iron export. Nature medicine 18, 291-295.
Li, Y., et al. (1997). A role for 12-lipoxygenase in nerve cell death caused by glutathione depletion. Neuron 19, 453-463.
Lipinski, C.A., et al. (2001). Experimental and computational approaches to estimate solubility and permeability in drug discovery and development settings. Advanced drug delivery reviews 46, 3-26.
Lo, M., et al. (2008). The xc-cystine/glutamate antiporter: a mediator of pancreatic cancer growth with a role in drug resistance. Br J Cancer. Aug. 5, 2008;99(3):464-72.
Lossi, L., et al. (2009). Cell death and proliferation in acute slices and organotypic cultures of mammalian CNS. Prog Neurobiol 88, 221-245.
Macarron, R., et al. (2011). Impact of high-throughput screening in biomedical research. Nature reviews Drug discovery 10, 188-195.
Moffat, J., et al. (2006). A lentiviral RNAi library for human and mouse genes applied to an arrayed viral high-content screen. Cell 124, 1283-1298.
Morrison, B., 3rd, et al. (2002). L-arginyl-3,4-spermidine is neuroprotective in several in vitro models of neurodegeneration and in vivo ischaemia without suppressing synaptic transmission. Br J Pharmacol 137, 1255-1268.
Mullen, A.R., et al. (2011). Reductive carboxylation supports growth in tumour cells with defective mitochondria. Nature. Nov. 20;481(7381):385-8.
Murphy, T.H., et al. (1989). Glutamate toxicity in a neuronal cell line involves inhibition of cystine transport leading to oxidative stress. Neuron 2, 1547-1558.
Ni Chonghaile, T., et al. (2011). Pretreatment mitochondrial priming correlates with clinical response to cytotoxic chemotherapy. Science, 334, 1129-1133.

(56) References Cited

OTHER PUBLICATIONS

Noraberg, J., et al. (2005). Organotypic hippocampal slice cultures for studies of brain damage, neuroprotection and neurorepair. Curr Drug Targets CNS Neurol Disord 4, 435-452.

Pagliarini, D.J., et al. (2008). A mitochondrial protein compendium elucidates complex I disease biology. Cell 134, 1 12-123.

Pinnix, Z.K., et al. (2010). Ferroportin and iron regulation in breast cancer progression and prognosis. Sci Transl Med 2, 43ra56.

Raj, L., et al. (2011). Selective killing of cancer cells by a small molecule targeting the stress response to ROS. Nature 475, 231-234.

Ramanathan, A., and Schreiber, S.L. (2009). Direct control of mitochondrial function by mTOR. Proc Natl Acad Sci USA 106, 22229-22232.

Ratan, R.R., et al. (1994). Oxidative stress induces apoptosis in embryonic cortical neurons. J Neurochem 62, 376-379.

Salahudeen, A.A., et al. (2009). An E3 ligase possessing an iron-responsive hemerythrin domain is a regulator of iron homeostasis. Science, 326, 722-726.

Sanchez, M., et al. (2011). Iron regulatory protein-1 and -2: transcriptome-wide definition of binding mRNAs and shaping of the cellular proteome by iron regulatory proteins. Blood, 118, e168-179.

Sato, H., et al. (1999). Cloning and expression of a plasma membrane cystine/glutamate exchange transporter composed of two distinct proteins. The Journal of biological chemistry 274, 1 1455-1 1458.

Shaw, AT., et al. (2011). Selective killing of K-ras mutant cancer cells by small molecule inducers of oxidative stress. Proc Natl Acad Sci U S A.

Sundstrom, L, et al. (2005). Organotypic cultures as tools for functional screening in the CNS. Drug discovery today 10, 993-1000.

Tan, S., et al. (1998). The regulation of reactive oxygen species production during programmed cell death. The Journal of Cell Biology 141, 1423-1432.

Thompson, C.B. (1995). Apoptosis in the pathogenesis and treatment of disease. Science 267, 1456-1462.

Trachootham, D., et al. (2006). Selective killing of oncogenically transformed cells through a ROS-mediated mechanism by beta-phenylethyl isothiocyanate. Cancer Cell 10, 241-252.

Vashisht, A.A., et al. (2009). Control of iron homeostasis by an iron-regulated ubiquitin ligase. Science 326, 718-721.

Vigil, D., et al. (2010). Ras superfamily GEFs and GAPs: validated and tractable targets for cancer therapy? Nat Rev Cancer 10, 842-857.

Wang, Y., et al. (2009). Poly(ADP-ribose) signals to mitochondrial AIF: a key event in parthanatos. Exp Neurol 218, 193-202.

Watkins, P.A., et al. (2007). Evidence for 26 distinct acyl-coenzyme A synthetase genes in the human genome. J Lipid Res 48, 2736-2750.

Wise, D.R., et al. (2008). Myc regulates a transcriptional program that stimulates mitochondrial glutaminolysis and leads to glutamine addiction. Proc Natl Acad Sci U S A., 105, 18782-18787.

Wolpaw, A.J., et al. (2011). Modulatory profiling identifies mechanisms of small molecule-induced cell death. Proc Natl Acad Sci USA. Sep. 27;108(39):E771-80.

Yagoda, N., et al. (2007). RAS-RAF-MEK-dependent oxidative cell death involving voltage-dependent anion channels. Nature 447, 864-868.

Yang, W.S., and Stockwell, B.R. (2008). Synthetic lethal screening identifies compounds activating iron-dependent, nonapoptotic cell death in oncogen ic-RAS-harboring cancer cells. Chemistry & biology 15, 234-245.

Yonezawa, M., et al. (1996). Cystine deprivation induces oligodendroglial death: rescue by free radical scavengers and by a diffusible glial factor. J Neurochem 67, 566-573.

International Search Report and Written Opinion from the International Searching Authority, dated Jul. 19, 2013.

* cited by examiner

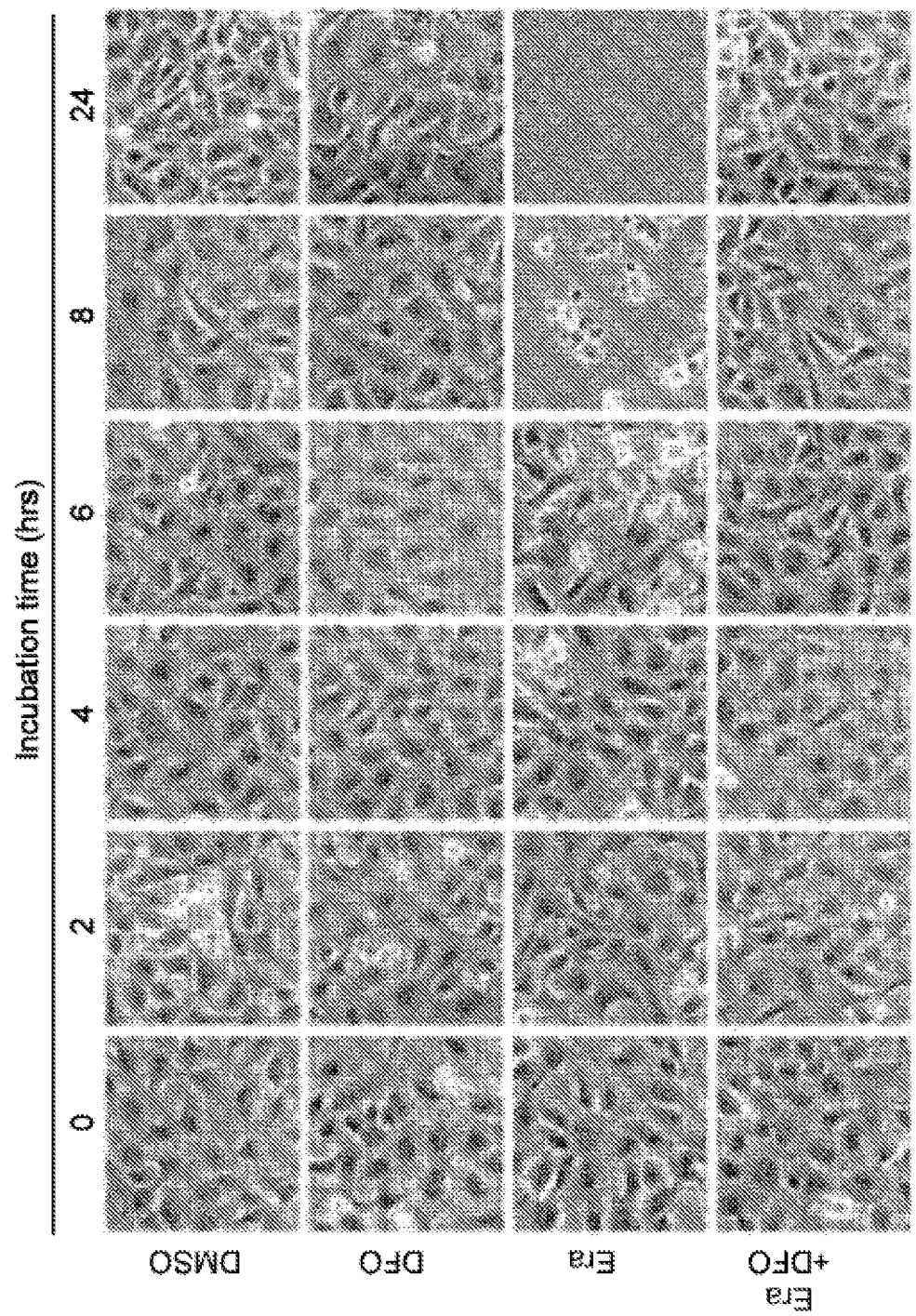

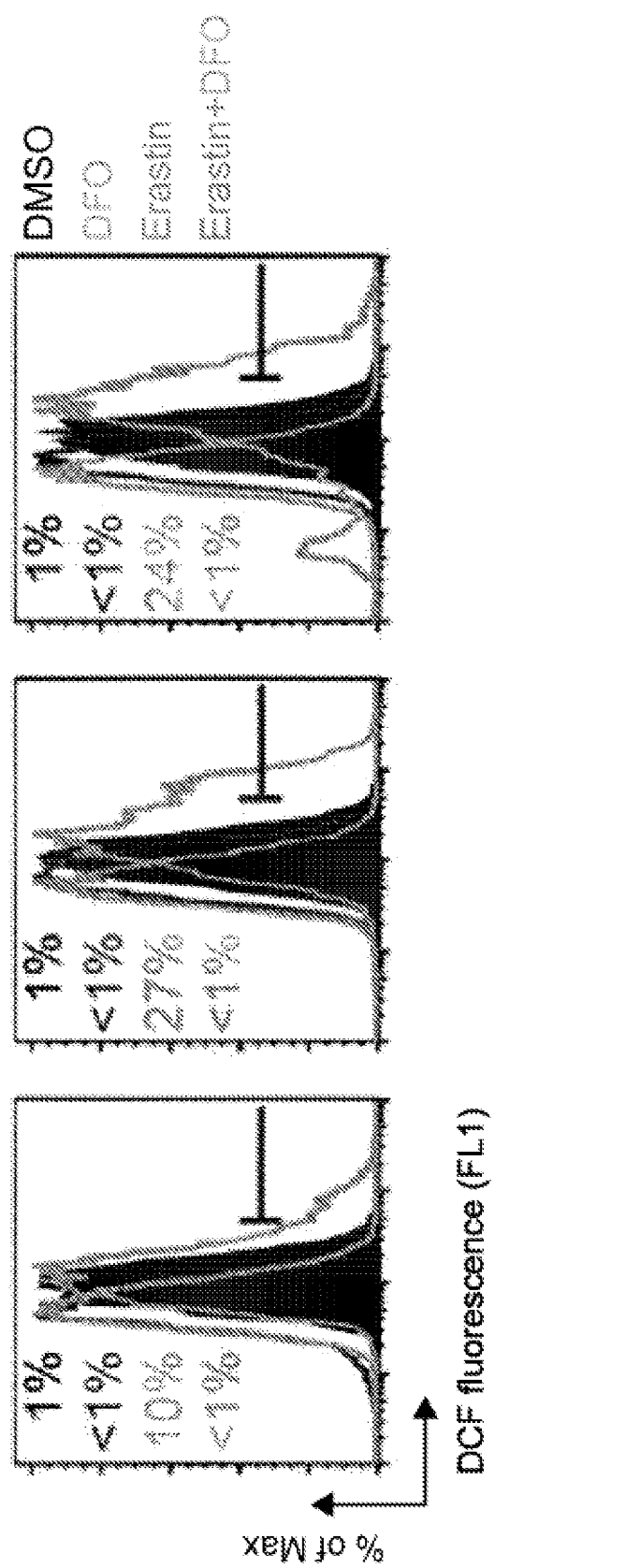

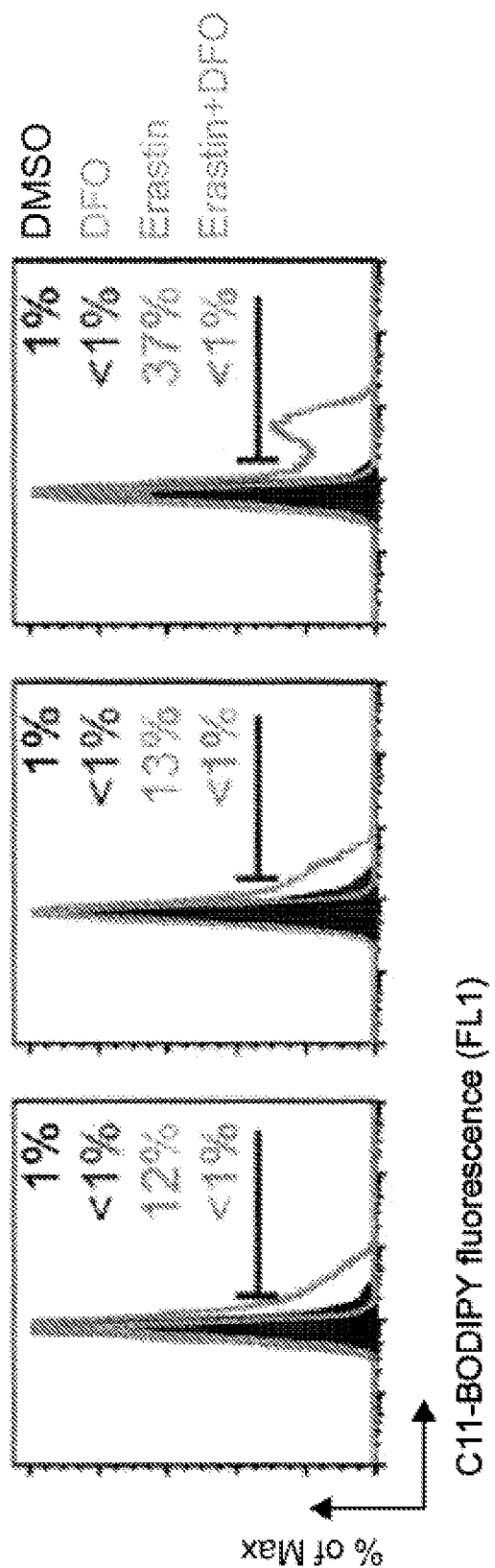

Erastin death inhibition

Fig. 6G Erastin affinity purification
BJeH  BJeLR
4  1  10
↓
SLC7A5
Fig. 6H  Metabolic profile: Jurkat T cells
(1 µM erastin, 25 minutes)
*System L substrates:*
| AA | Fold-chng | P value | Rank |
|---|---|---|---|
| Tyr | 0.81 | 0.0005 | 1/123 |
| Trp | 0.77 | 0.001 | 2/123 |
| Phe | 0.82 | 0.002 | 6/123 |
| Met | 0.83 | 0.002 | 7/123 |
| Ile/Leu | 0.86 | 0.004 | 12/123 |
| His | 0.80 | 0.06 | 50/123 |
*Non-system L substrates:*
| AA | Fold-chng | P value | Rank |
|---|---|---|---|
| Ser | 1.44 | 0.1 | 57/123 |
| Thr | 1.36 | 0.03 | 35/123 |
| Asn | 1.23 | 0.13 | 67/123 |
| Ala | 1.3 | 0.15 | 68/123 |
| Arg | 1.07 | 0.21 | 87/123 |

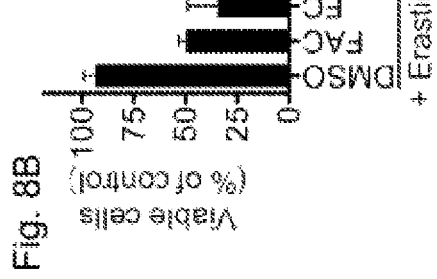
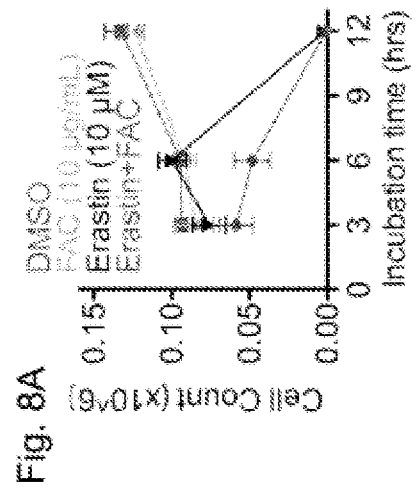
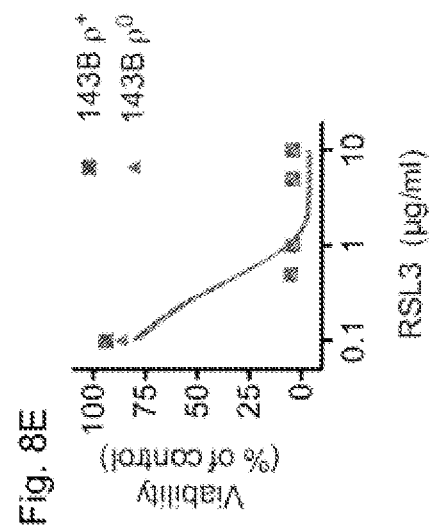
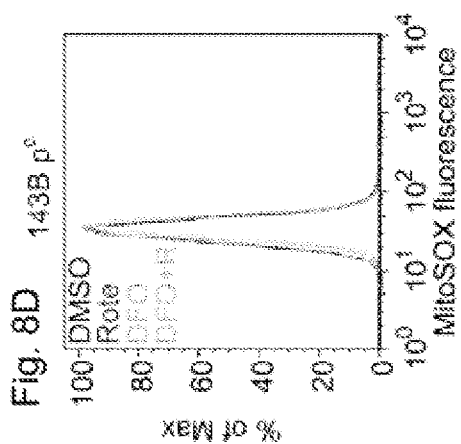
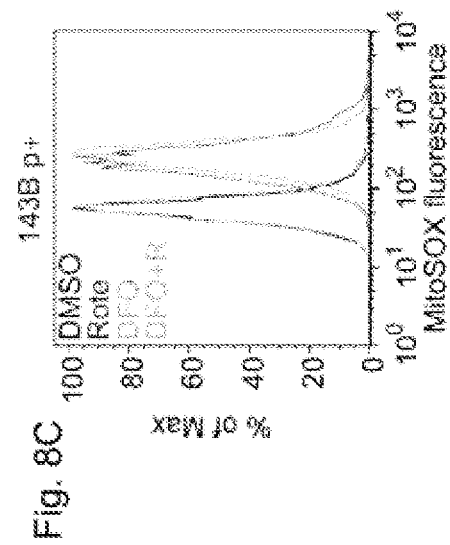

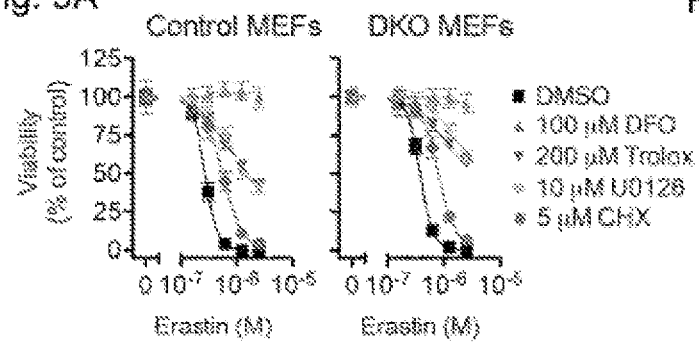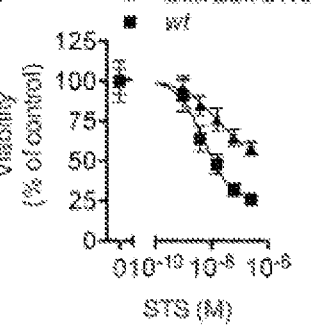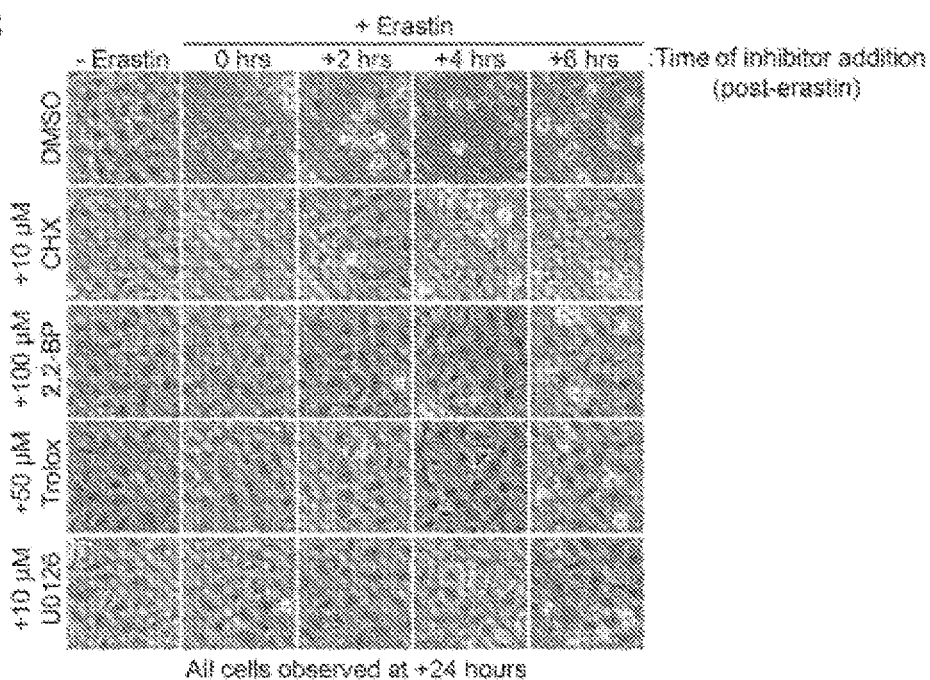

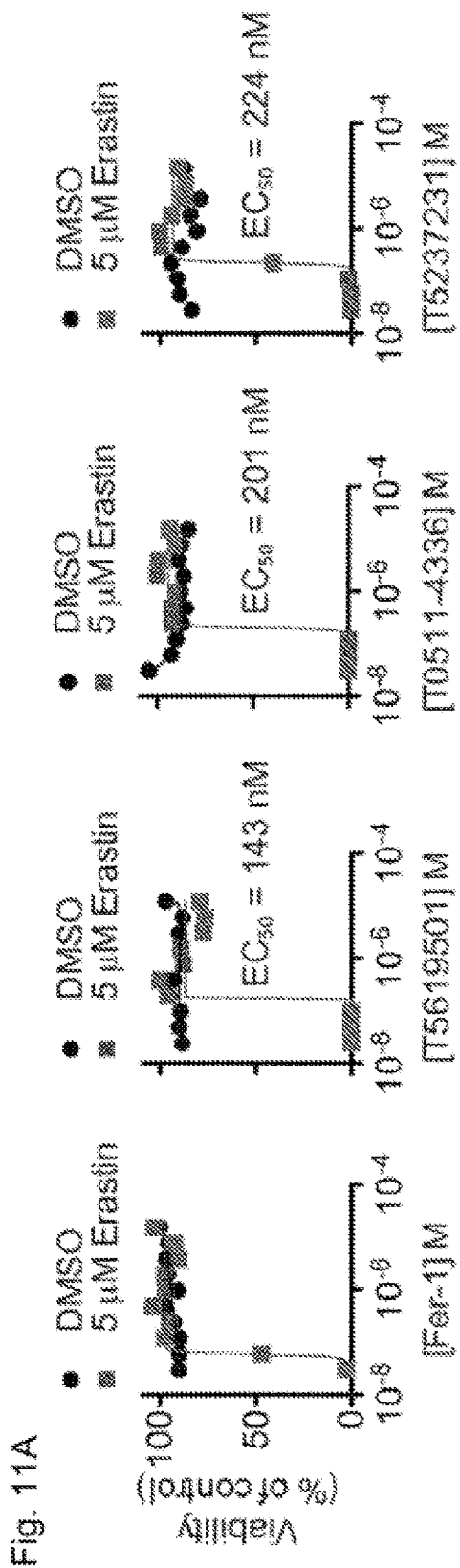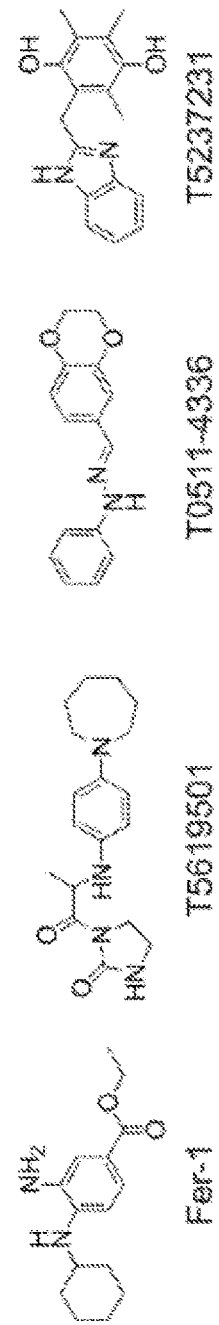
Fig. 11A
Fig. 11B

Fig. 11C

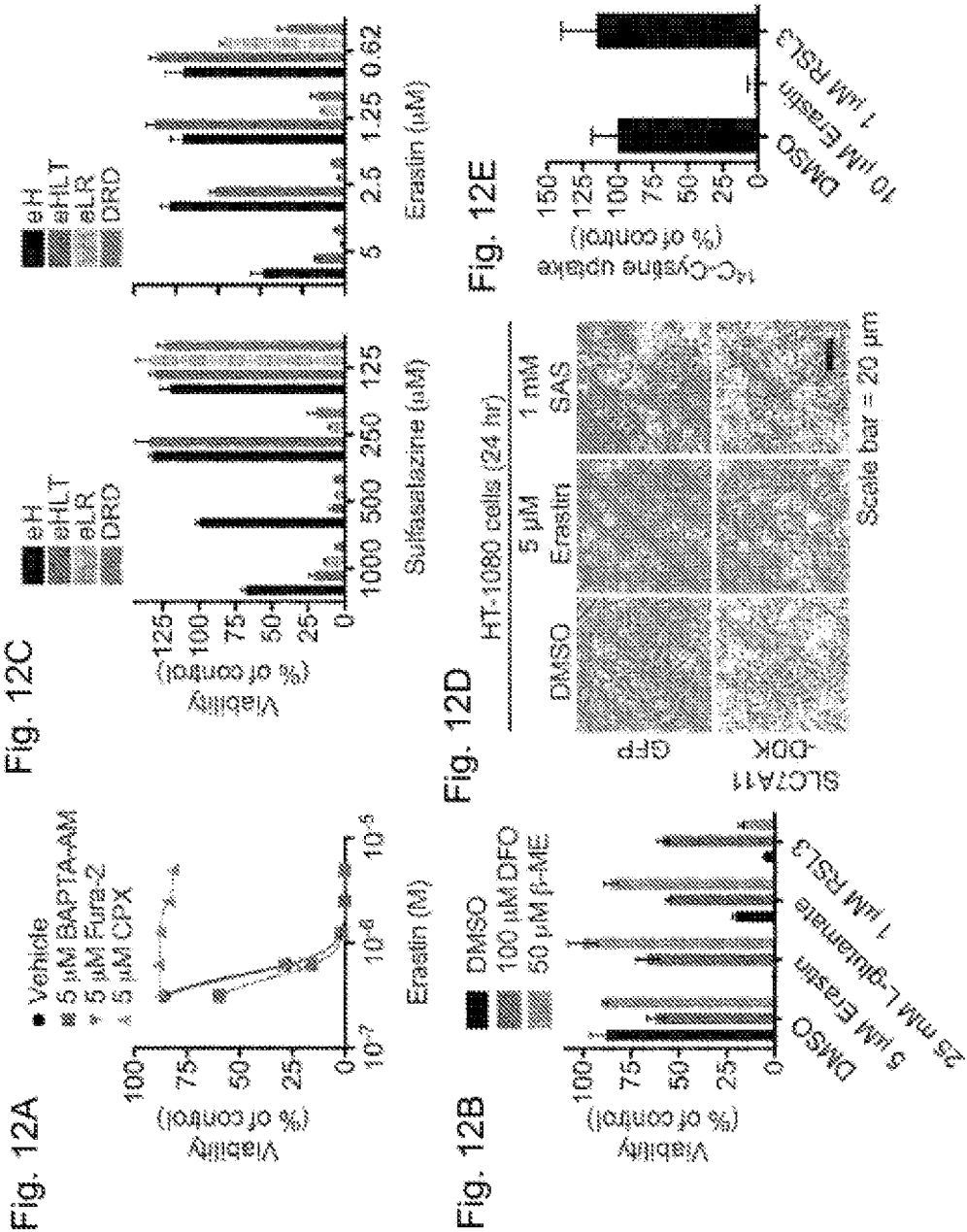

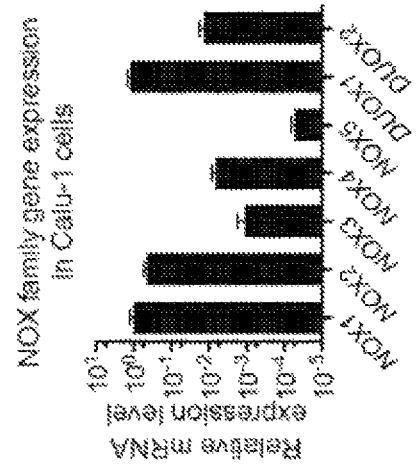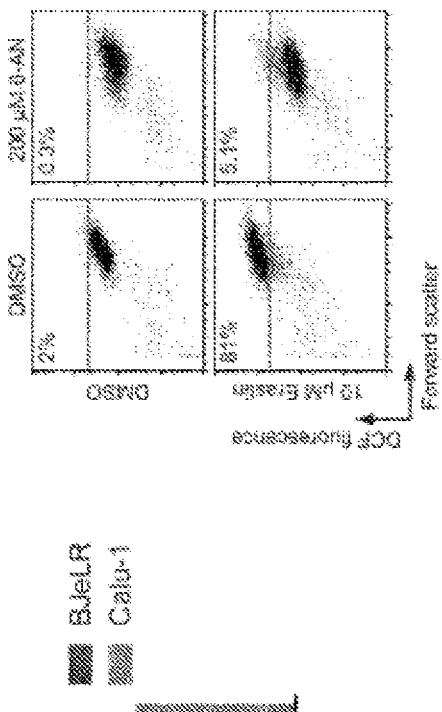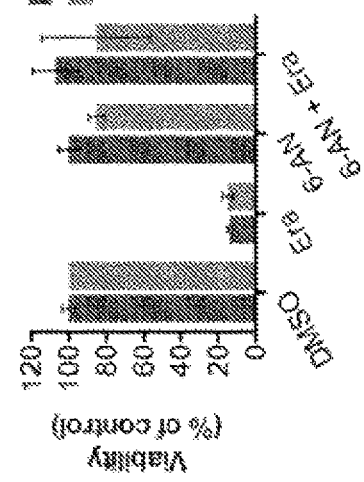

COMPOUNDS, COMPOSITIONS, AND METHODS FOR MODULATING FERROPTOSIS AND TREATING EXCITOTOXIC DISORDERS

CROSS-REFERENCE TO RELATED APPLICATIONS

The present application is a divisional application of U.S. application Ser. No. 14/390,256, filed Oct. 2, 2014, which is a National Stage of International Application No. PCT/US2013/035021, filed Apr. 2, 2013, which claims benefit to U.S. provisional application Ser. No. 61/619,315 filed Apr. 2, 2012. The entire contents of the above applications are incorporated by reference as if recited in full herein.

GOVERNMENT FUNDING

This invention was made with government support under grant number CA097061 awarded by the NIH. The government has certain rights in the invention.

INCORPORATION BY REFERENCE OF SEQUENCE LISTING

This application contains references to amino acids and/or nucleic acid sequences that have been filed concurrently herewith as sequence listing text file "0347521.txt", file size of 2 KB, created on Mar. 30, 2013. The aforementioned sequence listing is hereby incorporated by reference in its entirety pursuant to 37 C.F.R. § 1.52(e)(5).

FIELD OF INVENTION

The present invention provides, inter alia, a compound having the structure:

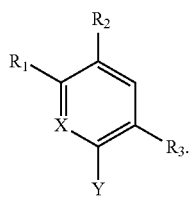

(I)

Also provided are compositions containing the compounds of the present invention, as well as methods of using the compounds and compositions of the present invention.

BACKGROUND OF THE INVENTION

Cell death is crucial for normal development, homeostasis and the prevention of hyper-proliferative diseases such as cancer (Fuchs and Steller, 2011; Thompson, 1995). It was once thought that almost all regulated cell death in mammalian cells resulted from the activation of caspase-dependent apoptosis (Fuchs and Steller, 2011; Thompson, 1995). More recently this view has been challenged by the discovery of several regulated non-apoptotic cell death pathways activated in specific disease states, including poly(ADP-ribose) polymerase-1 (PARP-1) and apoptosis inducing factor 1 (AIF1)-dependent parthanatos, caspase-1-dependent pyroptosis and receptor interacting protein kinase 1 (RIPK1)-dependent necroptosis (Bergsbaken et al., 2009; Christofferson and Yuan, 2010; Wang et al., 2009). It is believed that additional regulated forms of non-apoptotic cell death likely remain to be discovered that mediate cell death in other developmental or pathological circumstances.

The RAS family small GTPases (HRAS, NRAS and KRAS) are mutated in about 30% of all cancers (Vigil et al., 2010). Finding compounds that are selectively lethal to RAS-mutant tumor cells is, therefore, a high priority. Two structurally unrelated small molecules, named erastin and RSL3, were previously identified. These molecules were selectively lethal to oncogenic RAS-mutant cell lines, and together, they were referred to as RAS-selective lethal (RSL) compounds (Dolma et al., 2003; Yang and Stockwell, 2008). Using affinity purification, voltage dependent anion channels 2 and 3 (VDAC2/3) were identified as direct targets of erastin (Yagoda et al., 2007), but not RSL3. ShRNA and cDNA overexpression studies demonstrated that VDAC2 and VDAC3 are necessary, but not sufficient, for erastin-induced death (Yagoda et al., 2007), indicating that additional unknown targets are required for this process.

The type of cell death activated by the RSLs has been enigmatic. Classic features of apoptosis, such as mitochondrial cytochrome c release, caspase activation and chromatin fragmentation, are not observed in RSL-treated cells (Dolma et al., 2003; Yagoda et al., 2007; Yang and Stockwell, 2008). RSL-induced death is, however, associated with increased levels of intracellular reactive oxygen species (ROS) and is prevented by iron chelation or genetic inhibition of cellular iron uptake (Yagoda et al., 2007; Yang and Stockwell, 2008). In a recent systematic study of various mechanistically unique lethal compounds, the prevention of cell death by iron chelation was a rare phenomenon (Wolpaw et al., 2011), suggesting that few triggers can access iron-dependent lethal mechanisms.

Accordingly, there is a need for the exploration of various pathways of regulated cell death, as well as for compositions and methods for preventing the occurrence of regulated cell death. This invention is directed to meeting these and other needs.

SUMMARY OF THE INVENTION

Without being bound to a particular theory, the inventors hypothesized that RSLs, such as erastin, activate a lethal pathway that is different from apoptosis, necrosis and other well-characterized types of regulated cell death. It was found that erastin-induced death involves a unique constellation of morphological, biochemical and genetic features, which led to the name "ferroptosis" as a description for this phenotype. Small molecule inhibitors of ferroptosis that prevent ferroptosis in cancer cells, as well as glutamate-induced cell death in postnatal rat brain slices have been identified and disclosed herein. The inventors have found an underlying similarity between diverse forms of iron-dependent, non-apoptotic death and that the manipulation of ferroptosis may be exploited to selectively destroy RAS-mutant tumor cells or to preserve neuronal cells exposed to specific oxidative conditions.

In view of the foregoing, one embodiment of the present invention is a compound having the structure of formula (I):

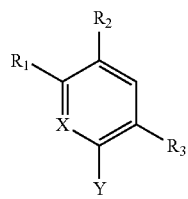

(I)

wherein

X is CH or N;

Y is H, halo, or $C_{1-4}$alkyl;

$R_1$ is selected from the group consisting of H, halo, cycloalkyl, and $NR_4R_5$;

$R_2$ is selected from the group consisting of $NR_6R_7$ and $NO_2$;

$R_3$ is selected from the group consisting of H,

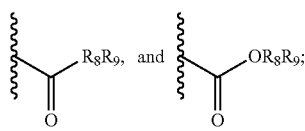

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

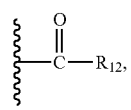

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, with the proviso that:

when $R_1$ is H, $R_3$ cannot be

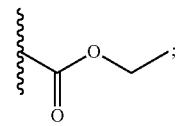 [SMILES: *C(=O)OCC]

when $R_1$ is

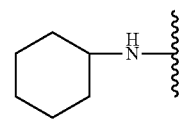

and $R_2$ is $NH_2$, $R_3$ cannot be

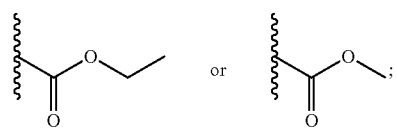

when $R_1$ is

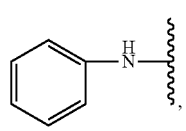 [SMILES: *Nc1ccccc1]

$R_3$ cannot be

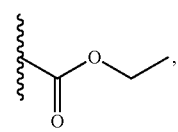 [SMILES: *C(=O)OCC]

when $R_1$ is

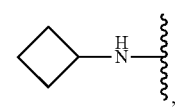 [SMILES: *NC1CCC1]

$R_3$ cannot be

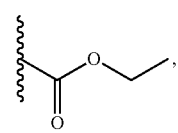 [SMILES: *C(=O)OCC]

when $R_1$ is Cl, X cannot be N, and both $R_1$ and Y cannot be F;

and pharmaceutically acceptable salts thereof, and individual enantiomers and diastereomers thereof.

Another embodiment of the present invention is a composition. This composition comprises a pharmaceutically acceptable carrier and a compound according to the present invention.

Yet another embodiment of the present invention is a method for treating or ameliorating the effects of an excitotoxic disorder in a subject in need thereof. This method comprises administering to the subject an effective amount of a compound having the structure of formula (I):

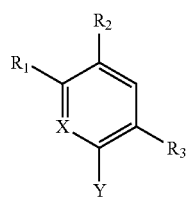
(I)

wherein
- X is CH or N;
- Y is H, halo, or $C_{1-4}$alkyl;
- $R_1$ is selected from the group consisting of H, halo, cycloalkyl, and $NR_4R_5$;
- $R_2$ is selected from the group consisting of $NR_6R_7$ and $NO_2$;
- $R_3$ is selected from the group consisting of H,

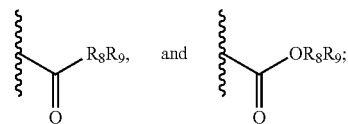

- $R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;
- $R_6$ and $R_7$ are independently selected from the group consisting of H, $C_{1-6}$alkyl, Boc, O, $COOR_{12}$,

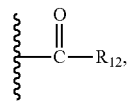

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;
- $R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;
- $R_{10}$ and $R_{11}$ are independently selected from H and Boc; and
- $R_{12}$ is a $C_{1-4}$alkyl optionally substituted with aryl, and pharmaceutically acceptable salts thereof, and individual enantiomers and diastereomers thereof.

An additional embodiment of the present invention is a method for treating or ameliorating the effects of an excitotoxic disorder in a subject in need thereof. This method comprises administering to the subject an effective amount of a composition comprising a pharmaceutically acceptable carrier and a compound having the structure (I):

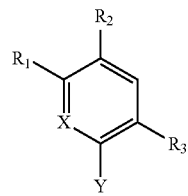
(I)

wherein
- X is CH or N;
- Y is H, halo, or $C_{1-4}$alkyl;
- $R_1$ is selected from the group consisting of H, halo, cycloalkyl, and $NR_4R_5$;
- $R_2$ is selected from the group consisting of $NR_6R_7$ and $NO_2$;
- $R_3$ is selected from the group consisting of H,

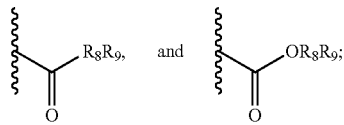

- $R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;
- $R_6$ and $R_7$ are independently selected from the group consisting of H, $C_{1-6}$alkyl, Boc, O, $COOR_{12}$,

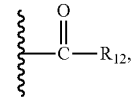

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;
- $R_8$ and $R_9$ are independently selected from the group consisting of no atom, O, N, $NHR_{12}$, $C_{1-10}$ alkyl, and $C_{1-10}$ ether, wherein the alkyl and the ether are option ally substituted with NH$_2$, NHBoc, or C$_{3-12}$cycloalkyl, wherein one or more of the ring carbons of the cycloalkyl are optionally substituted with one or more heteroatoms;

R$_{10}$ and R$_{11}$ are independently selected from H and Boc; and

R$_{12}$ is a C$_{1-4}$alkyl optionally substituted with aryl, and pharmaceutically acceptable salts thereof, and individual enantiomers and diastereomers thereof.

Another embodiment of the present invention is a method of modulating ferroptosis in a subject in need thereof. This method comprises administering to the subject an effective amount of a ferroptosis inhibitor.

A further embodiment of the present invention is a method of reducing reactive oxygen species (ROS) in a cell. This method comprises contacting a cell with a ferroptosis modulator.

Another embodiment of the present invention is a method for treating or ameliorating the effects of a neurodegenerative disease in a subject in need thereof. This method comprises administering to the subject an effective amount of a compound having the structure:

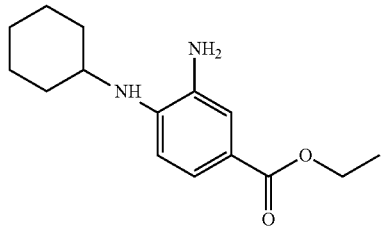 [SMILES: CCOC(=O)c1ccc(NC2CCCCC2)c(N)c1]

and pharmaceutically acceptable salts thereof.

A further embodiment of the present invention is a compound. The compound has the structure selected from the group consisting of:

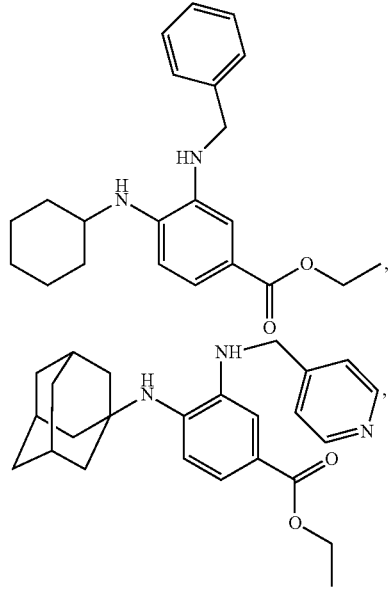

and pharmaceutically acceptable salts thereof.

BRIEF DESCRIPTION OF THE DRAWINGS

FIG. 1A to FIG. 1F shows that erastin-induced death triggers the accumulation of cytosolic ROS whose production can be inhibited by the iron chelator deferoxamine (DFO). FIG. 1A shows representative microscopy images of HT-1080 cell viability over time+/−erastin (Era, 10 µM) and deferoxamine (DFO, 100 µM). FIGS. 1B and 1C show cytosolic and lipid ROS production assessed over time (2, 4 and 6 hours) by flow cytometry using H$_2$DCFDA and C11-BODIPY. FIG. 1D shows mitochondrial ROS assessed in HT-1080 cells treated for 6 hours with erastin+/−DFO, as above, or with rotenone (250 nM)+/−DFO. In FIGS. 1A-D, representative data from one of four experiments are shown. FIG. 1E shows erastin-induced death in 143B ρ$^0$ and ρ$^+$ cells. FIG. 1F shows mtDNA-encoded transcript levels in ρ$^0$ and ρ$^+$ cells. Results in FIGS. 1E and 1F are mean±SD from one of three representative experiments.

FIG. 2A shows a transmission electron microscopy image of BJeLR cells treated with DMSO (10 hours), erastin (37 µM, 10 hours), staurosporine (STS, 0.75 µM, 8 hours), H$_2$O$_2$ (16 mM, 1 hour) and rapamycin (Rap, 100 nM, 24 hours). Single white arrowheads show shrunken mitochondria, paired white arrowheads show chromatin condensation, black arrowheads show cytoplasmic and organelle swelling, plasma membrane rupture, and black arrow shows formation of double-membrane vesicles. A minimum of 10 cells per treatment condition were examined. FIG. 2B shows normalized ATP levels in HT-1080 and BJeLR cells treated as in FIG. 2A with the indicated compounds. Representative data (mean±SD) from one of three independent experiments are shown. FIG. 2C shows modulatory profiling of known small molecule cell death inhibitors in HT-1080, BJ-eLR and Calu-1 cells treated with erastin (10 µM, 24 hours). FIG. 2D shows the effect of inhibitors on H$_2$DCFDA-sensitive ROS production in HT-1080 cells treated for 4 hours. FIG. 2E shows modulatory profiling of ciclopirox olamine (CPX), DFO, ebselen (Ebs), trolox (Tlx), U0126 and CHX on oxidative and non-oxidative lethal agents.

FIG. 3A shows an outline of the MitoCarta shRNA screen and confirmation pipeline. FIGS. 3B and 3C show six high confidence genes required for erastin-induced ferroptosis. FIG. 3B shows the viability of HT-1080 cells infected with shRNAs for 72 hours and treated with erastin (10 µM, 24 hours). FIG. 3C shows the mRNA levels for hairpins shown in FIG. 3B determined using RT-qPCR. Data in FIGS. 3B and 3C are mean±SD from one of three experiments. The sequences of various clones of shRNA listed in FIGS. 3B and 3C are as follows: the sequence for sh263-VDAC3 is shown in SEQ ID NO:1, the sequence for sh548-RPL8 is shown in SEQ ID NO:2, the sequence for sh440-ATP5G3 is shown in SEQ ID NO:3, the sequence for sh978-TTC35 is shown in SEQ ID NO:4, the sequence for sh2326-IREB2 is shown in SEQ ID NO:5, the sequence for sh1776-ACSF2 is shown in SEQ ID NO:6, and the sequence for sh332-CS is shown in SEQ ID NO:7. FIGS. 3D and 3E show the effect of shRNA-mediated silencing of high-confidence genes using the best hairpin identified by mRNA silencing efficiency in FIG. 3C on cell viability. FIG. 3D shows the viability of various cell lines treated with a lethal dose of erastin (indicated in parentheses) for 24 hours. FIG. 3E shows the viability of HT-1080 cells treated with various death-inducing or cytostatic compounds. For FIGS. 3D and 3E, % rescue was computed relative to each shRNA alone+DMSO. FIG. 3F is a cartoon outline of glutamine (Gln) metabolism. Shaded box indicates mitochondria. FIG. 3G shows images of HT-1080 cells treated with aminooxy acetic acid (AOA)+/−dimethyl alphaketoglutarate (DMK)+/−erastin.

FIG. 4A shows the structure of ferrostatin-1 (Fer-1). FIG. 4B shows the effect of resynthesized Fer-1 (0.5 µM) on the lethality of various compounds in HT-1080 cells. FIG. 4C shows the effect of Fer-1 and U0126 on ERK phosphorylation in HT-1080 cells. FIG. 4D shows the effect of DFO, CHX, trolox (Tlx) and Fer-1 on HT-1080 cell proliferation over 48 hours as assessed by Vi-Cell. FIG. 4E shows the effect of Fer-1 (0.5 µM) on erastin (10 µM)-induced ROS production in HT-1080 cells (4 hour treatment). FIG. 4F shows cell-free antioxidant potential monitored by changes in the absorbance at 517 nm of the stable radical DPPH. FIG. 4G shows the dose-response relationship for inhibition of erastin (10 µM, 24 hours)-induced death in HT-1080 cells by Fer-1 and analogs. FIG. 4H shows the structure of various compounds listed in FIG. 4G. FIG. 4I shows the correlation between predicted partition coefficient (log P) and the ability of various Fer-1 analogs to prevent erastin-induced death. FIG. 4J shows the dose-response relationship for inhibition of erastin (10 µM, 24 hours)-induced death by various antioxidants. FIG. 4K shows a plot of predicted partition coefficient (log P) and ability of various antioxidants to prevent erastin-induced death. Data in FIGS. 4B, 4D, 4F, 4G, and 4J represent mean±SD from one of three representative experiments.

FIG. 5A is a cartoon outline of the hippocampal slice procedure used herein. FIG. 5B shows bright-field and fluorescent images of propidium iodide (PI) staining of treated hippocampal slices. Slices were treated with glutamate (5 mM, 3 hours)+/−Fer-1 (2 µM), CPX (5 µM) or MK-801 (10 µM). Representative images from 1 one 6 slices per condition are shown. FIGS. 5C-E show quantification of the effects depicted in FIG. 5B. Data were analyzed using a two-way ANOVA (brain region×drug treatment) followed by Bonferroni post-tests. *: $P<0.05$, : $P<0.01$, *: $P<0.001$.

FIG. 6A to FIG. 6I shows that erastin inhibits the activity of system $x_c^-$. FIG. 6A shows the modulatory profile of HT-1080 cells treated with different lethal compounds and inhibitors. FIG. 6B is a cartoon depicting the composition and function of system L and system $x_c^-$. Cys: cystine, NAA: neutral amino acids. FIG. 6C shows SLC7A11 mRNA levels in compound (6 hours)-treated HT-1080 cells determined by RT-qPCR. FIGS. 6D and 6E show the effect of silencing SLC7A11 using siRNA on erastin (10 µM, 8 hours)-induced death (FIG. 6D) and mRNA levels (FIG. 6E) in HT-1080 cells. FIG. 6F shows Na$^+$-independent [$^{14}$C] cystine uptake by HT-1080 cells in response to various drugs. FIG. 6G shows identification of SLC7A5 as the lone target identified by erastin affinity purification in both BJeH and BJeLR cells. FIG. 6H shows the metabolic profiling of system L and non-system L substrate amino acid levels in erastin-treated Jurkat cells. FIG. 6I shows the effect of L-glutamic acid (L-Glu, 12.5 mM) and D-phenylalanine (D-Phe, 12.5 mM) on erastin-induced death in HT-1080 cells.

FIG. 7A shows the outline of the NOX (NADPH oxidase) pathway. Inhibitors are shown in gray. FIG. 7B shows the effect of NOX pathway inhibitors on erastin-induced death in Calu-1 and HT-1080 cells. GKT: GKT137831. FIGS. 7C and 7D show the effect of shRNA silencing of the PPP enzymes glucose-6-phosphate dehydrogenase (G6PD) and phosphogluconate dehydrogenase (PGD) on viability of erastin (2.5 µM)-treated Calu-1 cells. Infection with shRNA targeting VDAC2 was used as a positive control. Relative mRNA levels in (FIG. 7D) were assessed by qPCR following shRNA knockdown. Data in FIGS. 7B, 7C, and 7D represents mean±SD. FIG. 7E shows a model of ferroptosis pathway. The core ferroptotic lethal mechanism is in the shaded portion.

FIG. 8A to FIG. 8E shows that RSLs trigger iron-dependent cell death independent of the mitochondrial electron transport chain. FIG. 8A shows the viability of HT-1080 cells treated with erastin+/−ferric ammonium citrate (FAC) as assessed in triplicate by Vi-Cell. FIG. 8B shows the viability of HT-1080 cells treated with DMSO or erastin+/− FAC, ferric citrate (FC), iron chloride hexahydrate (IHC), manganese chloride (Mn), nickel sulfate hexahydrate (Ni), cobalt chloride hexahydrate (Co) or copper sulfate (Cu). FAC was used at 10 µg/mL, all other metals were used at 25 µM. Cell viability was assessed by Trypan Blue exclusion (Vi-Cell) in triplicate and the effects of the erastin+metal combination were expressed as a percentage of the DMSO+ metal viability alone. FIGS. 8C and 8D show mitochondrial superoxide levels in 143B cells assessed by flow cytometry using MitoSOX. Treatments used: 250 nM rotenone (Rote), 100 µM DFO alone or in combination, as indicated. FIG. 8E shows the viability of 143B $\rho^+$ and $\rho^0$ cells treated for 24 hours with RSL3 and assessed by Alamar Blue. All experiments were repeated two to four times with similar results, and representative data from one experiment are shown. Data in FIGS. 8A, 8B and 8E represent mean±SD from multiple replicates within one experiment.

FIG. 9A to FIG. 9C shows that ferroptosis occurs in mouse embryonic fibroblasts (MEFs), independent of Bax and Bak, and can be attenuated by the late addition of inhibitors. FIG. 9A shows the viability of SV40-transformed MEFs (control and Bax/Bak double knockout, DKO) that were treated with erastin+/−DFO, Trolox, U0126 or cycloheximide (CHX) for 24 hours as indicated. FIG. 9B shows the viability of wild-type and DKO MEFs that were treated with staurosporine (STS) for 24 hours at the indicated concentrations to induce apoptosis. Bax/Bak double knockout MEFs are more resistant to STS, as expected. In FIGS. 9A and 9B, cell viability was assessed by Alamar Blue. Experiments were repeated twice with similar results and representative data from one experiment are shown. All values are mean±SD from multiple replicates within each experiment. FIG. 9C shows microscopy images of cells that were treated+/−erastin and co-treated with the indicated inhibitors. Inhibitors were added either at the same time as erastin (0 hours) or 2-6 hours later (+2, +4, +6 hours). 2,2-bipyridyl (2,2-BP) is a membrane permeable iron chelator. All cells were photographed 24 hours after the start of the experiment. This experiment was repeated three times with similar results, and representative data from one experiment is shown.

In FIGS. 10A-10C, HT-1080 cells were infected with shRNAs targeting IREB2 and FBXL5 for 3 days and then examined for gene expression or drug sensitivity. FIGS. 10A and 10B show reciprocal transcriptional regulation of iron-regulated genes induced by silencing of IREB2 and FBXL5 as assessed by RT-qPCR. DFO treatment (48 hours) was used as a control for changes in gene expression. ISCU, FTH1, FTL and TFRC are known iron-regulated genes (Sanchez et al., 2011). FIG. 10C shows silencing of FBXL5 sensitizes cells to erastin-induced death. FIG. 10D shows that aminooxyacetic acid (AOA), but not dichloroacetic acid (DCA), inhibits erastin-induced death in HT-1080 and BJeLR cells. All data are mean±SD from multiple replicates within one experiment. All experiments were performed 2-4 times with similar results. Representative data from one experiment are shown.

FIG. 11A to FIG. 11C shows Fer-1, and Fer-1 structure-activity relationship (SAR) analysis. FIG. 11A shows that the re-testing in 10-point, 2-fold dilution series of the top four compounds from a LOC (Lead Optimized Compound) library screen validated to suppress erastin-induced death in HT-1080 cells. FIG. 11B shows the structure of these top 4 compounds. FIG. 11C shows the effect of varying the Fer-1 structure on the ability of such compounds to inhibit death in erastin (10 μM)-treated HT-1080 cells. Cell viability was assessed by Alamar Blue in quadruplicate. $EC_{50}$ values (nM) were computed from dose response curves using Prism. Log P (S log P) values were computed using Molecular Operating Environment.

FIG. 12A to FIG. 12E shows the analysis of the role of calcium and system $x_c^-$ in ferroptosis. FIG. 12A shows the viability of HT-1080 cells treated for 24 hours with erastin+/−DMSO, the calcium chelators BAPTA-AM or Fura-2, or, as a positive control for death rescue, the iron chelator ciclopirox olamine (CPX), at the indicated concentration. FIG. 12B shows the viability of HT-1080 cells treated for 24 hours with erastin, monosodium L-glutamic acid or RSL3+/−inhibitors using Alamar Blue. FIG. 12C shows that sulfasalazine, like erastin, displays RAS-selective lethal properties in the BJ cell series assay. For FIGS. 12A-12C, values represent mean±SD from multiple replicates within one experiment. The entire experiment was repeated twice and representative data from one experiment are shown. FIG. 12D shows microscopy images of HT-1080 cells that were transfected for 48 hours with either a control plasmid (pMaxGFP) or pCMV6-SLC7A11-DDK then treated with DMSO, erastin or SAS, as indicated, and photographed. FIG. 12E shows [$^{14}$C]-cystine uptake into HT-1080 cells measured under Na$^+$-free conditions in response to DMSO, erastin and RSL3. Data represents mean±SD, n=3.

FIG. 13A to FIG. 13C shows that erastin-induced death is prevented by inhibition of the PPP/NOX pathway. FIG. 13A shows relative expression of NOX family catalytic subunit mRNAs in Calu-1 cells assessed by RT-qPCR. FIG. 13B shows the viability of Calu-1 and BJeLR cells in response to erastin (10 μM)+/−the PPP inhibitor 6-aminonicotinamde (6-AN, 200 μM) after 24 hours by Vi-Cell. Data in FIGS. 13A and 13B represent mean±SD of replicates from one experiment. FIG. 13C shows $H_2DCFDA$-reactive ROS measured in BJeLR cells that were treated for 8.5 hours, as indicated, prior to the onset of overt death in these cells. Experiments were performed at 3 times with similar results, and representative data from one experiment are shown.

DETAILED DESCRIPTION OF THE INVENTION

Figure 1D:
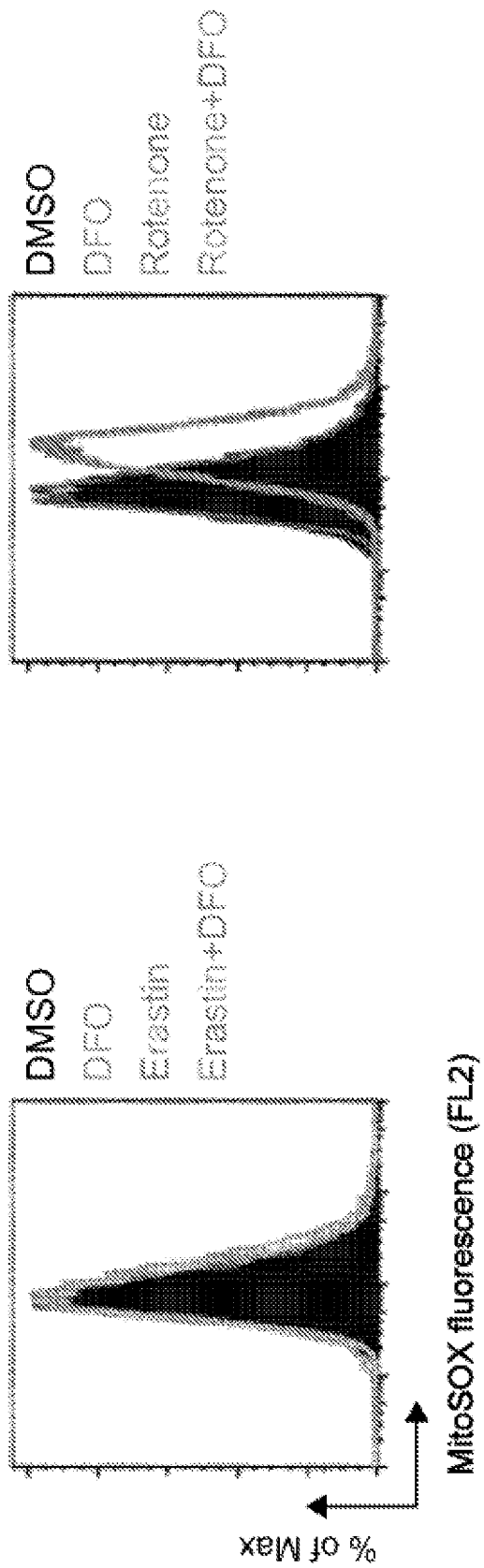
Figure 1E:
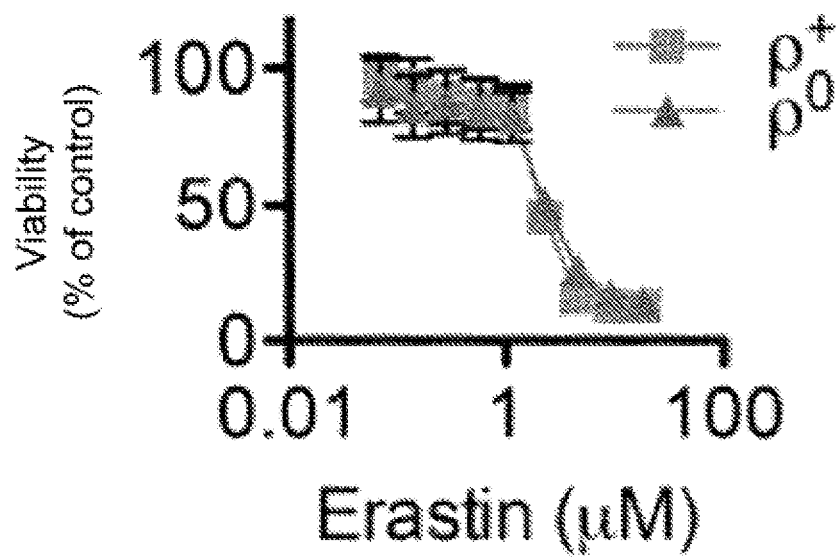
Figure 1F:
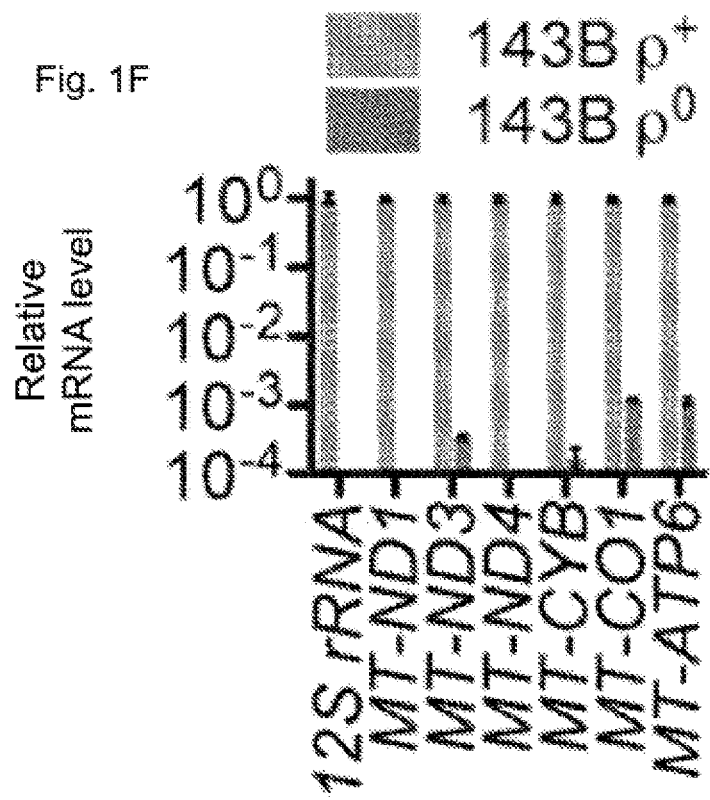

One embodiment of the present invention is a compound having the structure of formula (I):

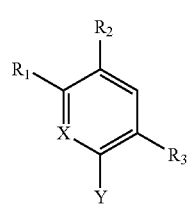

wherein

X is CH or N;

Y is H, halo, or $C_{1-4}$alkyl;

$R_1$ is selected from the group consisting of H, halo, cycloalkyl, and $NR_4R_5$;

$R_2$ is selected from the group consisting of $NR_6R_7$ and $NO_2$;

$R_3$ is selected from the group consisting of H,

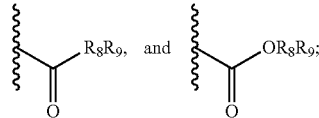

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

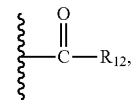

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, with the proviso that:

when $R_1$ is H, $R_3$ cannot be

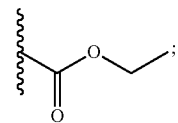 [SMILES: *C(=O)OCC]

when R₁ is

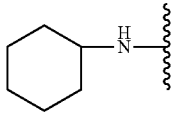 [SMILES: *NC1CCCCC1]

and R₂ is NH₂, R₃ cannot be

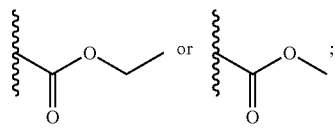

when R₁ is

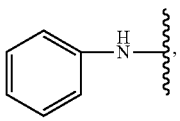

R₃ cannot be

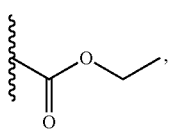

when R₁ is

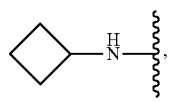

R₃ cannot be

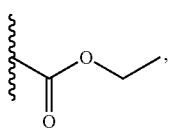

when R₁ is Cl, X cannot be N, and
both R₁ and Y cannot be F;
and pharmaceutically acceptable salts thereof, and individual enantiomers and diastereomers thereof.

To clarify, when more than one pendant group is present, each pendant group may be the same or different. For example, if there are two pendant groups on e.g., the alkyl-aryl, each pendant group may be the same (e.g., both pendant groups may be F atoms) or each pendant group may be different (e.g., one pendant group may be an F atom while the other is a Br atom).

In one aspect of this embodiment, the compound has the structure of formula II:

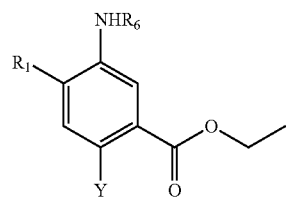

(II)

wherein
Y is Cl or methyl;
R₁ is selected from the group consisting of H, halo, cycloalkyl, and NR₄R₅;
R₄ and R₅ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, NR₁₀R₁₁, Boc, COOR₁₂, and $C_{1-8}$alkyl;
R₁₀ and R₁₁ are independently selected from H and Boc;
R₆ is selected from the group consisting of H, $C_{1-6}$alkyl, Boc, O, COOR₁₂,

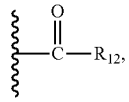

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, NO₂, $C_{1-4}$ ether, $C_{1-4}$ ester, OCOOR₁₂, and $C_{1-8}$alkyl, which $C_{1-8}$alkyl is optionally further substituted with one or more halo; and
R₁₂ is a $C_{1-4}$alkyl optionally substituted with aryl, and pharmaceutically acceptable salts thereof, and individual enantiomers and diastereomers thereof.

Preferably, R₆ is an alkyl-aryl with a pendent group. Also preferably, R₁ is cyclohexylamino or admantylamino.

In another aspect of this embodiment, the compound has the structure of formula III:

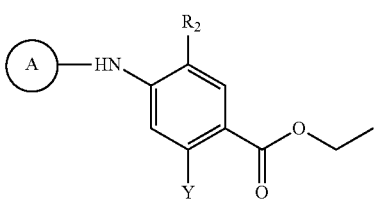

(III)

wherein
Y is Cl or methyl;

is selected from the group consisting of H, $C_{1-8}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl; and $R_{10}$ and $R_{11}$ are independently selected from H and Boc, $R_2$ is selected from the group consisting of $NR_6R_7$ and $NO_2$;

$R_6$ and $R_7$ are independently selected from the group consisting of H, $C_{1-6}$alkyl, Boc, O, $COOR_{12}$,

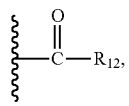

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_{12}$ is a $C_{1-4}$alkyl optionally substituted with aryl, and pharmaceutically acceptable salts thereof, and individual enantiomers and diastereomers thereof.

Preferably,

is cyclohexyl or adamantyl. Also preferably, $R_6$ is an alkyaryl with a pendant group, and $R_7$ is H.

In yet another aspect of this embodiment, the compound has the structure of formula IV:

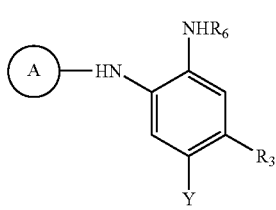

(IV)

wherein
Y is Cl or methyl;

is selected from the group consisting of H, $C_{1-8}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, and $C_{1-8}$alkyl, $R_3$ is selected from the group consisting of H,

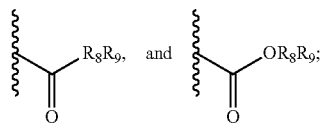

$R_6$ is selected from the group consisting of H, $C_{1-6}$alkyl, Boc, O, $COOR_{12}$,

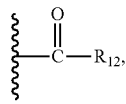

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, and pharmaceutically acceptable salts thereof, and individual enantiomers and diastereomers thereof.

Preferably,

is cyclohexyl or adamantyl. Also preferably, $R_6$ is an alkyaryl with a pendant group.

In another preferred embodiment, the compound is selected from the group consisting of:

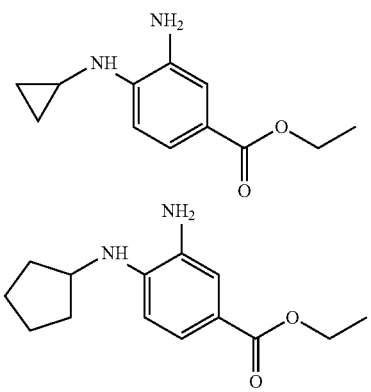

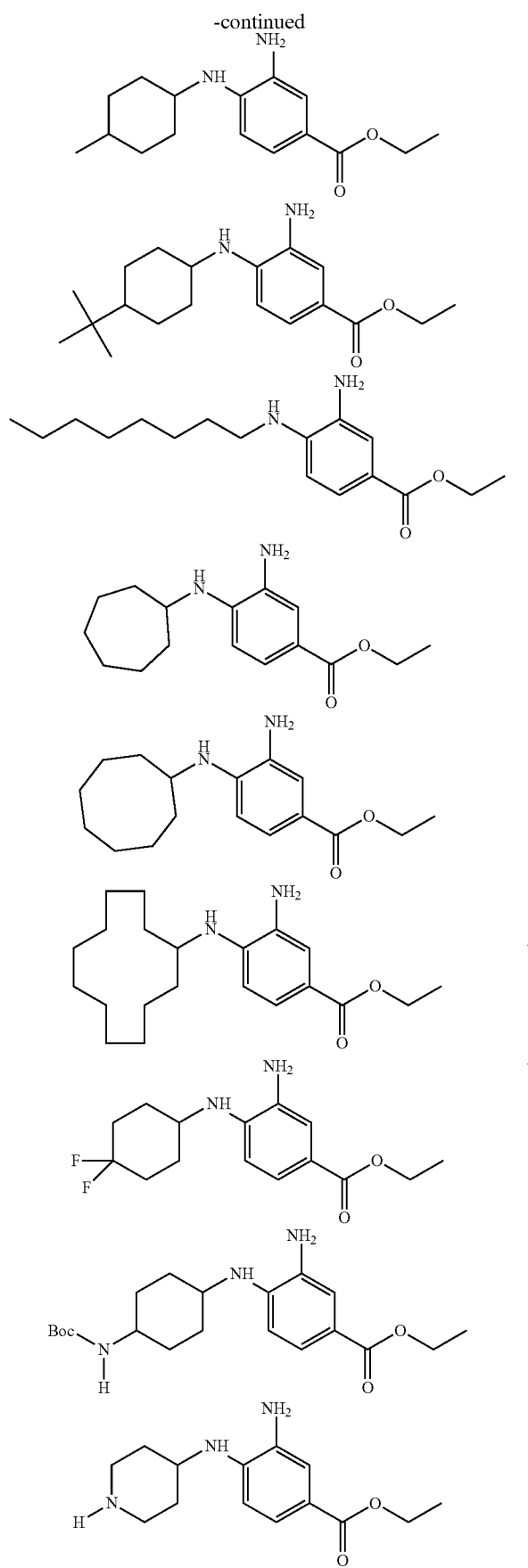
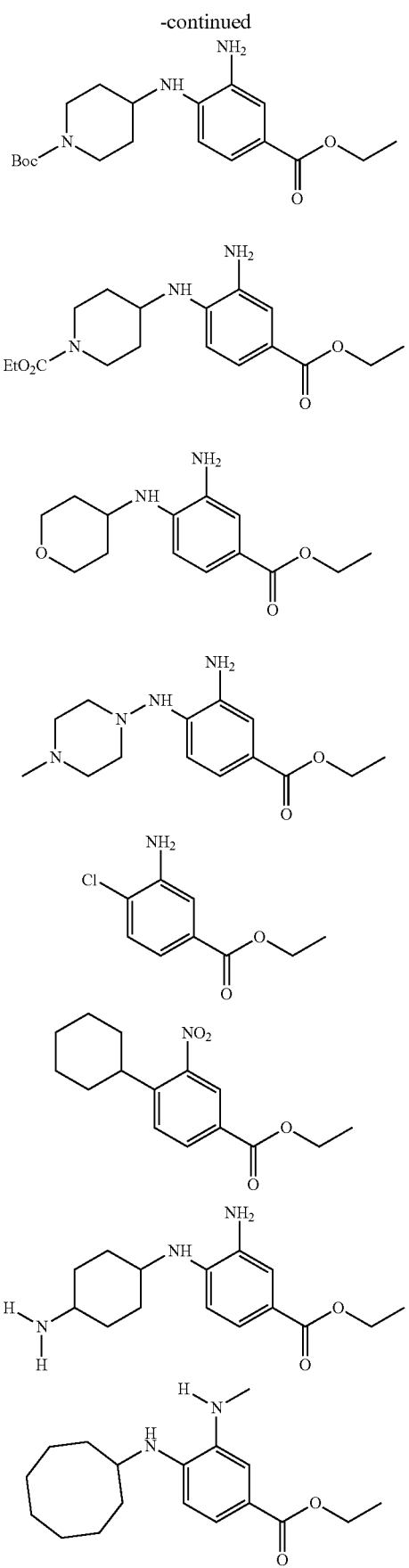

-continued
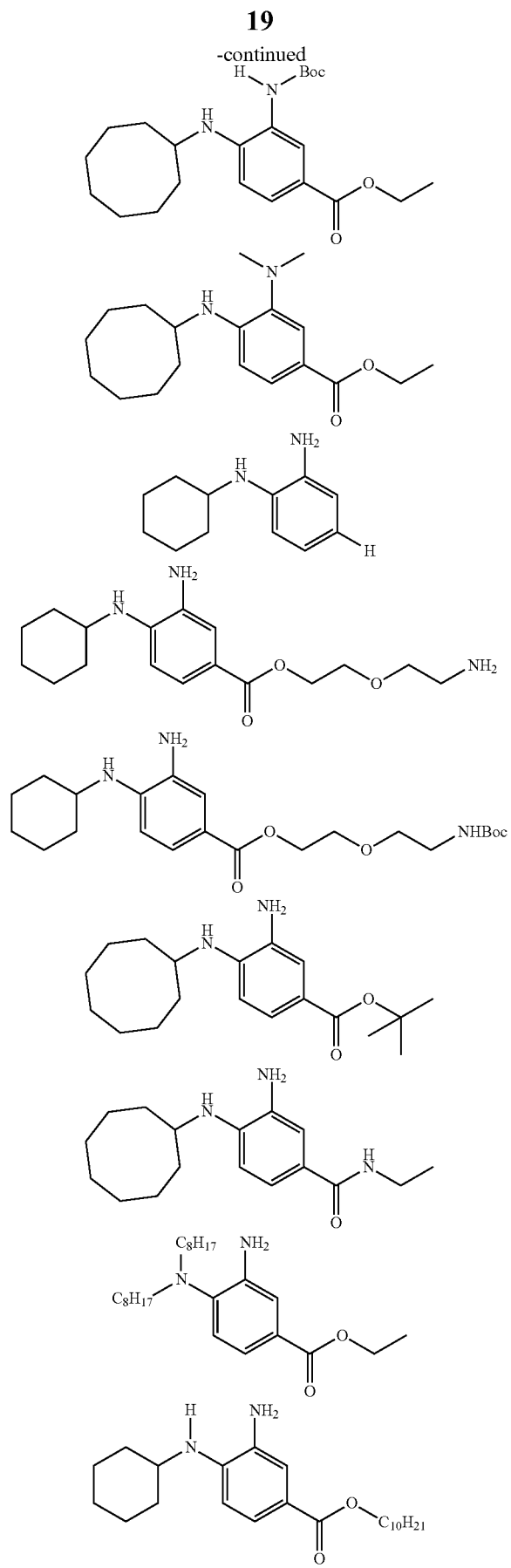
-continued
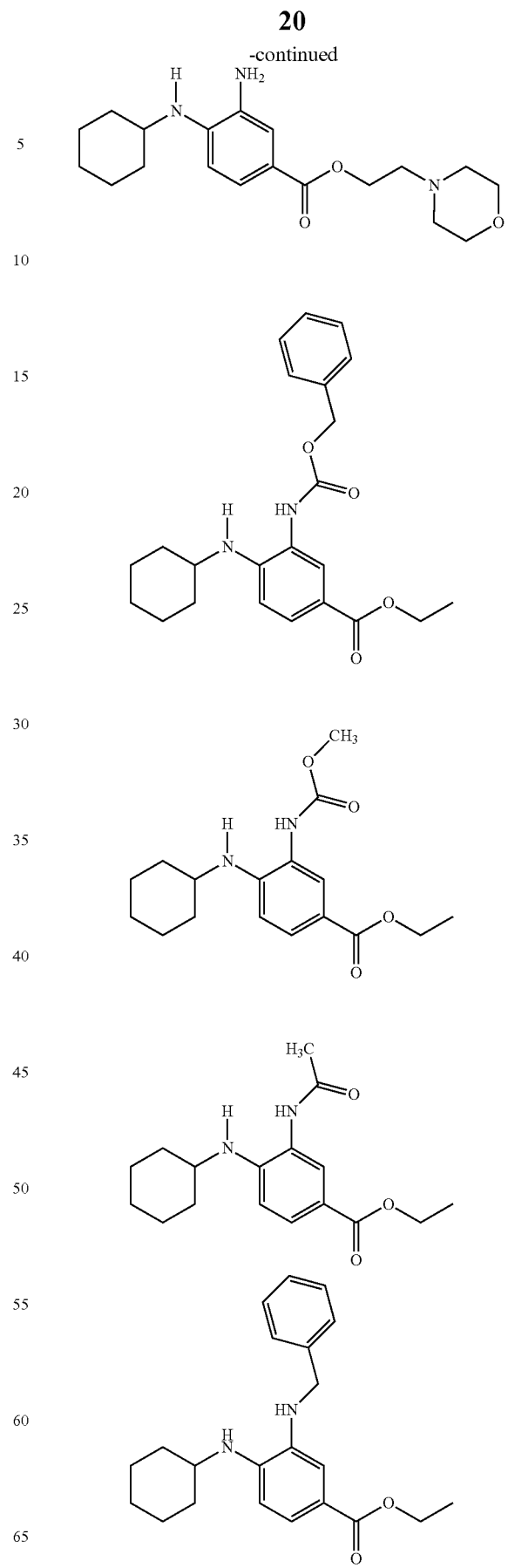

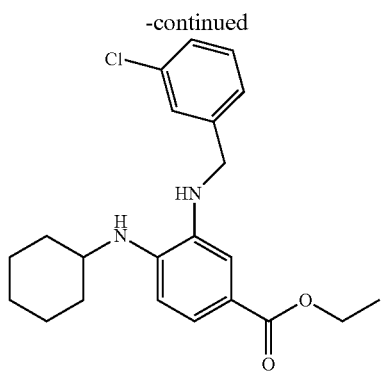
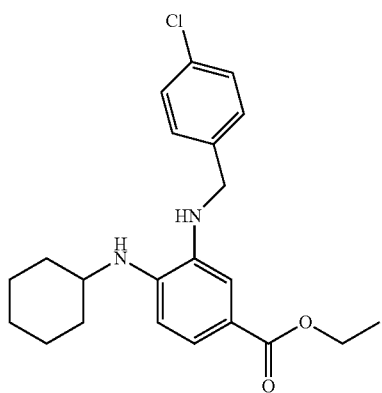
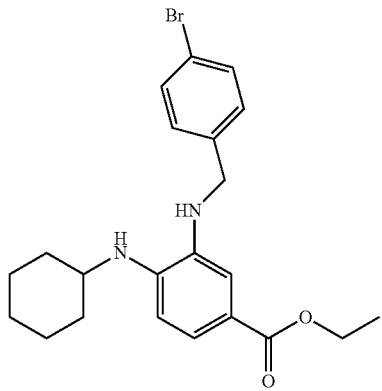
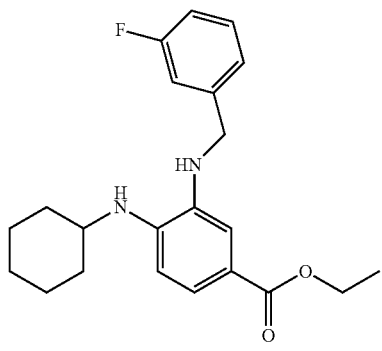
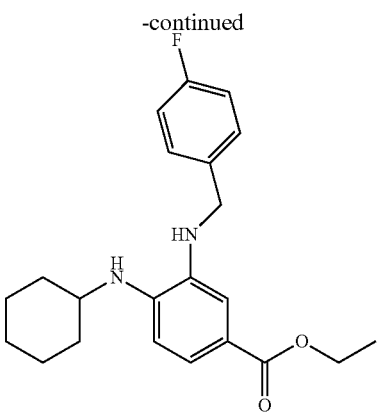
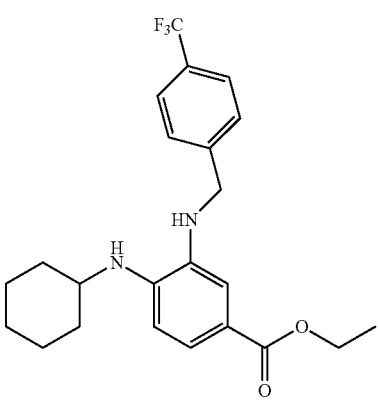
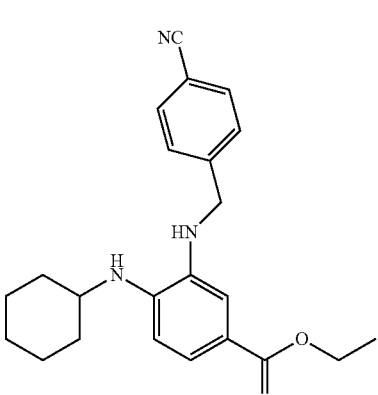
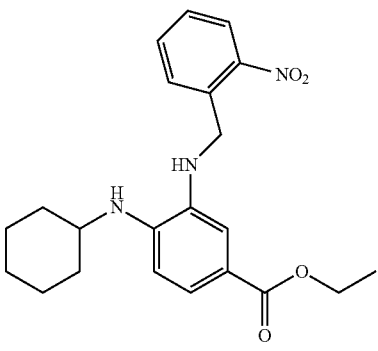

-continued
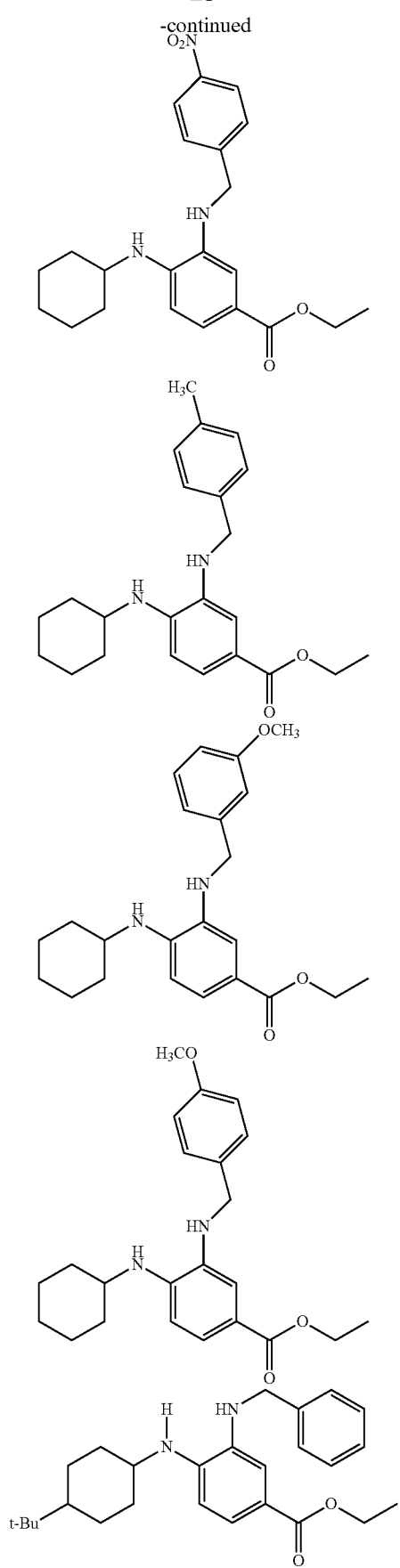
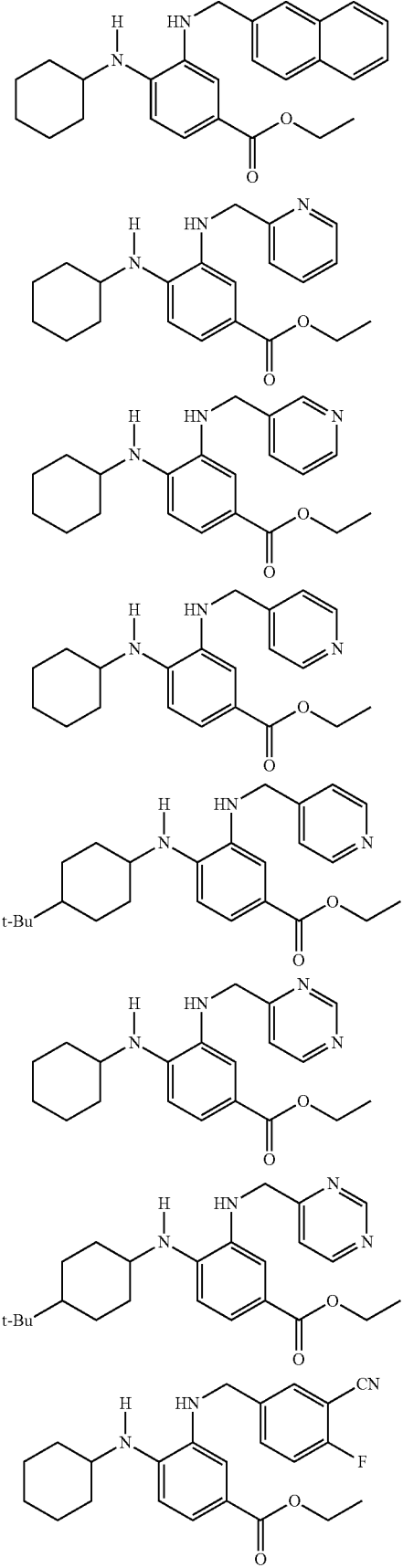

-continued
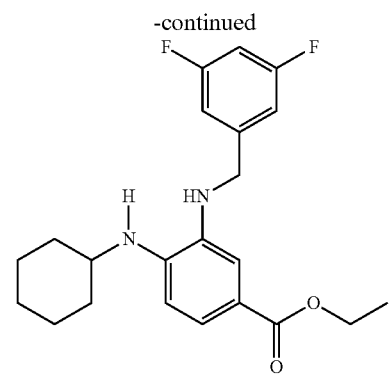
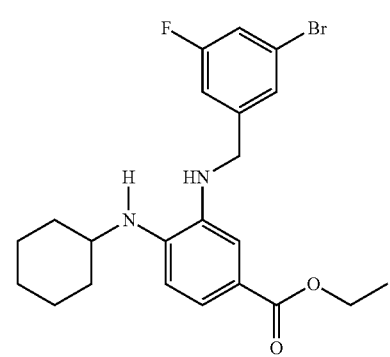
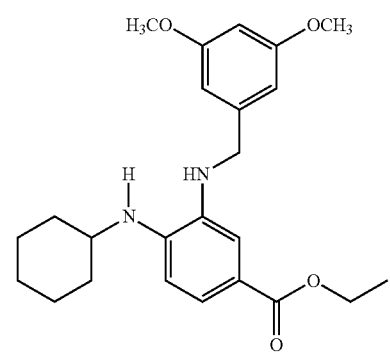
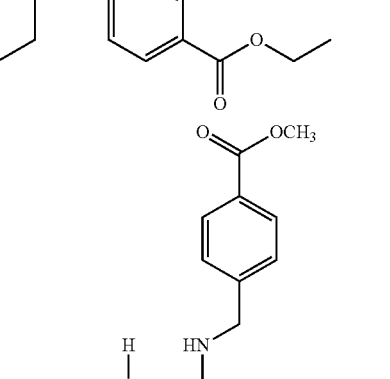
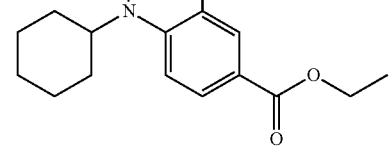
-continued
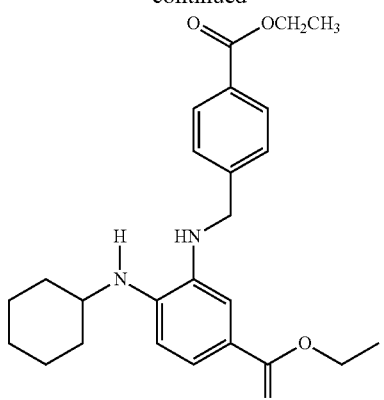
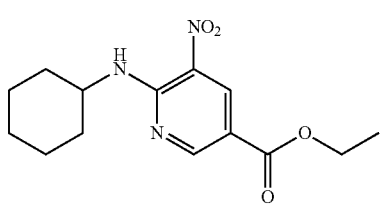
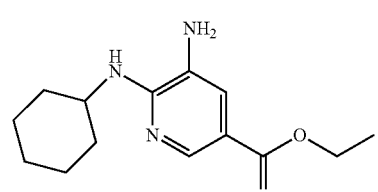
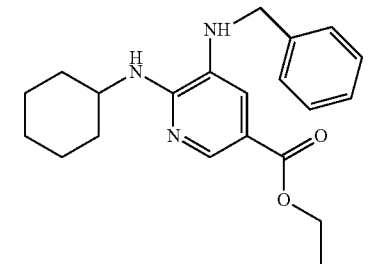
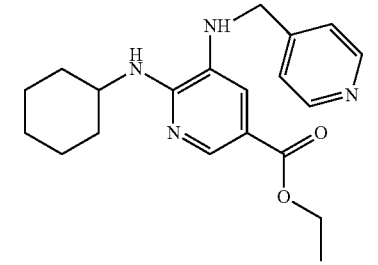
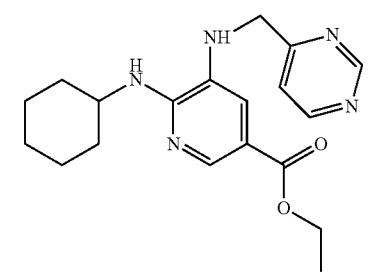

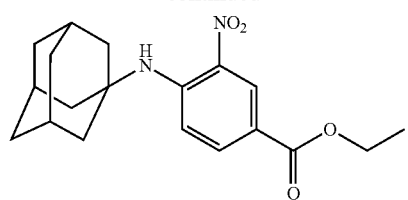
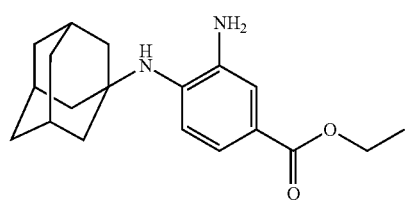
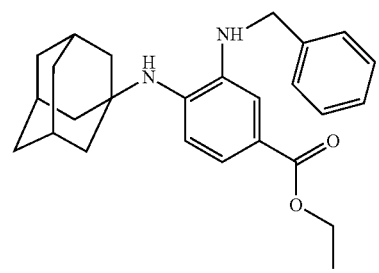
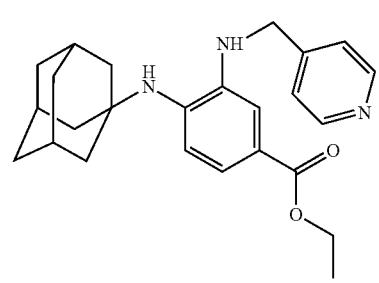
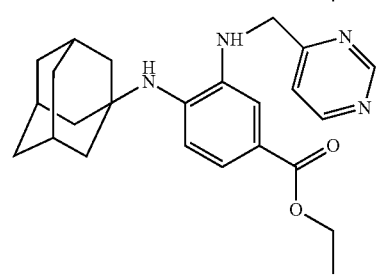
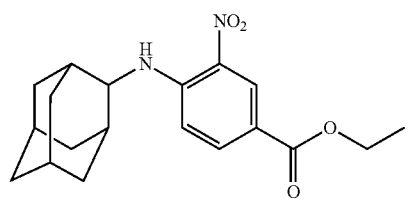
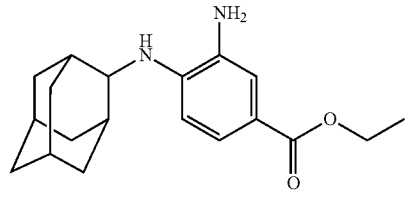
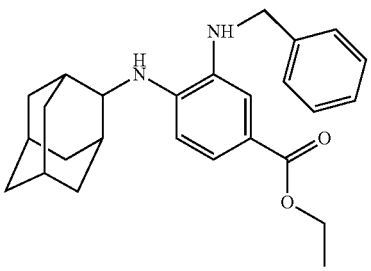
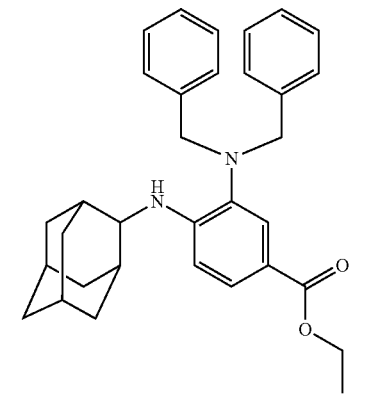
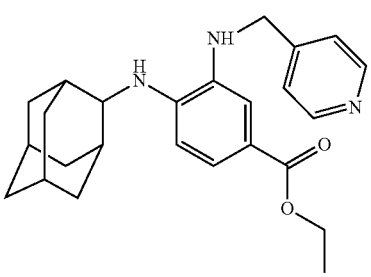
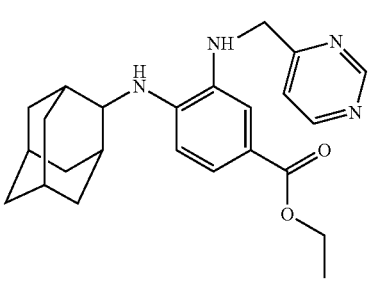
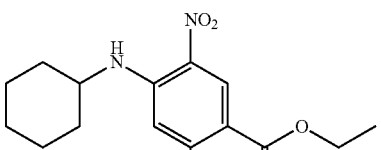
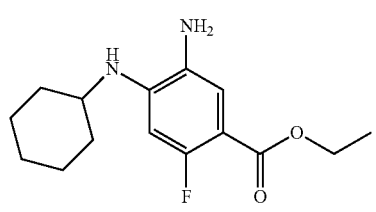

and pharmaceutically acceptable salts thereof, and individual enantiomers and diastereomers thereof.

In yet another preferred embodiment, the compound is selected from the group consisting of:

31
-continued
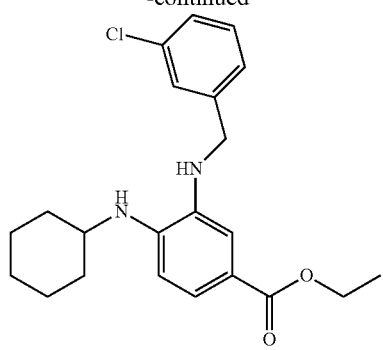
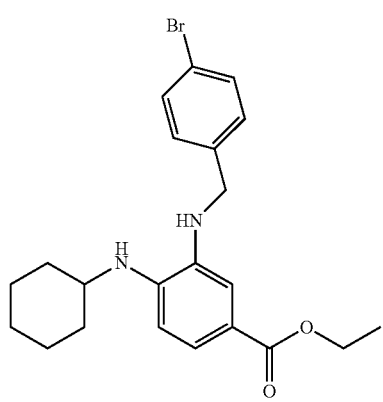
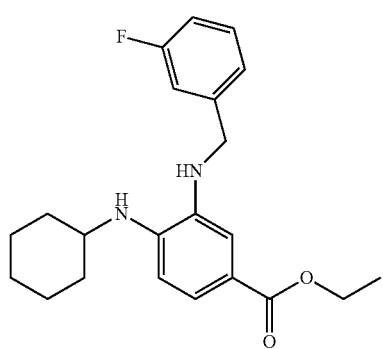
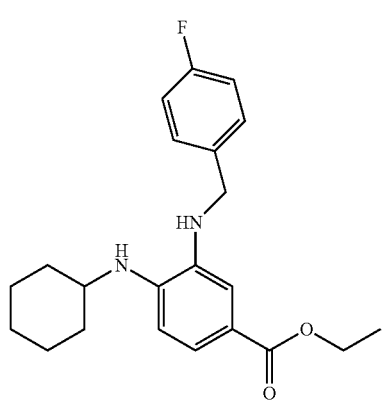
32
-continued
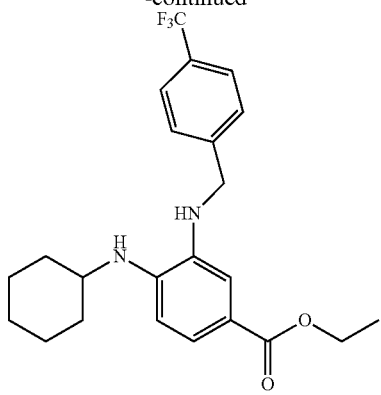
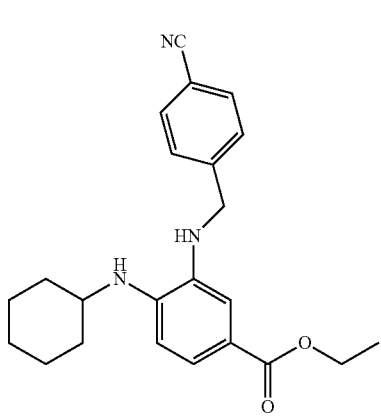
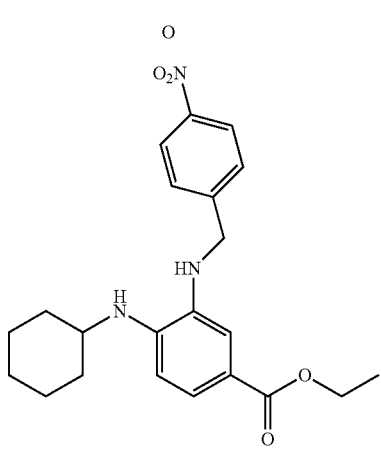
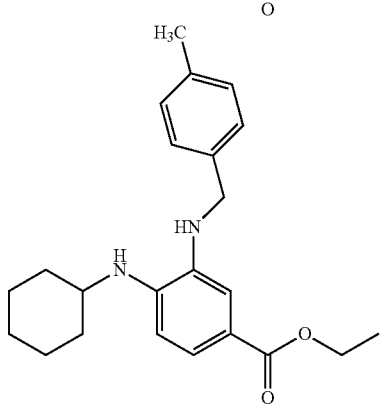

33
-continued
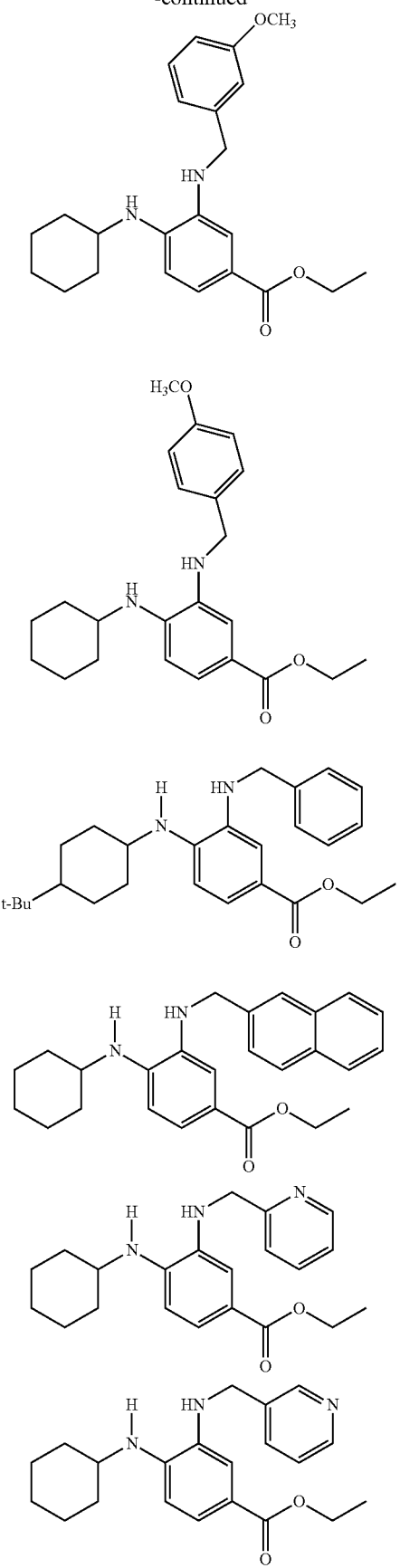
34
-continued
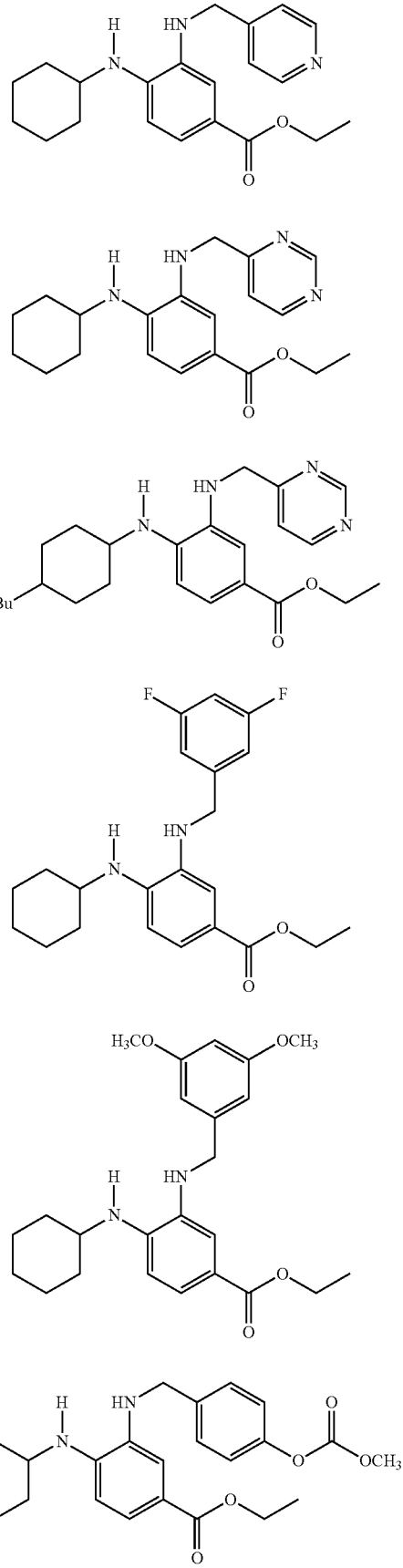

-continued
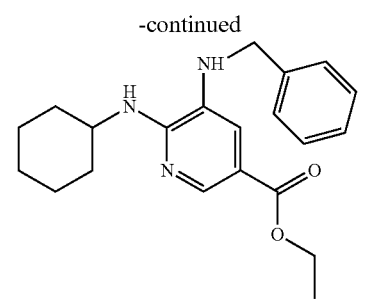
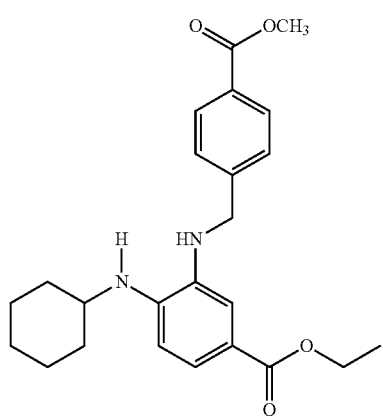
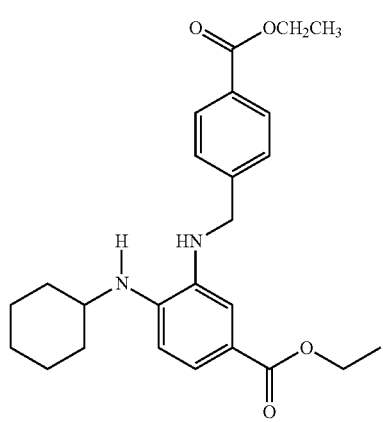
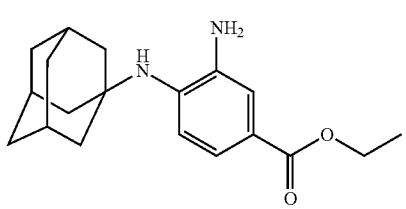
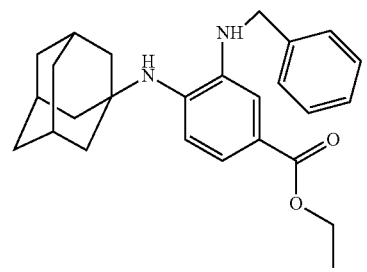
-continued
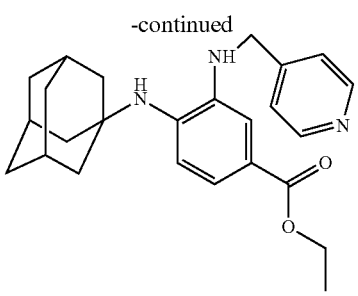
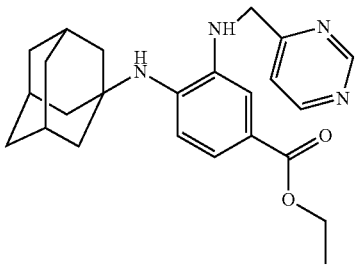
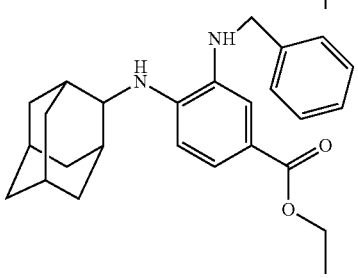
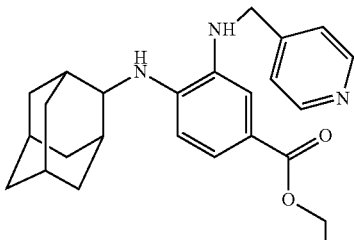
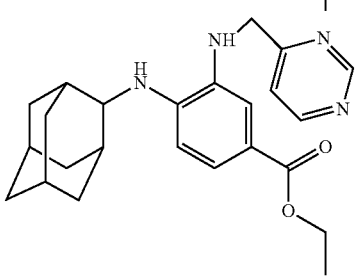
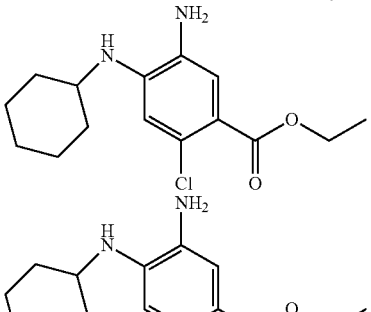

and pharmaceutically acceptable salts thereof, or individual enantiomers and diastereomers thereof.

Another embodiment of the present invention is a composition. This composition comprises a pharmaceutically acceptable carrier and one or more compounds according to the present invention.

Yet another embodiment of the present invention is a method for treating or ameliorating the effects of an excitotoxic disorder in a subject in need thereof. This method comprises administering to the subject an effective amount of a compound having the structure of formula (I):

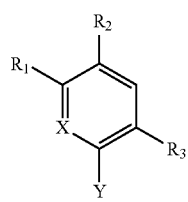
(I)

wherein
X is CH or N;
Y is H, halo, or $C_{1-4}$alkyl;
$R_1$ is selected from the group consisting of H, halo, cycloalkyl, and $NR_4R_5$;
$R_2$ is selected from the group consisting of $NR_6R_7$ and $NO_2$;
$R_3$ is selected from the group consisting of H,

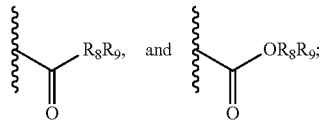

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;
$R_6$ and $R_7$ are independently selected from the group consisting of H, $C_{1-6}$alkyl, Boc, O, $COOR_{12}$,

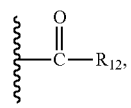

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;
$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;
$R_{10}$ and $R_{11}$ are independently selected from H and Boc; and
$R_{12}$ is a $C_{1-4}$alkyl optionally substituted with aryl, and pharmaceutically acceptable salts thereof, and individual enantiomers and diastereomers thereof.

In one aspect of this embodiment, the compound has the structure of formula II:

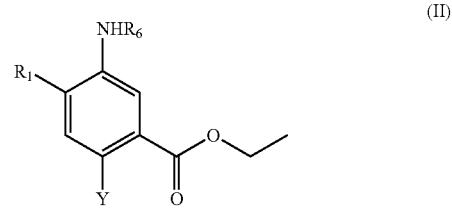
(II)

wherein
Y is Cl or methyl;
$R_1$ is selected from the group consisting of H, halo, cycloalkyl, and $NR_4R_5$;
$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;
$R_{10}$ and $R_{11}$ are independently selected from H and Boc;
$R_6$ is selected from the group consisting of H, $C_{1-6}$alkyl, Boc, O, $COOR_{12}$,

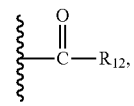

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo; and
$R_{12}$ is a $C_{1-4}$alkyl optionally substituted with aryl, and pharmaceutically acceptable salts thereof, and individual enantiomers and diastereomers thereof.

Preferably, $R_6$ is an alkyl-aryl with a pendent group. Also preferably, $R_1$ is cyclohexylamino or admantylamino.

In another aspect of this embodiment, the compound has the structure of formula III:

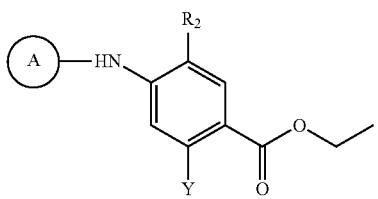
(III)

wherein
Y is Cl or methyl;

is selected from the group consisting of H, $C_{1-8}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl; and $R_{10}$ and $R_{11}$ are independently selected from H and Boc, $R_2$ is selected from the group consisting of $NR_6R_7$ and $NO_2$;

$R_6$ and $R_7$ are independently selected from the group consisting of H, $C_{1-6}$alkyl, Boc, O, $COOR_{12}$,

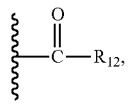

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_{12}$ is a $C_{1-4}$alkyl optionally substituted with aryl, and pharmaceutically acceptable salts thereof, and individual enantiomers and diastereomers thereof.

Preferably,

is cyclohexyl or adamantyl. Also preferably, $R_6$ is an alkyaryl with a pendant group, and $R_7$ is H.

In yet another aspect of this embodiment, the compound has the structure of formula IV:

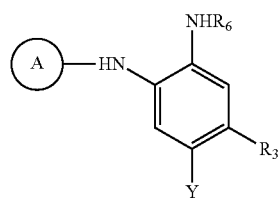
(IV)

wherein
Y is Cl or methyl;

is selected from the group consisting of H, $C_{1-8}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, and $C_{1-8}$alkyl, $R_3$ is selected from the group consisting of H,

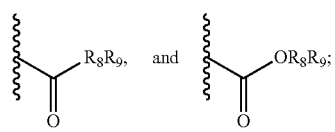

$R_6$ is selected from the group consisting of H, $C_{1-6}$alkyl, Boc, O, $COOR_{12}$,

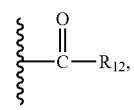

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, and pharmaceutically acceptable salts thereof, and individual enantiomers and diastereomers thereof.

Preferably,
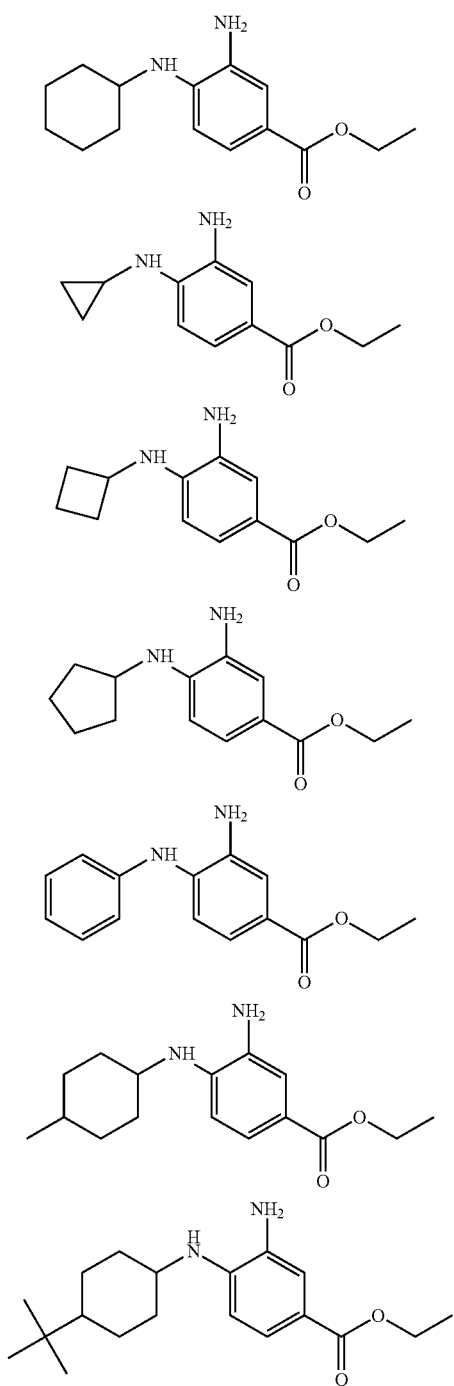
is cyclohexyl or adamantyl. Also preferably, $R_6$ is an alkyaryl with a pendant group.
In a further aspect of this embodiment, the compound is selected from the group consisting of:
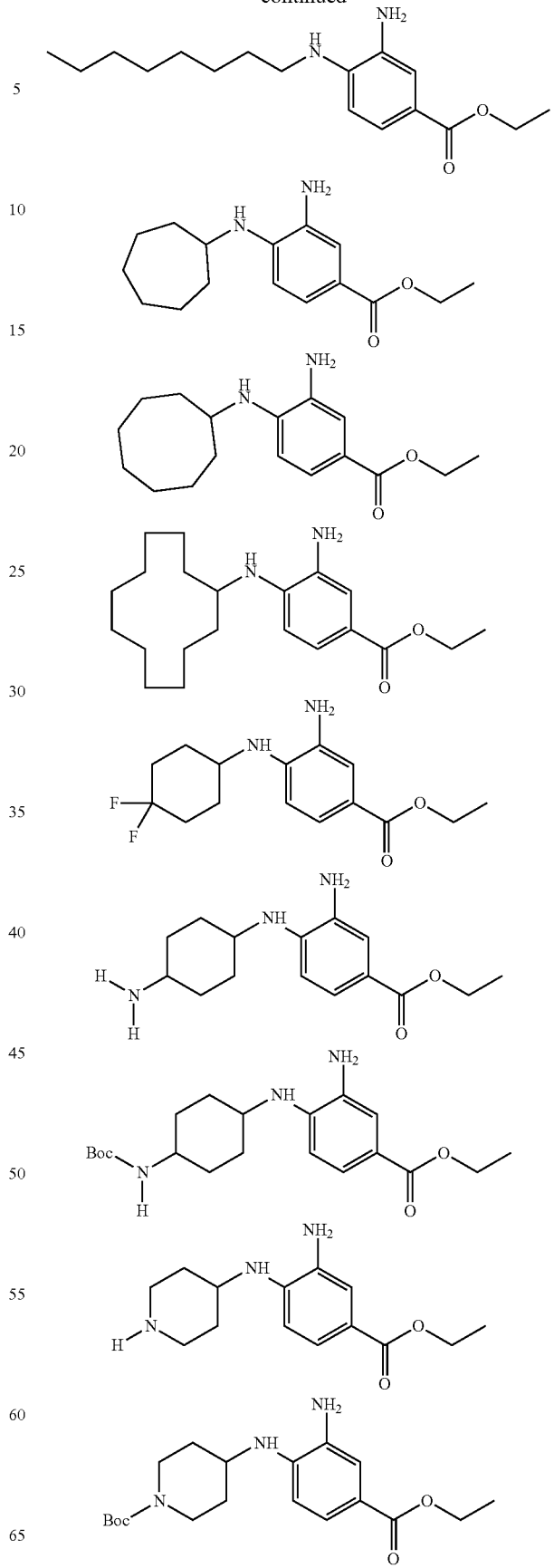

-continued
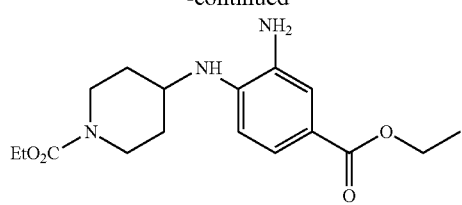
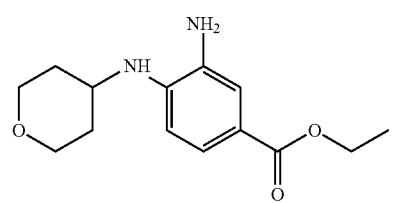
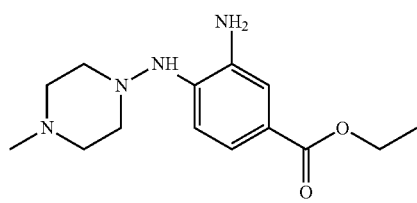
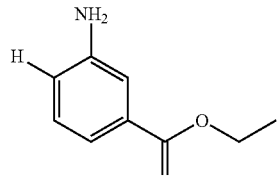
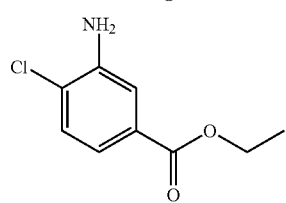
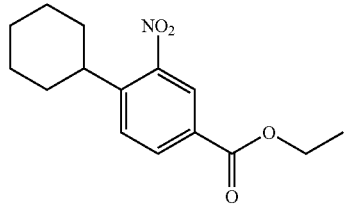
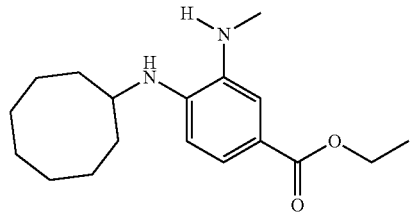
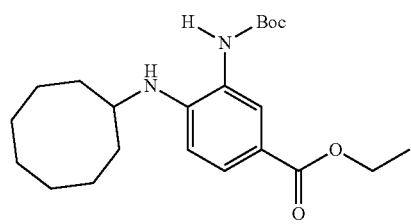
-continued
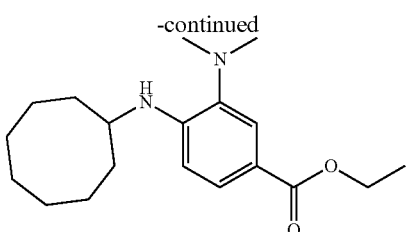
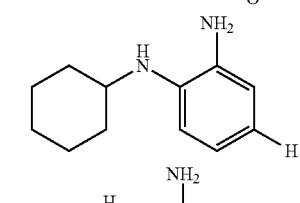
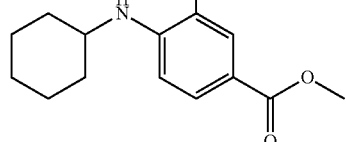
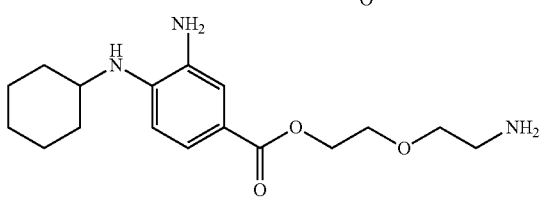
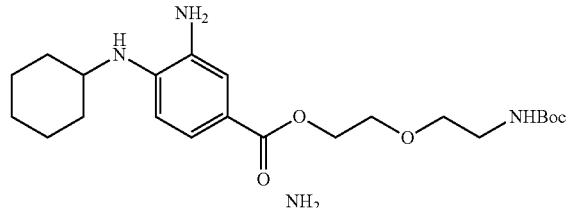
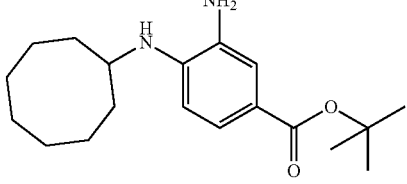
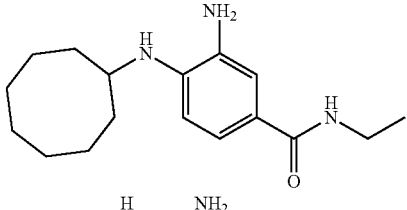
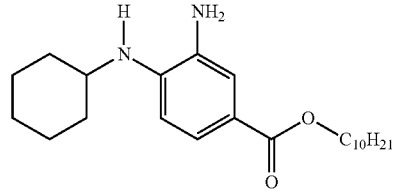
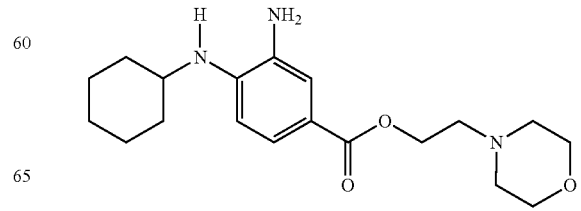

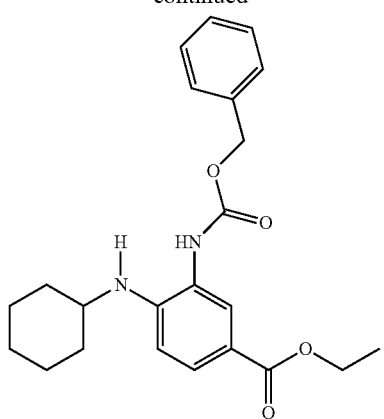
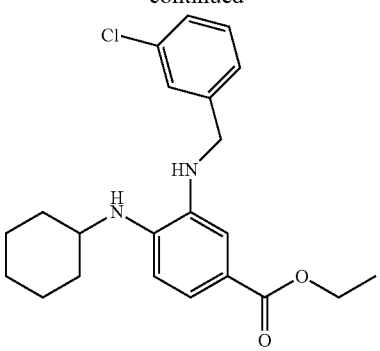
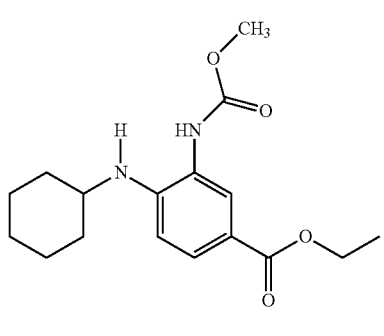
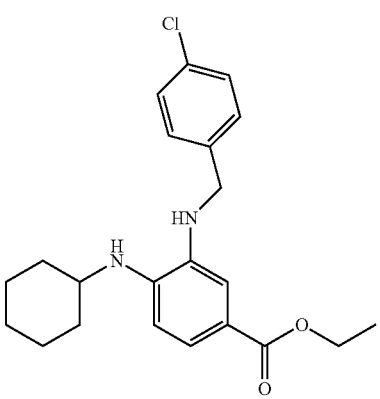
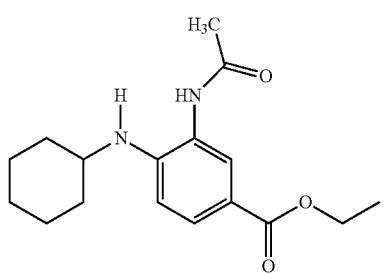
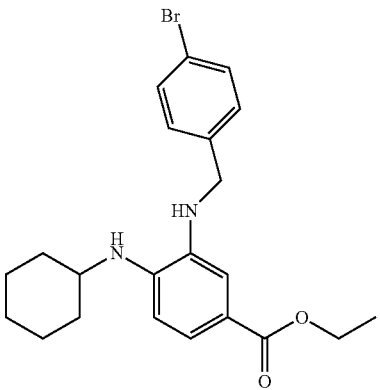
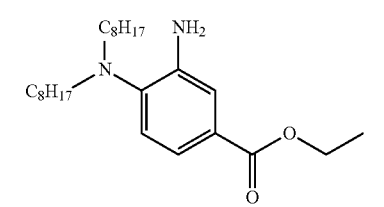
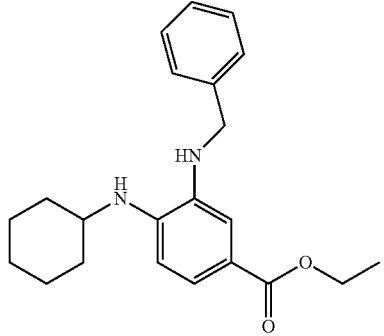
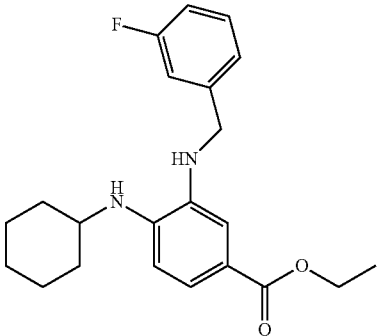

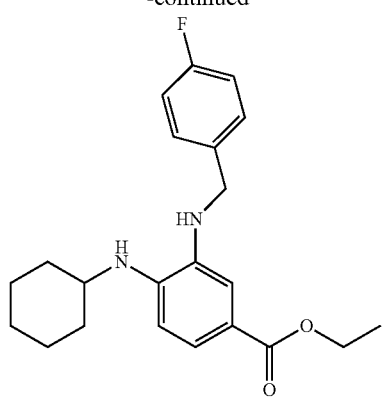
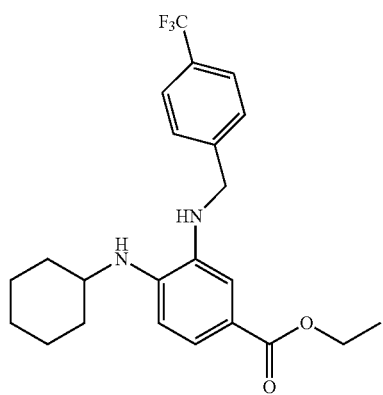
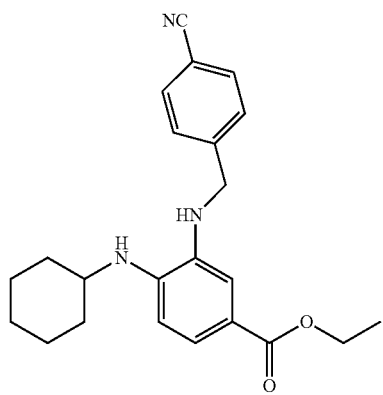
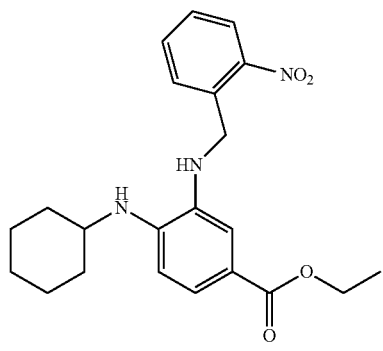
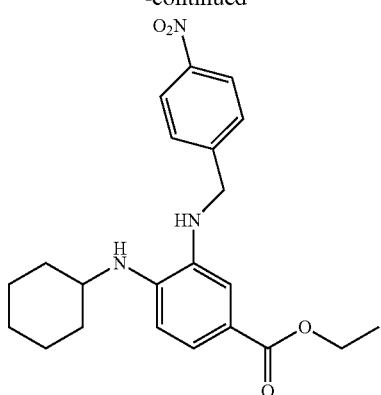
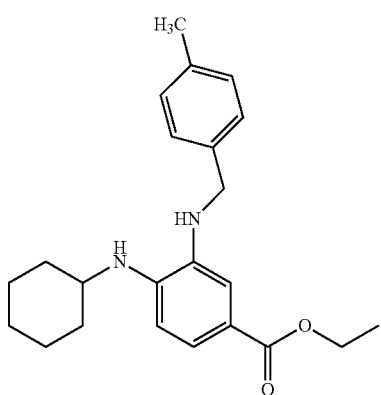
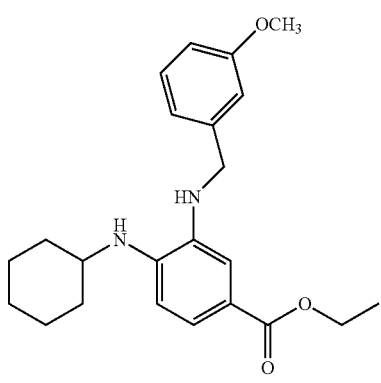
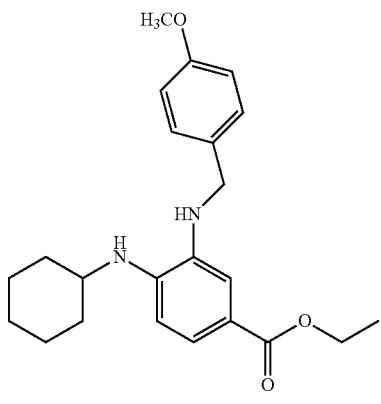

49
-continued
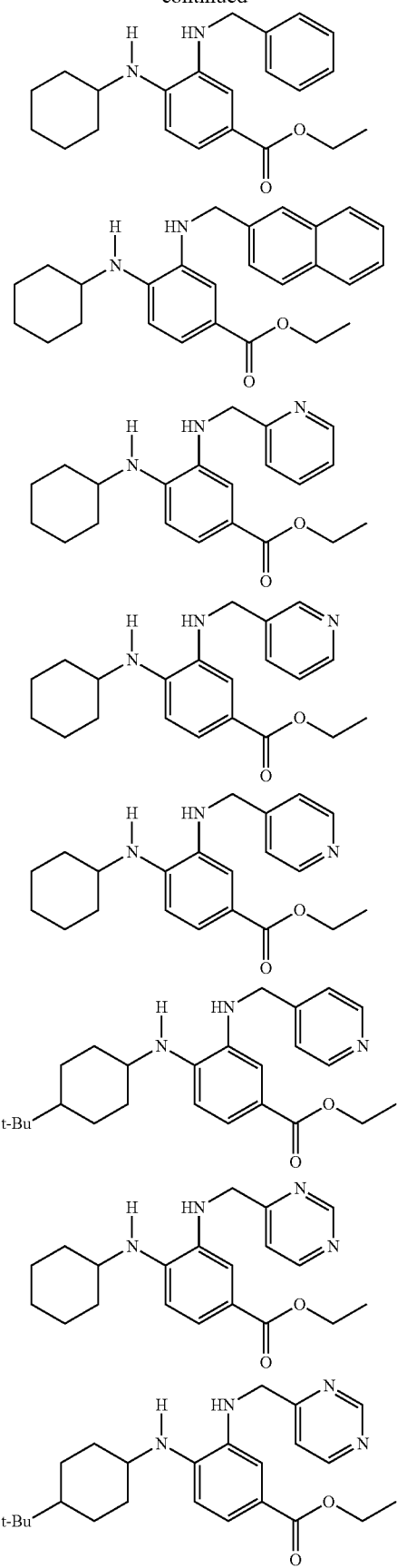
50
-continued
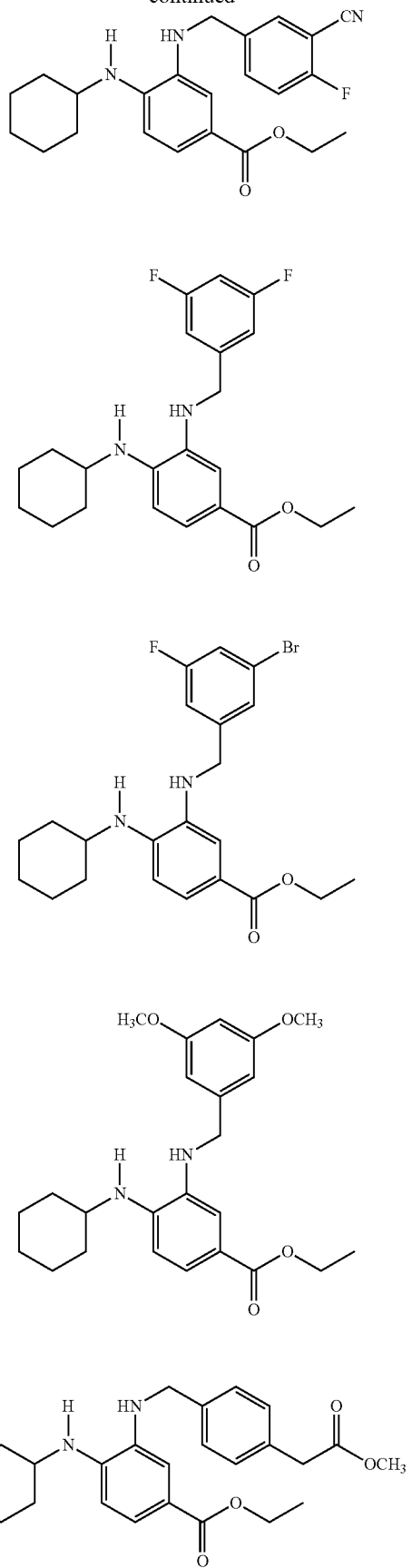

51
-continued
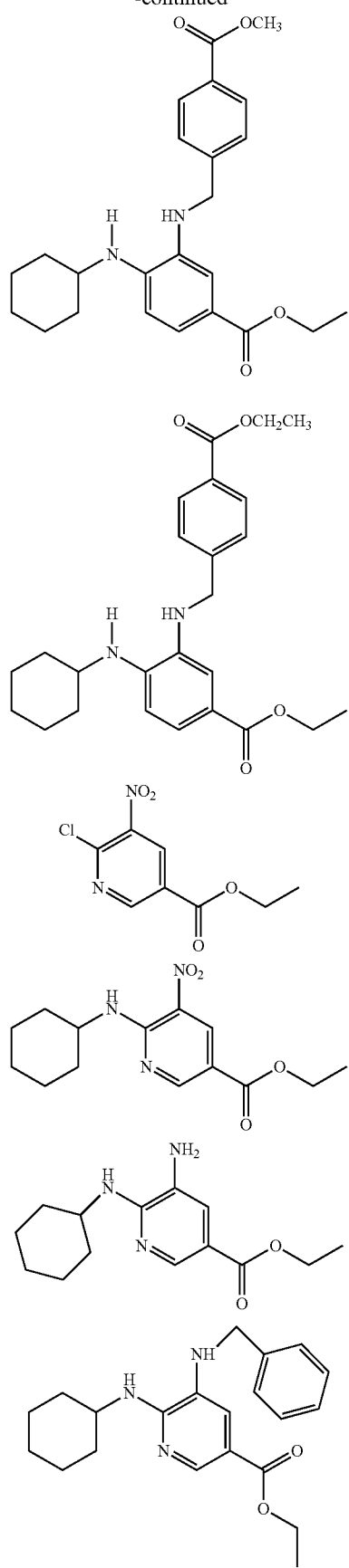
52
-continued
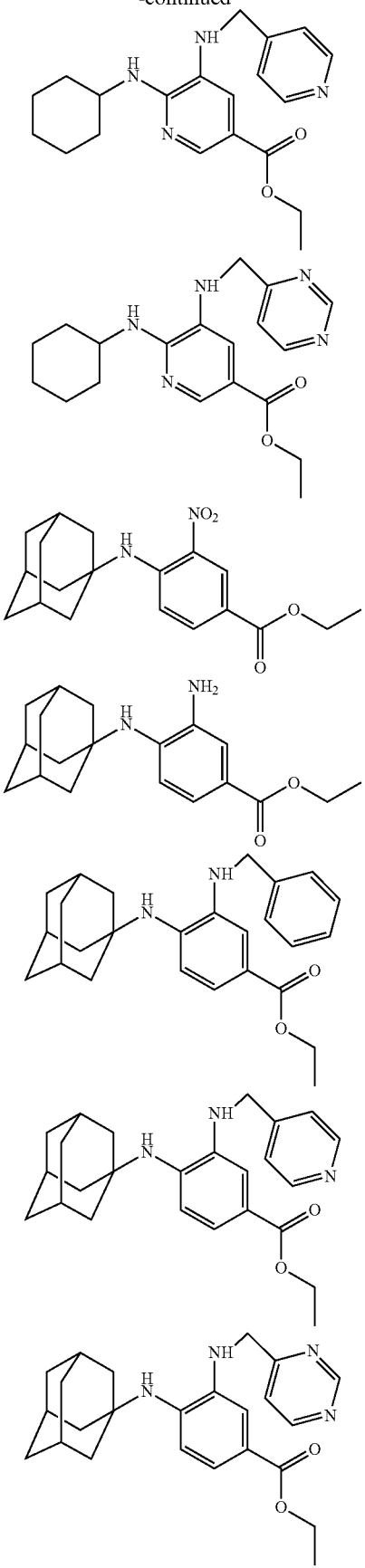

53
-continued
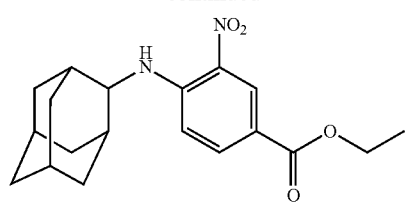
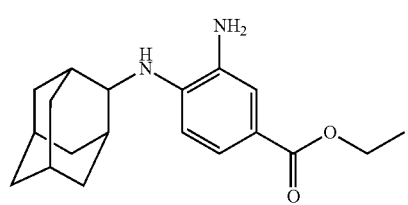
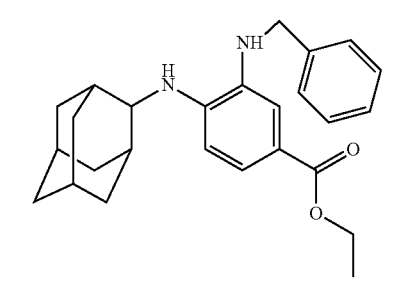
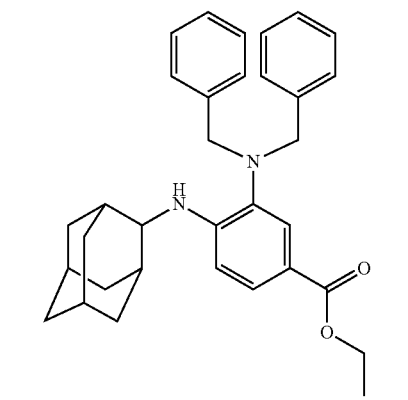
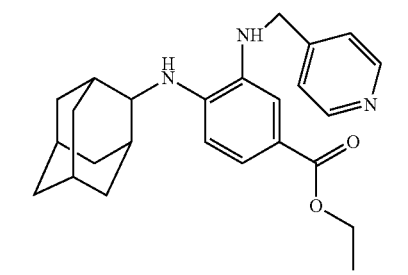
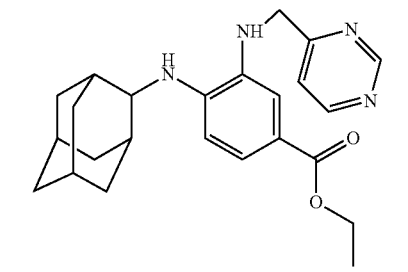
54
-continued
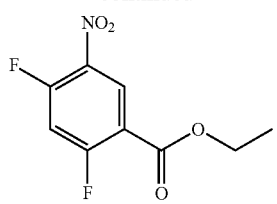
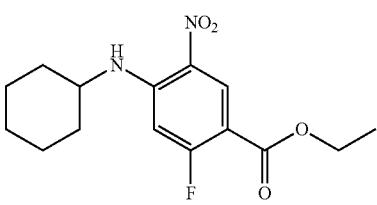
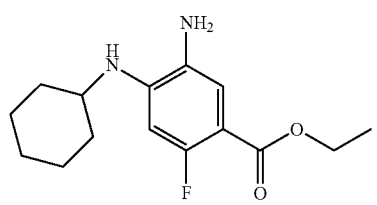
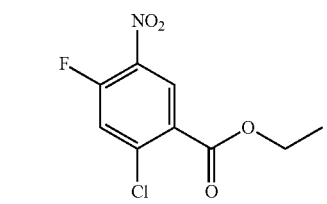
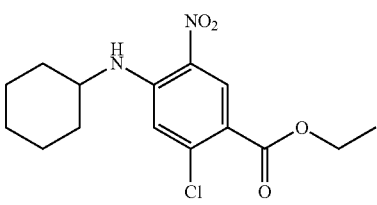
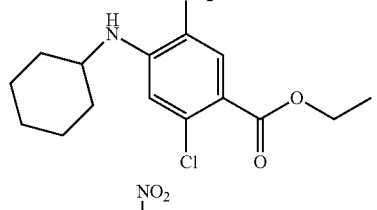
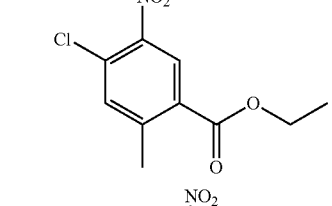
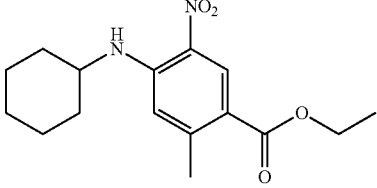

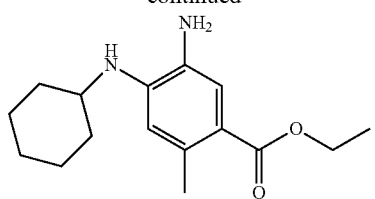
and pharmaceutically acceptable salts thereof, and individual enantiomers and diastereomers thereof.
In another aspect of this embodiment, the compound is selected from the group consisting of:
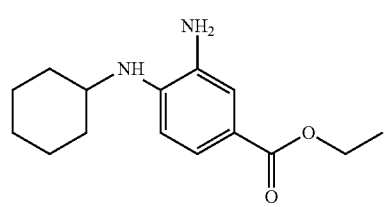
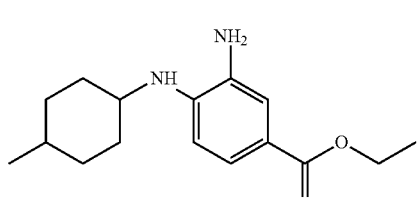
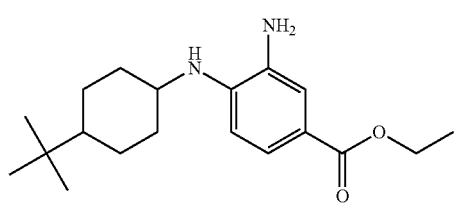
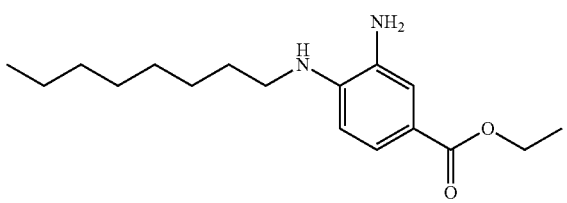
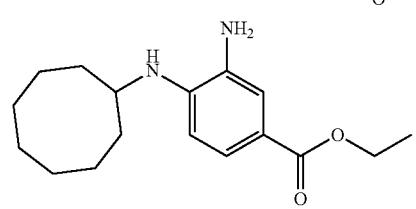
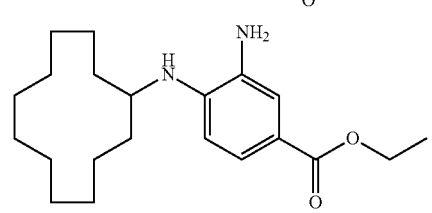
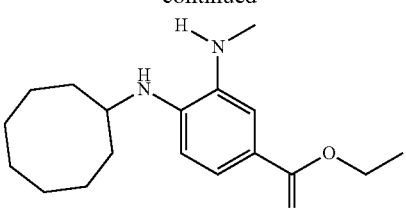
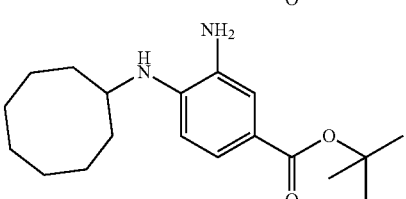
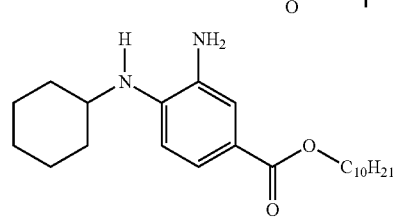
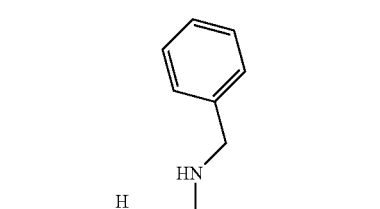
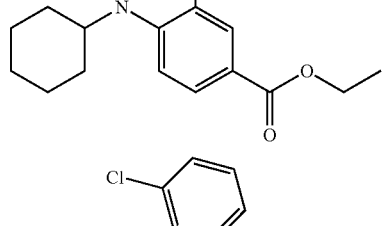
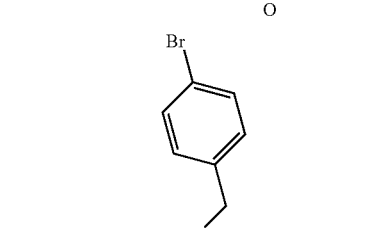

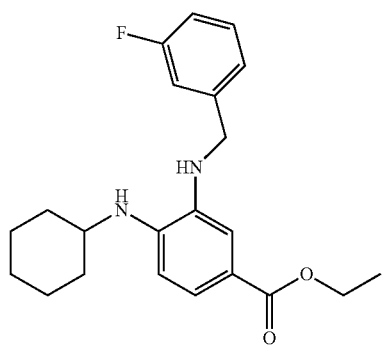
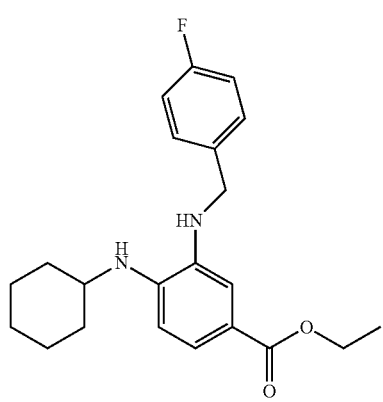
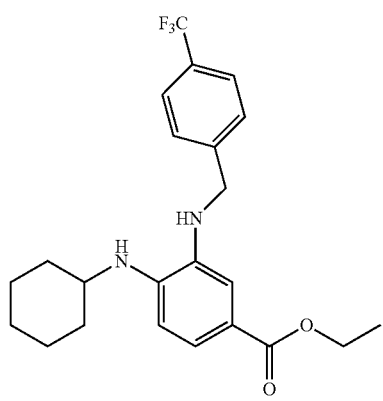
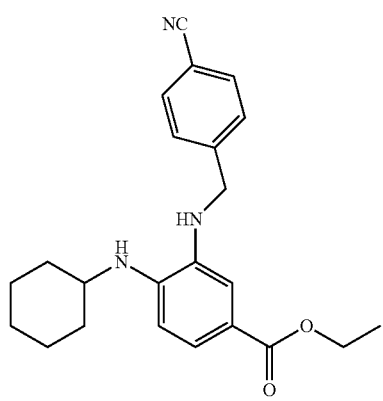
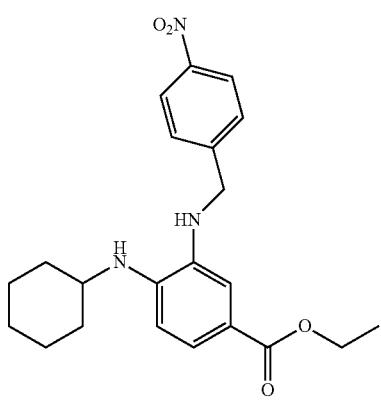
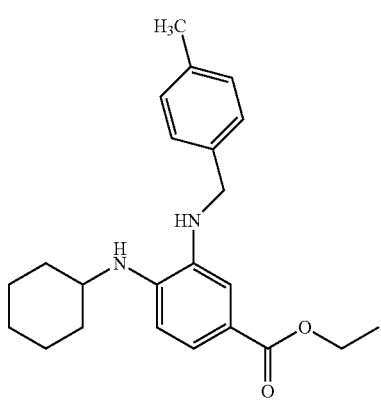
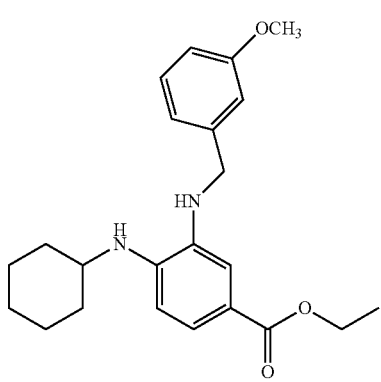
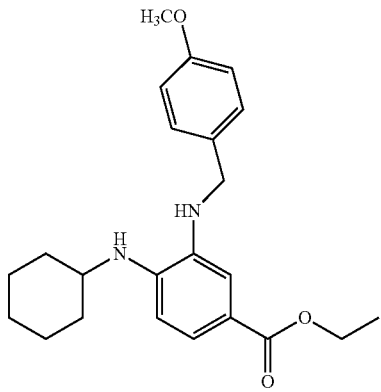

-continued
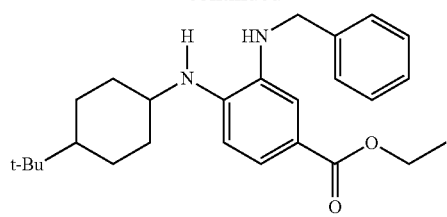
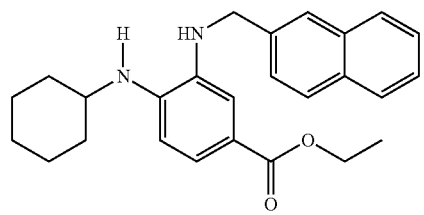
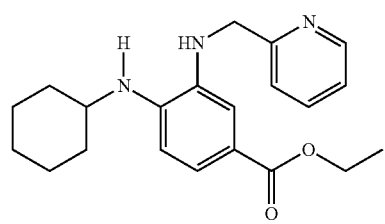 [SMILES: CCOC(=O)c1ccc(NC2CCCCC2)c(NCc2ccncn2)c1]
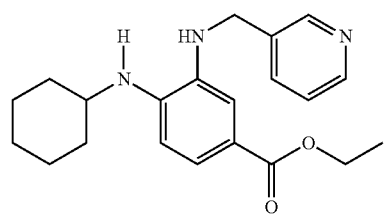
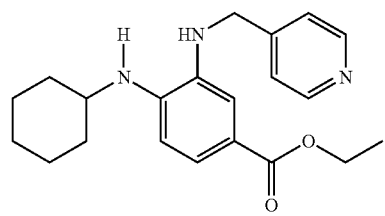
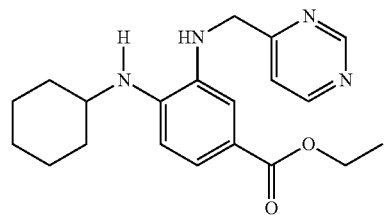
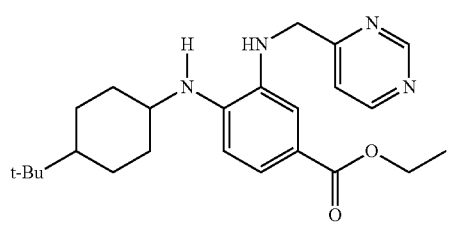
-continued
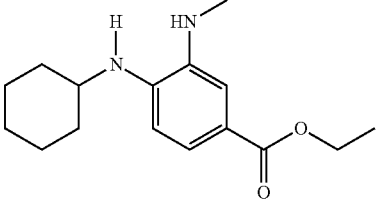
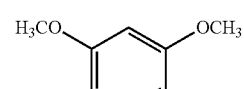
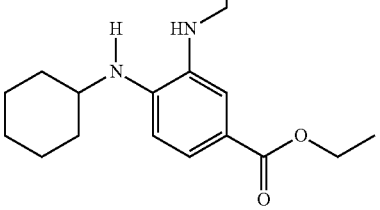
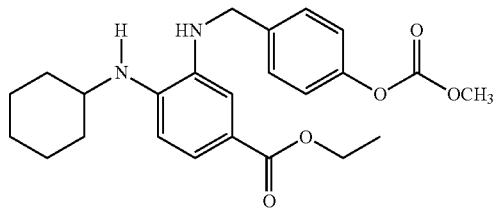
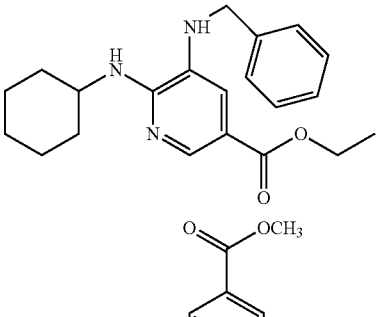
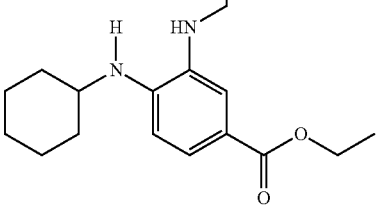

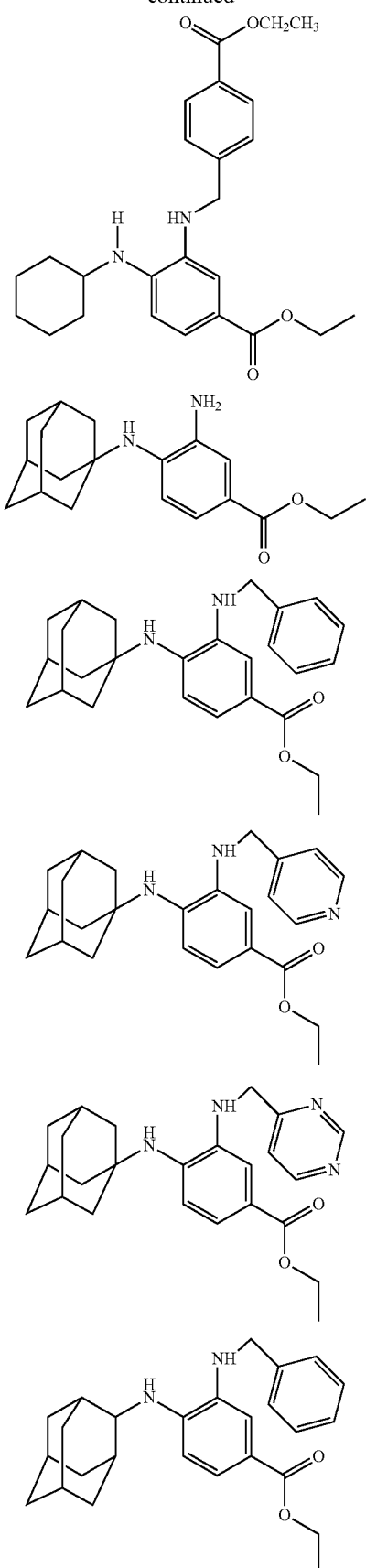
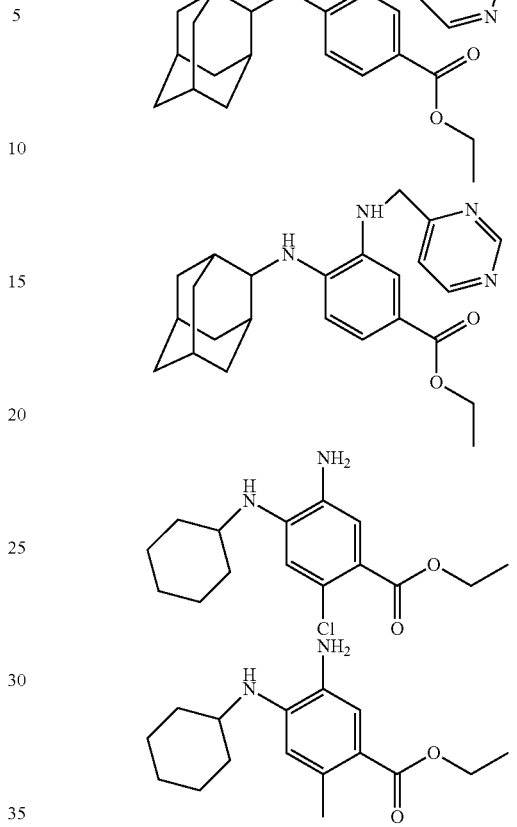

and pharmaceutically acceptable salts thereof, and individual enantiomers and diastereomers thereof.

As used herein, an "excitotoxic disorder" means a disease related to the death of central neurons that are mediated by excitatory amino acids (such as glutamate). Excitotoxic disorders within the scope of the present invention include diseases involving oxidative cell death. As used herein, "oxidative" cell death means cell death associated with increased levels of intracellular reactive oxygen species (ROS). In the present invention, "reactive oxygen species" means chemically reactive molecules, such as free radicals, containing oxygen. Non-limiting examples of ROS include oxygen ions and peroxides.

Non-limiting examples of excitotoxic disorders according to the present invention include epilepsy, stroke, myocardial infarction, type I diabetes, and neurodegenerative disease. Non-limiting examples of neurodegenerative diseases according to the present invention include Alzheimer's, Parkinson's, Amyotrophic lateral sclerosis, Friedreich's ataxia, Multiple sclerosis, Huntington's Disease, Transmissible spongiform encephalopathy, Charcot-Marie-Tooth disease, Dementia with Lewy bodies, Corticobasal degeneration, Progressive supranuclear palsy, and Hereditary spastic paraparesis.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include rats, mice, rabbits, guinea pigs, etc.

In one aspect of this embodiment, the method further comprises co-administering, together with one or more compounds or compositions of the present invention, to the subject an effective amount of one or more of the following: 5-hydroxytryptophan, Activase, AFQ056 (Novartis Corp., New York, N.Y.), Aggrastat, Albendazole, alpha-lipoic acid/L-acetyl carnitine, Alteplase, Amantadine (Symmetrel), amlodipine, Ancrod, Apomorphine (Apokyn), Arimoclomol, Arixtra, Armodafinil, Ascorbic acid, Ascriptin, Aspirin, atenolol, Avonex, baclofen (Lioresal), Banzel, Benztropine (Cogentin), Betaseron, BGG492 (Novartis Corp., New York, N.Y.), Botulinum toxin, Bufferin, Carbatrol®, Carbidopa/levodopa immediate-release (Sinemet), Carbidopa/levodopa oral disintegrating (Parcopa), Carbidopa/levodopa/Entacapone (Stalevo), CERE-110: Adeno-Associated Virus Delivery of NGF (Ceregene, San Diego, Calif.), cerebrolysin, CinnoVex, citalopram, citicoline, Clobazam, Clonazepam, Clopidogrel, clozapine (Clozaril), Coenzyme Q, Creatine, dabigatran, dalteparin, Dapsone, Davunetide, Deferiprone, Depakene®, Depakote ER®, Depakote®, Desmoteplase, Diastat, Diazepam, Digoxin, Dilantin®, Dimebon, dipyridamole, divalproex (Depakote), Donepezil (Aricept), EGb 761, Eldepryl, ELND002 (Elan Pharmaceuticals, Dublin, Ireland), Enalapril, enoxaparin, Entacapone (Comtan), epoetin alfa, Eptifibatide, Erythropoietin, Escitalopram, Eslicarbazepine acetate, Esmolol, Ethosuximide, Ethyl-EPA (Miraxion™), Exenatide, Extavia, Ezogabine, Felbamate, Felbatol®, Fingolimod (Gilenya), fluoxetine (Prozac), fondaparinux, Fragmin, Frisium, Gabapentin, Gabitril®, Galantamine, Glatiramer (Copaxone), haloperidol (Haldol), Heparin, human chorionic gonadotropin (hCG), Idebenone, Inovelon®, insulin, Interferon beta 1a, Interferon beta 1b, ioflupane 123I (DATSCAN®), IPX066 (Impax Laboratories Inc., Hayward, Calif.), JNJ-26489112 (Johnson and Johnson, New Brunswick, N.J.), Keppra®, Klonopin, Lacosamide, L-Alpha glycerylphosphorylcholine, Lamictal®, Lamotrigine, Levetiracetam, liraglutide, Lisinopril, Lithium carbonate, Lopressor, Lorazepam, losartan, Lovenox, Lu AA24493, Luminal, LY450139 (Eli Lilly, Indianapolis, Ind.), Lyrica, Masitinib, Mecobalamin, Memantine, methylprednisolone, metoprolol tartrate, Minitran, Minocycline, mirtazapine, Mitoxantrone (Novantrone), Mysoline®, Natalizumab (Tysabri), Neurontin®, Niacinamide, Nitro-Bid, Nitro-Dur, nitroglycerin, Nitrolingual, Nitromist, Nitrostat, Nitro-Time, Norepinephrine (NOR), Carbamazepine, octreotide, Onfi®, Oxcarbazepine, Oxybutinin chloride, PF-04360365 (Pfizer, New York, N.Y.), Phenobarbital, Phenytek®, Phenytoin, piclozotan, Pioglitazone, Plavix, Potiga, Pramipexole (Mirapex), pramlintide, Prednisone, Primidone, Prinivil, probenecid, Propranolol, PRX-00023 (EPIX Pharmaceuticals Inc.), PXT3003, Quinacrine, Ramelteon, Rasagiline (Azilect), Rebif, ReciGen, remacemide, Resveratrol, Retavase, reteplase, riluzole (Rilutek), Rivastigmine (Exelon), Ropinirole (Requip), Rotigotine (Neupro), Rufinamide, Sabril, safinamide (EMD Serono, Rockland, Mass.), Salagen, Sarafem, Selegiline (I-deprenyl, Eldepryl), SEN0014196 (Siena Biotech, Siena, Italy), sertraline (Zoloft), Simvastatin, Sodium Nitroprussiate (NPS), sodium phenylbutyrate, Stanback Headache Powder, Tacrine (Cognex), Tamoxifen, tauroursodeoxycholic acid (TUDCA), Tegretol®, Tenecteplase, Tenormin, Tetrabenazine (Xenazine), THR-18 (Thrombotech Ltd.), Tiagabine, Tideglusib, tirofiban, tissue plasminogen activator (tPA), tizanidine (Zanaflex), TNKase, Tolcapone (Tasmar), Tolterodine, Topamax®, Topiramate, Trihexyphenidyl (formerly Artane), Trileptal®, ursodiol, Valproic Acid, valsartan, Varenicline (Pfizer), Vimpat, Vitamin E, Warfarin, Zarontin®, Zestril, Zonegran®, Zonisamide, Zydis selegiline HCL Oral disintegrating (Zelapar), and combinations thereof.

For example, to treat or ameliorate the effects of epilepsy, a subject may be administered an effective amount of one or more compounds or compositions of the present invention and, e.g., one or more of the following: Albendazole, Banzel, BGG492 (Novartis Corp., New York, N.Y.) Carbamazepine, Carbatrol®, Clobazam, Clonazepam, Depakene®, Depakote®, Depakote ER®, Diastat, Diazepam, Dilantin®, Eslicarbazepine acetate, Ethosuximide, Ezogabine, Felbatol®, Felbamate, Frisium, Gabapentin, Gabitril®, Inovelon®, JNJ-26489112 (Johnson and Johnson, New Brunswick, N.J.) Keppra®, Keppra XR™, Klonopin, Lacosamide, Lamictal®, Lamotrigine, Levetiracetam, Lorazepam, Luminal, Lyrica, Mysoline®, Memantine, Neurontin®, Onfi®, Oxcarbazepine, Phenobarbital, Phenytek®, Phenytoin, Potiga, Primidone, probenecid, PRX-00023 (EPIX Pharmaceuticals Inc, Lexington, Mass.), Rufinamide, Sabril, Tegretol®, Tegretol XR®, Tiagabine, Topamax®, Topiramate, Trileptal®, Valproic Acid, Vimpat, Zarontin®, Zonegran®, and Zonisamide.

To treat or ameliorate the effects of stroke, a subject may be administered an effective amount of one or more compounds or compositions of the present invention and, e.g., one or more of the following: Aspirin, dipyridamole, Clopidogrel, tissue plasminogen activator (tPA), Warfarin, dabigatran, Heparin, Lovenox, citicoline, L-Alpha glycerylphosphorylcholine, cerebrolysin, Eptifibatide, Escitalopram, Tenecteplase, Alteplase, Minocycline, Esmolol, Sodium Nitroprussiate (NPS), Norepinephrine (NOR), Dapsone, valsartan, Simvastatin, piclozotan, Desmoteplase, losartan, amlodipine, Ancrod, human chorionic gonadotropin (hCG), epoetin alfa (EPO), Galantamine, and THR-18 (Thrombotech Ltd., Ness Ziona, Israel).

To treat or ameliorate the effects of myocardial infarction, a subject may be administered an effective amount of one or more compounds or compositions of the present invention and, e.g., one or more of the following: lisinopril, atenolol, Plavix, metoprolol tartrate, Lovenox, Lopressor, Zestril, Tenormin, Prinivil, aspirin, Arixtra, clopidogrel, Salagen, nitroglycerin, metoprolol tartrate, heparin, Nitrostat, Nitro-Bid, Stanback Headache Powder, nitroglycerin, Activase, Nitrolingual, nitroglycerin, fondaparinux, Lopressor, heparin, nitroglycerin TL, Nitro-Time, Nitromist, Ascriptin, alteplase, Retavase, TNKase, Bufferin, Nitro-Dur, Minitran, reteplase, tenecteplase, clopidogrel, Fragmin, enoxaparin, dalteparin, tirofiban, and Aggrastat.

To treat or ameliorate the effects of type I diabetes, a subject may be administered an effective amount of one or more compounds or compositions of the present invention and, e.g., one or more of the following: insulin, such as regular insulin (Humulin R, Novolin R, others), insulin isophane (Humulin N, Novolin N), insulin lispro (Humalog), insulin aspart (NovoLog), insulin glargine (Lantus) and insulin detemir (Levemir), octreotide, pramlintide, and liraglutide.

To treat or ameliorate the effects of Alzheimer's disease, a subject may be administered an effective amount of one or more compounds or compositions of the present invention and, e.g., one or more of the following: Donepezil (Aricept), Rivastigmine (Exelon), Galantamine (Razadyne), Tacrine (Cognex), Memantine (Namenda), Vitamin E, CERE-110: Adeno-Associated Virus Delivery of NGF (Ceregene), LY450139 (Eli Lilly), Exenatide, Varenicline (Pfizer), PF-04360365 (Pfizer), Resveratrol, and Donepezil (Eisai Korea).

To treat or ameliorate the effects of Parkinson's disease, a subject may be administered an effective amount of one or more compounds or compositions of the present invention and, e.g., one or more of the following: Carbidopa/levodopa immediate-release (Sinemet), Carbidopa/levodopa oral disintegrating (Parcopa), Carbidopa/levodopa/Entacapone (Stalevo), Ropinirole (Requip), Pramipexole (Mirapex), Rotigotine (Neupro), Apomorphine (Apokyn), Selegiline (I-deprenyl, Eldepryl), Rasagiline (Azilect), Zydis selegiline HCL Oral disintegrating (Zelapar), Entacapone (Comtan), Tolcapone (Tasmar), Amantadine (Symmetrel), Trihexyphenidyl (formerly Artane), Benztropine (Cogentin), IPX066 (Impax Laboratories Inc.), Rasagiline (Teva Neuroscience, Inc.), ioflupane 123I (DATSCAN®), safinamide (EMD Serono), and Pioglitazone.

To treat or ameliorate the effects of amyotrophic lateral sclerosis, a subject may be administered an effective amount of one or more compounds or compositions of the present invention and, e.g., one or more of the following: riluzole (Rilutek), Lithium carbonate, Arimoclomol, Creatine, Tamoxifen, Mecobalamin, Memantine (Ebixa), and tauroursodeoxycholic acid (TUDCA).

To treat or ameliorate the effects of Friedreich's ataxia, a subject may be administered an effective amount of one or more compounds or compositions of the present invention and, e.g., one or more of the following: Idebenone, Coenzyme Q, 5-hydroxytryptophan, Propranolol, Enalapril, Lisinopril, Digoxin, Erythropoietin, Lu AA24493, Deferiprone, Varenicline, IVIG, Pioglitazone, and EGb 761.

To treat or ameliorate the effects of multiple sclerosis, a subject may be administered an effective amount of one or more compounds or compositions of the present invention and, e.g., one or more of the following: Avonex, Betaseron, Extavia, Rebif, Glatiramer (Copaxone), Fingolimod (Gilenya), Natalizumab (Tysabri), Mitoxantrone (Novantrone), baclofen (Lioresal), tizanidine (Zanaflex), methylprednisolone, CinnoVex, ReciGen, Masitinib, Prednisone, Interferon beta 1a, Interferon beta 1b, and ELND002 (Elan Pharmaceuticals).

To treat or ameliorate the effects of Huntington's disease, a subject may be administered an effective amount of one or more compounds or compositions of the present invention and, e.g., one or more of the following: Tetrabenazine (Xenazine), haloperidol (Haldol), clozapine (Clozaril), clonazepam (Klonopin), diazepam (Valium), escitalopram (Lexapro), fluoxetine (Prozac, Sarafem), sertraline (Zoloft), valproic acid (Depakene), divalproex (Depakote), lamotrigine (Lamictal), Dimebon, AFQ056 (Novartis), Ethyl-EPA (Miraxion™), SEN0014196 (Siena Biotech), sodium phenylbutyrate, citalopram, ursodiol, minocycline, remacemide, and mirtazapine.

To treat or ameliorate the effects of transmissible spongiform encephalopathy, a subject may be administered an effective amount of one or more compounds or compositions of the present invention and e.g., Quinacrine.

To treat or ameliorate the effects of Charcot-Marie-Tooth disease, a subject may be administered an effective amount of one or more compounds or compositions of the present invention and, e.g., one or more of the following: ascorbic acid and PXT3003.

To treat or ameliorate the effects of dementia with Lewy bodies, a subject may be administered an effective amount of one or more compounds or compositions of the present invention and, e.g., one or more of the following: Aricept, Galantamine, Memantine, Armodafinil, Donepezil, and Ramelteon.

To treat or ameliorate the effects of corticobasal degeneration, a subject may be administered an effective amount of one or more compounds or compositions of the present invention and, e.g., one or more of the following: Davunetide and Coenzyme Q10.

To treat or ameliorate the effects of progressive supranuclear palsy, a subject may be administered an effective amount of one or more compounds or compositions of the present invention and, e.g., one or more of the following: Tideglusib, Rasagiline, alpha-lipoic acid/L-acetyl carnitine, Riluzole, Niacinamide, and Rivastigmine.

To treat or ameliorate the effects of hereditary spastic paraparesis, a subject may be administered an effective amount of one or more compounds or compositions of the present invention and, e.g., one or more of the following: Baclofen, Tizanidine, Oxybutinin chloride, Tolterodine, and Botulinum toxin.

In the present invention, one or more compounds or compositions may be co-administered to a subject in need thereof together in the same composition, simultaneously in separate compositions, or as separate compositions administered at different times, as deemed most appropriate by a physician.

In yet another aspect of this embodiment, the subject is a mammal. Preferably, the subject is a human, a veterinary animal, or an agricultural animal. More preferably, the subject is a human.

In the present invention, an "effective amount" or "therapeutically effective amount" of a compound or composition, is an amount of such a compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of the subject, and like factors well known in the arts of, e.g., medicine and veterinary medicine. In general, a suitable dose of a compound or composition according to the invention will be that amount of the compound or composition, which is the lowest dose effective to produce the desired effect with no or minimal side effects. The effective dose of a compound or composition according to the present invention may be administered as two, three, four, five, six or more sub-doses, administered separately at appropriate intervals throughout the day.

A suitable, non-limiting example of a dosage of a compound according to the present invention or a composition comprising such a compound, is from about 1 ng/kg to about 1000 mg/kg, such as from about 1 mg/kg to about 100 mg/kg, including from about 5 mg/kg to about 50 mg/kg. Other representative dosages of a compound or a composition of the present invention include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

An additional embodiment of the present invention is a method for treating or ameliorating the effects of an excitotoxic disorder in a subject in need thereof. This method comprises administering to the subject an effective amount of a composition comprising a pharmaceutically acceptable carrier and a compound having the structure (I):

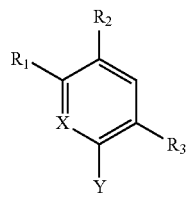

wherein
X is CH or N;
Y is H, halo, or $C_{1-4}$alkyl;
$R_1$ is selected from the group consisting of H, halo, cycloalkyl, and $NR_4R_5$;
$R_2$ is selected from the group consisting of $NR_6R_7$ and $NO_2$;
$R_3$ is selected from the group consisting of H,

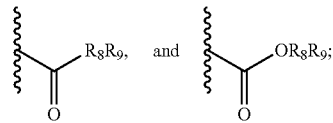

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;
$R_6$ and $R_7$ are independently selected from the group consisting of H, $C_{1-6}$alkyl, Boc, O, $COOR_{12}$,

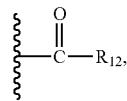

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ether, $C_{1-4}$ ester, $OCOOR_{12}$, and $C_{1-8}$alkyl, which $C_{1-8}$alkyl is optionally further substituted with one or more halo;
$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;
$R_{10}$ and $R_{11}$ are independently selected from H and Boc; and
$R_{12}$ is a $C_{1-4}$alkyl optionally substituted with aryl,
and pharmaceutically acceptable salts thereof, and individual enantiomers and diastereomers thereof.

In this embodiment, the subjects, excitotoxic disorders, and additional compositions that may be co-administered to the subject are as set forth above.

In one aspect of this embodiment, the compound has the structure of formula II:

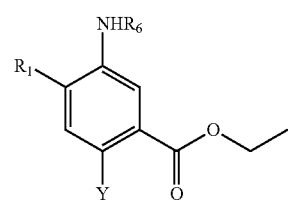

wherein
Y is Cl or methyl;
$R_1$ is selected from the group consisting of H, halo, cycloalkyl, and $NR_4R_5$;
$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;
$R_{10}$ and $R_{11}$ are independently selected from H and Boc;
$R_6$ is selected from the group consisting of H, $C_{1-6}$alkyl, Boc, O, $COOR_{12}$,

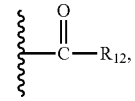

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ether, $C_{1-4}$ ester, $OCOOR_{12}$, and $C_{1-8}$alkyl, which $C_{1-8}$alkyl is optionally further substituted with one or more halo; and $R_{12}$ is a $C_{1-4}$alkyl optionally substituted with aryl, and pharmaceutically acceptable salts thereof, and individual enantiomers and diastereomers thereof.

Preferably, $R_6$ is an alkyl-aryl with a pendent group. Also preferably, $R_1$ is cyclohexylamino or admantylamino.

In another aspect of this embodiment, the compound has the structure of formula III:

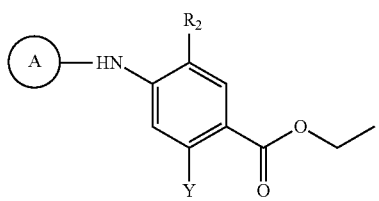

(III)

wherein
Y is Cl or methyl;

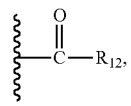

is selected from the group consisting of H, $C_{1-8}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl; and $R_{10}$ and $R_{11}$ are independently selected from H and Boc, $R_2$ is selected from the group consisting of $NR_6R_7$ and $NO_2$;

$R_6$ and $R_7$ are independently selected from the group consisting of H, $C_{1-6}$alkyl, Boc, O, $COOR_{12}$, $$\overset{O}{\underset{}{\overset{\|}{\underset{}{-C-R_{12},}}}}$$

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_{12}$ is a $C_{1-4}$alkyl optionally substituted with aryl, and pharmaceutically acceptable salts thereof, and individual enantiomers and diastereomers thereof.

Preferably,

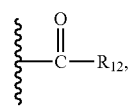

is cyclohexyl or adamantyl. Also preferably, $R_6$ is an alkyaryl with a pendent group, and $R_7$ is H.

In yet another aspect of this embodiment, the compound has the structure of formula IV:

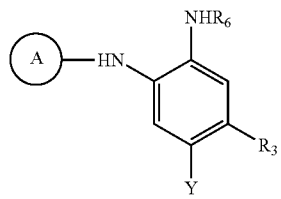

(IV)

wherein
Y is Cl or methyl;

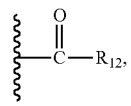

is selected from the group consisting of H, $C_{1-8}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, and $C_{1-8}$alkyl, $R_3$ is selected from the group consisting of H,

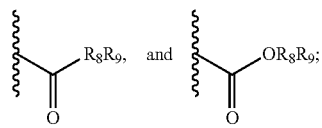

$R_6$ is selected from the group consisting of H, $C_{1-6}$alkyl, Boc, O, $COOR_{12}$, $$\overset{O}{\underset{}{\overset{\|}{\underset{}{-C-R_{12},}}}}$$

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, and pharmaceutically acceptable salts thereof, and individual enantiomers and diastereomers thereof.

Preferably, 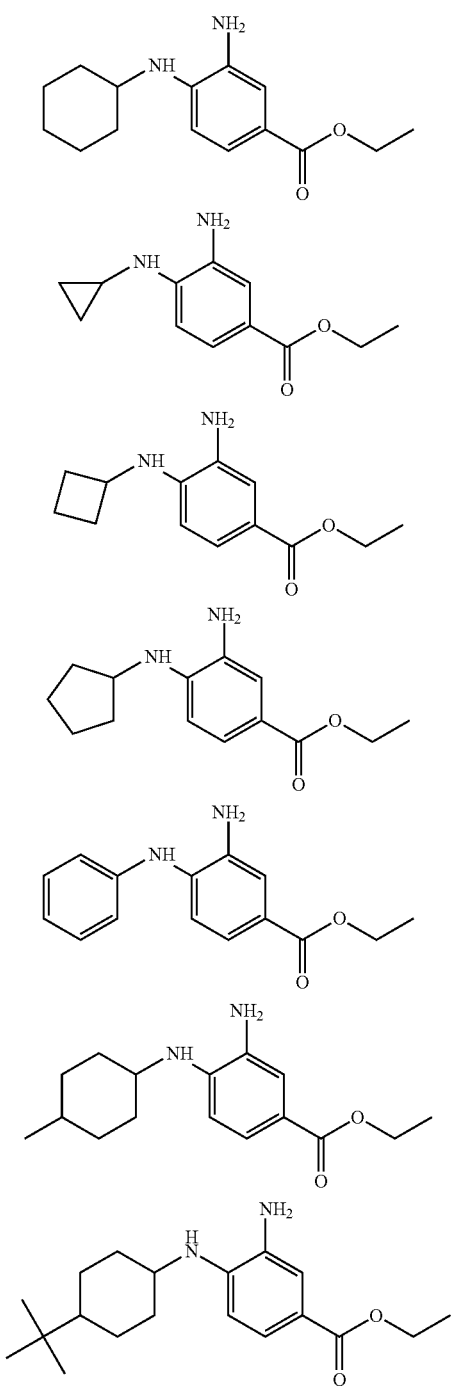 is cyclohexyl or adamantyl. Also preferably, $R_6$ is an alkyaryl with a pendant group.
In another aspect of this embodiment, the compound is selected from the group consisting of:
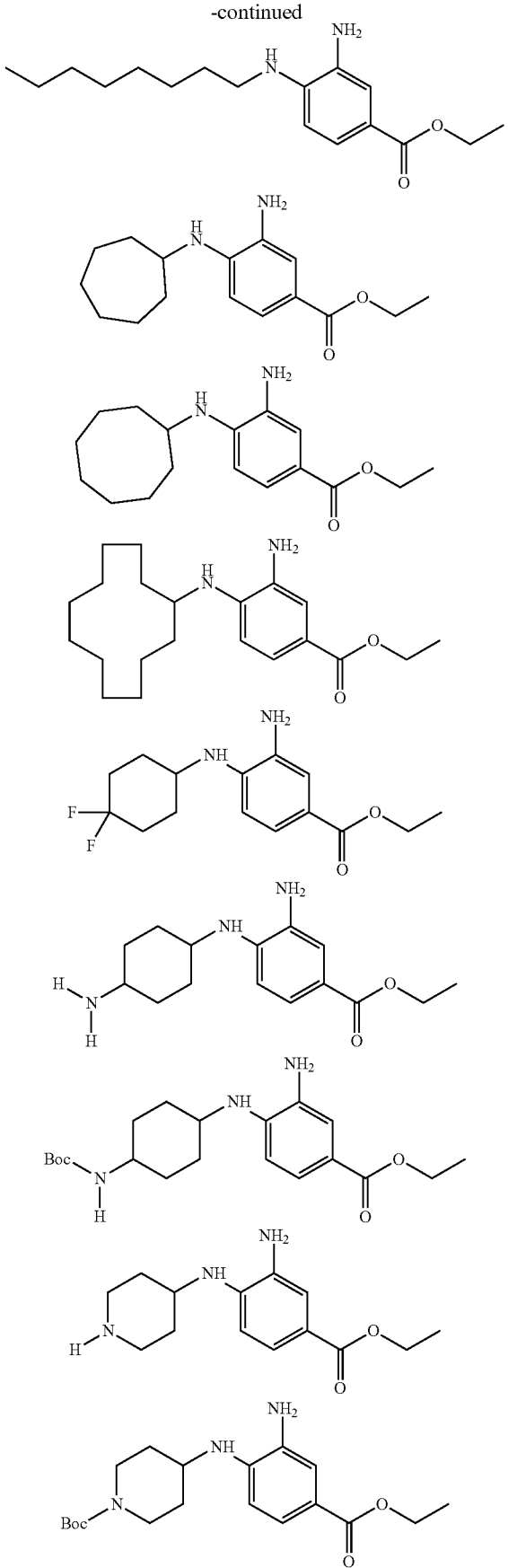

-continued
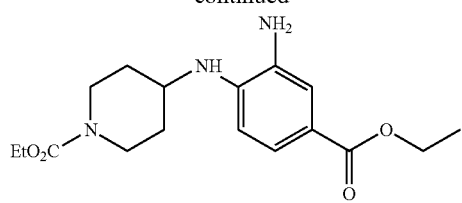
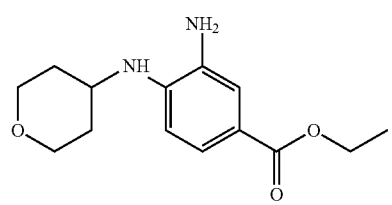
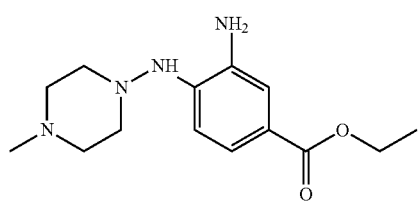
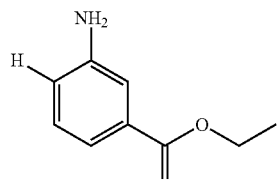
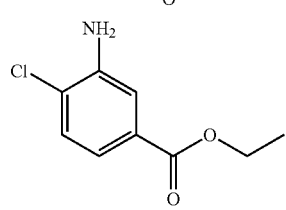
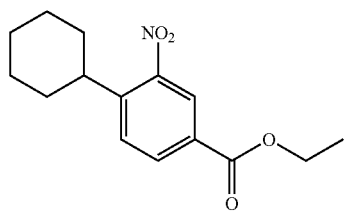
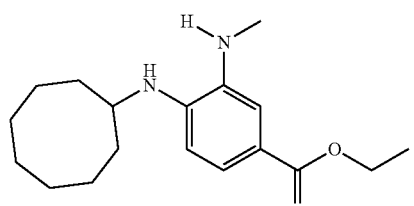
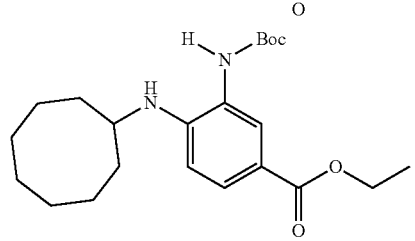
-continued
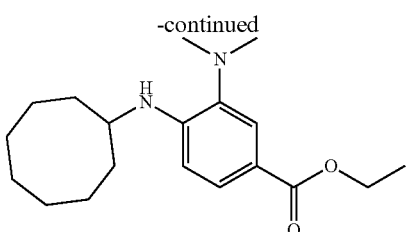
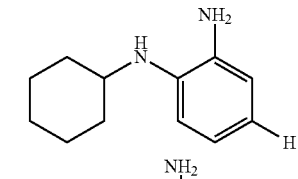
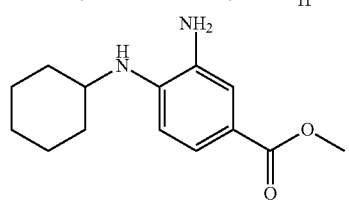
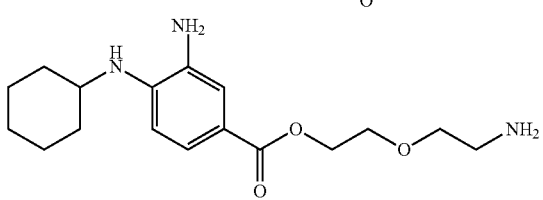
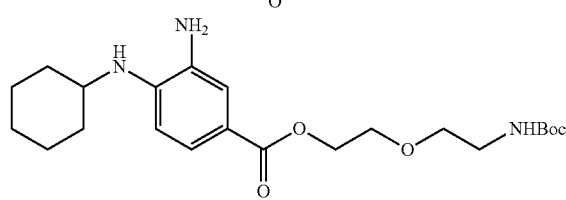
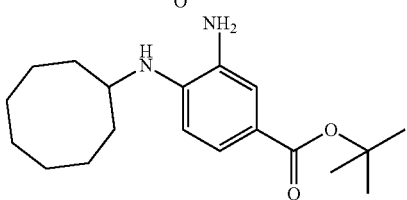
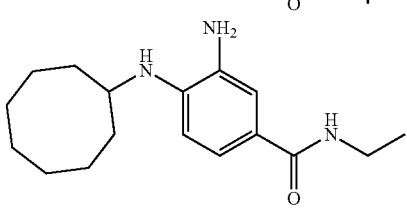
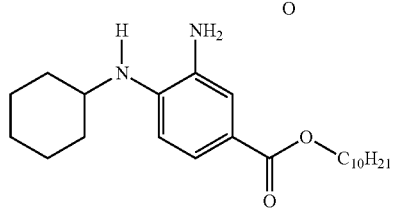
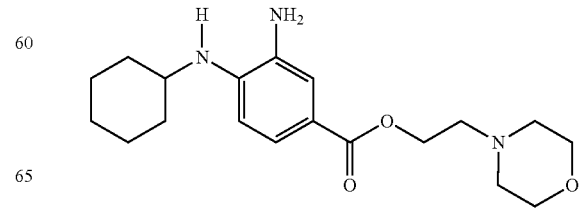

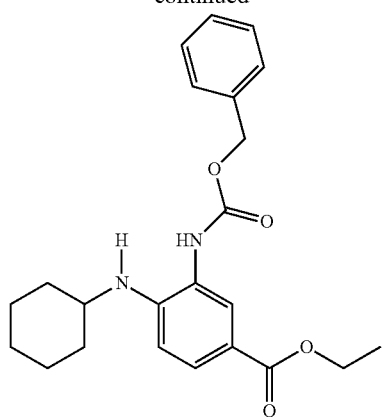
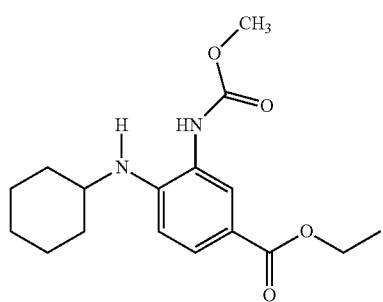
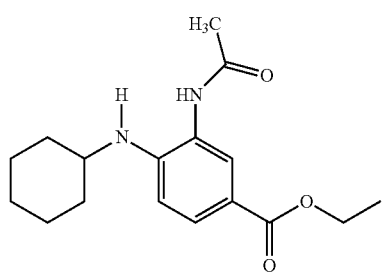
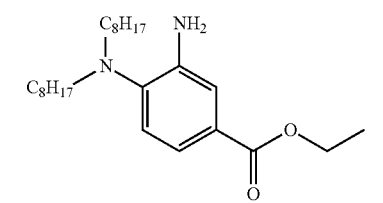
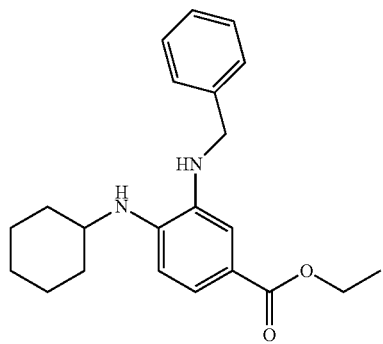
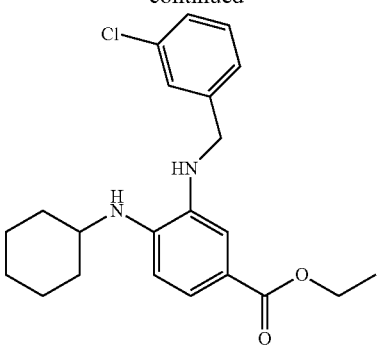
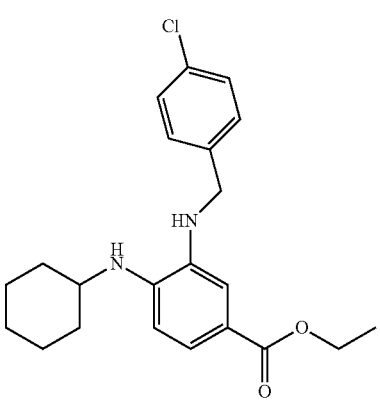
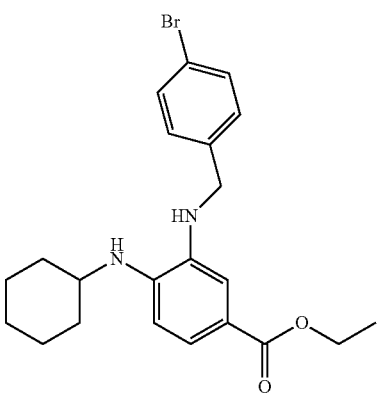

77
-continued
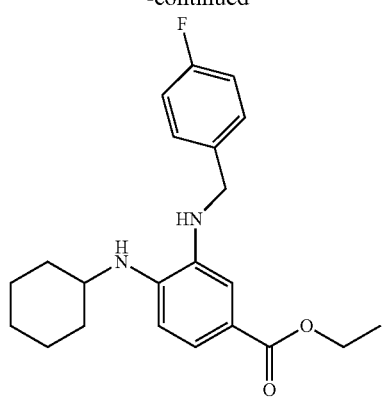
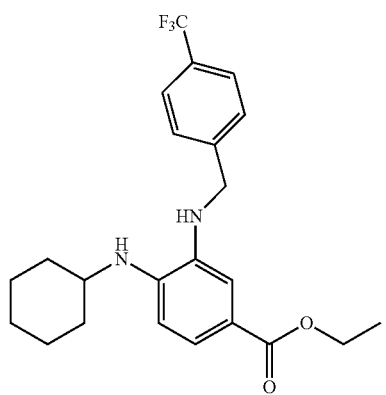
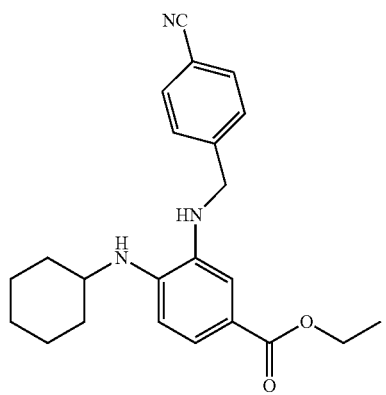
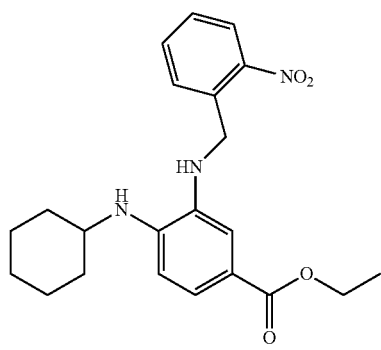
78
-continued
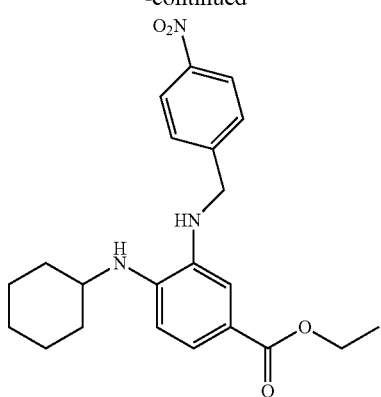
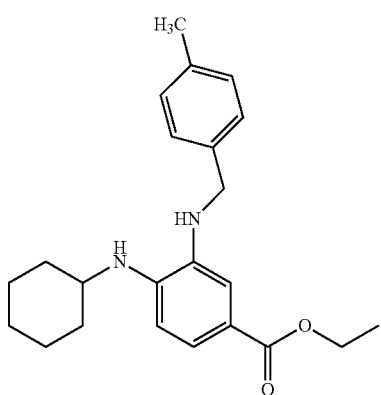
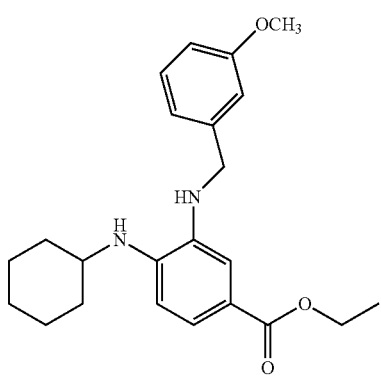
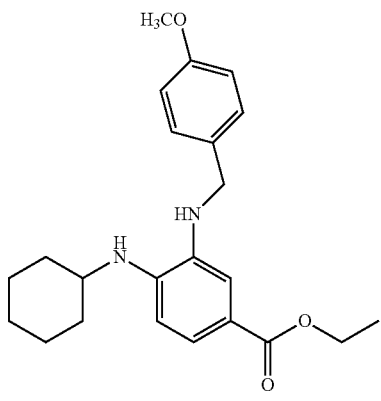

-continued
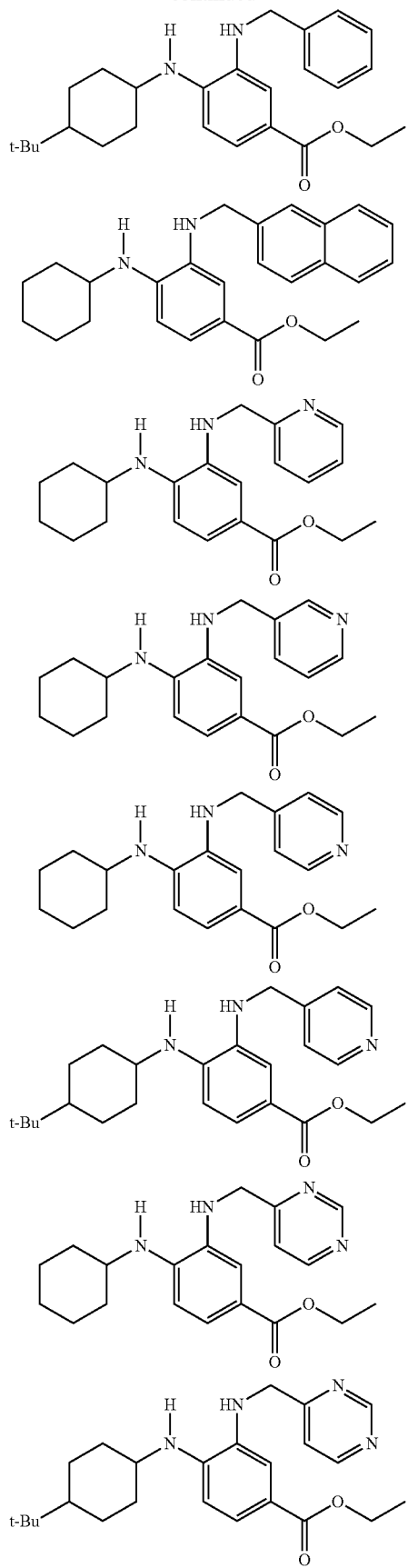
-continued
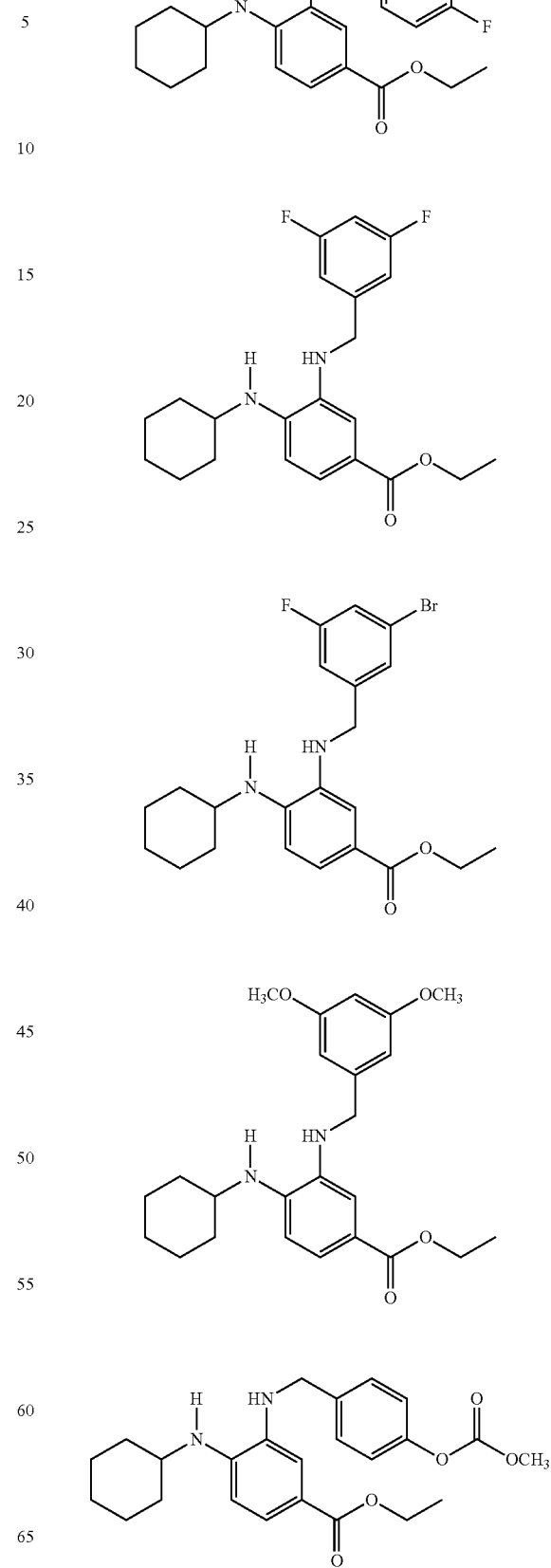

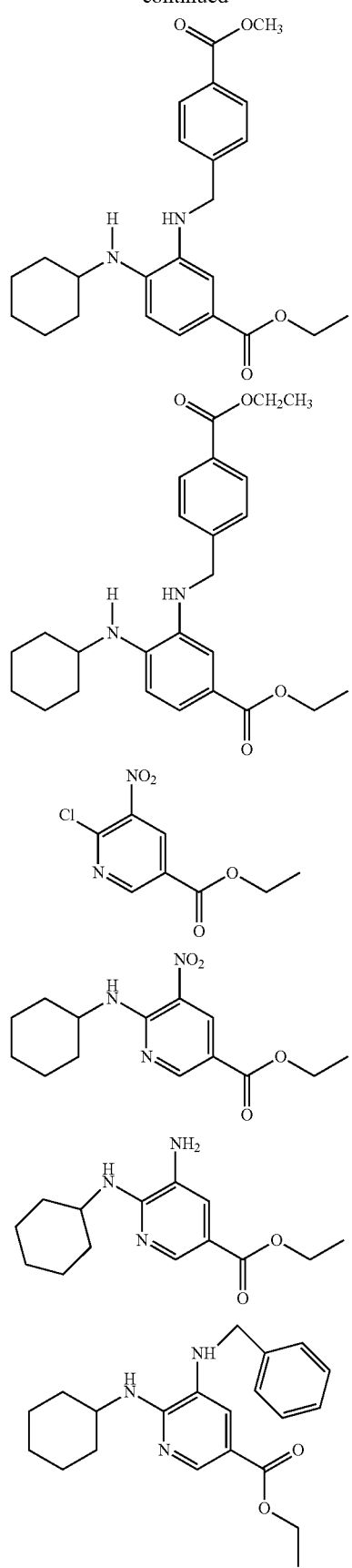
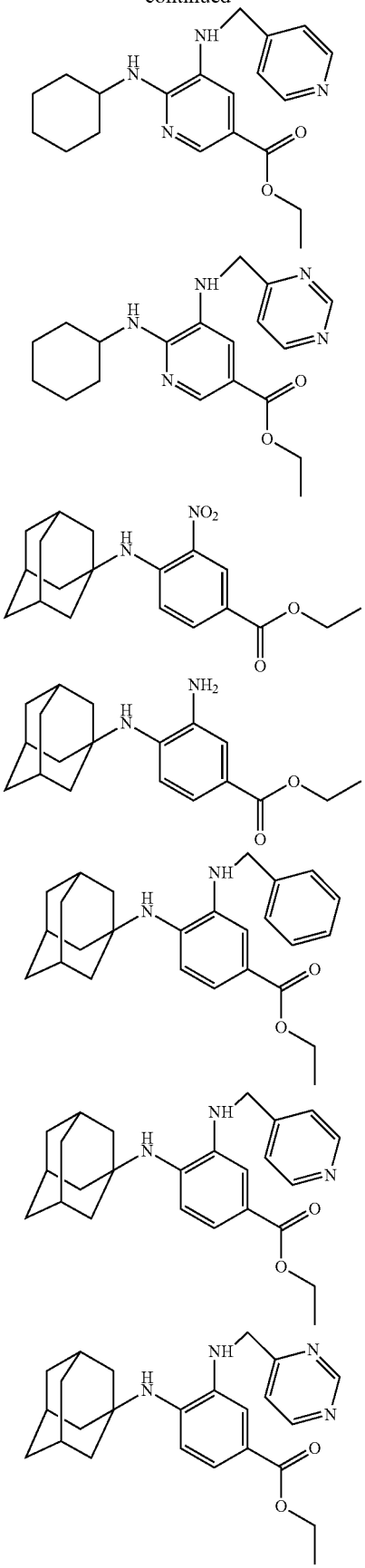

-continued
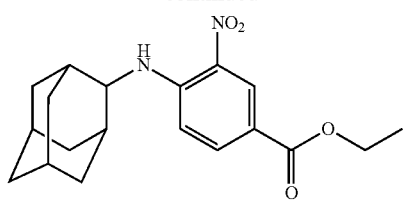
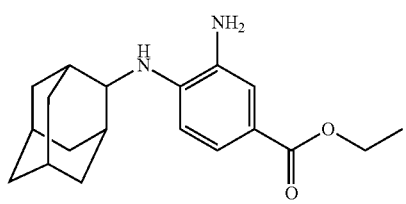
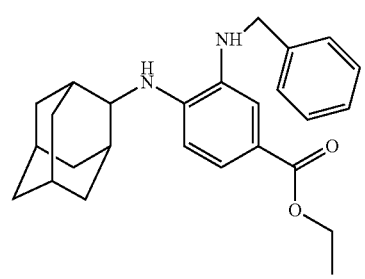
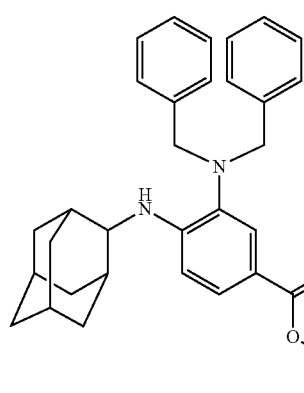
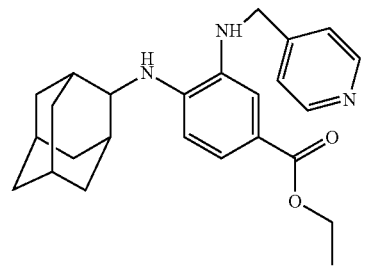
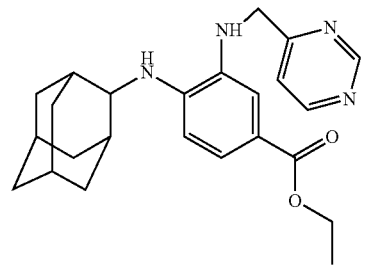
-continued
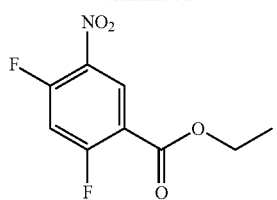
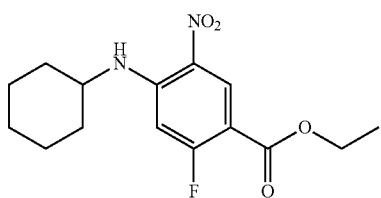
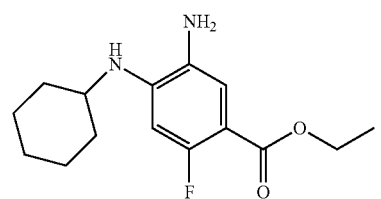
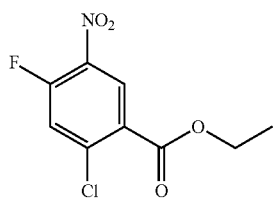
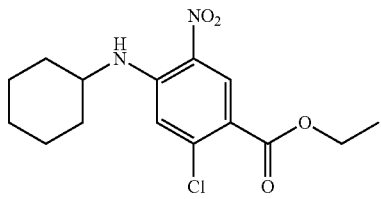
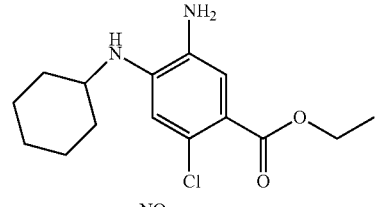
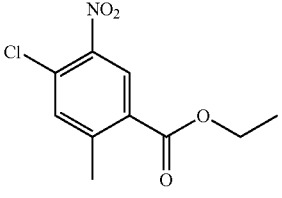
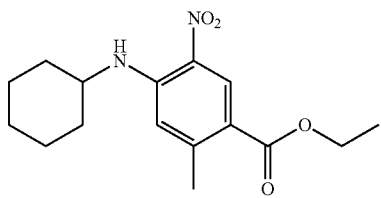

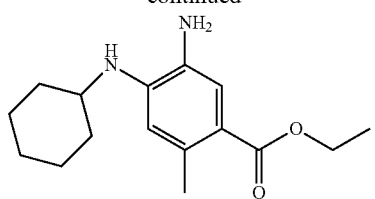
and pharmaceutically acceptable salts thereof, and individual enantiomers and diastereomers thereof.
Preferably, the compound is selected from the group consisting of:
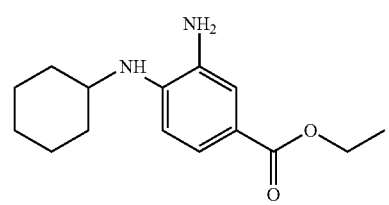
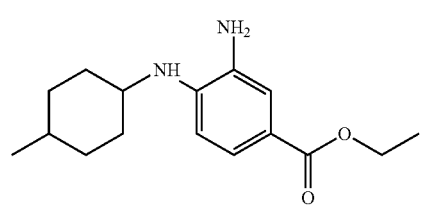
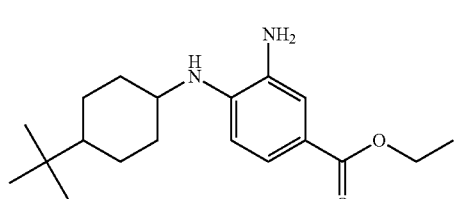
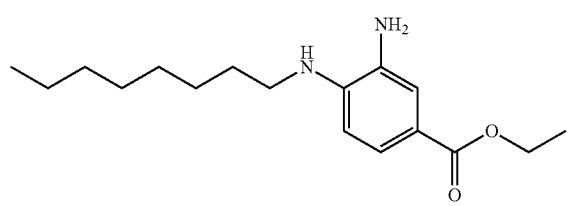
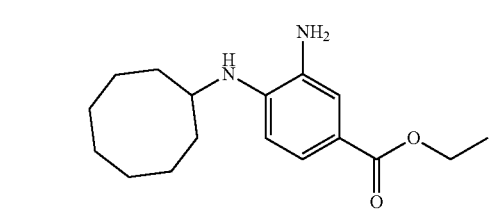
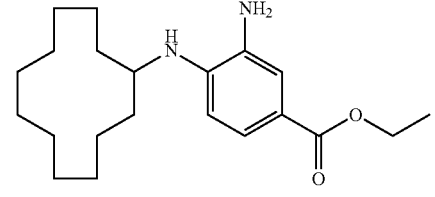
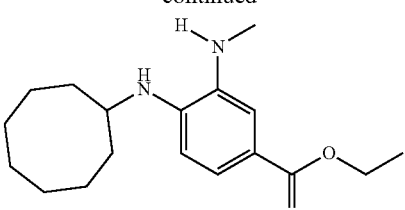
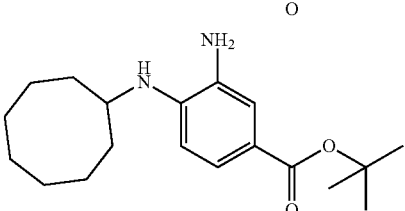
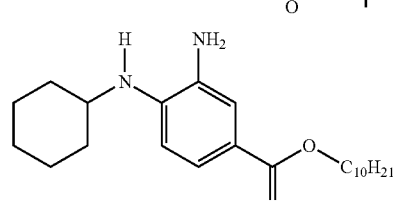
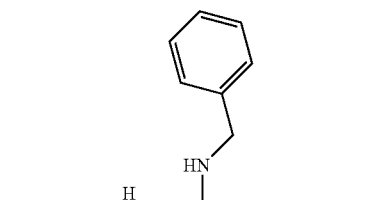
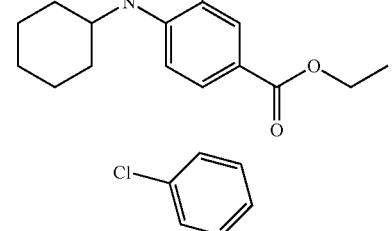
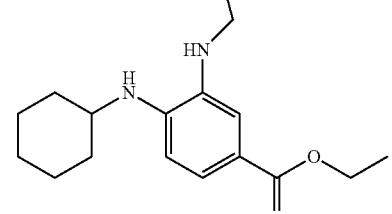
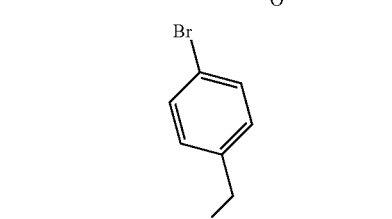
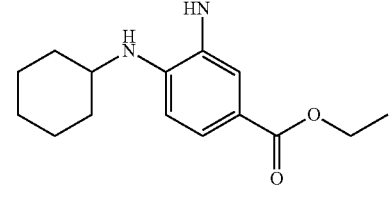

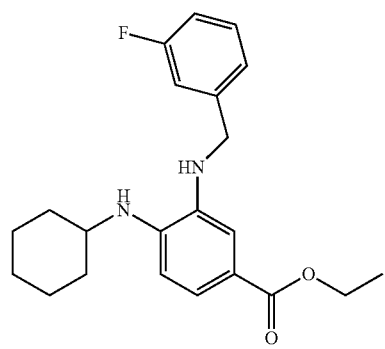
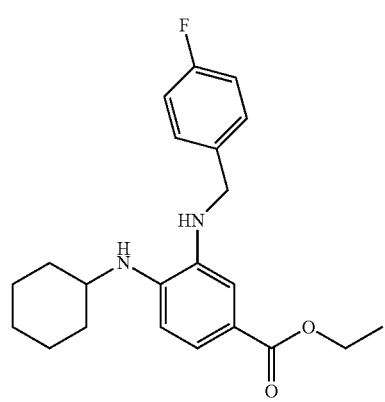
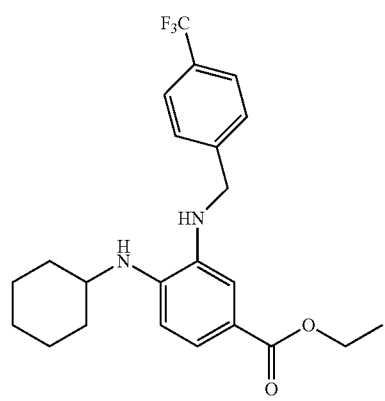
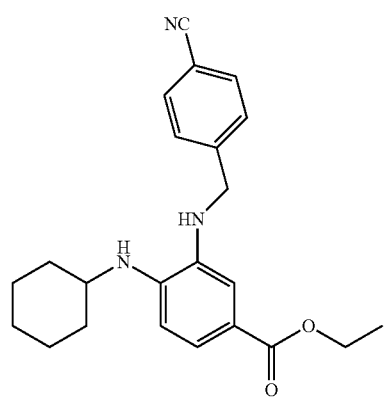
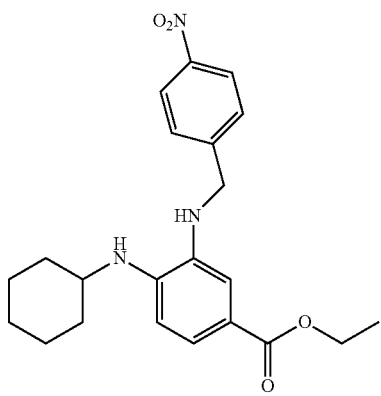
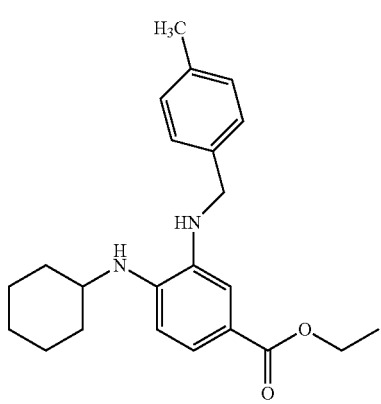
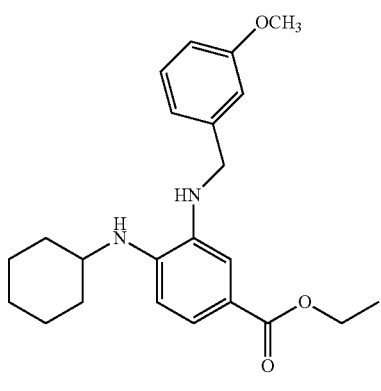
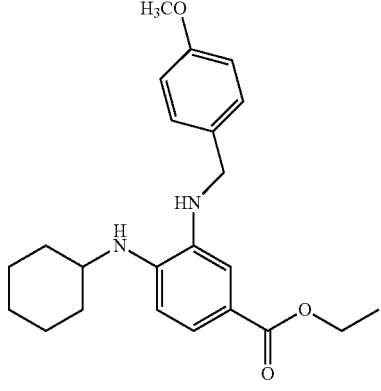

-continued
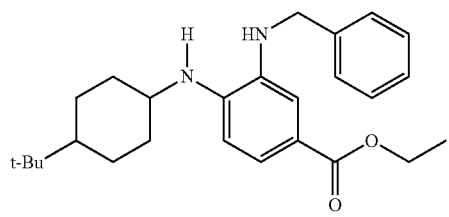
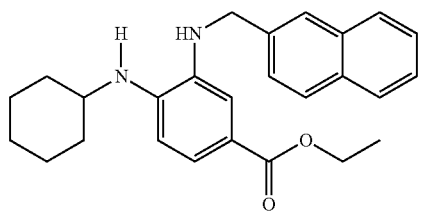
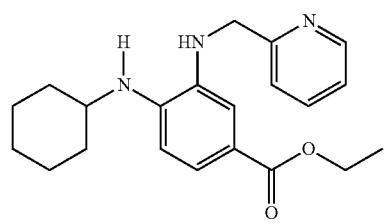
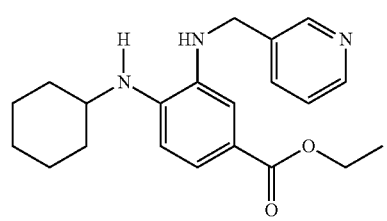
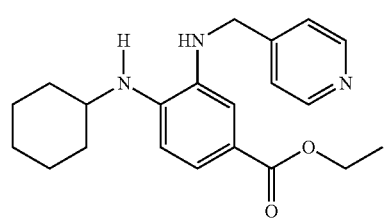
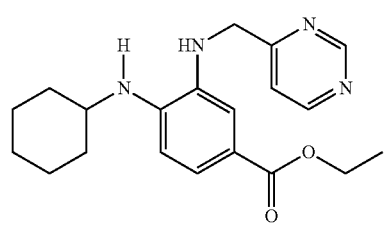
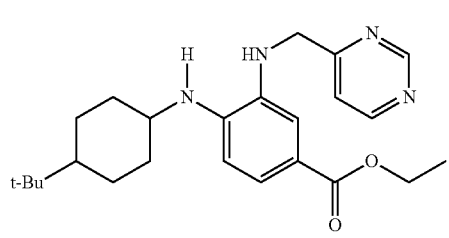
-continued
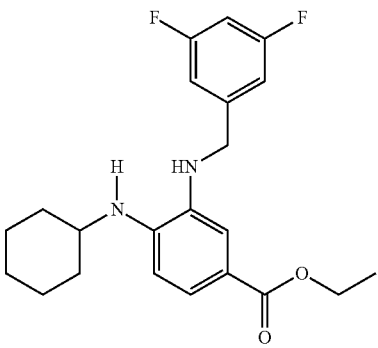
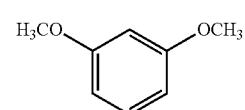
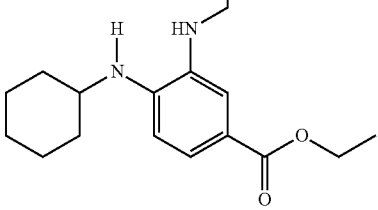
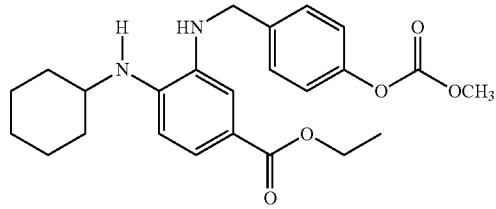
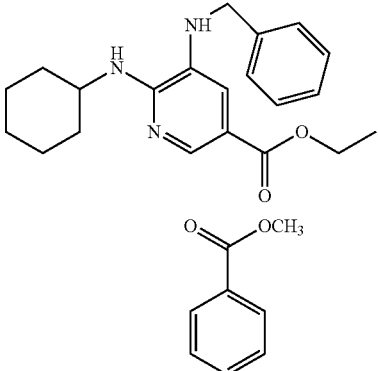
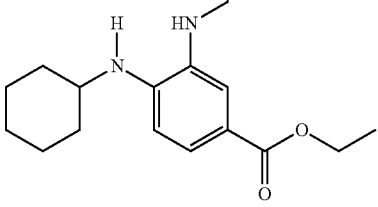

91
-continued

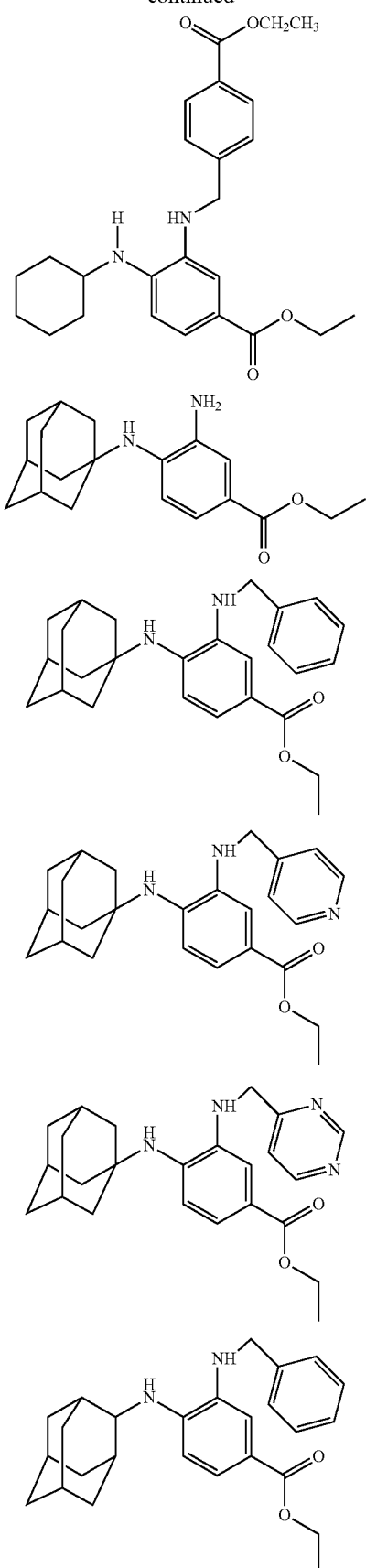

92
-continued

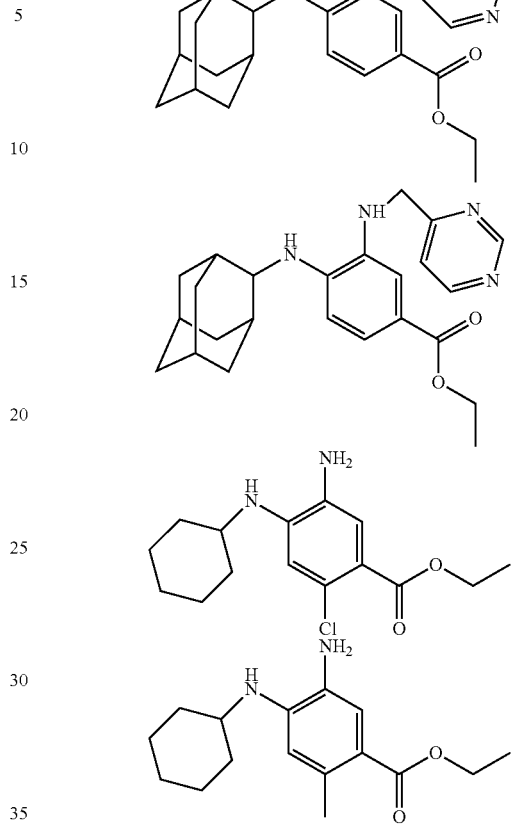

and pharmaceutically acceptable salts thereof, and individual enantiomers and diastereomers thereof.

Another embodiment of the present invention is a method of modulating ferroptosis in a subject in need thereof. This method comprises administering to the subject an effective amount of a ferroptosis inhibitor.

As used herein, "ferroptosis" means regulated cell death that is iron-dependent. Ferroptosis is characterized by the overwhelming, iron-dependent accumulation of lethal lipid reactive oxygen species. Ferroptosis is distinct from apoptosis, necrosis, and autophagy. Assays for ferroptosis are as disclosed herein, for instance, in the Examples section.

In one aspect of this embodiment, the ferroptosis inhibitor comprises a compound having the structure of formula (I):

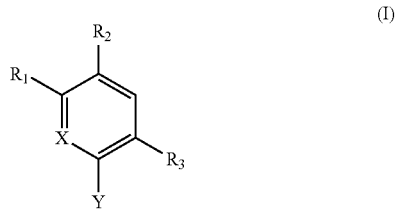

(I)

wherein
X is CH or N;
Y is H, halo, or $C_{1-4}$alkyl;
$R_1$ is selected from the group consisting of H, halo, cycloalkyl, and $NR_4R_5$;

$R_2$ is selected from the group consisting of $NR_6R_7$ and $NO_2$;

$R_3$ is selected from the group consisting of H,

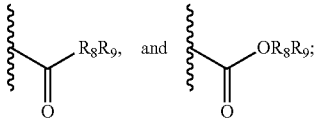

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

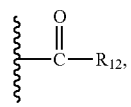

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, and pharmaceutically acceptable salts thereof, and individual enantiomers and diastereomers thereof.

Preferred compounds that fall within the structure of formula I are as set forth above.

A further embodiment of the present invention is a method of reducing reactive oxygen species (ROS) in a cell. This method comprises contacting a cell with a ferroptosis modulator. As used herein, the terms "modulate", "modulating" and grammatical variations thereof mean to change, such as decreasing or reducing the occurrence of ferroptosis.

In one aspect of this embodiment, the ferroptosis modulator is a ferroptosis inhibitor, which comprises a compound having the structure of formula (I):

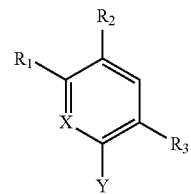

wherein
X is CH or N;
Y is H, halo, or $C_{1-4}$alkyl;
$R_1$ is selected from the group consisting of H, halo, cycloalkyl, and $NR_4R_5$;
$R_2$ is selected from the group consisting of $NR_6R_7$ and $NO_2$;
$R_3$ is selected from the group consisting of H,

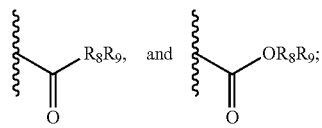

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

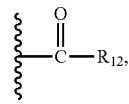

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, and pharmaceutically acceptable salts thereof, and individual enantiomers and diastereomers thereof.

Preferred compounds that fall within the structure of formula I are as set forth above.

Another embodiment of the present invention is a method for treating or ameliorating the effects of a neurodegenerative disease in a subject in need thereof. This method comprises administering to the subject an effective amount of a compound having the structure:

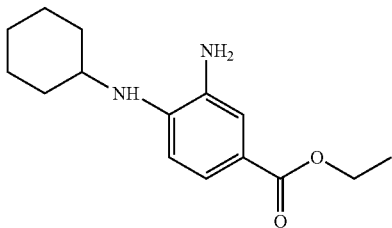 [SMILES: CCOC(=O)c1ccc(NC2CCCCC2)c(N)c1]

and pharmaceutically acceptable salts thereof.

Preferred compounds that fall within the structure of formula I are as set forth above.

In this embodiment, the subjects, the neurodegenerative diseases, and additional compositions that may be co-administered to the subject are as set forth above.

A further embodiment of the present invention is a compound. This compound has the structure selected from the group consisting of:

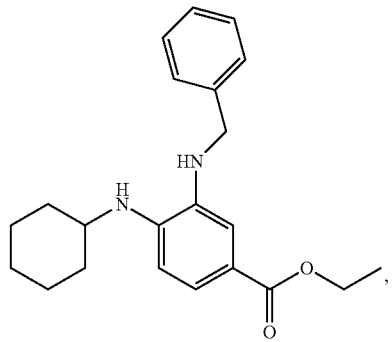

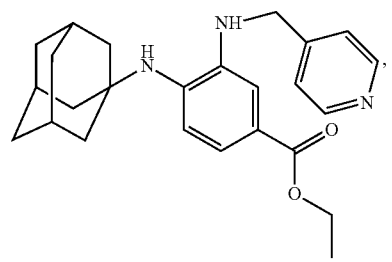

and pharmaceutically acceptable salts thereof.

An additional embodiment of the present invention is a method for treating or ameliorating the effects of a neurodegenerative disease in a subject in need thereof. This method comprise administering to the subject an effective amount of a compound having the structure selected from the group consisting of:

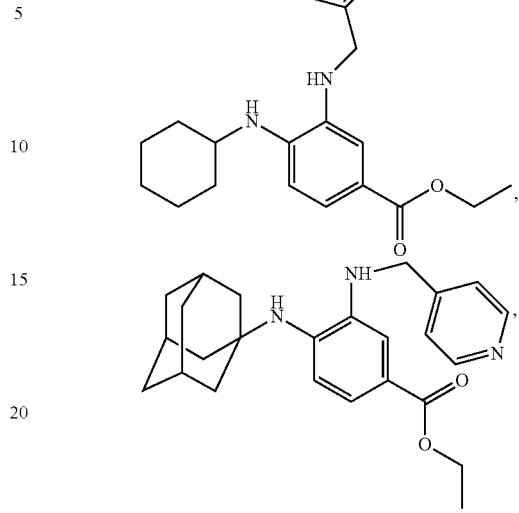

and pharmaceutically acceptable salts thereof.

In this embodiment, the subjects, the neurodegenerative diseases, and additional compositions that may be co-administered to the subject are as set forth above.

As used herein, a "pharmaceutically acceptable salt" means a salt of the compounds of the present invention which are pharmaceutically acceptable, as defined herein, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

A composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition of the present invention may be administered in conjunction with other treatments. A composition of the present invention maybe encapsulated or otherwise protected against gastric or other secretions, if desired.

The compositions of the invention are pharmaceutically acceptable and comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, Pa.). More generally, "pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers are well known in the art (see, e.g., Remington, The Science and Practice of Pharmacy ($21^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The compositions of the invention may, optionally, contain additional ingredients and/or materials commonly used in such compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteriaretaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

In the foregoing embodiments, the following definitions apply.

The term "alkyl" refers to the radical of saturated aliphatic groups that does not have a ring structure, including straight-chain alkyl groups, and branched-chain alkyl groups. In certain embodiments, a straight chain or branched chain alkyl has 12 or fewer carbon atoms in its backbone (e.g., $C_1$-$C_{12}$ for straight chains, $C_3$-$C_{12}$ for branched chains).

Moreover, unless otherwise indicated, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Indeed, unless otherwise indicated, all groups recited herein are intended to include both substituted and unsubstituted options. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aromatic, or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

The term "cycloakyl", as used herein, refers to the radical of saturated aliphatic groups having a ring structure, including cycloalkyl (alicyclic) groups, alkyl-substituted cycloalkyl groups, and cycloalkyl-substituted alkyl groups. Certain cycloalkyls have from 3-12 carbon atoms in their ring structure, including 5, 6, 7, 8, 9, 10, 11, or 12 carbons in the ring structure. Cycloalkyls can be further substituted with alkyls, alkenyls, alkoxys, alkylthios, aminoalkyls, carbonyl-substituted alkyls, —$CF_3$, —CN, and the like. As used herein, the "pendant group" of a cycloalkyl refers to any atom(s) or functional group(s) that are attached to the ring atom.

The term "$C_{x-y}$" when used in conjunction with a chemical moiety, such as, alkyl and cycloalkyl, is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc.

The term "aryl" as used herein includes substituted or unsubstituted single-ring aromatic groups in which each atom of the ring is carbon, or nitrogen (if ring carbons are substituted). Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "alkyl-aryl" refers to an alkyl group substituted with at least one aryl group. As used herein, the "pendant group" of a alkyl-aryl refers to any atom(s) or functional group(s) that are attached to the ring atom.

The term "Boc", as used herein, refers to the tert-butyloxycarbonyl group.

The term "ester" as used herein, includes the group —C(O)OR$^7$ wherein R$^7$ represents a hydrocarbyl group, including $C_{1-3}$ alkyl.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical, and substituted or unsubstituted. Specifically included in this definition is the group $C_{1-3}$alkyl-O—$C_{1-3}$alkyl-R, where R is $NH_2$ or NHBoc. An example of such a group is —$CH_2CH_2$—O—$CH_2$—$CH_2$—$NH_2$. Examples of ethers include, but are not limited to, alkyl-O-alkyl, heterocycle-O-heterocycle and aryl-O-heterocycle. Ethers also include "alkoxy" groups, which may be represented by the general formula —O-alky, as well as "alkoxyalkyl" groups, which may be represented by the general formula alkyl-O-alkyl.

The terms "halo" and "halogen" are used interchangeably herein and mean halogen and include chloro, fluoro, bromo, and iodo.

The term "heteroatom" as used herein means an atom of any element other than carbon or hydrogen. Preferred heteroatoms are nitrogen, oxygen, and sulfur; more preferably, nitrogen and oxygen.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As used herein, the term "substituent," means H, cyano, oxo, nitro, acyl, acylamino, halogen, hydroxy, amino acid, amine, amide, carbamate, ester, ether, carboxylic acid, thio, thioalkyl, thioester, thioether, $C_{1-8}$ alkyl, $C_{1-8}$alkoxy, $C_{1-8}$alkenyl, $C_{1-8}$aralkyl, 3- to 12-membered carbocyclic, 3- to 12-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

As set forth previously, unless specifically stated as "unsubstituted," references to chemical moieties herein are understood to include substituted variants. For example, reference to an "aryl" group or moiety implicitly includes both substituted and unsubstituted variants.

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that to the extent compounds of the present invention have a chiral center, they may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:
  i) physical separation of crystals—a technique whereby macroscopic crystals of the individual enantiomers are manually separated. This technique can be used if crystals of the separate enantiomers exist, i.e., the material is a conglomerate, and the crystals are visually distinct;
  ii) simultaneous crystallization—a technique whereby the individual enantiomers are separately crystallized from a solution of the racemate, possible only if the latter is a conglomerate in the solid state;
  iii) enzymatic resolutions—a technique whereby partial or complete separation of a racemate by virtue of differing rates of reaction for the enantiomers with an enzyme;
  iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts as disclosed in more detail herein or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The stereoisomers may also be separated by usual techniques known to those skilled in the art including fractional crystallization of the bases or their salts or chromatographic techniques such as LC or flash chromatography. The (+) enantiomer can be separated from the (−) enantiomer using techniques and procedures well known in the art, such as that described by J. Jacques, et al., antiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

The following examples are provided to further illustrate the methods of the present invention. These examples are illustrative only and are not intended to limit the scope of the invention in any way.

EXAMPLES

Example 1

Experimental Procedures

Analysis of Reactive Oxygen Species Production

The day before the experiment, 200,000 cells/well were seeded in 6-well dishes (Corning Inc., Corning, N.Y.). The day of the experiment, cells were treated with test compounds for the indicated times, then harvested by trypsinization, resuspended in 500 µL Hanks Balanced Salt Solution (HBSS, Gibco, Invitrogen Corp., Carlsbad, Calif.) containing either $H_2DCFDA$ (25 µM), C11-BODIPY (581/591) (2 µM) or MitoSOX (5 µM) (all from Molecular Probes, Invitrogen) and incubated for 10 minutes at 37° C. in a tissue culture incubator. Cells were then resuspended in 500 µL of fresh HBSS, strained through a 40 µM cell strainer (BD Falcon, BD Biosciences, San Jose, Calif.), and analyzed using a flow cytometer (FACSCalibur or Accuri C6, BD Biosciences), which was equipped with 488-nm laser for excitation. Data was collected from the FL1 ($H_2DCFDA$, C11-BODIPY) or FL2 channel (MitoSOX). A minimum of 10,000 cells were analyzed per condition.

Cancer Cell Viability Measurements

Cell viability was typically assessed in 384-well format by Alamar Blue (Invitrogen) fluorescence (ex/em 530/590) measured on a Victor3 platereader (Perkin Elmer, Waltham, Mass.). In some experiments, Trypan Blue dye exclusion counting was performed using an automated cell counter (ViCell, Beckman-Coulter Inc., Brea, Calif.). Cell viability in test conditions is reported as a percentage relative to the negative control treatment.

shRNA Screening

An arrayed collection of 6,528 shRNA hairpins derived from The RNAi Consortium (TRC) collection targeting 1,087 genes, kindly provided by Vamsi Mootha and Joshua Baughman (MIT), was screened in 384-well plate format (Corning) using both Calu-1 and HT-1080 cells. ShRNAs targeting GFP and RFP, randomly distributed through each plate, served as negative controls. 400 cells per well were infected in duplicate for 48 hours with 2 µL shRNA-containing viral supernatant, selected for 24 hours in puromycin (1.5 µg/mL), then treated with DMSO, erastin (7.3 µM) or staurosporine (STS) (1 µM) for 24 hours. Cell viability was determined using Alamar Blue. For each hairpin within each treatment condition, a cell death rescue score was computed as the ratio of the average viability of the two replicates to the average viability of the within-plate negative controls. These scores were used to compare the effects between compounds. To identify genes required for ferroptosis, individual hairpins were scored as hits if they displayed an average death suppression ≥3 median average deviations from the median within-plate or screen-wide negative control values. 51 candidate genes were identified with the same two (or more) unique hairpins per gene called as hits in both the Calu-1 and HT-1080 screens. For each candidate gene, confirmation studies using RT-qPCR analysis of mRNA silencing was performed in HT-1080 cells using freshly prepared virus as described in more detail below.

[$^{14}$C]Cystine Uptake Assay 200,000 HT-1080 cells/well were seeded overnight in 6-well dishes (Corning). The next day, cells were washed twice in pre-warmed Na$^+$-free uptake buffer (137 mM choline chloride, 3 mM KCl, 1 mM CaCl$_2$, 1 mM MgCl$_2$, 5 mM D-glucose, 0.7 mM K$_2$HPO$_4$, 10 mM HEPES, pH 7.4), then incubated for 10 minutes at 37° C. in 1 mL of uptake buffer, to deplete cellular amino acids. At this point, in each well the buffer was replaced with 600 µL uptake buffer containing compound and 0.12 µCi (80-110 mCi/mmol) of L-[3,3'-$^{14}$C]-cystine (Perkin Elmer) and incubated for 3 minutes at 37° C. Cells were then washed three times with ice-cold uptake buffer and lysed in 500 µL 0.1 M NaOH. To this lysate was added 15 mL of scintillation fluid and radioactive counts per minute were obtained using a scintillation counter. All measurements were performed in triplicate for each condition.

Statistical Analyses

All statistical analyses were performed using Prism 5.0c (GraphPad Software Inc., La Jolla, Calif.).

Chemicals

Erastin was synthesized as described (Yagoda et al., 2007). RSL3 was obtained from Leadgen Laboratories (Orange, Conn.). Rapamycin was obtained from Cell Signaling Technologies (Danvers, Mass.), z-VAD-fmk was from BioMol (Enzo Life Sciences, Inc., Farmingdale, N.Y.), ALLN and E64D were from CalBiochem (Merck KGaA, Darmstadt, Germany), bafilomycin A1 and U0126 were from LC Laboratories (Woburn, Mass.), BAPTA-AM and Fura-2 were from Invitrogen. GKT137831 was the generous gift of GenKyoTex S.A. (Geneva, Switzerland). Unless otherwise indicated, all other compounds were from Sigma (St. Louis, Mo.).

Cell Lines and Media

The following engineered human foreskin fibroblasts were obtained from Robert Weinberg (Whitehead Institute): BJeH, BJeHLT, BJeLR, DRD. BJeH cells express human telomerase (hTERT), BJeHLT express hTERT plus the large and small T oncoproteins (LT, ST), BJeLR express hTERT, LT, ST and an oncogenic HRAS allele (HRAS$^{V12}$), DRD cells express an alternative suite of oncoproteins: hTERT, ST, dominant-negative p53, cyclin D1, and a mutant form of CDK4, along with HRAS$^{V12}$. MEFs (Bax$^{-/-}$Bak$^{-/-}$ and wild-type) were obtained from Craig Thompson (Sloan Kettering), 143B.TK-mtDNA-depleted rho zero ($\rho^0$) and matching parental $\rho^+$ cells were obtained from Eric Schon (Columbia University), TC32 and SK-ES-1 were obtained from Stephen Lessnick (Huntsman Cancer Institute, Salt Lake City). HT-1080, Calu-1, U2OS and 293-T cells were obtained from American Type Culture Collection.

BJ series cell lines were grown in DMEM High-Glucose media (Gibco, Invitrogen Corp., Carlsbad, Calif.) plus 20% M199 (Sigma) and 15% heat-inactivated fetal bovine serum (FBS). HT-1080 cells were grown in DMEM High-Glucose media (Gibco) supplemented with 10% FBS and 1% non-essential amino acids (Gibco). Calu-1 and U2OS cells were grown in McCoy's 5A media (Gibco) supplemented with 10% fetal bovine serum. SK-ES-1 cells were grown in McCoy's 5A supplemented with 1.5 mM L-glutamine+15% FBS. 293-T and TC32 cells were grown in DMEM High-Glucose supplemented with 10% FBS. When used for transfections to generate virus, 293-T cells were seeded in the above media lacking antibiotics. 293-T viral collection media contained 30% HyClone FBS. MEFs were grown in DMEM supplemented with 10% fetal calf serum. 143B cells were grown in DMEM High-Glucose supplemented with 10% FBS. 143B $\rho^0$ cells were grown in the above media supplemented with 100 µg/mL uridine. The rho zero status of the 143B $\rho^0$ cell lines was confirmed using RT-qPCR by showing little or no mRNA expression for 7 mtDNA-encoded transcripts in the $\rho^0$ cell lines. All cell lines were grown in humidified tissue culture incubators (Thermo Scientific) at 37° C. with 5% CO$_2$. Except where indicated, all medias were supplemented with penicillin and streptomycin (Gibco).

Light Microscopy

Phase contrast images were acquired using an AMG EVOS FL (Advanced Microscopy Group) microscope equipped with a 10× phase-contrast objective. Three independent fields were acquired for each experimental condition. Representative samples from one field of view are shown.

Transmission Electron Microscopy

BJeLR cells were plated at 100,000 cells/dish in 35 mm tissue culture dishes. After 12 hours, cells were treated with vehicle (DMSO; 10 hours), erastin (37 µM; 10 hours), staurosporine (750 nM; 8 hours), hydrogen peroxide (16 mM; 1 hour) or rapamycin (100 nM; 24 hours). Cells were fixed with 2.5% glutaraldehyde in 0.1 M Sorenson's buffer (0.1 M H$_2$PO$_4$, 0.1 M HPO$_4$ (pH 7.2)) for at least 1 hour, and then treated with 1% OsO$_4$ in 0.1 M Sorenson's buffer for 1 hour. Enblock staining used 1% tannic acid. After dehydration through an ethanol series, cells were embedded in Lx-112 (Ladd Research Industries, Williston, Vt.) and Embed-812 (Electron Microscopy Sciences, Hatfield, Pa.). Thin sections were cut on an MT-7000 ultramicrotome, stained with 1% uranyl acetate and 0.4% lead citrate, and examined under a Jeol JEM-1200 EXII electron microscope. Pictures were taken on an ORCA-HR digital camera (Hamamatsu Corp., Bridgewater, N.J.) at 5,000-50,000-fold magnification, and measurements were made using the AMT Image Capture Engine.

Measurement of ATP Levels

ATP levels were evaluated using the ApoSENSOR ATP Assay Kit (Biovision Inc., Milpitas, Calif.) according to the manufacturer's instructions. 2000 HT-1080 or BJeLR cells were seeded in 96-well white bottom plates (Falcon). Cells were treated 12 hours later with compound as above for the TEM. Prior to luminescence measurement, medium was removed and cells were lysed and incubated with ATP Monitoring Enzyme. Luminescence was measured using a Victor3 platereader equipped with an infrared emission filter every 30 seconds for 10 minutes. Typically the first reading was used for data analysis. Parallel cell culture treatments were performed in 96-well clear bottom plates and cell viability was determined using Alamar Blue. These values were used to normalize ATP levels to cell viability.

Modulatory Profiling of Small Molecule Inhibitors

The following small molecule inhibitors were tested in a ten-point, four-fold dilution series for their ability to prevent erastin-induced death in HT-1080, Calu-1 and BJ-eLR cells (high dose of dilution series in brackets): carbobenzyloxy-valyl-alanyl-aspartyl-[O-methyl]-fluoromethylketone (z-VAD-fmk, 184 µM), necrostatin-1 (Nec-1, 19.3 µM), cyclosporine A (CspA, 33.2 µM), N-Acetyl-Leu-Leu-Nle- CHO (ALLN, 40 µM), (2S,3S)-trans-epoxysuccinyl-L-leucylamido-3-methylbutane ethyl ester (E64d, 400 µM), bafilomycin A1 (Baf A1, 4 µM), 3-methyladenine (3-MA, 6.25 mM), chloroquine (Chq, 250 µM), deferoxamine (DFO, 400), 6-hydroxy-2,5,7,8-tetramethylchroman-2-carboxylic acid (trolox, 320 µM), 1,4-diamino-2,3-dicyano-1,4-bis(2-aminophenylthio)butadiene (U0126, 52.4 µM) and cycloheximide (5.6 µM). The day before the experiment, cells were seeded in black, 384-well clear bottom plates (Corning) at a density of 1,000 cells/well using a Beckman Biomek FX Workstation. All compounds (except 3-methyladenine and chloroquine, which were diluted in water) were diluted in DMSO at 250 times the final highest test concentration, and aliquoted across a 384-well plate (Greiner, Monroe, N.C.). A ten-point, 4-fold dilution series of each inhibitor in DMSO was made using a multichannel pipette. Replicates of this mother plate were stored at −20° C. On the day of the experiment, a fresh inhibitor plate was thawed and diluted 25-fold into DMEM in a 384 deep well 'daughter' plate (Greiner), using a Biomek FX. Medium was removed from cells and replaced with 36 µL medium containing DMSO (0.1%) or erastin (10 µM final concentration). Using the Biomek FX, 4 µL were then transferred from each inhibitor daughter plate into the DMSO-containing or erastin-containing assay plates. For 3-methyladenine and chloroquine, inhibitors were prepared fresh in media at 10-fold the final concentration in the presence of DMSO or 10 µM erastin. These solutions were manually pipetted onto cells in 384-well format. Assay plates were incubated at 37° C. for 24 hours. Viability was assessed using Alamar Blue.

Computation of Modulatory Effects

The modulatory effect ($M_e$) for drug-drug interactions was computed as follows. First, plate-based background correction was performed using Alamar Blue values from empty (cell-free) wells included on each plate. Next, within each experiment, 100% viability is determined as the average Alamar Blue score for cells treated with modulator=DMSO and lethal=DMSO, and all Alamar Blue values were scaled from 0 to 1 with the DMSO×DMSO condition=1. The individual effects of each modulator and lethal (e.g. in the presence of DMSO) at all tested doses were then ascertained. Using these data, the "expected" effect on viability ($B_{Exp}$) for each modulator (M)×lethal (L) combination were modeled using the Bliss formula for drug interactions (M+L−M*L). Next, $B_{Exp}$ was compared to the actual observed viability. For each informative drug-drug interaction (i.e. modulator="DFO", modulator concentration=100 µM, lethal=Erastin) the modulatory effect ($M_e$) was equivalent to the maximum observed deviation, positive or negative, from $B_{Exp}$. By default, $M_e$ in DMSO-treated cells is equal to 0. This formula was empirically determined to provide a useful measure of modulation that is robust to differences in the shapes of individual dose-response curves for different inhibitors and lethal molecules. $M_e$ values for each inhibitor-lethal drug combination were hierarchically clustered and plotted as a heatmap using the heatmaps.2 function of the gplots library in R.

Modulatory Profile of Lethal Small Molecules

The following lethal molecules were compared in a ten-point, two-fold dilution series modulatory profiling assay (high dose of dilution series in brackets): erastin (20 µM), RSL3 (5 µM), hydrogen peroxide ($H_2O_2$, 5 mM), artesunate (200 µM), phenylarsine oxide (PAO, 1 µM), taxol (0.5 µM), suberoylanilide hydroxamic acid (SAHA, 50 µM), trichostatin A (2.5 µM), doxorubicin (2 µM), fenretinide (50 µM), staurosporine (STS, 0.5 µM), brefeldin A (10 µM), β-lapachone (25 µM), bortezomib (5 µM), carbonyl cyanide m-chlorophenyl hydrazine (CCCP, 50 µM), 2-methoxyestradiol (2-ME, 50 µM), rotenone (2 µM), helenaline (50 µM), sulfasalazine (SAS, 1 mM) and phenethyl isothiocyanate (PEITC, 50 µM).

The comparative analysis of the lethal effects of various molecules was conducted as above for the inhibitors experiment with the following modifications. All lethal molecules were tested in a ten point, two-fold dilution series. Inhibitors were made in media at 1× final concentration. The growth media was removed from the plates, and 36 µL media+inhibitor (or DMSO) was added back to the plate+4 µL from the 10× lethal stock plate. Cell viability and modulatory effects ($M_e$) were computed as above, to obtain the maximum deviation from $B_{Exp}$ produced by each modulator across the different lethal small molecule concentrations.

Arrayed shRNA Screen: Data Analysis and Hit Selection.

ShRNA screening and follow-up studies identified 51 initial candidate suppressor genes, each represented by 2 hairpins common to both cell lines. These candidates were re-tested. For 50 of these genes, fresh virus (see below) was prepared for the top two scoring shRNA hairpins. The resistance in HT-1080 cells infected with these hairpins in response to up to 10 µM erastin was re-tested. In parallel, target knockdown was validated for each shRNA hairpin by RT-qPCR. From the initial set of suppressor genes, high confidence genes were selected using the following criteria: (1) the degree of death suppression was consistent across two independent replicates in the re-testing phase; (2) the level of death suppression was at least 50% of that observed in the sh263-VDAC3 positive control at the highest dose of erastin (10 µM); (3) at least one of two shRNA hairpins must reduce the level of mRNA <50% of control, and (4) an inverse correlation must exist between erastin resistance and mRNA levels (providing a strong measure of confidence in the on-target nature of the shRNAs used). Finally, whether each hairpin had been reported as independently validated was determined on The RNAi Consortium/Sigma website. By intersecting the results of these confirmatory analyses, a final set of six high confidence genes was determined.

Arrayed shRNA Screen: shRNA Confirmation

For all candidate suppressors, individual "hit" shRNA hairpin sequences were non-overlapping (e.g. targeting unique sequences within the mRNA) and were confirmed using the siRNA-Check tool available from In Silico Solutions (Fairfax, Va.). Individual shRNAs are identified by the 3 or 4 number Clone ID suffixes assigned to each mRNA target sequences by TRC.

New virus were produced to validate erastin resistance and perform downstream analyses of target knockdown and functional effects in a 6-well format as follows. On Day 1, 170,000 293-T cells were seeded in antibiotic-free media into each well of a 6-well dish. On Day 2, these cells were transfected (Fugene, Roche) with 450 ng of shRNA plasmid DNA, 400 ng of pDelta8.9 helper plasmid and 45 ng of pVSVg helper plasmid. On Day 3, the media was switched to viral collection media. Virus was harvested the following morning and evening of Day 4 and then a final time the next morning of Day 5. The collected media was pooled, spun at 2,000 rpm for 5 minutes and the virus-containing supernatant aliquoted and stored at −80° C. This protocol was used for the production of virus in all other small-scale shRNA experiments as well (i.e. FIGS. 7C and 7D).

Six-well dish infections were performed as follows. On Day 1, 30,000 HT-1080 cells were seeded per well. On day 2, cells were infected with 150 µL of viral supernatant and spin infected as for 384-well plates.

Genetic Screeninq Follow-up Experiments: Cell Line and Lethal Compound Specificity Analysis These experiments were performed for all cell lines. Lethal compound experiments were performed in parallel by first re-arraying by hand virus prepared as described above for all suppressor hairpins in a single 384 deep well viral "mother plate" (Corning), including 3 independent copies of the negative control and positive controls (sh-Control and sh263-VDAC3). Each hairpin was arrayed in a block of 6 wells (2 across×3 down). For each experiment, cells were seeded at a standard density of 400 cells/well on Day 1. On Day 2, the media was removed either by flicking, (for HT-1080 cells in the lethal compound analysis) or using a BioMek FX (for the cell line analysis), and then replaced with 38 μl media containing 1× polybrene (8 μg/ml) using the BioMek. 2 μl viral soup was then transferred from each well of the viral mother plate to each well of the assay plate and a spin infection was performed as described above. On Day 3 (for the analysis of cell lines) or Day 4 (for the analysis of lethal compounds), the media+virus was removed using the BioMek and replaced with media+1.5 μg/ml puromycin. Next, for both experiments, on Day 5, the media was again removed using the BioMek and replaced with media+lethal compound. On Day 6, Alamar Blue was added as described above and the signal was measured 6 hours later. This experiment was repeated twice with similar results and representative data from one experiment is shown. Data for the best hairpin as defined by mRNA silencing levels in HT-1080 cells is disclosed herein. Similar results were obtained with the second best hairpins.

Reverse Transcription-Quantitative Polymerase Chain Reaction (RT-qPCR)

RNA was extracted using the Qiashredder and Qiagen RNeasy Mini kits (Qiagen) according to the manufacturer's protocol. 2 μg total RNA for each sample was used as input for each reverse transcription reaction, performed using the TaqMan RT kit (Applied Biosystems, Life Technologies Corp., Carlsbad, Calif.). Primer pairs were designed for target transcripts using Primer Express 2.0 (Applied Biosystems). Quantitative PCR reactions were performed using the Power SYBR Green PCR Master Mix (Applied Biosystems). Triplicate samples per condition were analyzed on an Applied Biosystems 7300 qPCR instrument using absolute quantification settings. Differences in mRNA levels compared to HPRT1 or ACTB internal reference control were computed between control and experimental conditions using the ΔΔCt method.

LOC Library Construction

The LOC (Lead Optimized Compound) library is composed of 9,517 compounds selected from a starting pool of 3,372,615 compounds available through a variety of commercial libraries (Asinex, Moscow, Russia; Life Chemicals, Burlington, ON, Canada; Enamine Ltd., Kiev, Ukrain; TimTec, Newark, Del.; InterBioScreen Ltd., Moscow, Russia; Chembridge Corp., San Diego, Calif.). The starting pool was generated in silico by downloading structure files for available compounds from all vendors. From this pool, the application of Lipinski's rules (Lipinski et al., 2001) and other relevant physicochemical descriptors consistent with drug-like candidates (molecular weight>235, number of rotatable bonds<5, topological polar surface area<70 $Å^2$, aqueous solubility>0.5 mM) reduced the total number of compounds to 58,786. The total number of compounds was further reduced to 45,395 by filtering out compounds containing nitro and nitroso groups, reactive moieties, ketones and aldehydes, imines, scaffolds unsuitable for further modification, organometallic compounds and thiols. From this set, the final collection was derived by eliminating multiple copies of highly similar compounds (Tanimoto coefficient). All computational analyses were performed using MOE2008.10 (Chemical Computing Group, Montreal, Canada) on a MacPro with 2×2.93 GHz Quad-Core Intel Xeon CPUs. At this point, 5 mg of each compound was obtained from their respective suppliers and dissolved in DMSO at a standard concentration of 4 mg/mL. Aliquots of each compound were then arrayed into individual wells of several 384 shallow well "mother" plates (Grenier) using a BioMek liquid handling robot and frozen at −80° C. until use.

LOC Library Screening

The LOC library was screened over the course of several days. 384-well glass bottom assay plates (Corning) were seeded with 1,000 HT-1080 cells/well the day before the experiment. The day of the experiment, LOC mother plates were thawed at room temperature for 1 hour and spun at 1000 rpm for 1 minute prior to use. Using a BioMek liquid handing robot, 2 μL of compound solution from each LOC library mother plate was transferred to a 384 deep well "daughter" plate (Grenier) containing 148 μL of cell culture media. The cell culture media in each assay plate was then removed by flicking and, using a BioMek FX, replaced with 36 μL of growth media containing erastin (5 μM final). To this was added 4 μL of the drug solution from the daughter plate, for a final screening concentration of 5.3 μg/mL for each LOC library compound. 4 wells containing DMSO alone (no erastin), 4 wells containing 100 μM DFO alone (no erastin), 4 wells containing erastin plus DMSO, and 4 wells containing erastin plus 100 μM DFO (positive control) were included as controls on each plate. Each drug daughter plate was aliquoted separately to duplicate assay plates. Plates were then spun briefly (1000 rpm, 5 seconds) and returned to the 37° C. tissue culture incubator. 24 hours later, cell viability was assessed by Alamar Blue as described above.

LOC Library Screen Hit Identification and Confirmation

Candidate hits from the LOC library screen were identified. First, values for each duplicate screening plate were averaged. Next, a growth rescue score consisting of the ratio of the viability of each LOC compound+erastin versus the DMSO+erastin treatment within each plate was computed. These plate-based growth rescue scores were rank ordered from highest to lowest. The top 336 ranked compounds, derived from the same LOC library plates used for screening, were then re-tested in HT-1080 cells in a 10-point, 2-fold dilution series against erastin (5 μM) as described above for the modulatory profiling experiments. For the top 50 most potent compound inhibitors of erastin-induced death identified in this experiment, fresh compound in powder form was re-ordered from the respective vendors, the powder was re-dissolved in DMSO as above, and the 10-point, 2-fold dilution series experiment in HT-1080 cells repeated. Fer-1 proved to be the most potent of the re-tested compounds in this experiment and was selected for more detailed study.

Western Blotting

Cells were trypsinized, pelleted, and washed once in PBS. Cells were lysed for 20 minutes in buffer containing: 50 mM HEPES pH 7.4, 40 mM NaCl, 2 mM EDTA, 0.5% Triton X-100, 1.5 mM sodium orthovanadate, 50 mM NaF, 10 mM sodium pyrophosphate, 10 mM sodium β-glycerophosphate, and protease inhibitor tablet (Roche, Nutley, N.J.). Unlysed cells and debris were pelleted for 10 minutes at 10,000 rpm in a benchtop microcentrifuge at 4° C., and the supernatant was removed and mixed with 5×SDS loading buffer. Samples were separated by SDS-polyacrylamide gel electrophoresis. Western transfer was performed using the iBlot system (Invitrogen). Membrane was blocked for 1 hour in Licor Odyssey Blocking Buffer (LI-COR) and incubated in primary antibody overnight at 4° C. Following three 5-minute washes in Tris-buffered saline (pH 7.4) with 1% Tween-20 (TBS-T), membrane was incubated with secondary antibodies for 45 minutes in the dark. The membrane was washed again in TBST for three 5-minute washes with protection from light and scanned using the Odyssey Imaging System (LI-COR). Antibodies used were as follows: rabbit anti-phospho p42/44 MAPK (Cell Signaling Technology, #9101) and rabbit anti-p42/44 MAPK (Cell Signaling Technology, #9102). The secondary antibody was IR dye 800CW goat anti-rabbit IgG (LI-COR).

2,2-diphenyl-1-picrylhydrazyl (DPPH) assay

The stable radical DPPH (Blois, 1958) was dissolved in methanol to a final concentration of 0.05 mM. 1 mL of DPPH solution was added to 2 µL of each test compound dissolved in DMSO. The final concentration of each test compound was 0.05 mM. Samples were inverted several times and allowed to incubate at room temperature for 10 minutes. Samples were then aliquoted to white 96-well solid-bottom dishes (Corning) and absorbance at 517 nm was recorded using a TECAN M200 plate reader. All values were normalized to background (methanol only). The experiment was repeated twice. Results within each trial normalized to DMSO (=1.0), then averaged across trials.

Analysis of Cell Death in Rat Brain Slices: Organotypic Hippocampal Slice Cultures (OHSCs)

OHSCs were cultured as previously described (Morrison et al., 2002) with approval from Columbia University's Institutional Animal Care and Use Committee (IACUC). Briefly, Sprague Dawley rat pups (P8-P10) were rapidly decapitated, and the hippocampus placed in ice-cold Gey's balanced salt solution (Sigma). 400 µm thick sections were cut using a McIlwain tissue chopper and immediately plated on Millicell cell culture inserts (Millipore, Billerica, Mass.) in Neurobasal (Invitrogen) media supplemented with B27 (1×, Invitrogen), GlutaMAX (1 mM, Invitrogen), and D-glucose (4.5 mg/mL, Sigma) at 37° C. and 5% $CO_2$. After 2 days in vitro (DIV), the media was changed to medium containing serum comprised of 50% DMEM (Sigma), 25% heat-inactivated horse serum (Sigma), 25% Hank's balanced salt solution (Sigma), GlutaMAX (1 mM, Invitrogen), and D-glucose (4.5 mg/mL, Sigma). Medium was changed every 2-3 days.

Analysis of Cell Death in Rat Brain Slices: Excitotoxic Injury

After 10-14 DIV, OBSCs were exposed to an excitotoxic injury consisting of a 3 hour exposure to 5 mM L-glutamate in SFM (Morrison et al., 2002). Only healthy OHSCs defined as those with less than 5% cell death in all regions of the hippocampus (DG, CA3, CA1) pre-injury were used for experiments. After the 3 hour exposure, the cultures were placed in fresh serum free media (SFM) containing 75% DMEM, 25% Hank's balanced salt solution, GlutaMAX (1 mM), D-glucose (4.5 mg/mL) until cell death was quantified at 24 hours. If drugs were added, they were added at the same time as glutamate.

Analysis of Cell Death in Rat Brain Slices: Cell Death Assessment

Quantification of cell death has been described previously (Cater et al., 2007; Morrison et al., 2002). Brightfield images of the hippocampal cultures were taken before injury for identification of regions of interest (ROI) including the dentate gyrus (DG), CA3 and CA1. Propidium iodide (PI, Invitrogen) was used as a fluorescent signal for cell death, and images were taken before the induction of injury and 24 hours following injury. For PI imaging, the cultures were transferred to SFM supplemented with 5 µg/mL PI. After a 30 minute incubation, brightfield and PI images were acquired. All images were captured on an Olympus IX-80 fluorescent microscope fitted with a 175 W Xenon Arc lamp (Perkin Elmer), CoolSNAP ES camera (Photometrics, Tucson, Ariz.), and standard rhodamine optics (excitation 556-580 nm; emission 590-630 nm; PI exposure 2 seconds, brightfield exposure 3 miliseconds). Metamorph image analysis software was used to determine the ROI in the brightfield image, and this ROI was transferred to the PI image taken before and 24 hours after injury. Percentage cell death was expressed as the number of pixels in the ROI above a threshold in the PI fluorescent image divided by the total number of pixels in the ROI.

Oncogenic-RAS-Selective Lethal Assay

Analysis of oncogenic-RAS-selective lethality in BJeH, BJeHLT, BJeLR and DRD cells was performed as described previously (Yang and Stockwell, 2008).

siRNA Gene Silencing

All siRNAs were obtained from Qiagen. 50,000 HT-1080 cells were seeded in antibiotic-free HT-1080 media into each well of a 6-well tissue culture dish (Corning) the day before the start of the experiment. The next day, cells were transfected with 2 nM of siRNAs (final concentration/well) using Lipofectamine RNAiMAX (Invitrogen) according to the manufacturer's protocols. The media was replaced with fresh antibiotic-containing HT-1080 media the following day. Parallel cultures were assayed for gene expression after 48 hours using RT-qPCR and for cell viability in response to drug treatment at 72 hours post-transfection.

Plasmids and Transfection pMaxGFP plasmid was from Amaxa (Lonza Group Ltd., Basel, Switzerland). pCMV6-SLC7A11-DDK was from Origene Technologies (Rockville, Md.). 50,000 HT-1080 cells were seeded in 6-well dishes (Corning) the day before the experiment in regular HT-1080 media. The next day, cells were transfected with 0.5 µg plasmid DNA/well using Lipofectamine LTX (Invitrogen) according to the manufacturer's protocol. 72 hours post-transfection, cell viability was assessed by microscopy in response to erastin and sulfasalazine.

Identification of SLC7A5 as an Erastin Target in BJeH and BJeLR Cells

Affinity chromatography and mass spectrometry were used to identify proteins that bound an active (lethal) erastin analog (erastin-A6) and an inactive control (erastin-B2) in lysates from oncogenic HRAS-mutant BJeLR cells and HRAS-wild-type BJeH cells (2 independent experimental replicates for each cell line) (Yagoda et al., 2007). Previously, the analyses on targets bound by active erastin-A6 were done in BJeLR versus BJeH cells, on the assumption that such targets were most likely to mediate oncogenic-RAS-selective lethality (Yagoda et al., 2007). However, given that erastin was lethal to various cells, including some that lack mutant HRAS, the data were re-analyzed in order to look for targets bound by active erastin-A6 (but not inactive erastin-B2) in both cells types, as follows. First the two experimental replicates were merged on the basis of protein reference IDs to identify high confidence targets for each erastin analog in both cell lines. Any proteins also bound by inactive erastin-B2 (i.e. non-specific interactions) were then eliminated from the erastin-A6 target lists. Next, the lists of proteins uniquely bound by active erastin-A6 in BJeH cells (gi|4506675 [RPN1], gi|4505773 [PHB], gi|1174469 [STT3A], gi|14017819 [LRRIQ1], gi|12643412

[SLC7A5]) and BJeLR cells (gi|1172554 [VDAC2], gi|19923753 [SLC16A1], gi|11281610 [TECR], gi|23308572 [MBOAT7], gi|4759086 [SEC22B], gi|7448310 [TSPO], gi|4507943 [XPO1], gi|21361181 [ATP1A1], gi|29029559 [CSEL1], gi|23308577 [PHGDH], gi|1362789 [PRKDC], gi|12643412 [SLC7A5]) were compared. This new analysis identified SLC7A5 as the lone protein bound by active erastin-A6 in both cell types. Of note, VDAC2 was identified in both experimental replicates for erastin-A6-treated BJeLR cells, but annotated with two different identifiers (gi|4507881 and gi|1172554). Also of note, SLC3A2 was identified in one replicate of erastin-A6-treated BJeLR cells.

Analysis of Metabolic Profiling Data for Erastin-treated Jurkat Cells

Ramanathan and Schreiber isolated a total of 123 metabolites from Jurkat T cells treated with erastin (1 µM, 25 minutes) or vehicle control (Ramanathan and Schreiber, 2009). These authors previously reported on a subset (11/123) of the metabolites that are specifically related to mitochondrial metabolism and glycolytic pathway function (FIG. 6, (Ramanathan and Schreiber, 2009)). The complete (123 metabolite) normalized dataset was obtained, and the data were ranked by the observed significance (P values) of the change in abundance between erastin-treated and control samples. The substrate specificity of system L has previously been established (Kanai and Endou, 2003).

Software

Flow cytometry data was analyzed using FloJo (9.3.2, Tree Star, Inc., Ashland, Oreg.). Chemical structures were drawn using ChemDraw Ultra (Cambridgesoft, Cambridge, Mass.). Computational determination of log P (S log P function) was performed using MOE 2010.10 (Chemical Computing Group, Montreal, Calif.). Viability data was analyzed using Excel (Microsoft Corp., Seattle, Oreg.). Summary data and heatmaps were generated using R. Dose-response curves were computed by 4-parameter logistic regression in Prism 5.0c (GraphPad Software). Images were manipulated using Photoshop CS4 and Illustrator CS4 (Adobe, San Jose, Calif.).

Example 2

Synthesis of Ferrostatin-1 and its Analogs

Chromatography

Merck pre-coated 0.25 mm silica plates containing a 254 nm fluorescence indicator were used for analytical thin-layer chromatography. Flash chromatography was performed on 230-400 mesh silica (SiliaFlash® P60) from Silicycle.

Nuclear Magnetic Resonance (NMR)

NMR spectra were obtained on a Bruker DPX 300 or 400 MHz spectrometer. CI-MS spectra were taken on a Nermag R-10-10 instrument.

Chemicals

Unless otherwise indicated, all other compounds were from Sigma (St. Louis, Mo.).

General Synthetic Scheme

General Scheme: General synthetic scheme for the synthesis of Ferrostatin-1 and other ferrostatins.

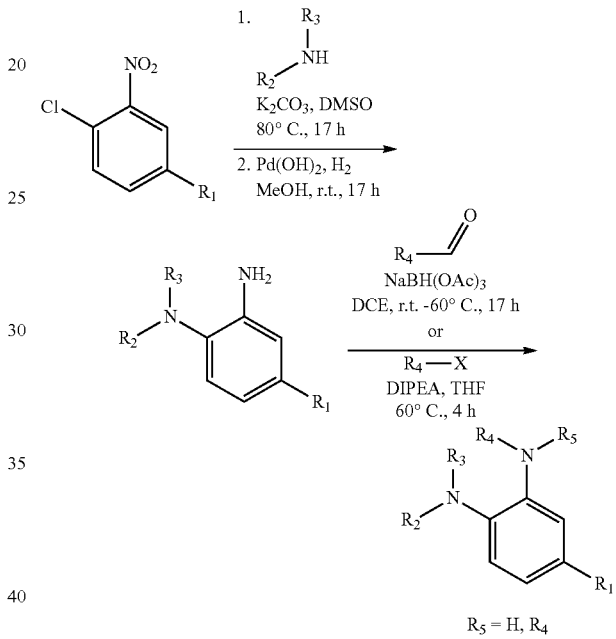

Ferrostatin-1: $R_1 = CO_2Et$; $R_2$ = cyclohexyl; $R_3$ = H.

General Procedure A (ArS$_N$2 Reaction) (Beaulieu et al., 2003)

To the ethyl 4-chloro-3-nitrobenzoate (1 equiv., 200 mg, 0.871 mmol) in dry DMSO (2 mL) was added K$_2$CO$_3$ (2 equiv., 240.8 mg, 1.742 mmol) and various amines (1.2 equiv., 119.5 µL, 1.045 mmol). The mixture was stirred for 17 hours at 60° C. The solution was poured in water, and the organic layer was extracted three times with ethyl acetate. After drying with anhydrous magnesium sulfate, the solvents were removed under vacuum. The residue was purified by flash-column chromatography on silica gel to provide the desired ethyl 4-(substituted-amino)-3-nitrobenzoate derivatives. (Tables 1-3)

General Procedure B (Hydrogenolysis)

The ethyl 4-(substituted-amino)-3-nitrobenzoates (130 mg, 0.445 mmol) were dissolved in MeOH (10 mL) and hydrogenated (H$_2$ gas) over 10% Pd(OH)$_2$ on charcoal (90 mg) for 17 hours at room temperature. The solution was filtered through a pad of celite, and volatiles were removed under vacuum. The residue was purified by flash-column chromatography on silica gel to provide the desired Ferrostatin-1 derivatives.

General Procedure C (Reductive Amination Reaction) (Abdel-Magid et al., 1996)

A representative example is the reductive amination of Fer-1 with benzaldehyde.

Method I: the ethyl 3-amino-4-(cyclohexylamino)benzoate (Fer-1) (100 mg, 0.382 mmol, 1 equiv) and benzaldehyde (39 µL, 0.382 mmol, 1 equiv) were heated in DCE for 1 hour at 80° C. in the presence of molecular sieve (4 Å), and then the mixture was cooled down to room temperature before addition of the $NaBH(OAc)_3$ in small portions over 3 hours. The reaction mixture was stirred at room temperature under a nitrogen atmosphere for 17 hours. The reaction mixture was quenched with aqueous saturated $NaHCO_3$, and the product was extracted with EtOAc. The EtOAc extract was dried ($MgSO_4$), and the solvent was evaporated. The residue was purified by flash-column chromatography on silica gel to provide the desired ethyl 3-(benzylamino)-4-(cyclohexylamino)benzoate (SRS11-92, Table 7, entry 1).

Method II: To the ethyl 3-amino-4-(cyclohexylamino) benzoate (Fer-1) (100 mg, 0.382 mmol, 1 equiv) and benzaldehyde (39 µL, 0.382 mmol, 1 equiv) in DCE was added $NaBH(OAc)_3$ (129.5 mg, 0.611 mmol, 1.6 equiv). The reaction mixture was treated in the same way as in method I.

General Procedure D (Alkylation Reaction)

A representative example is the methylation of the SRS8-70 (Table 1, entry 18) using methyl iodide. To the ethyl 3-amino-4-(cyclooctylamino)benzoate (SRS8-70; 58 mg, 0.199 mmol) in DMF (1 mL), MeI (28 µL, 0.398 mmol) and $K_2CO_3$ (82 mg, 0.508 mmol) were added. The mixture was stirred at 40° C. for 6 hours then poured in water. The organic layer was extracted with EtOAc then dried under $MgSO_4$, and the solvent was evaporated. The residue was purified by flash-column chromatography on silica gel to provide the desired ethyl 4-(cyclooctylamino)-3-(dimethylamino)benzoate (SRS9-01).

General Procedure E (Addition of the Fer-1 to an Acylchloride, Alkyl-, Benzyl-chloroformates)

A representative example is the addition of aniline of the Fer-1 to the benzylchloroformate. To the ethyl 3-amino-4-(cyclohexylamino)benzoate (Fer-1; SRS8-28; 22 mg, 0.084 mmol) in THF (1 mL), benzylchloroformate (24 µL, 0.168 mmol) and DIPEA (44 µL, 0.252 mmol) were added at 0° C. The mixture was stirred at room temperature for 17 hours then poured in water. The organic layer was extracted with EtOAc then dried under $MgSO_4$, and the solvent was evaporated. The residue was purified by flash-column chromatography on silica gel to provide the desired ethyl 3-(benzyloxycarbonylamino)-4-(cyclohexylamino)benzoate (SRS11-89, Table 6, entry 1).

TABLE 1

Synthetic scheme of Ferrostatin-1 analogs with various hydrophobic chains.

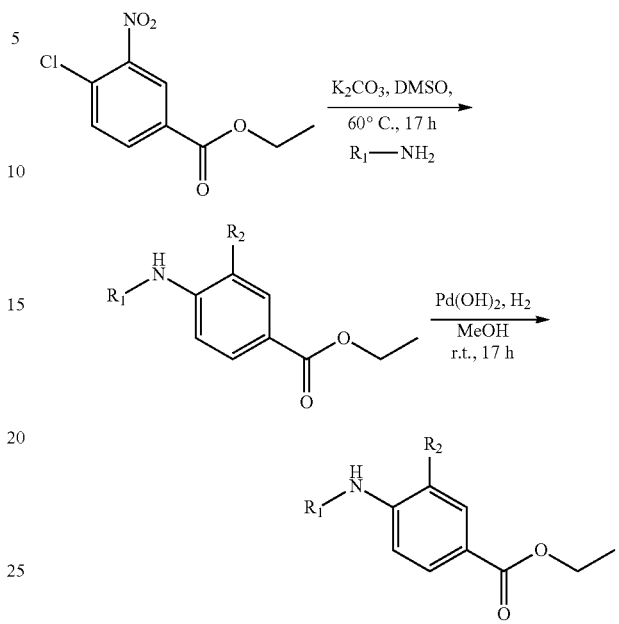

| Entry | R1 | R2 | Name |
|---|---|---|---|
| 1 | cyclopropyl | $NO_2$ | SRS8-66 |
| 2 | cyclopropyl | $NH_2$ | SRS8-72 |
| 3 | cyclobutyl | $NO_2$ | SRS8-65 |
| 4 | cyclobutyl | $NH_2$ | SRS8-71 |
| 5 | cyclopentyl | $NO_2$ | SRS8-67 |
| 6 | cyclopentyl | $NH_2$ | SRS8-73 |
| 7 | cyclohexyl | $NO_2$ | SRS8-24 |
| 8 | cyclohexyl | $NH_2$ | Fer-1 (SRS8-28) |
| 9 | phenyl | $NO_2$ | SRS8-33 |
| 10 | phenyl | $NH_2$ | SRS8-42 |

TABLE 1-continued

Synthetic scheme of Ferrostatin-1 analogs with various hydrophobic chains.

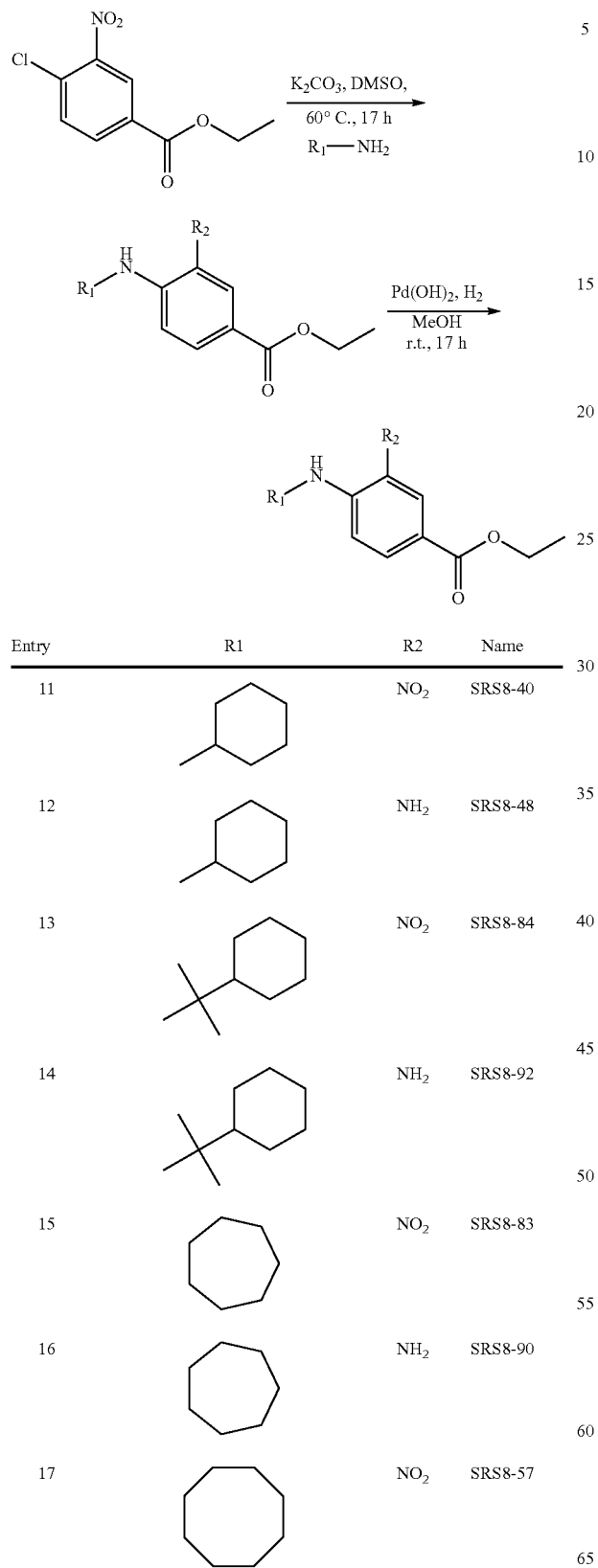

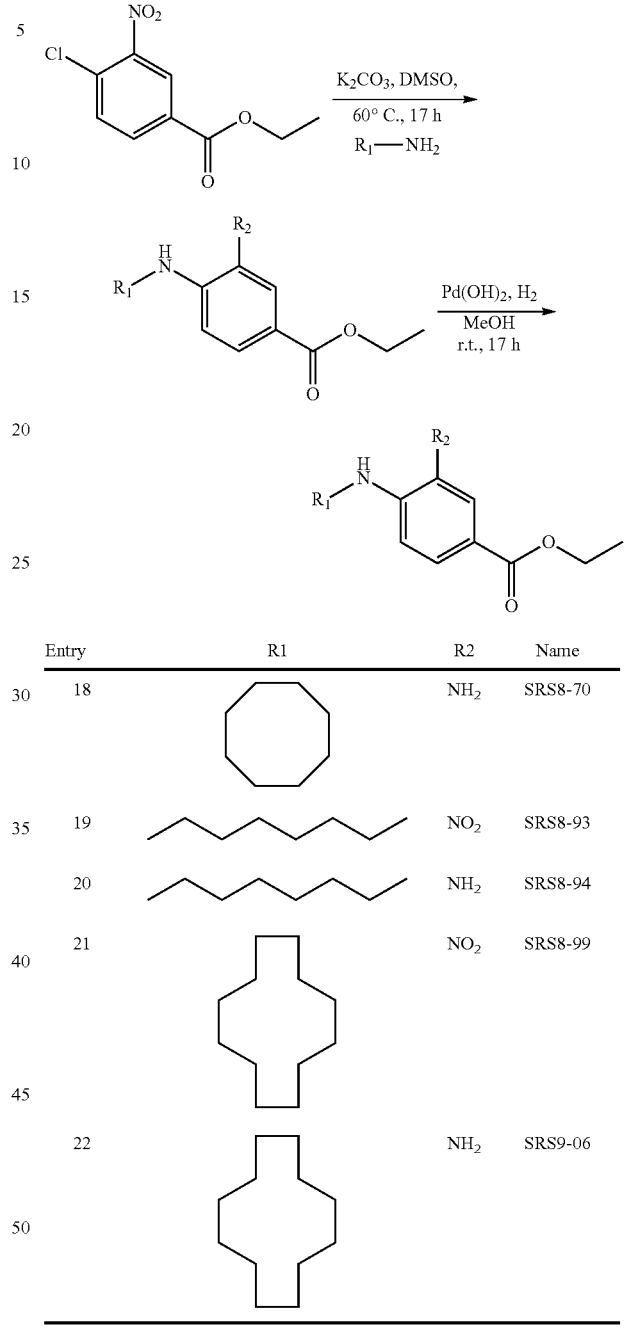

Synthesis of ethyl 4-(cyclopropylamino)-3-nitrobenzoate (SRS8-66, Table 1, Entry 1)

Following the above general procedure A with the ethyl 4-chloro-3-nitrobenzoate (300 mg, 1.306 mmol), $K_2CO_3$ (541.0 mg, 3.919 mmol) and cyclopropylamine (108.6 μL, 1.045 mmol), the crude reaction mixture was purified by column chromatography (hexane:ethylacetate=50:1) to give the ethyl 4-(cyclopropylamino)-3-nitrobenzoate (SRS8-66) (213.0 mg, 0.848 mmol, 65%). $^1$H NMR (CDCl$_3$, 400 MHz, ppm) δ 8.86 (s, 1H), 8.36 (b, NH), 8.10 (d, J=9.2 Hz, 1H), 7.33 (d, J=9.2 Hz, 1H), 4.37 (q, J=7.2 Hz, 2H), 2.64 (m, 1H), 1.37 (t, J=7.2 Hz, 3H), 0.98 (m, 2H), 0.70 (m, 2H); MS (APCI+, M+1) 251.16.

Synthesis of ethyl 3-amino-4-(cyclopropylamino)benzoate (SRS8-72, Table 1, Entry 2)

Following the above general procedure B with the ethyl 4-(cyclopropylamino)-3-nitrobenzoate (SRS8-66) (124 mg, 0.494 mmol), and hydrogen gas ($H_2$ gas) over 10% Pd(OH)$_2$ on charcoal (45 mg), the crude reaction mixture was purified by column chromatography (dichloromethane:methanol=20:1) to provide the desired Ferrostatin-1 analog, the ethyl 3-amino-4-(cyclopropylamino)benzoate, (SRS8-72) (81 mg, 0.370 mmol, 74%). $^1$H NMR (CDCl$_3$, 400 MHz, ppm) δ 7.60 (s, 1H), 7.40 (b, NH), 7.01 (d, J=9.2 Hz, 1H), 6.57 (d, J=9.2 Hz, 1H), 4.37 (q, J=7.2 Hz, 2H), 3.16 (m, 1H), 1.37 (t, J=7.2 Hz, 3H), 1.05 (m, 2H), 0.80 (m, 2H); MS (APCI+, M+1) 221.18.

Synthesis of ethyl 4-(cyclobutylamino)-3-nitrobenzoate (SRS8-65, Table 1, Entry 3)

Following the above general procedure A with the ethyl 4-chloro-3-nitrobenzoate (300 mg, 1.306 mmol), K$_2$CO$_3$ (541.7 mg, 3.915 mmol) and cyclobutylamine (134.3 µL, 1.567 mmol), the crude reaction mixture was purified by column chromatography (hexane:ethylacetate=50:1) to give the ethyl 4-(cyclobutylamino)-3-nitrobenzoate (SRS8-65) (262 mg, 0.99 mmol, 76%). $^1$H NMR (CDCl$_3$, 400 MHz, ppm) δ 8.89 (s, 1H), 8.43 (b, NH), 8.06 (d, J=9.2 Hz, 1H), 6.74 (d, J=9.2 Hz, 1H), 4.34 (q, J=7.2 Hz, 2H), 2.57 (m, 1H), 1.90 (m, 2H), 1.70 (m, 2H), 1.36 (t, J=7.2 Hz, 3H); MS (APCI+, M+1) 265.19.

Synthesis of ethyl 3-amino-4-(cyclobutylamino)benzoate (SRS8-71, Table 1, Entry 4)

Following the above general procedure B with the ethyl 4-(cyclobutylamino)-3-nitrobenzoate (SRS8-65) (175 mg, 0.66 mmol), and hydrogen gas ($H_2$ gas) over 10% Pd(OH)$_2$ on charcoal (66 mg), the crude reaction mixture was purified by column chromatography (dichloromethane:methanol=20:1) to provide the desired Ferrostatin-1 analog, the ethyl 3-amino-4-(cyclobutylamino)benzoate, (SRS8-71) (124.1 mg, 0.528 mmol, 80%). $^1$H NMR (CDCl$_3$, 400 MHz, ppm) δ 7.56 (d, J=8.0 Hz, 1H), 7.40 (s, 1H), 6.48 (d, J=8.0 Hz, 1H), 4.32 (q, J=7.2 Hz, 2H), 3.98 (m, 1H), 2.46 (m, 2H), 1.85 (m, 2H) 1.34 (t, J=7.2 Hz, 3H); MS (APCI+, M+1) 235.20.

Synthesis of ethyl 4-(cyclopentylamino)-3-nitrobenzoate (SRS8-67, Table 1, Entry 5)

Following the above general procedure A with the ethyl 4-chloro-3-nitrobenzoate (300 mg, 1.306 mmol), K$_2$CO$_3$ (541.7 mg, 3.915 mmol) and cyclopentylamine (155.2 µL, 1.567 mmol), the crude reaction mixture was purified by column chromatography (hexane:ethylacetate=10:1) to give the ethyl 4-(cyclopentylamino)-3-nitrobenzoate (SRS8-67) 284 mg, 1.018 mmol, 78%). $^1$H NMR (CDCl$_3$, 400 MHz, ppm) δ 8.87 (s, 1H), 8.40 (b, NH), 8.04 (d, J=9.2 Hz, 1H), 6.90 (d, J=9.2 Hz, 1H), 4.36 (q, J=7.2 Hz, 2H), 4.01 (m, 1H), 2.11 (m, 2H), 1.83-1.58 (m, 6H), 1.37 (t, J=7.2 Hz, 3H); MS (APCI+, M+1) 279.19.

Synthesis of ethyl 3-amino-4-(cyclobutylamino)benzoate (SRS8-73, Table 1, Entry 6)

Following the above general procedure B with the ethyl 4-(cyclopentylamino)-3-nitrobenzoate (SRS8-67) (125 mg, 0.448 mmol), and hydrogen gas ($H_2$ gas) over 10% Pd(OH)$_2$ on charcoal (44.5 mg), the crude reaction mixture was purified by column chromatography (dichloromethane:methanol=20:1) to provide the desired Ferrostatin-1 analog, the ethyl 3-amino-4-(cyclopentylamino)benzoate, (SRS8-73) (94 mg, 0.378 mmol, 85%). $^1$H NMR (CDCl$_3$, 400 MHz, ppm) δ 7.59 (d, J=8.4 Hz, 1H), 7.40 (s, 1H), 6.61 (d, J=8.4 Hz, 1H), 4.32 (q, J=7.2 Hz, 2H), 3.86 (br, 1H), 3.84 (m, 1H), 3.25 (br, 2H), 2.06 (m, 2H), 1.74-1.55 (m, 4H), 1.53 (m, 2H), 1.35 (t, J=7.2 Hz, 3H); MS (APCI+, M+1) 249.17.

Synthesis of ethyl 4-(cyclohexylamino)-3-nitrobenzoate (SRS8-24, Table 1, Entry 7)

Following the above general procedure A with the ethyl 4-chloro-3-nitrobenzoate (200 mg, 0.871 mmol), K$_2$CO$_3$ (240.8 mg, 1.742 mmol) and cyclohexylamine (119.55 µL, 1.045 mmol), the crude reaction mixture was purified by column chromatography (hexane:ethyl acetate=10:1) to provide the desired ethyl 4-(cyclohexylamino)-3-nitrobenzoate compound (SRS8-24) (198 mg, 0.678 mmol, 77%). $^1$H NMR (CDCl$_3$, 400 MHz, ppm) δ 8.87 (s, 1H), 8.42 (b, NH), 8.02 (d, J=8.8 Hz, 1H), 6.87 (d, J=8.8 Hz, 1H), 4.35 (q, J=7.2 Hz, 2H), 3.58 (m, 1H), 2.06 (m, 2H), 1.83 (m, 2H), 1.70-1.40 (s, 6H), 1.37 (t, J=7.2 Hz, 3H); MS (APCI+, M+1) 293.16.

Synthesis of ethyl 3-amino-4-(cyclohexylamino)benzoate (Ferrostatin-1; SRS8-28, Table 1, Entry 8)

Following the above general procedure B with the ethyl 4-(cyclohexylamino)-3-nitrobenzoate (130 mg, 0.445 mmol) and hydrogen gas ($H_2$ gas) over 10% Pd(OH)2 on charcoal (90 mg) for 17 hours at room temperature, the crude reaction mixture was purified by column chromatography (dichloromethane:methanol=20:1) to provide the desired ethyl 3-amino-4-(cyclohexylamino)benzoate (Ferrostatin-1; SRS8-28, Table 1, entry 8); (100 mg, 0.380 mmol, 85%). $^1$H NMR (CDCl$_3$, 400 MHz, ppm) δ 7.59 (d, J=8.4 Hz, 1H), 7.43 (s, 1H), 6.59 (d, J=8.4 Hz, 1H), 5.29 (br, NH2), 4.32 (q, J=7.2 Hz, 2H), 3.35 (b, 1H), 2.10 (m, 2H), 1.79 (m, 2H), 1.68 (m, 1H), 1.43-1.23 (m, 8H); MS (APCI+, M+1) 263.18.

Synthesis of ethyl 3-nitro-4-(phenylamino)benzoate (SRS8-33, Table 1, Entry 9)

Following the above general procedure A with the ethyl 4-chloro-3-nitrobenzoate (300 mg, 1.306 mmol), K$_2$CO$_3$ (541.7 mg, 3.915 mmol) and aniline (120 µL, 1.567 mmol), the crude reaction mixture was purified by column chromatography (hexane:ethylacetate=50:1) to give the ethyl 3-nitro-4-(phenylamino)benzoate (SRS8-33) (168 mg, 0.587 mmol, 45%). $^1$H NMR (CDCl$_3$, 400 MHz, ppm) δ 9.82 (br, 1H), 8.95 (s, 1H), 8.01 (d, J=8.8 Hz, 1H), 8.01-7.20 (m, 5H), 7.19 (d, J=8.8 Hz, 1H), 4.40 (q, J=7.2 Hz, 2H), 1.41 (t, J=7.2 Hz, 3H); MS (APCI+, M+1) 287.22.

Synthesis of ethyl 3-amino-4-(phenylamino)benzoate (SRS8-42, Table 1, Entry 10)

Following the above general procedure B with the ethyl 4-(phenylamino)-3-nitrobenzoate (SRS8-67) (60 mg, 0.209 mmol), and hydrogen gas ($H_2$ gas) over 10% Pd(OH)2 on charcoal (21 mg), the crude reaction mixture was purified by column chromatography (dichloromethane:methanol=40:1) to provide the desired Ferrostatin-1 analog, the ethyl 3-amino-4-(phenylamino)benzoate, (SRS8-42) (33.7 mg, 0.131 mmol, 64%). $^1$H NMR (CDCl$_3$, 400 MHz, ppm) δ 7.49-7.29 (m, 6H), 6.94 (m, 2H), 4.33 (q, J=7.2 Hz, 2H), 1.36 (t, J=7.2 Hz, 3H); MS (APCI+, M+1) 257.18.

Synthesis of ethyl 4-(4-methylcyclohexylamino)-3-nitrobenzoate (SRS8-40, Table 1, Entry 11)

Following the above general procedure A with the ethyl 4-chloro-3-nitrobenzoate (300 mg, 1.306 mmol), K$_2$CO$_3$ (541.7 mg, 3.915 mmol) and 4-methylcyclohexylamine (177.5 μL, 1.567 mmol), the crude reaction mixture was purified by column chromatography (hexane:ethyl acetate=5:1) to provide the desired ethyl 4-(4-methylcyclohexylamino)-3-nitrobenzoate compound (SRS8-40) (354 mg, 1.153 mmol, 88%). $^1$H NMR (CDCl$_3$, 400 MHz, ppm) δ 8.87 (s, 1H), 8.42 (b, NH), 8.02 (d, J=8.8 Hz, 1H), 6.87 (d, J=8.8 Hz, 1H), 4.35 (q, J=7.2 Hz, 2H), 3.58 (m, 1H), 2.06 (m, 2H), 1.83 (m, 2H), 1.70-1.40 (s, 6H), 1.37 (t, J=7.2 Hz, 2H), 0.93 (d, J=6.4 Hz, 3H); MS (APCI+, M+1) 307.16.

Synthesis of ethyl 3-amino-4-(4-methylcyclohexylamino)benzoate (SRS8-48, Table 1, Entry 12)

Following the above general procedure B with the ethyl 4-(4-methylcyclohexylamino)-3-nitrobenzoate (171 mg, 0.559 mmol) and hydrogen gas ($H_2$ gas) over 10% Pd(OH)$_2$ on charcoal (56 mg) for 17 hours at room temperature, the crude reaction mixture was purified by column chromatography (dichloromethane:methanol=20:1) to provide the desired ethyl 3-amino-4-(4-methylcyclohexylamino)benzoate (SRS8-48) (137 mg, 0.495 mmol, 89%). $^1$H NMR (CDCl$_3$, 400 MHz, ppm) δ 7.58 (d, J=8.4 Hz, 1H), 7.40 (s, 1H), 6.58 (d, J=8.4 Hz, 1H), 4.31 (q, J=7.2 Hz, 2H), 3.81 (b, 1H), 3.25 (m, 3H), 2.12 (m, 2H), 1.77 (m, 2H), 1.37-1.33 (m, 1H), 1.25-1.10 (m, 4H), 0.93 (d, J=6.4 Hz, 3H); MS (APCI+, M+1) 277.18.

Synthesis of ethyl 4-(4-tert-butylcyclohexylamino)-3-nitrobenzoate (SRS8-84, Table 1, Entry 13)

Following the above general procedure A with the ethyl 4-chloro-3-nitrobenzoate (300 mg, 1.306 mmol), K$_2$CO$_3$ (541.7 mg, 3.915 mmol) and 4-methylcyclohexylamine (243 mg, 1.567 mmol), the crude reaction mixture was purified by column chromatography (hexane:ethyl acetate 20:1) to provide the desired ethyl 4-(4-tert-butylcyclohexylamino)-3-nitrobenzoate compound (SRS8-84) (350 mg, 1.003 mmol, 77%). $^1$H NMR (CDCl$_3$, 400 MHz, ppm) δ 8.89 (s, 1H), 8.34 (b, NH), 8.03 (d, J=8.8 Hz, 1H), 6.89 (d, J=8.8 Hz, 1H), 4.38 (q, J=7.2 Hz, 2H), 3.46 (m, 1H), 2.22 (m, 2H), 1.92 (m, 2H), 1.42-1.14 (s, 8H), 0.95 (s, 9H); MS (APCI+, M+1) 349.17.

Synthesis of ethyl 3-amino-4-(4-tert-butylcyclohexylamino)benzoate (SRS8-92, Table 1, Entry 14)

Following the above general procedure B with the ethyl 4-(4-tert-butylcyclohexylamino)-3-nitrobenzoate (216 mg, 0.618 mmol) and hydrogen gas ($H_2$ gas) over 10% Pd(OH)$_2$ on charcoal (62 mg) for 17 hours at room temperature, the crude reaction mixture was purified by column chromatography (dichloromethane:methanol=20:1) to provide the desired ethyl 3-amino-4-(4-tert-butylcyclohexylamino)benzoate (SRS8-92) (157 mg, 0.492 mmol, 80%). $^1$H NMR (CDCl$_3$, 400 MHz, ppm) δ 7.57 (d, J=8.4 Hz, 1H), 7.40 (s, 1H), 6.59 (d, J=8.4 Hz, 1H), 4.31 (q, J=7.2 Hz, 2H), 3.86 (br, 1H), 3.23 (m, 3H), 2.18 (m, 2H), 1.85 (m, 2H), 1.35 (t, J=7.2 Hz, 3H), 1.18-1.14 (m, 5H), 0.87 (d, J=6.4 Hz, 3H); MS (APCI+, M+1) 319.40.

Synthesis of ethyl 4-(cycloheptylamino)-3-nitrobenzoate (SRS8-83, Table 1, Entry 15)

Following the above general procedure A with the ethyl 4-chloro-3-nitrobenzoate (300 mg, 1.306 mmol), K$_2$CO$_3$ (541.7 mg, 3.915 mmol) and cycloheptylamine (199.4 μL, 1.045 mmol), the crude reaction mixture was purified by column chromatography (hexane:ethyl acetate=20:1) to provide the desired ethyl 4-(cycloheptylamino)-3-nitrobenzoate compound (SRS8-83) (373 mg, 1.068 mmol, 82%). $^1$H NMR (CDCl$_3$, 400 MHz, ppm) δ 8.87 (s, 1H), 8.42 (br, 1H), 8.03 (d, J=8.4 Hz, 1H), 6.80 (d, J=8.4 Hz, 1H), 4.36 (q, J=7.2 Hz, 2H), 3.76 (m, 1H), 2.05 (m, 2H), 1.97-1.63 (m, 10H), 1.38 (t, J=7.2 Hz, 3H); MS (APCI+, M+1) 349.17.

Synthesis of ethyl 3-amino-4-(cycloheptylamino)benzoate (SRS8-90, Table 1, Entry 16)

Following the above general procedure B with the ethyl 4-(cycloheptylamino)-3-nitrobenzoate (200 mg, 0.65 mmol) and hydrogen gas ($H_2$ gas) over 10% Pd(OH)$_2$ on charcoal (65 mg) for 17 hour at room temperature, the crude reaction mixture was purified by column chromatography (dichloromethane:methanol=20:1) to provide the desired ethyl 3-amino-4-(cycloheptylamino)benzoate (SRS8-90) (155 mg, 0.559 mmol, 86%). $^1$H NMR (CDCl$_3$, 400 MHz, ppm) δ 7.58 (d, J=8.4 Hz, 1H), 7.41 (s, 1H), 6.50 (d, J=8.4 Hz, 1H), 4.31 (q, J=7.2 Hz, 2H), 3.96 (br, 1H), 3.25 (m, 1H), 3.22 (m, 2H), 2.04 (m, 2H), 1.85 (m, 2H), 1.71-1.52 (m, 10H), 1.36 (t, J=7.2 Hz, 3H); MS (APCI+, M+1) 277.33.

Synthesis of ethyl 4-(cyclooctylamino)-3-nitrobenzoate (SRS8-57, Table 1, Entry 17)

Following the above general procedure A with the ethyl 4-chloro-3-nitrobenzoate (300 mg, 1.306 mmol), K$_2$CO$_3$ (541.7 mg, 3.915 mmol) and cyclooctylamine (216.8 μL, 1.567 mmol), the crude reaction mixture was purified by column chromatography (hexane:ethyl acetate=20:1) to provide the desired ethyl 4-(cyclooctylamino)-3-nitrobenzoate compound (SRS8-57) (360 mg, 1.123 mmol, 86%). $^1$H NMR (CDCl$_3$, 400 MHz, ppm) δ 8.88 (s, 1H), 8.45 (br, 1H), 8.03 (d, J=8.4 Hz, 1H), 6.81 (d, J=8.4 Hz, 1H), 4.37 (q, J=7.2

Hz, 2H), 3.78 (m, 1H), 2.05 (m, 2H), 1.97-1.63 (m, 12H), 1.38 (t, J=7.2 Hz, 3H); MS (APCI+, M+1) 291.27. MS (APCI+, M+1) 321.17.

Synthesis of ethyl 3-amino-4-(cyclooctylamino)benzoate (SRS8-70, Table 1, Entry 18)

Following the above general procedure B with the ethyl 4-(cyclooctylamino)-3-nitrobenzoate (194 mg, 0.604 mmol) and hydrogen gas ($H_2$ gas) over 10% Pd(OH)2 on charcoal (60 mg) for 17 hours at room temperature, the crude reaction mixture was purified by column chromatography (dichloromethane:methanol=20:1) to provide the desired ethyl 3-amino-4-(cyclooctylamino)benzoate (SRS8-70) (156 mg, 0.536 mmol, 89%). $^1$H NMR (CDCl$_3$, 400 MHz, ppm) δ 7.60 (d, J=8.4 Hz, 1H), 7.41 (s, 1H), 6.52 (d, J=8.4 Hz, 1H), 4.32 (q, J=7.2 Hz, 2H), 3.91 (br, 1H), 3.56 (m, 1H), 3.22 (br, 2H), 1.92 (m, 2H), 1.76-1.57 (m, 12H), 1.36 (t, J=7.2 Hz, 3H); MS (APCI+, M+1) 291.27.

Synthesis of ethyl 4-(octylamino)-3-nitrobenzoate (SRS8-93, Table 1, Entry 19)

Following the above general procedure A with the ethyl 4-chloro-3-nitrobenzoate (300 mg, 1.306 mmol), K$_2$CO$_3$ (541.7 mg, 3.915 mmol) and octylamine (259 µL, 1.567 mmol), the crude reaction mixture was purified by column chromatography (hexane:ethyl acetate 20:1) to provide the desired ethyl 4-(octylamino)-3-nitrobenzoate compound (SRS8-93) (354 mg, 1.097 mmol, 84%). $^1$H NMR (CDCl$_3$, 400 MHz, ppm) δ 8.85 (s, 1H), 8.33 (br, 1H), 8.03 (d, J=8.4 Hz, 1H), 6.84 (d, J=8.4 Hz, 1H), 4.34 (q, J=7.2 Hz, 2H), 3.34 (t, J=6.8 Hz, 2H), 1.71 (m, 2H), 1.42-1.36 (m, 13H), 0.87 (t, J=6.8 Hz, 3H); MS (APCI+, M+1) 291.27. MS (APCI+, M+1) 323.26.

Synthesis of ethyl 3-amino-4-(octylamino)benzoate (SRS8-94, Table 1, Entry 20)

Following the above general procedure B with the ethyl 4-(octylamino)-3-nitrobenzoate (90 mg, 0.278 mmol) and hydrogen gas ($H_2$ gas) over 10% Pd(OH)$_2$ on charcoal (30 mg) for 17 hours at room temperature, the crude reaction mixture was purified by column chromatography (dichloromethane:methanol=20:1) to provide the desired ethyl 3-amino-4-(octylamino)benzoate (SRS8-94) (73 mg, 0.250 mmol, 90%). $^1$H NMR (CDCl$_3$, 400 MHz, ppm) δ 7.61 (d, J=8.4 Hz, 1H), 7.41 (s, 1H), 6.59 (d, J=8.4 Hz, 1H), 4.32 (q, J=7.2 Hz, 2H), 3.17 (t, J=7.2 Hz, 2H), 1.70 (m, 2H), 1.43-1.30 (m, 13H), 0.90 (t, J=6.8 Hz, 3H); MS (APCI+, M+1) 293.28.

Synthesis of ethyl 4-(cyclododecylamino)-3-nitrobenzoate (SRS8-99, Table 1, Entry 21)

Following the above general procedure A with the ethyl 4-chloro-3-nitrobenzoate (300 mg, 1.306 mmol), K$_2$CO$_3$ (541.0 mg, 3.919 mmol) and cyclododecylamine (479.04 mg, 2.613 mmol), the crude reaction mixture was purified by column chromatography (hexane:ethyl acetate 20:1) to provide the desired ethyl 4-(cyclododecylamino)-3-nitrobenzoate compound (SRS8-99) (177 mg, 0.470 mmol, 36%). $^1$H NMR (CDCl$_3$, 400 MHz, ppm) δ 8.87 (s, 1H), 8.40 (br, 1H), 8.04 (d, J=8.4 Hz, 1H), 6.86 (d, J=8.4 Hz, 1H), 4.34 (q, J=7.2 Hz, 2H), 3.78 (m, 1H), 1.78-1.38 (m, 25H); MS (APCI+, M+1) 377.31.

Synthesis of ethyl 3-amino-4-(cyclododecylamino)benzoate (SRS9-06, Table 1, Entry 21)

Following the above general procedure B with the ethyl 4-(cyclododecylamino)-3-nitrobenzoate (130 mg, 0.445 mmol) and hydrogen gas ($H_2$ gas) over 10% Pd(OH)$_2$ on charcoal (34.4 mg) for 17 hours at room temperature, the crude reaction mixture was purified by column chromatography (dichloromethane:methanol=20:1) to provide the desired ethyl 3-amino-4-(cyclododecylamino)benzoate (SRS9-06) (95.4 mg, 0.275 mmol, 80%). $^1$H NMR (CDCl$_3$, 400 MHz, ppm) δ 7.61 (d, J=8.4 Hz, 1H), 7.42 (s, 1H), 6.60 (d, J=8.4 Hz, 1H), 4.32 (q, J=7.2 Hz, 2H), 3.60 (m, 2H), 3.20 (br, 2H), 1.69-1.27 (m, 26H); MS (APCI+, M+1) 347.34.

TABLE 2

Synthesis of Ferrostatin-1 analogs with various cyclic compounds.

| Entry | R1 | R2 | Name |
|---|---|---|---|
| 1 |  | NO$_2$ | SRS8-34 |
| 2 |  | NH$_2$ | SRS8-41 |
| 3 | 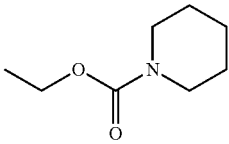 | NO$_2$ | SRS8-45 |

TABLE 2-continued

Synthesis of Ferrostatin-1 analogs with various cyclic compounds.

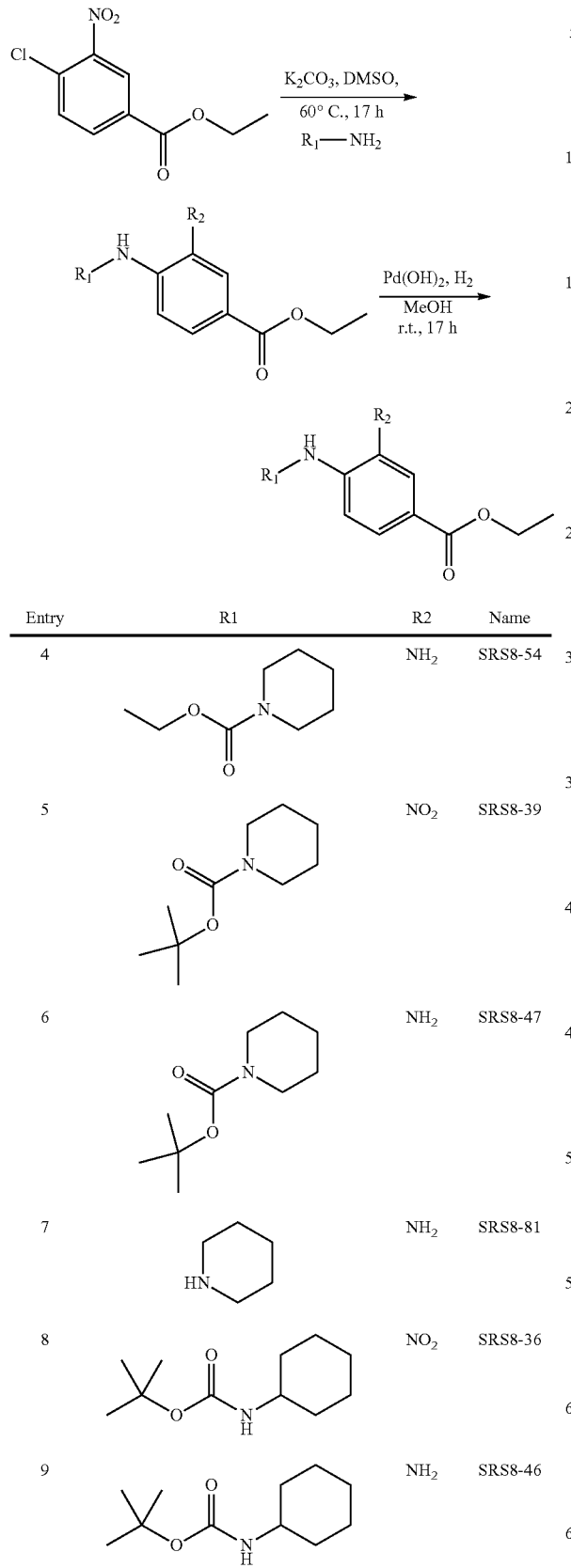
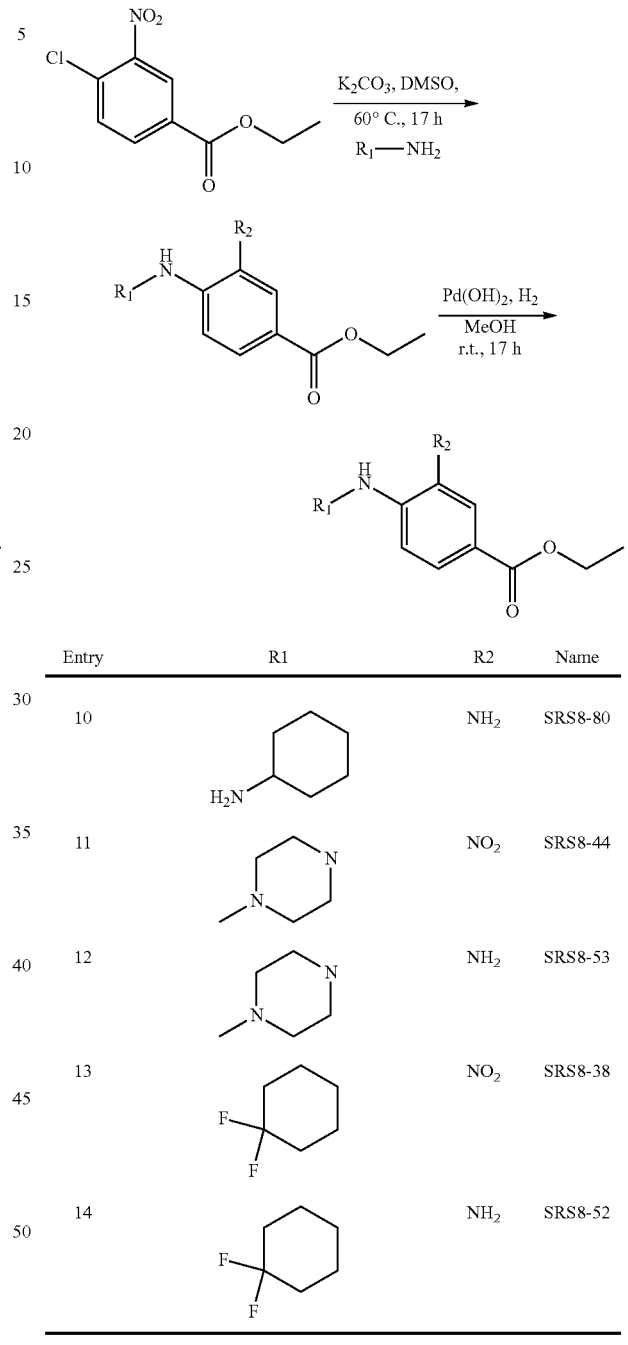

| Entry | R1 | R2 | Name |
|---|---|---|---|
| 4 | ethyl piperidine-1-carboxylate | NH₂ | SRS8-54 |
| 5 | tert-butyl piperidine-1-carboxylate | NO₂ | SRS8-39 |
| 6 | tert-butyl piperidine-1-carboxylate | NH₂ | SRS8-47 |
| 7 | piperidine | NH₂ | SRS8-81 |
| 8 | tert-butyl cyclohexylcarbamate | NO₂ | SRS8-36 |
| 9 | tert-butyl cyclohexylcarbamate | NH₂ | SRS8-46 |
| 10 | cyclohexylamine | NH₂ | SRS8-80 |
| 11 | 1-methylpiperazine | NO₂ | SRS8-44 |
| 12 | 1-methylpiperazine | NH₂ | SRS8-53 |
| 13 | 1,1-difluorocyclohexane | NO₂ | SRS8-38 |
| 14 | 1,1-difluorocyclohexane | NH₂ | SRS8-52 |

Synthesis of ethyl 3-nitro-4-(tetrahydro-2H-pyran-4-ylamino)benzoate (SRS8-34, Table 2, Entry 1)

Following the above general procedure A with the ethyl 4-chloro-3-nitrobenzoate (300 mg, 1.306 mmol), K₂CO₃ (541.0 mg, 3.919 mmol) and tetrahydro-2H-pyran-4-ylamino amine (162.3 µL, 1.567 mmol), the crude reaction mixture was purified by column chromatography (hexane: ethyl acetate 10:1) to provide the desired ethyl 3-nitro-4-(tetrahydro-2H-pyran-4-ylamino)benzoate compound (SRS8-34) (295 mg, 1.003 mmol, 77%). $^1$H NMR (CDCl$_3$, 400 MHz, ppm) δ 8.71 (s, 1H), 8.28 (br, 1H), 7.92 (d, J=8.8

Hz, 1H), 6.83 (d, J=8.8 Hz, 1H), 4.26 (q, J=7.2 Hz, 2H), 3.95 (m, 2H), 3.75 (m, 1H), 3.51 (m, 2H), 2.01 (m, 2H), 1.64 (m, 2H), 1.37 (t, J=7.2 Hz, 3H); MS (APCI+, M+1) 295.24.

Synthesis of ethyl 3-amino-4-(tetrahydro-2H-pyran-4-ylamino)benzoate (SRS8-41, Table 2, Entry 2)

Following the above general procedure B with the ethyl 4-(tetrahydro-2H-pyran-4-ylamino)-3-nitrobenzoate (148 mg, 0.503 mmol) and hydrogen gas (H$_2$ gas) over 10% Pd(OH)$_2$ on charcoal (50 mg) for 17 hours at room temperature, the crude reaction mixture was purified by column chromatography (dichloromethane:methanol=20:1) to provide the desired ethyl 3-amino-4-(tetrahydro-2H-pyran-4-ylamino) benzoate (SRS8-41) (112.8 mg, 0.427 mmol, 85%). $^1$H NMR (CDCl$_3$, 400 MHz, ppm) δ 7.59 (d, J=8.0 Hz, 1H), 7.43 (s, 1H), 6.61 (d, J=8.0 Hz, 1H), 4.32 (q, J=7.2 Hz, 2H), 4.02 (m, 2H), 3.91 (br, 1H), 3.58-3.52 (m, 3H), 3.23 (br, 1H), 1.54 (m, 4H), 1.35 (t, J=7.2 Hz, 3H); MS (APCI+, M+1) 265.25.

Synthesis of ethyl 4-(4-(ethoxycarbonyl)-2-nitrophenylamino)piperidine-1-carboxylate (SRS8-45, Table 2, Entry 3)

Following the above general procedure A with the ethyl 4-chloro-3-nitrobenzoate (300 mg, 1.306 mmol), K$_2$CO$_3$ (541.0 mg, 3.919 mmol) and ethyl 4-aminopiperidine-1-carboxylate (269 μL, 1.568 mmol), the crude reaction mixture was purified by column chromatography (hexane:ethyl acetate 10:1) to provide the desired ethyl 4-(4-(ethoxycarbonyl)-2-nitrophenylamino) piperidine-1-carboxylate (SRS8-45) (452 mg, 1.234 mmol, 79%). $^1$H NMR (CDCl$_3$, 400 MHz, ppm) δ 8.88 (s, 1H), 8.38 (br, 1H), 8.06 (d, J=8.8 Hz, 1H), 6.89 (d, J=8.8 Hz, 1H), 4.37 (q, J=7.2 Hz, 2H), 4.18-4.13 (m, 4H), 3.76 (m, 1H), 3.11 (t, J=12.0 Hz, 2H), 2.08 (m, 2H), 1.64 (m, 2H), 1.37 (t, J=7.2 Hz, 3H), 1.28 (t, J=7.6 Hz, 3H); MS (APCI+, M+1) 366.29.

Synthesis of ethyl 4-(2-amino-4-(ethoxycarbonyl) phenylamino)piperidine-1-carboxylate (SRS8-54, Table 2, Entry 4)

Following the above general procedure B with the ethyl 4-(4-(ethoxycarbonyl)-2-nitrophenylamino)piperidine-1-carboxylate (SRS8-45) (307 mg, 0.838 mmol) and hydrogen gas (H$_2$ gas) over 10% Pd(OH)$_2$ on charcoal (84 mg) for 17 hours at room temperature, the crude reaction mixture was purified by column chromatography (dichloromethane:methanol=20:1) to provide the desired ethyl 3-amino-4-(4-methylpiperazin-1-ylamino) benzoate (SRS8-54) (140 mg, 0.416 mmol, 50%). $^1$H NMR (CDCl$_3$, 400 MHz, ppm) δ δ 7.57 (d, J=8.4 Hz, 1H), 7.41 (s, 1H), 6.58 (d, J=8.4 Hz, 1H), 4.31 (q, J=7.2 Hz, 2H), 4.18 (q, J=7.6 Hz, 2H), 4.05 (m, 2H), 3.50 (m, 1H), 3.26 (m, 2H), 2.96 (m, 2H), 2.05 (m, 2H), 1.35 (t, J=7.2 Hz, 3H), 1.28 (t, J=7.6 Hz, 3H); MS (APCI+, M+1) 336.20.

Synthesis of tert-butyl 4-(4-(ethoxycarbonyl)-2-nitrophenylamino)-piperidine-1-carboxylate (SRS8-39, Table 2, Entry 5)

Following the above general procedure A with the ethyl 4-chloro-3-nitrobenzoate (300 mg, 1.306 mmol), K$_2$CO$_3$ (541.0 mg, 3.919 mmol) and tert-butyl 4-aminopiperidine-1-carboxylate (314 mg, 1.568 mmol), the crude reaction mixture was purified by column chromatography (hexane: ethyl acetate 10:1) to provide the desired tert-butyl 4-(4-(ethoxycarbonyl)-2-nitrophenylamino)-piperidine-1-carboxylate (SRS8-39) (434 mg, 1.101 mmol, 84%). $^1$H NMR (CDCl$_3$, 400 MHz, ppm) δ 8.87 (s, 1H), 8.38 (br, 1H), 8.05 (d, J=8.8 Hz, 1H), 6.90 (d, J=8.8 Hz, 1H), 4.37 (q, J=7.2 Hz, 2H), 4.10 (m, 2H), 3.75 (m, 1H), 3.07 (m, 2H), 2.08 (m, 2H), 1.60-1.39 (m, 11H), 1.37 (t, J=7.2 Hz, 3H); MS (APCI+, M+1, M-Boc) 394.20; 294.26.

Synthesis of tert-butyl 4-(2-amino-4-(ethoxycarbonyl)phenylamino)-piperidine-1-carboxylate (SRS8-47, Table 2, Entry 6)

Following the above general procedure B with the tert-butyl 4-(4-(ethoxycarbonyl)-2-nitrophenylamino)-piperidine-1-carboxylate (SRS8-39) (340 mg, 0.863 mmol) and hydrogen gas (H$_2$ gas) over 10% Pd(OH)$_2$ on charcoal (86 mg) for 17 hours at room temperature, the crude reaction mixture was purified by column chromatography (dichloromethane:methanol=20:1) to provide the desired tert-butyl 4-(2-amino-4-(ethoxycarbonyl)phenylamino)piperidine-1-carboxylate (SRS8-47) (204 mg, 0.561 mmol, 65%). $^1$H NMR (CDCl$_3$, 400 MHz, ppm) δ 7.58 (d, J=8.4 Hz, 1H), 7.42 (s, 1H), 6.59 (d, J=8.4 Hz, 1H), 4.31 (q, J=7.2 Hz, 2H), 4.05 (m, 2H), 3.50 (m, 1H), 3.26 (m, 2H), 2.96 (m, 2H), 2.05 (m, 2H), 1.46 (s, 9H), 1.35 (t, J=7.2 Hz, 3H); MS (APCI+, M+1) 364.35.

Synthesis of ethyl 3-amino-4-(piperidin-4-ylamino)benzoate (SRS8-81, Table 2, Entry 7)

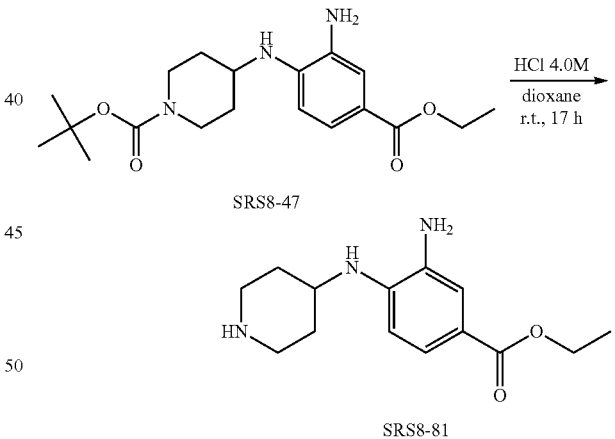

Scheme 1. Synthesis of Ferrostatin analog SRS8-81.

To the tert-butyl 4-(2-amino-4-(ethoxycarbonyl)phenylamino)piperidine-1-carboxylate (SRS8-47) (42 mg, 0.115 mmol) in dioxane (1 mL) was added HCl 4.0M in dioxane (0.5 mL) and stirred for 17 hours at room temperature. The solvent was removed under vacuum and the residue was poured in 10% Na$_2$CO$_3$. The organic layer was extracted with ethylacetate then dried over MgSO$_4$ before the solvent was removed under vacuum. The crude reaction mixture was purified by column chromatography (dichloromethane:methanol=20:1) to provide the desired ethyl 3-amino-4-(piperidin-4-ylamino)benzoate (SRS8-81) (26 mg, 0.099 mmol, 86%). $^1$H NMR (CDCl$_3$, 400 MHz, ppm) δ 7.57 (d, J=8.4 Hz, 1H), 7.43 (s, 1H), 6.60 (d, J=8.4 Hz, 1H), 4.33 (q, J=7.2 Hz, 2H), 3.70 (m, 2H), 3.48 (m, 1H), 3.19 (m, 2H), 2.99 (br, 2H), 2.78 (m, 2H), 2.12 (m, 2H), 1.35 (t, J=7.2 Hz, 3H); MS (APCI+, M+1) 364.35.

Synthesis of ethyl 4-(4-(tert-butoxycarbonyl)cyclohexylamino)-3-nitrobenzoate (SRS8-36, Table 2, Entry 8)

Following the above general procedure A with the ethyl 4-chloro-3-nitrobenzoate (300 mg, 1.306 mmol), $K_2CO_3$ (541.0 mg, 3.919 mmol) and tert-butyl 4-aminocyclohexylcarbamate (336 mg, 1.568 mmol), the crude reaction mixture was purified by column chromatography (hexane:ethyl acetate=5:1) to provide the desired ethyl 4-(4-(tert-butoxycarbonyl)cyclohexylamino)-3-nitrobenzoate (SRS8-36) (403 mg, 0.990 mmol, 76%). $^1$H NMR (CDCl$_3$, 400 MHz, ppm) δ 8.89 (s, 1H), 8.33 (br, 1H), 8.05 (d, J=8.8 Hz, 1H), 6.87 (d, J=8.8 Hz, 1H), 4.46 (br, 1H), 4.37 (q, J=7.2 Hz, 2H), 3.54 (m, 2H), 2.19 (m, 4H), 1.68-1.32 (m, 16H); MS (APCI+, M−100) 308.29.

Synthesis of ethyl 3-amino-4-(4-(tert-butoxycarbonyl)cyclohexylamino) benzoate (SRS8-46, Table 2, Entry 9)

Following the above general procedure B with the ethyl 4-(4-(tert-butoxycarbonyl)cyclohexylamino)-3-nitrobenzoate (SRS8-36) (320 mg, 0.786 mmol) and hydrogen gas (H$_2$ gas) over 10% Pd(OH)$_2$ on charcoal (78 mg) for 17 hours at room temperature, the crude reaction mixture was purified by column chromatography (dichloromethane:methanol=20:1) to provide the desired ethyl 3-amino-4-(4-(tert-butoxycarbonyl)cyclohexylamino) benzoate (SRS8-46) (240 mg, 0.636 mmol, 81%). $^1$H NMR (CDCl$_3$, 400 MHz, ppm) δ 7.58 (d, J=8.4 Hz, 1H), 7.41 (s, 1H), 6.56 (d, J=8.4 Hz, 1H), 4.46 (br, 1H), 4.30 (q, J=7.2 Hz, 2H), 3.90 (br, 1H), 3.48 (m, 1H), 3.28-3.20 (m, 3H), 2.17-2.04 (m, 4H), 1.45 (s, 9H), 1.37-1.24 (m, 7H); MS (APCI+, M+1) 378.36.

Synthesis of ethyl 3-amino-4-(4-aminocyclohexylamino)benzoate (SRS8-80, Table 2, Entry 10)

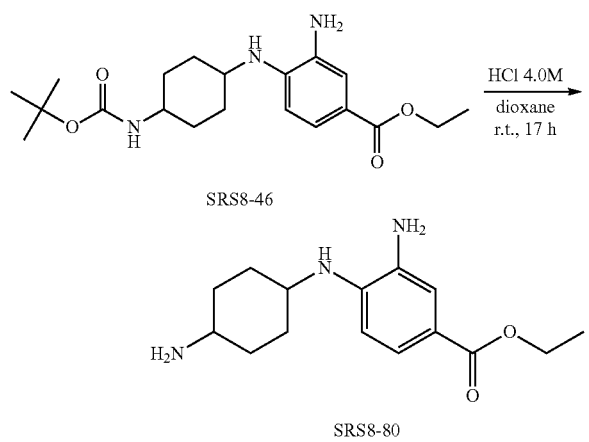

Scheme 2. Synthesis of Ferrostatin analog SRS8-80.

To the ethyl 3-amino-4-(4-(tert-butoxycarbonyl)cyclohexylamino) benzoate (SRS8-46) (35 mg, 0.093 mmol) in dioxane (1 mL) was added HCl 4.0M in dioxane (0.5 mL) and stirred for 17 hours at room temperature. The solvent was removed under vacuum and the residue was poured in 10% Na$_2$CO$_3$. The organic layer was extracted with ethylacetate then dried over MgSO$_4$ before the solvent was removed under vacuum. The crude reaction mixture was purified by column chromatography (dichloromethane:methanol=20:1) to provide the desired ethyl 3-amino-4-(4-aminocyclohexylamino)benzoate (SRS8-80) (22 mg, 0.079 mmol, 85%). $^1$H NMR (CDCl$_3$, 400 MHz, ppm) δ 7.59 (d, J=8.4 Hz, 1H), 7.42 (s, 1H), 6.59 (d, J=8.4 Hz, 1H), 4.32 (q, J=7.2 Hz, 2H), 3.71 (m, 2H), 3.31 (m, 2H), 2.83 (br, 2H), 2.18 (m, 4H), 1.99 (m, 4H), 1.35 (t, J=7.2 Hz, 3H); MS (APCI+, M+1) 378.20.

Synthesis of ethyl 4-(4-methylpiperazin-1-ylamino)-3-nitrobenzoate (SRS8-44, Table 2, Entry 11)

Following the above general procedure A with the ethyl 4-chloro-3-nitrobenzoate (300 mg, 1.306 mmol), $K_2CO_3$ (541.0 mg, 3.919 mmol) and 4-methylpiperazin-1-ylamine (188.7 μL, 1.568 mmol), the crude reaction mixture was purified by column chromatography (hexane:ethyl acetate 5:1) to provide the desired ethyl 4-(4-methylpiperazin-1-ylamino)-3-nitrobenzoate compound (SRS8-44) (266 mg, 0.862 mmol, 66%). $^1$H NMR (CDCl$_3$, 400 MHz, ppm) δ 8.60 (s, 1H), 8.28 (br, 1H), 7.92 (d, J=8.8 Hz, 1H), 6.98 (d, J=8.8 Hz, 1H), 4.23 (q, J=7.2 Hz, 2H), 2.95 (m, 4H), 2.75 (m, 4H), 2.31 (s, 3H), 1.27 (t, J=7.2 Hz, 3H); MS (APCI+, M+1) 309.26.

Synthesis of ethyl 3-amino-4-(4-methylpiperazin-1-ylamino)benzoate (SRS8-53, Table 2, Entry 12)

Following the above general procedure B with the ethyl 4-(4-methylpiperazin-1-ylamino)-3-nitrobenzoate (SRS8-44) (150 mg, 0.485 mmol) and hydrogen gas (H$_2$ gas) over 10% Pd(OH)$_2$ on charcoal (48.5 mg) for 17 hours at room temperature, the crude reaction mixture was purified by column chromatography (dichloromethane:methanol=20:1) to provide the desired ethyl 3-amino-4-(4-methylpiperazin-1-ylamino) benzoate (SRS8-53) (95 mg, 0.340 mmol, 70%). $^1$H NMR (CDCl$_3$, 400 MHz, ppm) δ 7.49 (d, J=8.0 Hz, 1H), 7.38 (s, 1H), 6.97 (d, J=8.0 Hz, 1H), 4.58 (br, 1H), 4.32 (q, J=7.2 Hz, 2H), 3.71 (br, 2H), 3.00-2.60 (m, 4H), 2.60-2.40 (m, 4H), 2.32 (s, 3H), 1.36 (t, J=7.2 Hz, 3H); MS (APCI+, M+1) 279.20.

Synthesis of ethyl 4-(4,4-difluorocyclohexylamino)-3-nitrobenzoate (SRS8-38, Table 2, Entry 13)

Following the above general procedure A with the ethyl 4-chloro-3-nitrobenzoate (300 mg, 1.306 mmol), $K_2CO_3$ (541.0 mg, 3.919 mmol) and 4,4-difluorocyclohexanamine hydrochloride (269 mg, 1.568 mmol), the crude reaction mixture was purified by column chromatography (hexane:ethyl acetate 10:1) to provide the desired ethyl 4-(4,4-difluorocyclohexylamino)-3-nitrobenzoate compound (SRS8-38) (316 mg, 0.960 mmol, 56%). $^1$H NMR (CDCl$_3$, 400 MHz, ppm) δ 8.88 (s, 1H), 8.40 (br, 1H), 8.06 (d, J=8.8 Hz, 1H), 6.88 (d, J=8.8 Hz, 1H), 4.36 (q, J=7.2 Hz, 2H), 3.74

(m, 1H), 2.15 (m, 4H), 2.04-1.63 (m, 4H), 1.37 (t, J=7.2 Hz, 3H); MS (APCI+, M+1) 329.26.

Synthesis of ethyl 3-amino-4-(4,4-difluorocyclohexylamino)benzoate (SRS8-52, Table 2, Entry 14)

Following the above general procedure B with the ethyl 4-(4,4-difluorocyclohexylamino)-3-nitrobenzoate (SRS8-38) (185 mg, 0.563 mmol) and hydrogen gas ($H_2$ gas) over 10% Pd(OH)$_2$ on charcoal (56 mg) for 17 hours at room temperature, the crude reaction mixture was purified by column chromatography (dichloromethane:methanol=20:1) to provide the desired ethyl 3-amino-4-(4,4-difluorocyclo-hexylamino)benzoate (SRS8-52) (147 mg, 0.491 mmol, 87%). $^1$H NMR (CDCl$_3$, 400 MHz, ppm) δ 7.62 (d, J=8.0 Hz, 1H), 7.46 (s, 1H), 6.62 (d, J=8.0 Hz, 1H), 4.34 (q, J=7.2 Hz, 2H), 3.94 (br, 1H), 3.52 (m, 1H), 3.28 (br, 1H), 2.16 (m, 4H), 1.92 (m, 2H), 1.28 (m, 2H), 1.37 (t, J=7.2 Hz, 3H); MS (APCI+, M+1) 299.26.

Synthesis of ethyl 3-amino-4-chlorobenzoate (SRS8-62, Entry 3, Table 3)

Following the above general procedure B with ethyl 4-chloro-3-nitrobenzoate (200 mg, 0.871 mmol) and hydrogen gas ($H_2$ gas) over 10% Pd(OH)2 on charcoal (87 mg) for 17 hours at room temperature, the crude reaction mixture was purified by column chromatography (dichloromethane:methanol=20:1) to provide the desired ethyl 3-amino-4-chlorobenzoate (SRS8-62) (164 mg, 0.824 mmol, 95%). $^1$H NMR (CDCl$_3$, 400 MHz, ppm) δ 7.46 (s, 1H), 7.36 (d, J=8.0 Hz, 1H), 7.29 (d, J=8.0 Hz, 1H), 4.36 (q, J=7.2 Hz, 2H), 4.20 (br, 2H), 1.38 (t, J=7.2 Hz, 3H); MS (APCI+, M+1) 200.10; 202.26.

TABLE 3

Synthesis of Ferrostatin analogs.

| Entry | R$_1$ | R$_2$ | Name |
|---|---|---|---|
| 1 | cyclohexyl | NO$_2$ | SRS8-24[1] |
| 2 | H | NH$_2$ | CA[2] |
| 3 | Cl | NH$_2$ | SRS8-62[3] |

[1] Synthesis of SRS8-24 is shown in table 1, entry 4.
[2] CA: Commercially availabe compound.
[3] The synthesis of SRSs8-62 is shown in Scheme 3.

Scheme 3: Syntehsis of Ferrostatin-1 analog SRS8-62.

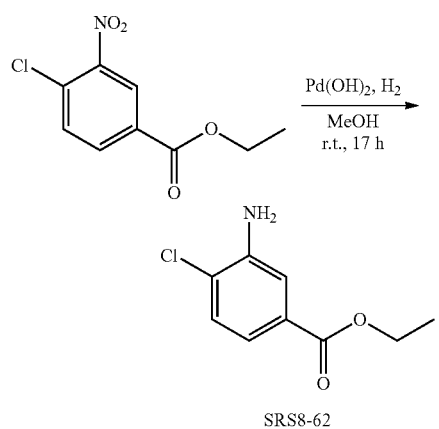

TABLE 4

Synthesis of Ferrostatin-1 analogs with various esters and amides

| Entry | R$_1$ | R$_2$ | R$_3$ | Name |
|---|---|---|---|---|
| 1 | cyclohexyl | NO$_2$ | H | SRS8-69 |
| 2 | cyclohexyl | NH$_2$ | H | SRS8-75 |
| 3 | cyclohexyl | NO$_2$ | CO$_2$CH$_3$ | SRS8-50 |
| 4 | cyclohexyl | NH$_2$ | CO$_2$CH$_3$ | SRS8-61 |
| 5 | cyclohexyl | NO$_2$ | CO$_2$CH$_2$CH$_2$OCH$_2$CH$_2$NHBoc | SRS8-25 |
| 6 | cyclohexyl | NH$_2$ | CO$_2$CH$_2$CH$_2$OCH$_2$CH$_2$NHBoc | SRS8-37 |

TABLE 4-continued

Synthesis of Ferrostatin-1 analogs with various esters and amides

| Entry | R₁ | R₂ | R₃ | Name |
|---|---|---|---|---|
| 7 | 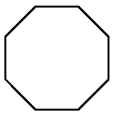 | NH₂ | CO₂CH₂CH₂OCH₂CH₂NH₂ | SRS8-43 |
| 8 | 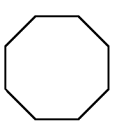 | NO₂ | CO₂C(CH₃)₃ | SRS8-86 |
| 9 | 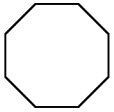 | NH₂ | CO₂C(CH₃)₃ | SRS8-87 |
| 10 | 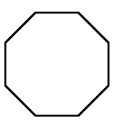 | NO₂ | CONC₂H₅ | SRS9-03 |
| 11 | 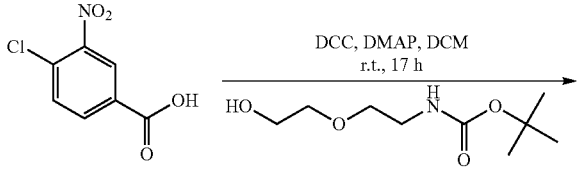 | NH₂ | CONC₂H₅ | SRS9-11 |

Synthesis of N-cyclohexyl-2-nitrobenzenamine (SRS8-69, Table 4, Entry 1)

Following the above general procedure A with the 1-chloro-2-nitrobenzene (200 mg, 1.419 mmol), $K_2CO_3$ (586 mg, 4.252 mmol) and cyclohexanamine (194.5 µL, 1.7 mmol), the crude reaction mixture was purified by column chromatography (hexane:ethyl acetate 10:1) to provide the desired N-cyclohexyl-2-nitrobenzenamine compound (SRS8-69) (279 mg, 1.262 mmol, 89%). $^1$H NMR (CDCl$_3$, 400 MHz, ppm) δ 8.19 (dd, J=1.6 Hz; 8.8 Hz, 1H), 7.42 (t, J=8.8 Hz, 1H), 6.88 (dd, J=1.6 Hz; 8.8 Hz, 1H), 6.60 (t, J=8.8 Hz, 1H), 3.54 (m, 1H), 2.09 (m, 2H), 1.82 (m, 2H), 1.70-1.31 (m, 5H); MS (APCI+, M+1) 221.17.

Synthesis of N1-cyclohexylbenzene-1,2-diamine (SRS8-75, Table 4, Entry 2)

Following the above general procedure B with the N-cyclohexyl-2-nitrobenzenamine (SRS8-69) (245 mg, 1.11 mmol) and hydrogen gas (H$_2$ gas) over 10% Pd(OH)$_2$ on charcoal (111 mg) for 17 hours at room temperature, the crude reaction mixture was purified by column chromatography (dichloromethane:methanol=20:1) to provide the desired N1-cyclohexylbenzene-1,2-diamine (SRS8-75) (182 mg, 0.953 mmol, 86%). $^1$H NMR (CDCl$_3$, 400 MHz, ppm) δ 6.87-6.68 (m, 4H), 3.32 (br, 3H), 2.13 (m, 1H), 1.84-1.70 (m, 3H), 1.45-1.24 (m, 6H); MS (APCI+, M+1) 191.16.

Synthesis of methyl 4-(cyclohexylamino)-3-nitrobenzoate (SRS8-50, Table 4, Entry 3)

Following the above general procedure A with the methyl 4-chloro-3-nitrobenzoate (300 mg, 1.391 mmol), $K_2CO_3$ (541.0 mg, 3.919 mmol) and cyclohexanamine (191 µL, 1.669 mmol), the crude reaction mixture was purified by column chromatography (hexane:ethyl acetate 20:1) to provide the desired methyl 4-(cyclohexylamino)-3-nitrobenzoate compound (SRS8-50) (345 mg, 1.237 mmol, 89%). $^1$H NMR (CDCl$_3$, 400 MHz, ppm) δ 8.88 (s, 1H), 8.43 (br, 1H), 8.01 (d, J=8.8 Hz, 1H), 6.69 (d, J=1.6 Hz; 8.8 Hz, 1H), 3.90 (s, 3H), 3.59 (m, 1H), 2.09 (m, 2H), 1.71 (m, 2H), 1.48-1.27 (m, 6H); MS (APCI+, M+1) 279.24.

Synthesis of methyl 3-amino-4-(cyclohexylamino)benzoate (SRS8-61, Table 4, Entry 4)

Following the above general procedure B with the methyl 4-(cyclohexylamino)-3-nitrobenzoate (SRS8-50) (335 mg, 1.206 mmol) and hydrogen gas (H$_2$ gas) over 10% Pd(OH)2 on charcoal (120 mg) for 17 hours at room temperature, the crude reaction mixture was purified by column chromatography (dichloromethane:methanol=20:1) to provide the desired methyl 3-amino-4-(cyclohexylamino)benzoate (SRS8-61) (269 mg, 1.085 mmol, 90%). $^1$H NMR (CDCl$_3$, 400 MHz, ppm) δ 7.58 (d, J=8.8 Hz, 1H), 7.42 (br, 1H), 6.60 (d, J=8.8 Hz, 1H), 3.85 (s, 3H), 3.83 (m, 1H), 3.36 (m, 2H), 2.18 (m, 2H), 1.80 (m, 2H), 1.48-1.20 (m, 6H); MS (APCI+, M+1) 249.22.

Synthesis of 2-(2-(tert-butoxycarbonyl)ethoxy)ethyl 4-chloro-3-nitrobenzoate (SRS8-19, Structure Shown Below)

Scheme 4. Synthesis of Ferrostatin precursor analog SRS8-19.

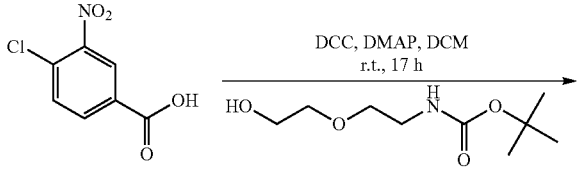

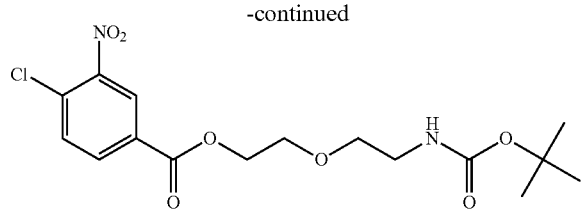

SRS8-19

To the 4-chloro-3-nitrobenzoic acid (500 mg, 2.487 mmol) in dichloromethane was added tert-butyl 2-(2-hydroxyethoxy)ethylcarbamate (459 mg, 2.238 mmol) and dimethylaminopyridine (DMAP) (61 mg, 0.497 mmol). At 0° C. the dicyclohexylcarbodiimide (DCC) (615.9 mg, 2.98 mmol). was added and the mixture was stirred for 17 hours. The precipitate was filtered out and the organic solvent was removed. The residue was purified by column chromatography (hexane:ethyl acetate 5:1) to provide the desired 2-(2-(tert-butoxycarbonyl)ethoxy)ethyl 4-chloro-3-nitrobenzoate SRS8-19 (685 mg, 1.765 mmol, 71%). $^1$H NMR (CDCl$_3$, 400 MHz, ppm) δ 8.40 (s, 1H), 8.09 (d, J=8.4 Hz, 1H), 7.57 (d, J=8.4 Hz, 1H), 4.98 (br, 1H), 4.43 (t, J=4.8 Hz, 2H), 3.73 (t, J=4.8 Hz, 2H), 3.50 (t, J=4.8 Hz, 1H), 3.24 (t, J=4.8 Hz, 1H), 1.32 (s, 9H); MS (APCI+, M+1; M+1-100) 389.19; 289.18

Synthesis of 2-(2-(tert-butoxycarbonyl)ethoxy)ethyl 4-(cyclohexylamino)-3-nitrobenzoate (SRS8-25, Table 4, Entry 5)

Following the above general procedure A with the 2-(2-(tert-butoxycarbonyl)ethoxy)ethyl 4-chloro-3-nitrobenzoate (SRS8-19) (300 mg, 0.773 mmol), K$_2$CO$_3$ (320 mg, 2.319 mmol) and cyclohexanamine (106.2 □L, 0.927 mmol), the crude reaction mixture was purified by column chromatography (hexane ethyl acetate 10:1) to provide the desired 2-(2-(tert-butoxycarbonyl)ethoxy)ethyl 4-(cyclohexylamino)-3-nitrobenzoate (SRS8-25) (247 mg, 0.546 mmol, 71%). $^1$H NMR (CDCl$_3$, 400 MHz, ppm) δ 8.88 (s, 1H), 8.40 (br, 1H), 8.03 (d, J=8.8 Hz, 1H), 6.89 (d, J=8.8 Hz, 1H), 4.88 (br, 1H), 4.45 (t, J=4.8 Hz, 2H), 3.79 (t, J=4.8 Hz, 2H), 3.60 (t, J=4.8 Hz, 1H), 3.57 (m, 1H), 3.34 (t, J=4.8 Hz, 1H), 2.08 (m, 2H), 1.71 (m, 2H), 1.44-1.27 (m, 15H); MS (APCI+, M−100) 352.19.

Synthesis of 2-(2-(tert-butoxycarbonyl) ethoxy)ethyl 3-amino-4-(cyclohexylamino)benzoate (SRS8-37, Table 4, Entry 6)

Following the above general procedure B with the 2-(2-(tert-butoxycarbonyl)ethoxy)ethyl 4-(cyclohexylamino)-3-nitrobenzoate (SRS8-25) (157 mg, 0.347 mmol) and hydrogen gas (H$_2$ gas) over 10% Pd(OH)2 on charcoal (35 mg) for 17 hours at room temperature, the crude reaction mixture was purified by column chromatography (dichloromethane:methanol=20:1) to provide the desired 2-(2-(tert-butoxycarbonyl) ethoxy)ethyl 3-amino-4-(cyclohexylamino)benzoate (SRS8-37) (143 mg, 0.338 mmol, 98%). $^1$H NMR (CDCl$_3$, 400 MHz, ppm) δ 7.59 (d, J=8.8 Hz, 1H), 7.42 (br, 1H), 6.58 (d, J=8.8 Hz, 1H), 4.97 (br, 1H), 4.39 (t, J=4.8 Hz, 2H), 3.76 (t, J=4.8 Hz, 2H), 3.59 (t, J=4.8 Hz, 1H), 3.30 (t, J=4.8 Hz, 1H), 3.28 (bs, 2H), 2.06 (m, 2H), 1.79 (m, 2H), 1.43-1.21 (m, 15H); MS (APCI+, M+1, M+1-Boc) 422.39; 422.32.

Synthesis of 2-(2-aminoethoxy)ethyl 3-amino-4-(cyclohexylamino)benzoate SRS8-43 (Table 4, Entry 7)

Scheme 5. Synthesis of Ferrostatin analog SRS8-43.

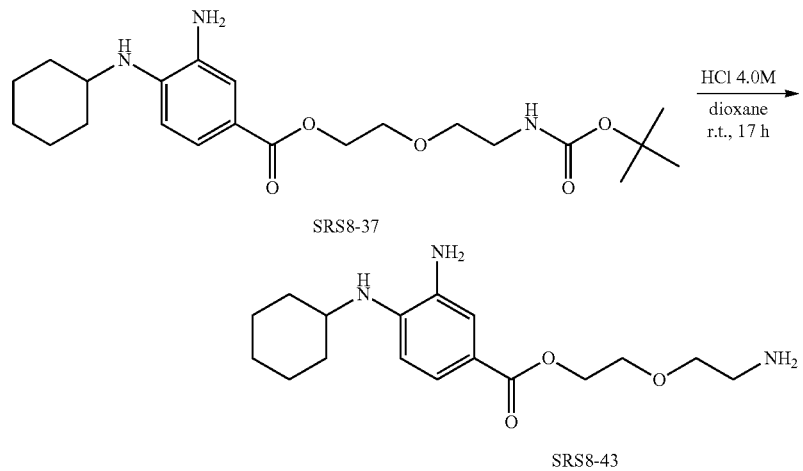

To the 2-(2-(tert-butoxycarbonyl)ethoxy)ethyl 3-amino-4-(cyclohexylamino)benzoate (SRS8-37) (93 mg, 0.22 mmol) in dioxane (2 mL) was added HCl 4.0 M in dioxane (1.1 mL) and stirred for 17 hours at room temperature. The solvent was removed under vacuum and the residue was poured in 10% Na$_2$CO$_3$. The organic layer was extracted with ethylacetate then dried over MgSO$_4$ before the solvent was removed under vacuum. The crude reaction mixture was purified by column chromatography (dichloromethane:methanol=20:1) to provide the desired 2-(2-aminoethoxy)ethyl 3-amino-4-(cyclohexylamino)benzoate (SRS8-43) (63 mg, 0.195 mmol, 89%). $^1$H NMR (CDCl$_3$, 400 MHz, ppm) δ 7.45 (d, J=8.4 Hz, 1H), 7.38 (s, 1H), 6.68 (d, J=8.4 Hz, 1H), 4.45 (t, J=4.8 Hz, 2H), 3.82 (t, J=4.8 Hz, 2H), 3.79 (br, 1H), 3.60 (t, J=4.8 Hz, 1H), 3.29 (m, 1H), 3.02 (m, 2H), 2.92 (br, 2H), 2.08 (m, 2H), 1.80 (m, 2H), 1.67-1.26 (m, 6H).

Synthesis of tert-butyl 4-(cyclooctylamino)-3-nitrobenzoate (SRS8-86, Table 4, Entry 8)

Following the above general procedure A with the tert-butyl 4-chloro-3-nitrobenzoate (400 mg, 1.556 mmol), K$_2$CO$_3$ (645 mg, 4.669 mmol) and cyclooctylamine (258.2 μL, 1.045 mmol), the crude reaction mixture was purified by column chromatography (hexane:ethyl acetate 10:1) to provide the desired tert-butyl 4-(cyclooctylamino)-3-nitrobenzoate compound (SRS8-86) (434 mg, 1.244 mmol, 80%). $^1$H NMR (CDCl$_3$, 400 MHz, ppm) δ 8.88 (s, 1H), 8.45 (br, 1H), 8.03 (d, J=8.4 Hz, 1H), 6.81 (d, J=8.4 Hz, 1H), 3.78 (m, 1H), 2.05 (m, 2H), 1.97-1.63 (m, 21H); MS (APCI+, M+1) 291.27. MS (APCI+, M+1) 349.17.

Synthesis of tert-butyl 3-amino-4-(cyclooctylamino)benzoate (SRS8-87, Table 4, Entry 9)

Following the above general procedure B with the tert-butyl 4-(cyclooctylamino)-3-nitrobenzoate compound (SRS8-86) (350 mg, 1.002 mmol) and hydrogen gas (H$_2$ gas) over 10% Pd(OH)$_2$ on charcoal (100 mg) for 17 hours at room temperature, the crude reaction mixture was purified by column chromatography (dichloromethane:methanol=20:1) to provide the desired tert-butyl 3-amino-4-(cyclooctylamino)benzoate (SRS8-87) (278 mg, 0.871 mmol, 87%). $^1$H NMR (CDCl$_3$, 400 MHz, ppm) δ 7.54 (d, J=8.4 Hz, 1H), 7.35 (s, 1H), 6.50 (d, J=8.4 Hz, 1H), 3.93 (br, 1H), 3.55 (m, 1H), 3.20 (br, 2H), 1.89 (m, 2H), 1.76-1.54 (m, 21H); MS (APCI+, M+1) 319.30.

Synthesis of 4-(cyclooctylamino)-N-ethyl-3-nitrobenzamide (SRS9-03, Table 4, Entry 10)

Following the above general procedure A with the 4-chloro-N-ethyl-3-nitrobenzamide (200 mg, 0.877 mmol), K$_2$CO$_3$ (363.7 mg, 2.631 mmol) and cyclooctylamine (145.6 μL, 1.052 mmol), the crude reaction mixture was purified by column chromatography (hexane:ethyl acetate 10:1) to provide the desired 4-(cyclooctylamino)-N-ethyl-3-nitrobenzamide compound (SRS9-03) (168 mg, 0.525 mmol, 60%). $^1$H NMR (CDCl$_3$, 400 MHz, ppm) δ 8.55 (s, 1H), 8.37 (br, 1H), 7.95 (d, J=8.4 Hz, 1H), 6.82 (d, J=8.4 Hz, 1H), 6.45 (m, 1H), 3.73 (m, 3H), 1.91-1.22 (m, 17H); MS (APCI+, M+1) 320.27.

Synthesis of 3-amino-4-(cyclooctylamino)-N-ethylbenzamide (SRS9-11, Table 4, Entry 11)

Following the above general procedure B with the 4-(cyclooctylamino)-N-ethyl-3-nitrobenzamide compound (SRS9-03) (200 mg, 0.625 mmol) and hydrogen gas (H$_2$ gas) over 10% Pd(OH)$_2$ on charcoal (62.5 mg) for 17 hours at room temperature, the crude reaction mixture was purified by column chromatography (dichloromethane:methanol=20:1) to provide the desired 3-amino-4-(cyclooctylamino)-N-ethylbenzamide (SRS9-11) (119 mg, 0.410 mmol, 66%). $^1$H NMR (CDCl$_3$, 400 MHz, ppm) δ 7.25 (d, J=8.4 Hz, 1H), 7.19 (s, 1H), 6.50 (d, J=8.4 Hz, 1H), 3.74 (br, 1H), 3.60 (m, 1H), 3.48 (br, 2H), 3.35 (q, J=6.4 Hz, 2H), 1.92-1.25 (m, 17H); MS (APCI+, M+1) 290.20.

Synthesis of Ferrostatin-1 Analogs with Various Substitutions on the Primary Amine Scheme 6: Synthesis of Ferrostatin-1 analogs with various substitutions on the primary amine.

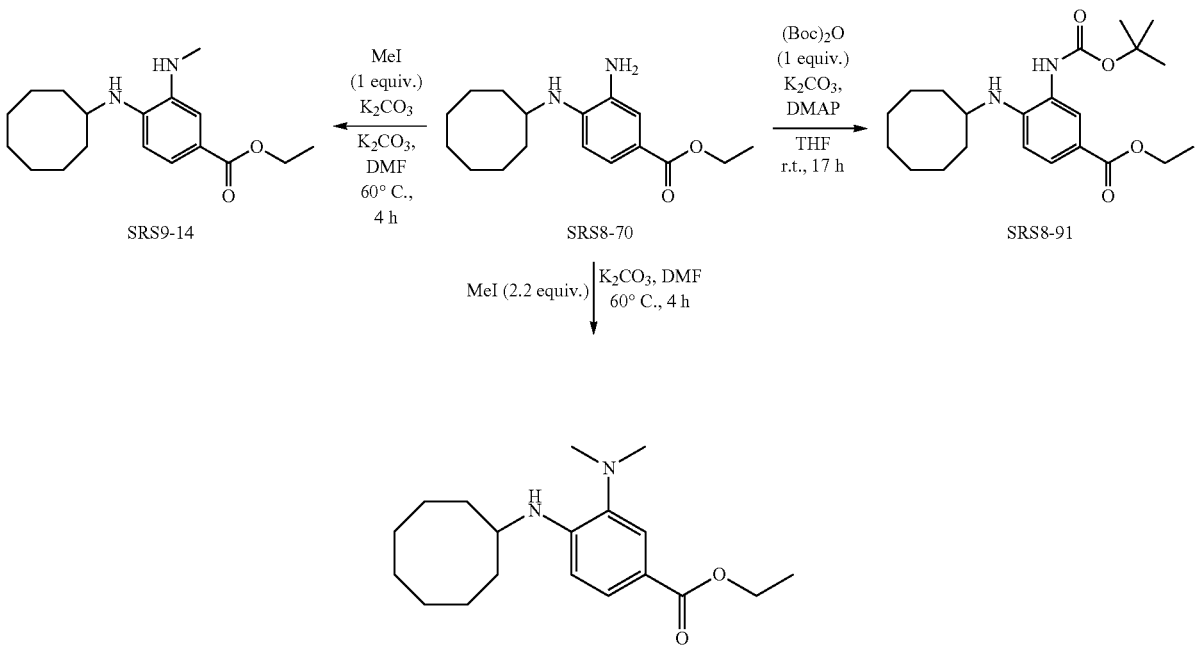

Synthesis of ethyl 3-(tert-butoxycarbonyl)-4-(cyclooctylamino)benzoate (SRS8-91, Scheme 6)

To the ethyl 3-amino-4-(cyclooctylamino)benzoate (26 mg, 0.089 mmol) in THF was added was di-tert-butyl dicarbonate (19.5 mg, 0.089 mmol) and 4-dimethylaminopyridine (DMAP) (2.2 mg, 0.018 mmol). The mixture was stirred at room temperature for 17 hours. The organic solvent was removed. The residue was purified by column chromatography (hexane:ethyl acetate 10:1) to provide the desired ethyl 3-(tert-butoxycarbonyl)-4-(cyclooctylamino)benzoate compound (SRS8-91) (18 mg, 0.046 mmol, 52%). $^1$H NMR (CDCl$_3$, 400 MHz, ppm) δ 8.53 (s, 1H), 7.93 (d, J=8.4 Hz, 1H), 7.07 (d, J=8.4 Hz, 1H), 4.65 (br, 1H), 4.37 (q, J=7.4 Hz, 2H), 3.80 (m, 1H), 1.98-1.37 (m, 26H); MS (APCI+, M+1; M+1-100) 391.19; 291.18.

Synthesis of ethyl 4-(cyclooctylamino)-3-(dimethylamino)benzoate (SRS9-01, Scheme 6)

To the ethyl 3-amino-4-(cyclooctylamino)benzoate (58 mg, 0.199 mmol) in DMF was added was MeI (27.3 µL, 0.438 mmol) and potassium carbonate (K$_2$CO$_3$) (82 mg, 0.597 mmol). The mixture was stirred at 60° C. for 4 hours then poured in water. The organic layer was extracted with ethylacetate and the solvent was removed. The residue was purified by column chromatography (hexane:ethyl acetate 10:1) to provide the desired ethyl 4-(cyclooctylamino)-3-(dimethylamino)benzoate compound (SRS9-01) (54 mg, 0.169 mmol, 85%). $^1$H NMR (CDCl$_3$, 400 MHz, ppm) δ 7.75 (d, J=8.4 Hz, 1H), 7.70 (s, 1H), 6.49 (d, J=8.4 Hz, 1H), 5.19 (br, 1H), 4.34 (q, J=7.4 Hz, 2H), 3.57 (m, 1H), 2.64 (s, 6H), 1.95-1.57 (m, 14H), 1.37 (t, J=7.4 Hz, 3H); MS (APCI+, M+1) 319.19.

Synthesis of ethyl 4-(cyclooctylamino)-3-(methylamino)benzoate (SRS9-14, Scheme 6)

To the ethyl 3-amino-4-(cyclooctylamino)benzoate (40 mg, 0.137 mmol) in DMF was added was 1 equivalent of MeI (8.6 µL, 0.137 mmol) and potassium carbonate (K$_2$CO$_3$) (37.9 mg, 0.274 mmol). The mixture was stirred at 60° C. for 4 hours then poured in water. The organic layer was extracted with ethylacetate and the solvent was removed. The residue was purified by column chromatography (hexane:ethyl acetate 20:1) to provide the desired ethyl 4-(cyclooctylamino)-3-(methylamino)benzoate compound (SRS9-14) (14 mg, 0.046 mmol, 34%). $^1$H NMR (CDCl$_3$, 400 MHz, ppm) δ 7.62 (d, J=8.4 Hz, 1H), 7.38 (s, 1H), 6.55 (d, J=8.4 Hz, 1H), 4.34 (q, J=7.4 Hz, 2H), 3.57 (m, 1H), 2.91 (s, 3H), 1.95-1.57 (m, 14H), 1.37 (t, J=7.4 Hz, 3H); MS (APCI+, M+1) 305.19.

TABLE 5

Synthetic scheme of Ferrostatin-1 analogs with various R3 substitutions.

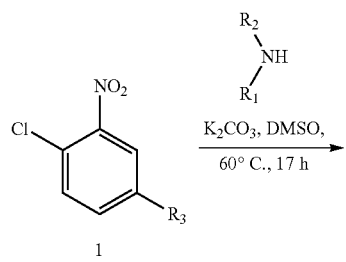

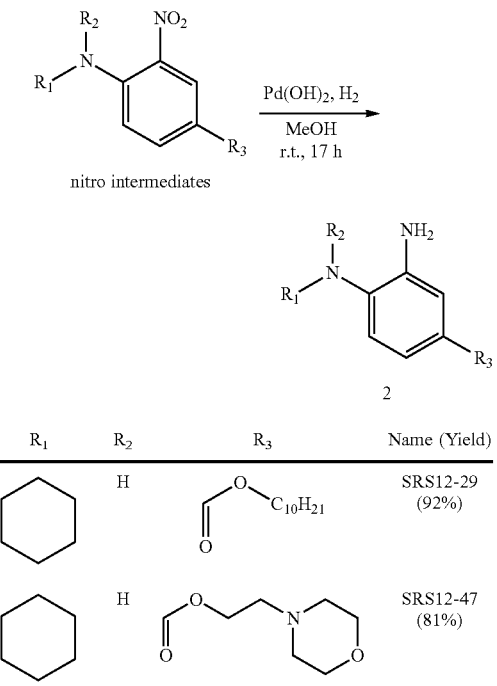

| Entry | R$_1$ | R$_2$ | R$_3$ | Name (Yield) |
|---|---|---|---|---|
| 1 | cyclohexyl | H | –O–C(=O)–C$_{10}$H$_{21}$ | SRS12-29 (92%) |
| 2 | cyclohexyl | H | –O–C(=O)–CH$_2$CH$_2$–morpholine | SRS12-47 (81%) |

Synthesis of decyl 3-amino-4-(cyclohexylamino)benzoate (SRS12-29, Table 5, Entry 1)

Following the above general procedure B, the crude reaction mixture was purified by column chromatography (dichloromethane:methanol=100:1) to provide the desired decyl 3-amino-4-(cyclohexylamino)benzoate (SRS12-29) (170 mg, 0.909 mmol, 91%). $^1$H NMR (CDCl$_3$, 400 MHz) δ 7.59 (d, J=8.4 Hz, 1H), 7.42 (s, 1H), 6.61 (d, J=8.4 Hz, 1H), 4.27-4.24 (m, 2H), 3.35 (b, 1H), 2.10-2.07 (m, 2H), 2.78-1.72 (m, 4H), 1.43-1.29 (m, 22H), 0.90-0.88 (m, 3H); $^{13}$C NMR (100 MHz, CDCl$_3$) δ 167.0, 141.2, 132.2, 124.2, 119.2, 118.7, 110.4, 64.5, 51.8, 33.1, 31.9, 29.55, 29.3, 28.9, 26.1, 25.8, 24.9, 22.7, 14.1; HRMS (FAB) calculated for C$_{23}$H$_{38}$N$_2$O$_2$: 374.56; found: 374.47.

Synthesis of 2-morpholinoethyl 3-amino-4-(cyclohexylamino)benzoate (SRS12-47, Table 5, Entry 2)

Following the above general procedure B, the crude reaction mixture was purified by column chromatography (dichloromethane:methanol=20:1) to provide the desired 2-morpholinoethyl 3-amino-4-(cyclohexylamino)benzoate (SRS12-47) (132 mg, 0.380 mmol, 84%). $^1$H NMR (CDCl$_3$, 400 MHz) δ 7.56 (d, J=5.0 Hz, 1H), 7.39 (d, J=2.0 Hz, 1H), 6.59 (d, J=8.4 Hz, 1H), 4.40 (t, J=6.0 Hz, 2H), 3.90 (b, NH), 3.73-3.71 (m, 4H), 3.33 (b, 1H), 3.19 (b, NH$_2$), 2.76 (t, J=6.0 Hz, 2H), 2.59-2.56 (m, 4H), 2.09-2.04 (m, 2H), 1.82-1.17 (m, 8H); 13C NMR (100 MHz, CDCl$_3$) δ 166.8, 142.3, 131.8, 124.5, 118.6, 117.9, 109.4, 67.0, 61.8, 57.3, 53.9, 51.3, 49.1, 34.0, 33.3, 25.8, 24.9; HRMS (FAB) calculated for C$_{19}$H$_{29}$N$_3$O$_3$: 347.45; found: 348.31.

TABLE 6

Synthesis of Ferrostatin analogs.

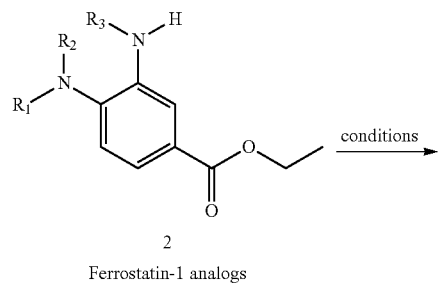

Conditions. Addition of Fer-1 to acylchloride, alkyl- or benzyl-chloroformates (1 equiv.), DIPEA, DCM, r.t., 17 h.

| Entry/Name (Yield) | $R_1$ | $R_2$ | $R_3$ | $R_4$ |
|---|---|---|---|---|
| 1 SRS11-89 (88%) | cyclohexyl | H | H | C(O)OCH₂Ph |
| 2 SRS11-97 (86%) | cyclohexyl | H | H | C(O)OCH₃ |
| 3 SRS11-98 (70%) | cyclohexyl | H | H | C(O)CH₃ |
| 4 SRS12-12 (89%) | $C_8H_{17}$ | $C_8H_{17}$ | H | H |

Synthesis of ethyl 3-(benzyloxycarbonylamino)-4-(cyclohexylamino)-benzoate (SRS11-89, Table 6, Entry 1)

Following the above general procedure E, the crude reaction mixture was purified by column chromatography (dichloromethane:methanol=200:1) to provide the desired ethyl 3-(benzyloxycarbonylamino)-4-(cyclohexylamino)-benzoate (SRS11-89) (29.4 mg, 0.074 mmol, 88%). $^1$H NMR (400 MHz, CDCl$_3$) δ 7.83 (d, J=10.3 Hz, 2H), 7.38 (s, 5H), 6.66 (d, J=8.5 Hz, 1H), 4.34-4.11 (m, 4H), 3.32 (s, 1H), 1.99 (s, 2H), 1.74 (s, 2H), 1.64 (s, 1H), 1.36 (t, J=7.1 Hz, 5H), 1.23-1.11 (m, 3H); $^{13}$C NMR (100 MHz, CDCl$_3$) δ 166.4, 154.6, 146.7, 136.0, 130.2, 128.6, 128.4, 121.0, 117.9, 110.6, 67.5, 60.3, 51.3, 33.0, 25.7, 24.8, 14.5; HRMS (FAB) calculated for $C_{23}H_{28}N_2O_4$: 396.48; found: 396.20.

Synthesis of ethyl 4-(cyclohexylamino)-3-(methoxycarbonylamino)benzoate (SRS11-97, Table 6, Entry 2)

Following the above general procedure E, the crude reaction mixture was purified by column chromatography (dichloromethane:methanol=200:1) to provide the desired ethyl 4-(cyclohexylamino)-3-(methoxycarbonylamino)-benzoate (SRS11-97) (23 mg, 0.074 mmol, 86%). $^1$H NMR (400 MHz, CDCl$_3$) δ 7.85 (s, 2H), 6.67 (d, J=9.0 Hz, 1H), 6.04 (s, 1H), 4.32 (q, J=7.1 Hz, 2H), 3.78 (s, 2H), 3.36 (s, 1H), 2.06 (d, J=12.4 Hz, 2H), 1.79 (d, J=13.4 Hz, 2H), 1.68 (d, J=12.6 Hz, 1H), 1.37 (t, J=7.1 Hz, 5H), 1.29-1.18 (m, 3H); $^{13}$C NMR (100 MHz, CDCl$_3$) δ 166.4, 155.9, 146.7, 130.2, 129.1, 121.1, 117.9, 110.5, 60.3, 52.8, 51.3, 33.1, 25.7, 24.8, 14.4; HRMS (FAB) calculated for $C_{17}H_{24}N_2O_4$: 320.38; found: 320.17.

Synthesis of ethyl 4-(cyclohexylamino)-3-ethanamidobenzoate (SRS11-98, Table 6, Entry 3)

Following the above general procedure E, the crude reaction mixture was purified by column chromatography (dichloromethane:methanol=200:1) to provide the ethyl 4-(cyclohexylamino)-3-ethanamidobenzoate (SRS11-98) (18 mg, 0.059 mmol, 70%). $^1$H NMR (400 MHz, CDCl$_3$) δ 7.82 (d, J=8.6 Hz, 1H), 7.75 (s, 1H), 6.68 (d, J=8.6 Hz, 1H), 4.57-4.46 (m, 1H), 4.33 (d, J=9.8 Hz, 2H), 3.35 (s, 1H), 2.22 (s, 3H), 2.04 (d, J=12.1 Hz, 2H), 1.88 (s, 1H), 1.79 (s, 3H), 1.38 (s, 4H), 1.24 (d, J=8.6 Hz, 3H); HRMS (FAB) calculated for $C_{17}H_{24}N_2O_3$: 304.38; found: 304.18.

Synthesis of ethyl 3-amino-4-(dioctylamino)benzoate (SRS12-12, Table 6, Entry 4)

Following the above general procedure B, the crude reaction mixture was purified by column chromatography (dichloromethane:methanol=20:1) to provide the desired ethyl 3-amino-4-(dioctylamino)benzoate (SRS12-12) (143 mg, 0.354 mmol, 89%). $^1$H NMR (400 MHz, CDCl$_3$) δ 7.41 (s, 2H), 7.03 (d, J=8.7 Hz, 1H), 4.34 (d, J=7.1 Hz, 2H), 2.95 (s, 3H), 1.38 (d, J=7.1 Hz, 6H), 1.24 (s, 22H), 0.87 (s, 3H); $^{13}$C NMR (100 MHz, CDCl$_3$) δ 166.9, 142.8, 142.3, 126.0, 121.8, 119.7, 116.1, 60.6, 52.8, 31.8, 29.4, 29.3, 27.2, 22.6, 14.4, 14.1.

TABLE 7

Synthesis of ferrostatin analogs

2a Ferrostatin-1 + R₁–CHO (NaBH(OAc)₃, DCE, r.t. –60° C., 17 h) or R₁–X (DIPEA, THF, 60° C., 4 h) → 3

| Entry | R1 | Name (Yield) |
|---|---|---|
| 1 | H₂C–C₆H₅ (benzyl) | SRS11-92 (95%) |
| 2 | H₂C–(3-Cl-C₆H₄) | SRS12-58 (90%) |
| 3 | H₂C–(4-Cl-C₆H₄) | SRS12-49 (91%) |
| 4 | H₂C–(4-Br-C₆H₄) | SRS12-35 (89%) |
| 5 | H₂C–(3-F-C₆H₄) | SRS12-57 (85%) |
| 6 | H₂C–(4-F-C₆H₄) | SRS12-33 (85%) |
| 7 | H₂C–(4-CF₃-C₆H₄) | SRS12-48 (86%) |
| 8 | H₂C–(4-CN-C₆H₄) | SRS12-50 (92%) |
| 9 | H₂C–(2-NO₂-C₆H₄) | SRS12-71 (94%) |
| 10 | H₂C–(4-NO₂-C₆H₄) | SRS12-36 (90%) |
| 11 | H₂C–(4-CH₃-C₆H₄) | SRS12-34 (94%) |
| 12 | H₂C–(3-OCH₃-C₆H₄) | SRS12-69 (85%) |
| 13 | H₂C–(4-OCH₃-C₆H₄) | SRS12-43 (86%) |

Synthesis of ethyl
3-(benzylamino)-4-(cyclohexylamino)benzoate
(SRS11-92, Table 7, Entry 1)

Following the above general procedure C or D, the crude reaction mixture was purified by column chromatography (dichloromethane:methanol=200:1) to provide the desired ethyl 3-(benzylamino)-4-(cyclohexylamino)benzoate (SRS11-92) (24.5 mg, 0.069 mmol, 91%). $^1$H NMR (CDCl$_3$, 400 MHz) δ 7.69-7.61 (m, 1H), 7.53-7.30 m, 6H), 6.71-6.62 (m, 1H), 4.40-4.28 (m, 4H), 3.97 (b, NH), 3.36 (b, 1H), 3.23 (m, NH), 2.17-2.03 (m, 2H), 1.87-1.76 (m, 2H), 1.75-1.66 (m, 1H), 1.47-1.34 (m, 5H), 1.32-1.19 (m, 3H); $^{13}$C NMR (100 MHz, CDCl3) δ 167.3, 142.0, 139.2, 134.8, 128.2, 127.44, 123.7, 118.8, 114.7, 109.3, 60.2, 51.4, 49.5, 33.3, 25.9, 25.0 14.5; HRMS (FAB) calculated for $C_{22}H_{28}N_2O_2$: 352.47; found: 352.22.

Synthesis of ethyl 3-(3-chlorobenzylamino)-4-(cyclohexylamino)benzoate (SRS12-58, Table 7, Entry 2)

Following the above general procedure C or D, the crude reaction mixture was purified by column chromatography (dichloromethane:methanol=200:1) to provide the desired ethyl 3-(3-chlorobenzylamino)-4-(cyclohexylamino)benzoate (SRS12-58) (39.5 mg, 0.103 mmol, 90%). $^1$H NMR (CDCl$_3$, 400 MHz) δ 7.63 (d, J=4.2 Hz, 1H), 7.43 (s, 2H), 7.30-7.28 (m, 3H), 6.65 (d, J=8.4 Hz, 1H), 4.35-4.30 (m, 4H), 3.37 (b, 1H), 2.14-2.05 (m, 2H), 1.87-1.76 (m, 2H), 1.75-1.67 (m, 1H), 1.47-1.36 (m, 5H), 1.29-1.24 (m, 3H); $^{13}$C NMR (100 MHz, CDCl$_3$) δ 167.2, 142.1, 141.3, 134.5, 134.4, 129.9, 128.1, 127.6, 126.2, 123.9, 118.9, 115.0, 110.0, 60.2, 51.5, 48.9, 33.3, 25.9, 24.9, 14.5; HRMS (FAB) calculated for $C_{22}H_{27}ClN_2O_2$: 386.91; found: 386.18.

Synthesis of ethyl 3-(4-chlorobenzylamino)-4-(cyclohexylamino)benzoate (SRS12-49, Table 7, Entry 3)

Following the above general procedure C or D, the crude reaction mixture was purified by column chromatography (dichloromethane:methanol=200:1) to provide the desired ethyl 3-(4-chlorobenzylamino)-4-(cyclohexylamino)benzoate (SRS12-49) (40 mg, 0.104 mmol, 91%). $^1$H NMR (CDCl$_3$, 400 MHz) δ 7.60 (d, J=8.0 Hz, 1H), 7.41 (s, 1H), 7.34 (s, 4H), 6.64 (d, J=8.3 Hz, 1H), 4.36-4.25 (m, 4H), 3.32 (b, 1H), 2.07-2.04 (m, 2H), 1.79-1.76 (m, 2H), 1.69-1.33 (5H), 1.26-1.20 (m, 3H); $^{13}$C NMR (100 MHz, CDCl$_3$) δ 167.2, 142.0, 137.7, 134.4, 133.2, 129.4, 128.8, 123.9, 118.9, 114.9, 109.5, 60.2, 51.4, 48.7, 33.3, 25.9, 24.9 14.5; HRMS (FAB) calculated for $C_{22}H_{27}ClN_2O_2$: 386.91; found: 386.17.

Synthesis of ethyl 3-((4-bromobenzyl)amino)-4-(cyclohexylamino)benzoate (SRS12-35, Table 7, Entry 4)

Following the above general procedure C or D, the crude reaction mixture was purified by column chromatography (dichloromethane:methanol=200:1) to provide the desired ethyl 3-((4-bromobenzyl)amino)-4-(cyclohexylamino)-benzoate (SRS12-35) (44 mg, 0.102 mmol, 89%). $^1$H NMR (CDCl$_3$, 400 MHz,) δ 7.62 (d, J=8.0 Hz, 1H), 7.50 (d, J=8.4 Hz, 2H), 7.42 (s, 1H), 7.31-7.28 (m, 2H), 6.64 (d, J=8.4 Hz, 1H), 4.35-4.28 (m, 4H), 3.35 (b, 1H), 2.10-2.07 (m, 2H), 1.81-1.59 (m, 4H), 1.44-1.35 (m, 4H), 1.28-1.22 (m, 3H); $^{13}$C NMR (100 MHz, CDCl$_3$) δ 167.2, 142.0, 138.2, 134.4, 131.7, 129.74, 123.9, 121.2, 118.9, 114.9, 109.5, 60.2, 51.4, 48.8, 33.3, 25.9, 24.9, 14.5; HRMS (FAB) calculated for $C_{22}H_{27}BrN_2O_2$: 431.37; found: 430.13.

Synthesis of ethyl 4-(cyclohexylamino)-3-(3-fluorobenzylamino)benzoate (SRS12-57, Table 7, Entry 5)

Following the above general procedure C or D, the crude reaction mixture was purified by column chromatography (dichloromethane:methanol=200:1) to provide the desired ethyl 4-(cyclohexylamino)-3-(3-fluorobenzylamino)-benzoate (SRS12-57) (36 mg, 0.097 mmol, 85%). $^1$H NMR (CDCl$_3$, 400 MHz) δ 7.62 (d, J=8.4 Hz, 1H), 7.43 (s, 1H), 7.34-7.31 (m, 1H), 7.21-7.20 (m, 1H), 7.16-7.13 (m, 1H), 7.03-6.99 (m, 1H), 6.65 (d, J=8.4 Hz, 1H), 4.35-4.30 (m, 4H), 3.94 (b, NH), 3.56 (b, 1H), 3.24 (b, NH), 2.15-2.03 (m, 2H). 1.88-1.75 (m, 2H), 1.76-1.66 (m, 1H), 1.49-1.33 (m, 5H). 1.32-1.19 (3H); $^{13}$C NMR (100 MHz, CDCl$_3$) δ 167.2, 164.3, 161.9, 142.1, 134.4, 130.1, 123.9, 123.5, 123.49, 118.9, 115.0, 114.9, 114.7, 114.4, 114.2, 109.5, 60.2, 51.4, 48.9, 33.3, 25.86, 24.9, 14.5; $^{19}$F (CDCl$_3$) δ−112.0; HRMS (FAB) calculated for $C_{22}H_{27}FN_2O_2$: 370.48; found: 370.20.

Synthesis of ethyl 4-(cyclohexylamino)-3-((4-fluorobenzyl)amino)benzoate (SRS12-33, Table 7, Entry 6)

Following the above general procedure C or D, the crude reaction mixture was purified by column chromatography (dichloromethane:methanol=200:1) to provide the desired ethyl 4-(cyclohexylamino)-3-((4-fluorobenzyl)amino)benzoate (SRS12-33) (36 mg, 0.097 mmol, 85%). $^1$H NMR (CDCl$_3$, 400 MHz) δ 7.62 (d, J=8.4 Hz, 1H), 7.45 (s, 1H), 7.41-7.38 (m, 2H), 7.07 (d, J=8.8 Hz, 2H), 6.65 (d, J=8.0 Hz, 1H), 4.36-4.288 (m, J=4H), 3.35 (b, 1H), 2.10-2.07 (m, 2H), 1.81-1.61 (m, 4H), 1.46-1.44 (m, 4H), 1.39 (t, J=7.2 Hz, 3H); $^{13}$C NMR (100 MHz, CDCl3) δ 167.3, 163.4, 161.0, 142.0, 134.5, 129.7, 123.8, 118.8, 115.4, 114.8, 109.4, 60.2, 51.4, 48.7, 33.3, 25.9, 25.0, 14.5; $^{19}$F (CDCl$_3$) δ −114.3; HRMS (FAB) calculated for $C_{22}H_{27}FN_2O_2$: 370.46; found: 371.13.

Synthesis of ethyl 4-(cyclohexylamino)-3-(4-(trifluoromethyl)benzylamino)-benzoate (SRS12-48, Table 7, Entry 7)

Following the above general procedure C or D, the crude reaction mixture was purified by column chromatography (dichloromethane:methanol=200:1) to provide the desired ethyl 4-(cyclohexylamino)-3-(4-(trifluoromethyl)benzylamino)-benzoate (SRS12-48, Table 7, entry 7) (41 mg, 0.098 mmol, 86%). $^1$H NMR (CDCl$_3$, 400 MHz) δ 7.61 (td, J=6.2, 2.9 Hz, 3H), 7.52 (d, J=8.0 Hz, 2H), 7.40 (d, J=1.9 Hz, 1H), 6.64 (d, J=8.4 Hz, 1H), 4.38 (s, 2H), 4.30 (q, J=7.1 Hz, 2H), 3.34 (b, 1H 2.11-2.03 (m, 2H), 1.84-1.74 (m, 2H). 1.70-1.66 (m, 1H), 1.43-1.32 (m, 5H). 1.2-1.17 (m, 3H); $^{13}$C NMR (100 MHz, CDCl$_3$) δ 167.2, 143.3, 142.1, 134.2, 128.2, 125.6, 124.0, 118.9, 115.0, 109.6, 60.2, 51.4, 50.8, 48.9, 33.3, 25.8, 24.9, 14.4; $^{19}$F (CDCl$_3$) δ −61.3; HRMS (FAB) calculated for $C_{23}H_{27}F_3N_2O_2$: 420.47; found: 420.22.

Synthesis of ethyl 3-(4-cyanobenzylamino)-4-(cyclohexylamino)benzoate (SRS12-50, Table 7, Entry 8)

Following the above general procedure C or D, the crude reaction mixture was purified by column chromatography (dichloromethane:methanol=200:1) to provide the desired ethyl 3-(4-cyanobenzylamino)-4-(cyclohexylamino)benzoate (SRS12-50, Table 7, entry 8) (39.7 mg, 0.105 mmol, 92%). $^1$H NMR (CDCl$_3$, 400 MHz) δ 7.61 (d, J=2.0 Hz, 2H), 7.59 (d, J=1.6 Hz, 1H), 7.50 (d, J=8.4 Hz, 2H), 7.33 (d, J=1.9 Hz, 1H), 6.64 (d, J=8.4 Hz, 1H), 4.40 (s, 2H), 4.29 (q, J=7.1 Hz, 2H), 3.34 (b, 1H), 2.09-2.04 (m, 2H), 1.77-1.32 (m, 8H), 1.27-1.21 (m, 3H); $^{13}$C NMR (100 MHz, CDCl$_3$) δ 167.1, 144.8, 142.1, 133.9, 132.4, 128.4, 124.1, 119.0, 118.8, 115.0, 111.2, 110.0, 60.2, 51.4, 48.8, 33.3, 25.9, 24.9, 14.4: HRMS (FAB) calculated for C23H27N3O2: 377.48; found: 377.39.

Synthesis of ethyl 4-(cyclohexylamino)-3-(2-nitrobenzylamino)benzoate (SRS12-71, Table 7, Entry 9)

Following the above general procedure C or D, the crude reaction mixture was purified by column chromatography (dichloromethane:methanol=200:1) to provide the desired ethyl 4-(cyclohexylamino)-3-(2-nitrobenzylamino)benzoate (SRS12-71, Table 7, entry 9) (71 mg, 0.179 mmol, 94%). $^1$H NMR (CDCl$_3$, 400 MHz) δ 7.99 (dd, J=8.1, 1.3 Hz, 1H), 7.62-7.58 (m, 1H), 7.57-7.54 (m, 1H), 7.52 (d, J=1.5 Hz, 1H), 7.44 (ddd, J=8.1, 7.1, 1.7 Hz, 1H), 7.32 (d, J=1.9 Hz, 1H), 6.65-6.58 (m, 1H), 4.58 (s, 2H), 4.28 (q, J=7.1 Hz, 2H), 4.08 (s, NH), 3.53 (s, NH), 3.39-3.27 (m, 1H), 2.06 (dd, J=12.5, 4.0 Hz, 2H), 2.11-2.02 (m, 2H), 1.82-1.73 (m, 2H), 1.71-1.62 (m, 2H), 1.39-1.31 (m, 4H), 1.28-1.22 (m, 3H), 1.27-1.16 (m, 3H); $^{13}$C NMR (100 MHz, CDCl$_3$) δ 167.1, 149.1, 142.9, 134.5, 133.6, 133.3, 131.1, 128.4, 124.9, 124.6, 118.6, 116.6, 109.7, 60.17, 51.42, 47.0, 33.2, 25.9, 24.9, 14.4; HRMS (FAB) calculated for C$_{22}$H$_{27}$N$_3$O$_4$: 397.47; found: 397.20.

Synthesis of ethyl 4-(cyclohexylamino)-3-((4-nitrobenzyl)amino)benzoate (SRS12-36, Table 7, Entry 10)

Following the above general procedure C or D, the crude reaction mixture was purified by column chromatography (dichloromethane:methanol=200:1) to provide the desired ethyl 4-(cyclohexylamino)-3-((4-nitrobenzyl)amino)benzoate (SRS12-36, Table 7, entry 10) (68 mg, 0.172 mmol, 90%). $^1$H NMR (CDCl$_3$, 400 MHz) δ 8.20 (d, J=8.6 Hz, 2H), 7.59 (dd, J=20.8, 8.4 Hz, 3H), 7.36 (d, J=14.1 Hz, 1H), 6.66 (d, J=8.4 Hz, 1H), 4.45 (s, 2H), 4.29 (q, J=7.0 Hz, 2H), 3.97 (s, 1H), 3.38 (d, J=12.9 Hz, NH+1H), 2.09 (d, J=10.1 Hz, 2H), 1.75 (dd, J=40.7, 13.0 Hz, 4H), 1.41-1.33 (m, 4H), 1.31-1.21 (m, 3H); $^{13}$C NMR (100 MHz, CDCl$_3$) δ 167.1, 146.8, 142.0, 133.8, 129.5, 128.4, 124.1, 123.9, 118.9, 114.9, 109.7, 60.3, 51.5, 48.5, 33.3, 25.9, 24.9, 14.5.

Synthesis of ethyl 4-(cyclohexylamino)-3-((4-methylbenzyl)amino)benzoate (SRS12-34, Table 7, Entry 11)

Following the above general procedure C or D, the crude reaction mixture was purified by column chromatography (dichloromethane:methanol=200:1) to provide the desired ethyl 4-(cyclohexylamino)-3-((4-methylbenzyl)amino)-benzoate (SRS12-34, Table 7, entry 11) (39 mg, 0.107 mmol, 94%). $^1$H NMR (CDCl$_3$, 400 MHz) δ 7.62 (d, J=8.0 Hz, 1H), 7.49 (s, 1H), 7.33 (d, J=8.0 Hz, 2H), 7.20 (d, J=7.6 Hz, 2H), 6.66 (d, J=8.4 Hz, 1H), 4.33 (q, J=6.8, 2H), 4.27 (s, 2H), 3.35 (b, 1H), 2.39 (s, 3H), 2.13-2.0 (m, 2H), 1.84-1.74 (m, 2H), 1.73-1.64 (m, 1H), 1.41-1.36 (m, 4H), 1.28-1.21 (m, 3H); $^{13}$C NMR (100 MHz, CDCl$_3$) δ 167.3, 141.8, 137.1, 136.1, 134.8, 129.3, 128.2, 123.6, 118.9, 114.7, 109.3, 60.2, 51.5, 49.25, 33.3, 25.9, 25.0, 21.1, 14.5; HRMS (FAB) calculated for C$_{23}$H$_{30}$N$_2$O$_2$: 366.50; found: 366.23.

Synthesis of ethyl 4-(cyclohexylamino)-3-(4-(methoxycarbonyl)-benzylamino)benzoate (SRS12-69, Table 7, Entry 12)

Following the above general procedure C or D, the crude reaction mixture was purified by column chromatography (dichloromethane:methanol=100:1) to provide the desired ethyl 4-(cyclohexylamino)-3-(4-(methoxycarbonyl)-benzylamino)benzoate (SRS12-69, Table 7, entry 12) (37 mg, 0.097 mmol, 85%). $^1$H NMR (CDCl$_3$, 400 MHz) δ 7.60 (ddd, J=8.4, 1.9, 1.0 Hz, 1H), 7.45 (d, J=1.8 Hz, 1H), 7.32-7.27 (m, 1H), 7.04-6.95 (m, 2H), 6.89-6.81 (m, 1H), 6.62 (dd, J=8.7, 1.3 Hz, 1H), 4.31 (tdd, J=7.2, 6.7, 1.2 Hz, 2H), 4.27 (s, 2H), 3.90 (s, NH), 3.82 (d, J=1.1 Hz, 3H), 3.33 (s, 1H), 2.09-2.02 (m, 2H), 1.82-1.73 (m, 2H), 1.71-1.63 (m, 1H), 1.45-1.32 (m, 5H), 1.26-1.17 (m, 3H); $^{13}$C NMR (100 MHz, CDCl$_3$) δ 167.3, 159.9, 141.9, 140.8, 134.7, 129.7, 123.7, 120.5, 118.9, 114.8, 113.8, 112.8, 109.4, 60.2, 55.2, 49.5, 33.3, 25.9, 25.0, 14.5; HRMS (FAB) calculated for C$_{23}$H$_{30}$N$_2$O$_3$: 382.50; found: 382.37.

Synthesis of ethyl 4-(cyclohexylamino)-3-((4-methoxybenzyl)amino)-benzoate (SRS12-43, Table 7, Entry 13)

Following the above general procedure C or D, the crude reaction mixture was purified by column chromatography (dichloromethane:methanol=100:1) to provide the desired ethyl 4-(cyclohexylamino)-3-((4-methoxybenzyl)amino)-benzoate (SRS12-43, Table 7, entry 13) (37.6 mg, 0.098 mmol, 86%). $^1$H NMR (CDCl$_3$, 400 MHz) δ 7.63 (d, J=8.4 Hz, 1H), 7.49 (s, 1H), 7.37 (d, J=8.4 Hz, 2H), 6.94 (d, J=8.8 Hz, 2H), 6.65 (d, J=8.4 Hz, 1 H), 4.5 (q, J=7.2, 2H), 4.26 (s, 2H), 3.85 (s, 3H), 3.35 (b, 1H), 2.10-2.07 (m, 2H), 1.82-1.60 (m, 4H), 1.47-1.33 (m, 4H), 1.30-1.27 (m, 3H); MS (APCI+, M+1) 382.86.

TABLE 8
Synthesis of ferrostatin analogs
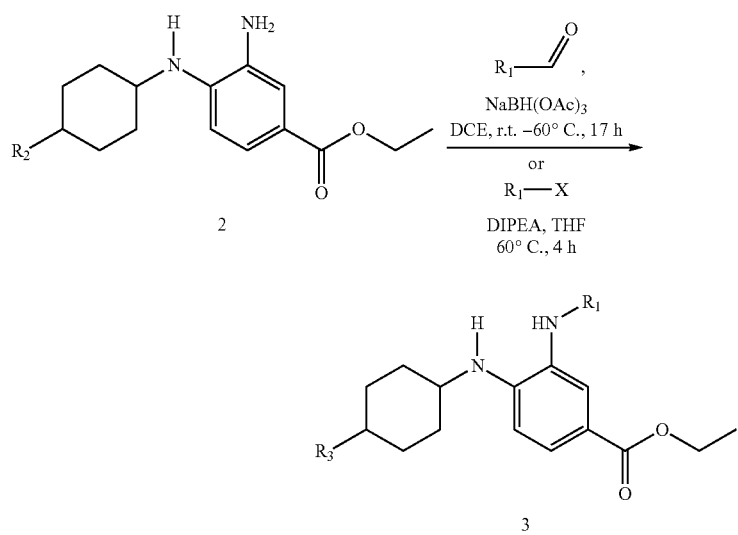
| Entry | R₁ | R₂ | Name (Yield) |
|---|---|---|---|
| 1 | H₂C-phenyl | tert-butyl | SRS13-29 (95%) |
| 2 | H₂C-(2-naphthyl) | H | SRS12-51 (91%) |
| 3 | H₂C-(2-pyridyl) | H | SRS12-46 (85%) |
| 4 | H₂C-(3-pyridyl) | H | SRS13-12 (87%) |
| 5 | H₂C-(4-pyridyl) R₁b | H | SRS12-45 (90%) |
| 6 | R₁b | tert-butyl | SRS13-30 (89%) |
| 7 | H₂C-(4-pyridyl) R₁c | H | SRS13-35 (92%) |
| 8 | R₁c | tert-butyl | SRS13-37 (88%) |
| 9 | H₂C-(2-fluoro-5-cyanophenyl) | H | SRS12-54 (85%) |

TABLE 8-continued

Synthesis of ferrostatin analogs

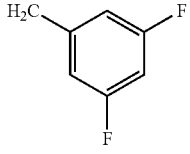

| Entry | R₁ | R₂ | Name (Yield) |
|---|---|---|---|
| 10 | 3,5-difluorobenzyl | H | SRS12-59 (86%) |
| 11 | 3-bromo-5-fluorobenzyl | H | SRS12-52 (89%) |
| 12 | 3,5-dimethoxybenzyl | H | SRS12-53 (85%) |
| 13 | 4-(methoxycarbonyloxy)benzyl | H | 4MO43 (55%) |
| 14 | $R_{1d}$ = 4-(alkoxycarbonyl)benzyl | H | SRS12-80; $R_2$ = $CH_3$ (86%) |
| 15 | $R_{1d}$ | H | SRS12-84; $R_2$ = $CH_2CH_3$ (88%) |

Synthesis of Single Isomer of ethyl 3-(benzylamino)-4-(4-tert-butylcyclohexylamino)benzoate (SRS13-29, Table 8, Entry 1)

Following the above general procedure C or D, the crude reaction mixture was purified by column chromatography (dichloromethane:methanol=200:1) to provide the desired ethyl 3-(benzylamino)-4-(4-tert-butylcyclohexylamino)-benzoate (SRS13-29, Table 8, entry 1) (60.9 mg, 0.149 mmol, 95%). ¹H NMR (CDCl₃, 400 MHz) δ 7.62 (d, J=8.3, 1H), 7.48-7.32 (m, 6H), 6.65 (d, J=8.3 Hz, 1H), 4.35-4.29 (m, 4H), 3.36 (b, 1H), 2.19 (s, 2H), 1.86 (s, 2H), 1.38 (t, J=7.1, 0.8 Hz, 3H), 1.22-1.15 (m, 4H), 1.09-1.03 (m, 1H), 0.90 (s, 9H); $^{13}$C NMR (100 MHz, CDCl$_3$) δ 167.3, 141.9, 139.2, 134.8, 128.7, 128.3, 127.5, 123.6, 118.8, 114.5, 109.3, 60.2, 52.1, 49.5, 47.6, 33.8, 32.4, 27.6, 26.2, 14.5; HRMS (FAB) calculated for C$_{26}$H$_{36}$N$_2$O$_2$: 408.58; found: 408.28.

Synthesis of ethyl 4-(cyclohexylamino)-3-(naphthalen-2-ylmethylamino)-benzoate (SRS12-51, Table 8, Entry 2)

Following the above general procedure C or D, the crude reaction mixture was purified by column chromatography (dichloromethane:methanol=200:1) to provide the desired ethyl 4-(cyclohexylamino)-3-(naphthalen-2-ylmethylamino)-benzoate (SRS12-51, Table 8, entry 2) (41.9 mg, 0.104 mmol, 91%). $^1$H NMR (CDCl$_3$, 400 MHz) δ 7.87-7.82 (m, 4H), 7.63-7.60 (m, 1H), 7.55 (d, J=5.0 Hz, 1H), 7.51 (s, 1H), 7.50-7.48 (m, 2H), 6.64 (d, J=8.4 Hz, 1H), 4.46 (s, 2H), 4.31 (q, J=7.1 Hz, 2H), 3.93 (s, NH,) 3.34 (b, 1H), 3.24 (b, NH), 2.09-2.03 (m, 2H), 1.79-1.63 (m, 3H), 1.45-1.33 (m, 5H), 1.27-1.19 (m, 3H); $^{13}$C NMR (100 MHz, CDCl$_3$) δ 167.3, 142.0, 136.7, 134.8, 133.5, 132.86, 128.4, 127.8, 127.7, 126.7, 126.4, 126.2, 125.9, 123.8, 118.9, 114.8, 109.4, 60.2, 51.4, 49.7, 33.3, 25.9, 25.0, 14.5; HRMS (FAB) calculated for C$_{26}$H$_{30}$N$_2$O$_2$: 402.53; found: 402.23.

Synthesis of ethyl 4-(cyclohexylamino)-3-(pyridin-2-ylmethylamino)-benzoate (SRS12-46, Table 8, Entry 3)

Following the above general procedure C or D, the crude reaction mixture was purified by column chromatography (dichloromethane:methanol=40:1) to provide the desired ethyl 4-(cyclohexylamino)-3-(pyridin-2-ylmethylamino)-benzoate (SRS12-46, Table 8, entry 3) (34 mg, 0.097 mmol, 85%). $^1$H NMR (CDCl$_3$, 400 MHz) δ 8.62 (d, J=4.4 Hz, 1H), 7.71-7.67 (m, 1H), 7.61-7.59 (m, 1H), 7.42 (s, 1H), 7.34 (d, J=8.0 Hz, 1H), 7.28 (s, 1H), 7.24-7.21 (m, 1H), 6.64 (d, J=8.4 Hz, 1H), 4.45 (s, 2H), 4.32 (q, J=7.2, 2H), 3.36 (b, 1H), 2.12-2.09 (m, 2H), 1.85-1.66 (m, 3H), 1.46-1.34 (m, 5H), 1.32-1.24 (m, 3H); $^{13}$C NMR (100 MHz, CDCl$_3$) δ 167.3, 158.1, 149.2, 142.1, 136.7, 134.6, 123.6, 122.3, 122.2, 118.6, 114.7, 109.2, 51.4, 50.1, 33.3, 26.1, 25.9, 25.0, 14.5; HRMS (FAB) calculated for C$_{21}$H$_{27}$N$_3$O$_2$: 353.46; found: 353.21.

Synthesis of ethyl 4-(cyclohexylamino)-3-(pyridin-3-ylmethylamino)-benzoate (SRS13-12)

Following the above general procedure C or D, the crude reaction mixture was purified by column chromatography (dichloromethane:methanol=40:1) to provide the desired ethyl 4-(cyclohexylamino)-3-((pyridin-4-ylmethyl)amino)-benzoate (SRS13-12, Table 8, entry 4) (35 mg, 0.099 mmol, 87%). $^1$H NMR (CDCl$_3$, 400 MHz) δ 8.70 (d, J=2.3 Hz, 1H), 8.59-8.56 (m, 1H), 7.75 (d, J=7.6 Hz, 1H), 7.64-7.53 (m, 1H), 7.44 (s, 1H), 7.37-7.26 (m, 1H), 6.66 (d, J=8.8 Hz, 1H), 4.36-4.31 (m, 4H) 3.39-3.33 (b, 1H), 2.13-2.01 (m, 2H), 1.87-1.75 (m, 2H), 1.71-1.66 (m, 1H), 1.43-1.33 (m, 5H), 1.30-1.20 (m, 3H); $^{13}$C NMR (100 MHz, CDCl$_3$) δ 167.2, 149.3, 148.6, 136.1, 134.0, 124.18, 123.7, 115.1, 112.3, 109.6, 60.3, 51.5, 46.9, 33.29, 31.3, 25.83, 24.9, 14.5; HRMS (FAB) calculated for C$_{21}$H$_{27}$N$_3$O$_2$: 353.46; found: 354.12.

Synthesis of ethyl 4-(cyclohexylamino)-3-((pyridin-4-ylmethyl)amino)-benzoate (SRS12-45, Table 8, Entry 5)

Following the above general procedure C or D, the crude reaction mixture was purified by column chromatography (dichloromethane:methanol=40:1) to provide the desired ethyl 4-(cyclohexylamino)-3-((pyridin-4-ylmethyl)amino)-benzoate (SRS12-45, Table 8, entry 5) (40 mg, 0.114 mmol, 90%). $^1$H NMR (CDCl$_3$, 400 MHz) δ 8.50 (d, J=1.2 Hz, 1H), 7.62 (d, J=7.6 Hz, 1H), 7.35 (s, 1H), 6.66 (d, J=8.4 Hz, 1H), 4.37-4.28 (m, 4H), 3.36 (b, 1H), 2.11-2.08 (m, 2H), 1.84-1.76 (m, 2H), 1.76-1.70 (m, 1H), 1.44-1.33 (m, 4H), 1.29-1.22 (m, 3H); $^{13}$C NMR (100 MHz, CDCl$_3$) δ 167.08, 150.04, 148.31, 142.06, 133.98, 124.05, 122.63, 118.98, 115.01, 109.73, 60.22, 51.44, 48.06, 33.34, 25.85, 24.91, 14.44: HRMS (FAB) calculated for C$_{21}$H$_{27}$N$_3$O$_2$: 353.46; found: 354.21.

Synthesis of ethyl 4-(4-tert-butylcyclohexylamino)-3-(pyridin-4-ylmethylamino)benzoate (SRS13-30, Table 8, Entry 6)

Following the above general procedure C or D, the crude reaction mixture was purified by column chromatography (dichloromethane:methanol=40:1) to provide the desired ethyl 4-(4-tert-butylcyclohexylamino)-3-(pyridin-4-ylmethylamino)benzoate (SRS13-30, Table 8, entry 6) (57 mg, 0.139 mmol, 89%). $^1$H NMR (CDCl$_3$, 400 MHz) δ 8.63-8.55 (m, 2H), 7.62 (dd, J=8.4, 1.9 Hz, 1H). 7.38-7.30 (m, 3H), 6.67 (d, J=8.4 Hz, 1H), 4.37 (s, 2H), 4.31 (q, J=7.1 Hz, 2H), 3.30-3.24 (m, 1H), 2.28-2.16 (m, 2H), 1.93-1.82 (m, 2H), 1.36 (t, J=7.1 Hz, 3H), 1.24-1.16 (m, 4H,), 1.11-1.05 (m, 1H), 0.91 (s, 9H); $^{13}$C NMR (100 MHz, CDCl$_3$) δ 167.1, 150.0, 148.3, 142.2, 134.0, 124.0, 122.6, 119.0, 114.9, 109.8, 60.2, 52.1, 48.1, 47.7, 33.9, 32.4, 27.6, 26.2, 14.4; HRMS (FAB) calculated for C$_{25}$H$_{35}$N$_3$O$_2$: 409.56; found: 409.27.

Synthesis of ethyl 4-(cyclohexylamino)-3-(pyrimidin-5-ylmethylamino)-benzoate (SRS13-35, Table 8, Entry 7)

Following the above general procedure C or D, the crude reaction mixture was purified by column chromatography (dichloromethane:methanol=40:1) to provide the desired ethyl 4-(cyclohexylamino)-3-(pyrimidin-5-ylmethylamino)-benzoate (SRS13-35, Table 8, entry 7) (62 mg, 0.175 mmol, 92%). $^1$H NMR (CDCl$_3$, 400 MHz) δ 9.17 (s, 1H), 8.63 (d, J=5.1 Hz, 1H), 7.57 (d, J=8.3 Hz, 1H), 7.34-7.27 (m, 2H), 6.62 (d, J=8.4 Hz, 1H), 4.41 (s, 2H), 4.26 (q, J=7.1 Hz, 2H), 4.15 (s, 2H), 3.34 (b, 1H), 2.07 (d, J=11.8 Hz, 2H), 1.77 (d, J=13.1 Hz, 2H), 1.66 (d, J=12.1 Hz, 1H), 1.39-1.21 (m, 8H); $^{13}$C NMR (100 MHz, CDCl$_3$) δ 167.1, 158.6, 157.0, 141.9, 133.8, 123.8, 119.3, 118.7, 114.4, 109.5, 60.2, 51.4, 49.3, 33.2, 25.8, 24.9, 14.5; HRMS (FAB) calculated for C$_{20}$H$_{26}$N$_4$O$_2$: 354.45; found: 354.20.

Synthesis of ethyl 4-(4-tert-butylcyclohexylamino)-3-(pyrimidin-5-ylmethylamino)benzoate (SRS13-37, Table 8, Entry 8)

Following the above general procedure C or D, the crude reaction mixture was purified by column chromatography (dichloromethane:methanol=40:1) to provide the desired ethyl 4-(4-tert-butylcyclohexylamino)-3-(pyrimidin-5-ylmethylamino)benzoate (SRS13-37, Table 8, entry 8) (56 mg, 0.137 mmol, 88%). $^1$H NMR (CDCl$_3$, 400 MHz) δ 9.23 (s, 1H), 8.74-8.64 (m, 1H), 7.62 (s, 1H), 7.41-7.31 (m, 2H), 6.66 (d, J=8.4 Hz, 1H), 4.47 (s, 2H), 4.31 (d, J=10.0 Hz, 2H), 4.04 (d, J=16.2 Hz, 2H), 2.23 (s, 2H), 1.89 (s, 2H), 1.35 (t, J=7.1 Hz, 3H), 1.21 (s, 4H), 1.09 (d, J=9.0 Hz, 1H), 0.92-0.088 (s, 9H); $^{13}$C NMR (100 MHz, CDCl$_3$) δ 166.9, 158.7, 157.1, 142.1, 133.8, 123.9, 119.3, 118.8, 114.6, 109.6, 60.2, 52.1, 49.3, 47.7, 33.8, 32.4, 27.6, 26.2, 14.5; HRMS (FAB) calculated for C$_{24}$H$_{34}$N$_4$O$_2$: 410.55; found: 410.27.

Synthesis of ethyl 3-(3-cyano-4-fluorobenzy-lamino)-4-(cyclohexylamino)-benzoate (SRS12-54, Table 8, Entry 9)

Following the above general procedure C or D, the crude reaction mixture was purified by column chromatography (dichloromethane:methanol=100:1) to provide the desired ethyl 3-(3-cyano-4-fluorobenzylamino)-4-(cyclohexy-lamino)-benzoate (SRS12-54, Table 8, entry 9) (38 mg, 0.096 mmol, 85%). $^1$H NMR (CDCl$_3$, 400 MHz) δ 7.70-7.65 (m, 1H), 7.62-7.60 (m, 2H), 7.31 (s, 1H), 7.20 (t, J=8.8 Hz, 1H), 6.65 (d, J=8.4 Hz, 1 H), 4.34-4.27 (m, 4H), 3.35 (b, 1H), 2.10-2.04 (m, 2H), 1.83-1.75 (m, 2H), 1.72-1.65 (m, 1H), 1.45-1.31 (m, 5H), 1.29-1.19 (m, 3H); $^{13}$C NMR (100 MHz, CDCl$_3$) δ 167.1, 163.7, 161.1, 142.1, 136.4, 134.4, 133.6, 132.5, 124.2, 118.9, 116.5, 115.0, 113.9, 109.8, 60.3, 51.5, 47.8, 33.4, 25.84, 24.9, 14.4; $^{19}$F (CDCl$_3$) δ −107.7; HRMS (FAB) calculated for C$_{23}$H$_{26}$FN$_3$O$_2$: 395.47; found: 395.08. Synthesis of ethyl 4-(cyclohexylamino)-3-(3,5-difluorobenzylamino)-benzoate (SRS12-59, Table 8, Entry 10)

Following the above general procedure C or D, the crude reaction mixture was purified by column chromatography (dichloromethane:methanol=200:1) to provide the desired ethyl 4-(cyclohexylamino)-3-(3,5-difluorobenzylamino)-benzoate (SRS12-59, Table 8, entry 10) (38 mg, 0.098 mmol, 86%). $^1$H NMR (CDCl$_3$, 400 MHz) δ 7.62 (d, J=8.0 Hz, 1H), 7.37 (s, 1H), 7.30-6.95 (d, J=6.8 Hz, 2H), 6.76-6.72 (m, 1H), 6.65 (d, J=8.4 Hz, 1H), 4.32-4.30 (m, 4H), 3.93 (b, NH), 3.36 (b, 1H), 3.28 (b, NH), 2.11-2.08 (m, 2H), 1.82-1.79 (m, 2H), 1.71-1.69 (m, 1H), 1.47-1.33 (m, 5H), 1.31-1.20 (m, 3H); $^{13}$C NMR (100 MHz, CDCl$_3$) δ 167.1, 164.5, 162.0, 143.4, 142.1, 134.0, 124.1, 118.9, 115.0, 110.5, 109.7, 102.7, 60.2, 51.4, 48.6, 33.3, 25.86, 24.9, 14.4; $^{19}$F (CDCl$_3$) δ −108.7; HRMS (FAB) calculated for C$_{22}$H$_{26}$F$_2$N$_2$O$_2$: 388.45; found: 388.00.

Synthesis of ethyl 3-(3-bromo-5-fluorobenzy-lamino)-4-(cyclohexylamino)-benzoate (SRS12-52, Table 8, Entry 11)

Following the above general procedure C or D, the crude reaction mixture was purified by column chromatography (dichloromethane:methanol=200:1) to provide the desired ethyl 3-(3-bromo-5-fluorobenzylamino)-4-(cyclohexy-lamino)-benzoate (SRS12-52, Table 8, entry 11) (46 mg, 0.102 mmol, 89%). $^1$H NMR (CDCl$_3$, 400 MHz) δ 7.60 7.61 (dd, J=8.4, 1.9 Hz, 1H), 7.35 (d, J=1.8 Hz, 2H), 7.17 (dt, J=8.1, 2.1 Hz, 1H), 7.06 (d, J=9.2 Hz, 1H), 6.64 (d, J=8.4 Hz, 1H), 4.33-4.27 (m, 4H), 3.91 (s, NH), 3.34 (b, 1H), 3.24 (s, NH), 2.12-2.03 (m, 2H), 1.84-1.75 (m, 2H), 1.72-1.65 (m, 1H), 1.45-1.32 (m, 5H), 1.29-1.21 (m, 3H); $^{13}$C NMR (100 MHz, CDCl$_3$) δ 167.1, 164.1, 161.6, 143.5, 142.1, 134.0, 126.7, 124.1, 122.7, 118.2, 115.1, 113.8, 109.7, 60.2, 51.5, 48.4, 33.3, 25.9, 24.9, 14.4; $^{19}$F (CDCl$_3$) −109.6; HRMS (FAB) calculated for C22H$_{26}$BrFN$_2$O$_2$: 449.36; found: 450.00.

Synthesis of ethyl 4-(cyclohexylamino)-3-(3,5-di-methoxybenzylamino)-benzoate (SRS12-53, Table 8, Entry 12)

Following the above general procedure C or D, the crude reaction mixture was purified by column chromatography (dichloromethane:methanol=200:1) to provide the desired ethyl 4-(cyclohexylamino)-3-(3,5-dimethoxybenzylamino)-benzoate (SRS12-53, Table 8, entry 12) (40 mg, 0.097 mmol, 85%). $^1$H NMR (CDCl$_3$, 400 MHz) δ 7.60 (dd, J=8.3, 1.9 Hz, 1H), 7.44 (d, J=2.0 Hz, 1H), 6.62 (d, J=8.4 Hz, 1H), 6.58 (d, J=2.3 Hz, 2H), 6.42-6.4 (m, 1H), 4.31 (q, J=7.1 Hz, 2H), 4.23 (s, 2H), 3.80 (s, 6H), 3.33 (b, 1H), 2.07-2.04 (m, 2H), 1.79-1.34 (m, 8H), 1.26-1.20 (m, 3H); MS (APCI+, M+1) 412.94

Synthesis of ethyl 4-(cyclohexylamino)-3-(4-(etha-noyloxy)benzylamino)-benzoate (4MO43, Table 8, Entry 13)

Following the above general procedure C or D, the crude reaction mixture was purified by column chromatography (dichloromethane:methanol=40:1) to provide the desired ethyl 4-(cyclohexylamino)-3-(4-(ethanoyloxy)benzy-lamino)-benzoate (4MO43, Table 8, entry 13) (40 mg, 0.097 mmol, 85%). $^1$H NMR (400 MHz, CDCl$_3$) δ 7.61 (dd, J=8.3, 1.9 Hz, 1H), 7.46-7.40 (m, 3H), 7.09 (d, J=8.5 Hz, 2H), 6.63 (d, J=8.5 Hz, 1H), 4.37-4.29 (m, 2H), 4.28 (s, 2H), 3.33 (s, 1H), 2.31 (s, 3H), 2.10-2.03 (m, 2H), 1.78 (d, J=13.4 Hz, 2H), 1.67 (d, J=12.8 Hz, 1H), 1.41 (s, 1H), 1.36 (t, J=7.1 Hz, 4H), 1.27-1.19 (m, 3H); $^{13}$C NMR (126 MHz, CDCl$_3$) δ 169.6, 167.3, 150.0, 142.0, 136.8, 134.61, 129.4, 123.8, 121.8, 118.8, 114.6, 109.3, 60.2, 51.5, 48.9, 33.4, 25.9, 25.0, 21.1, 14.5; HRMS (FAB) calculated for C$_{24}$H$_{30}$N$_2$O$_4$: 410.51; found: 410.22.

Synthesis of ethyl 4-(cyclohexylamino)-3-(4-(methoxycarbonyl)-benzylamino)benzoate (SRS12-80, Table 8, Entry 14)

Following the above general procedure C or D, the crude reaction mixture was purified by column chromatography (dichloromethane:methanol=40:1) to provide the desired ethyl 4-(cyclohexylamino)-3-(4-(methoxycarbonyl)-benzy-lamino)benzoate (SRS12-80, Table 8, entry 14) (40.2 mg, 0.098 mmol, 86%). $^1$H NMR (CDCl$_3$, 400 MHz) δ 8.07-7.99 (m, 2H), 7.60 (dd, J=8.4, 1.9 Hz, 1H), 7.51-7.44 (m, 2H), 7.40 (d, J=1.9 Hz, 1H), 6.64 (d, J=8.4 Hz, 1H), 4.37 (s, 2H), 4.30 (q, J=7.1 Hz, 2H), 3.92 (d, J=0.6 Hz, 3H), 3.89 (d, J=0.7 Hz, 1H), 3.39-3.29 (m, 1H), 2.11-2.02 (m, 2H), 1.83-1.73 (m, 2H), 1.72-1.62 (m, 1H), 1.48-1.30 (m, 5H), 1.30-1.16 (m, 3H); $^{13}$C NMR (100 MHz, CDCl$_3$) δ 167.2, 166.9, 144.5, 142.0, 134.3, 130.0, 128.7, 127.8, 123.9, 118.9, 114.9, 109.5, 60.2, 52.1, 51.4, 49.0, 33.3, 25.9, 24.9, 14.5; HRMS (FAB) calculated for C$_{24}$H$_{30}$N$_2$O$_4$: 410.51; found: 410.10.

Synthesis of ethyl 4-(cyclohexylamino)-3-(4-(ethoxycarbonyl)benzylamino)-benzoate (SRS12-84, Table 8, Entry 15)

Following the above general procedure C or D, the crude reaction mixture was purified by column chromatography (dichloromethane:methanol=40:1) to provide the desired ethyl 4-(cyclohexylamino)-3-(4-(ethoxycarbonyl)benzy-lamino)-benzoate (SRS12-84, Table 8, entry 15) (42.7 mg, 0.1 mmol, 88%). $^1$H NMR (CDCl$_3$, 400 MHz) δ 8.05 (d, J=8.3 Hz, 2H), 7.61 (dd, J=8.3, 1.9 Hz, 1H), 7.48 (d, J=8.3 Hz, 2H), 7.41 (d, J=1.8 Hz, 1H), 6.66-6.62 (m, 1H), 4.41-4.36 (m, 4H), 4.30 (t, J=7.1 Hz, 2H), 3.35 (s, 1H), 3.11 (d, J=7.5 Hz, 1H), 2.07 (d, J=12.8 Hz, 2H), 1.79 (d, J=13.4 Hz, 2H), 1.68 (d, J=13.0 Hz, 1H), 1.44-1.36 (m, 8H), 1.26 (d, J=7.9 Hz, 3H); $^{13}$C NMR (100 MHz, CDCl$_3$) δ 167.2, 166.4, 144.3, 142.0, 134.3, 129.9, 129.6, 128.7, 127.8, 123.9, 118.9, 114.9, 109.5, 60.9, 60.2, 57.8, 51.4, 49.0, 33.3, 25.9, 24.9, 14.5; HRMS (FAB) calculated for $C_{25}H_{32}N_2O_4$: 424.53; found: 424.12.

4.30-4.21 (m, 2H), 4.08-3.92 (m, 1H), 3.36 (s, 1H), 2.07-1.56 (m, 10H), 1.42-1.24 (m, 3H), MS (APCI+, M+1) 264.26.

Synthesis of ethyl 5-(benzylamino)-6-(cyclohexylamino)pyridine-3-carboxylate (SRS14-91, Scheme 7)

Following the above general procedure C or D, the crude reaction mixture was purified by column chromatography

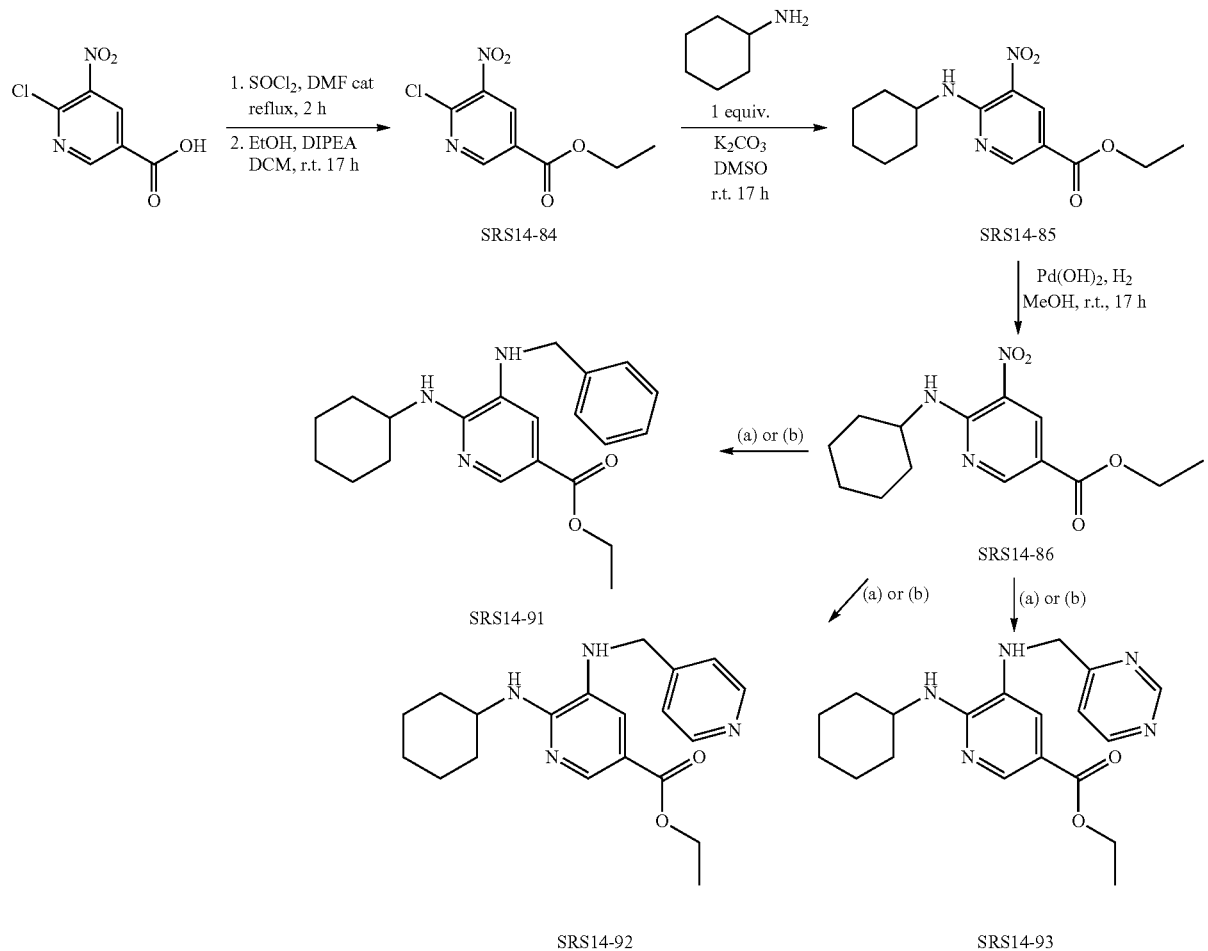

Scheme 7. Synthesis of Ferrostation analogs SRS14-86, SRS14-91, SRS14-92, SRS14-93. (a) alkylation reaction: arylhalide, DIPEA, THF, 60° C., 17 h. (b) reductive amination reaction: arylhaldehyde, NaBH(OAc)$_3$, molecular sieve (4 Å), DCE, r.t. to 80° C., 17 h.

Synthesis of ethyl 5-amino-6-(cyclohexylamino)pyridine-3-carboxylate (SRS14-86, Scheme 7)

Following the above general procedure A and B and starting from the ethyl ester (SRS14-84, Scheme 8), which was prepared from the corresponding acid, the crude reaction mixture was purified by column chromatography (dichloromethane:methanol=20:1) to provide the desired ethyl 5-amino-6-(cyclohexylamino)pyridine-3-carboxylate (SRS14-86, Scheme 8) (195 mg, 0.739 mmol, 85% (2 steps)). $^1$H NMR (400 MHz, CDCl$_3$) δ 8.42 (d, J=2.0 Hz, 1H), 7.36 (d, J=2.0 Hz, 1H), 4.78 (d, J=7.6 Hz, 1H), (dichloromethane:methanol=40:1) to provide the desired ethyl 5-(benzylamino)-6 (cyclohexylamino)-pyridine-3-carboxylate (SRS14-91, Scheme 8) (14.8 mg, 0.04 mmol, 53%). $^1$H NMR (500 MHz, CDCl$_3$) δ 8.49 (d, J=1.9 Hz, 1H), 7.40 (dd, J=34.8, 27.7 Hz, 5H), 4.59 (s, 1H), 4.47-4.25 (m, 4H), 4.08 (s, 1H), 2.11-1.51 (m, 10H), 1.38 (t, J=11.5, 4.4 Hz, 3H); MS (APCI+, M+1) 354.66.

Synthesis of ethyl 6-(cyclohexylamino)-5-(pyridin-4-ylmethylamino)pyridine-3-carboxylate (SRS14-92, Scheme 7)

Following the above general procedure C or D, the crude reaction mixture was purified by column chromatography (dichloromethane:methanol=20:1) to provide the desired ethyl 6-(cyclohexylamino)-5-(pyridin-4-ylmethylamino)-pyridine-3-carboxylate (SRS14-92, Scheme 8) (16 mg, 0.045 mmol, 54%), $^1$H NMR (400 MHz, CDCl$_3$) δ 8.55 (d, J=50.9 Hz, 3H), 7.46-7.15 (m, 3H), 4.67 (s, 1H), 4.40-4.25 (m, 2H), 4.07 (s, 2H), 2.10-1.62 (m, 10H), 1.40-1.19 (m, 3H); MS (APCI+, M+1) 355.36.

Synthesis of ethyl 6-(cyclohexylamino)-5-(pyrimidin-4 ylmethylamino)-pyridine-3-carboxylate (SRS14-93, Scheme 7)

Following the above general procedure C or D, the crude reaction mixture was purified by column chromatography (dichloromethane:methanol=15:1) to provide the desired ethyl 6-(cyclohexylamino)-5-(pyrimidin-4 ylmethylamino)-pyridine-3-carboxylate (SRS14-93, Scheme 8) (18 mg, 0.051 mmol, 58%). $^1$H NMR (500 MHz, CDCl$_3$) δ 9.26 (s, 1H), 8.74 (d, J=5.1 Hz, 1H), 8.49 (d, J=1.8 Hz, 1H), 7.37 (d, J=5.1 Hz, 1H), 7.32 (d, J=1.8 Hz, 1H), 4.40 (d, J=40.5 Hz, 2H), 4.34 (dd, J=14.2, 7.1 Hz, 2H), 4.11 (s, 1H), 2.11-1.48 (m, 10H), 1.42-1.31 (m, 3H); MS (APCI+, M+1) 356.26.

Synthesis of ethyl 3-amino-4-(1-adamantylamino)benzoate (SRS15-18, Scheme 8)

Following the above general procedure A and B and starting from the commercially available ethyl 4-chloro-3-nitrobenzoate (Scheme 8), the crude reaction mixture was purified by column chromatography (dichloromethane:methanol=40:1) to provide the desired ethyl 3-amino-4-(1-adamantylamino)-benzoate (SRS15-18, Scheme 9) (649 mg, 2.067 mmol, 95% (2 steps)). $^1$H NMR (500 MHz, CDCl$_3$) δ 7.52 (d, J=8.1 Hz, 1H), 7.43 (s, 1H), 6.93 (d, J=8.1 Hz, 1H), 4.34-4.27 (m, 2H), 2.15-1.72 (m, 15H), 1.36, (t, J=6.6 Hz, 3H); MS (APCI+, M+1) 315.36.

Synthesis of ethyl 3-(benzylamino)-4-(1-adamantylamino)benzoate (SRS15-23, Scheme 8)

Following the above general procedure C or D, the crude reaction mixture was purified by column chromatography (dichloromethane:methanol=100:1) to provide the desired ethyl 3-(benzylamino)-4-(1-adamantylamino)benzoate (SRS15-23, Scheme 9) (26 mg, 0.064 mmol, 68%). $^1$H NMR Scheme 8. Synthesis of Ferrostation analogs SRS15-18, SRS15-23, SRS15-24, SRS15-25. (a) alkylation reaction: arylhalide, DIPEA, THF, 60° C., 17 h. (b) reductive amination reaction: arylhaldehyde, NaBH(OAc)$_3$, molecular sieve (4 Å), DCE, r.t. to 80° C., 17 h.

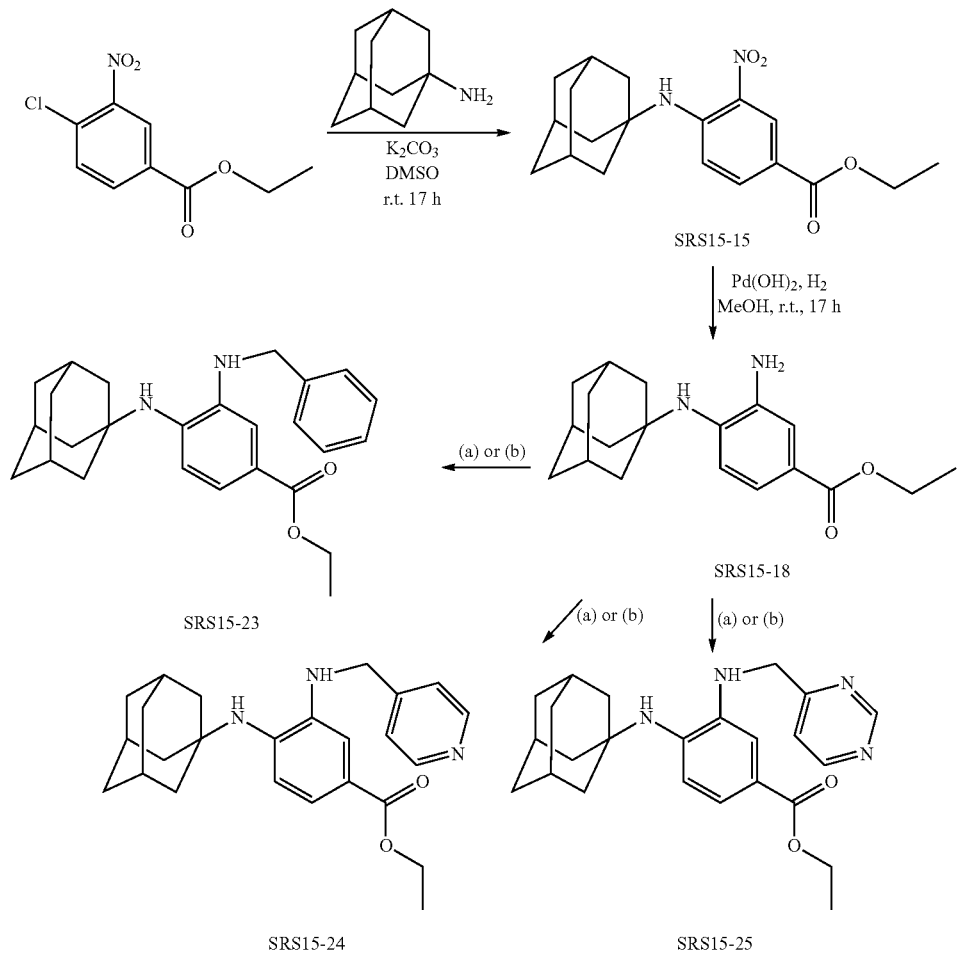

(400 MHz, CDCl₃) δ 7.54 (dd, J=8.1, 1.5 Hz, 1H), 7.49-7.27 (m, 7H), 6.98 (dd, J=11.3, 4.7 Hz, 1H), 4.37-4.28 (m, 4H), 3.69 (s, 1H), 2.16 (s, 3H), 1.98 (s, 6H), 1.72 (s, 6H), 1.38 (ddd, J=7.1, 5.8, 1.6 Hz, 3H); MS (APCI+, M+1) 405.36.

Synthesis of ethyl 4-(1-adamantylamino)-3-((pyridin-4-ylmethyl)amino)-benzoate (SRS15-24, Scheme 8)

Following the above general procedure C or D, the crude reaction mixture was purified by column chromatography (dichloromethane:methanol=40:1) to provide the desired ethyl 4-(1-adamantylamino)-3-((pyridin-4-ylmethyl)amino)-benzoate (SRS15-24, Scheme 9) (27 mg, 0.066 mmol, 70%). ¹H NMR (400 MHz, CDCl₃) δ 8.61 (s, 2H), 7.53 (d, J=8.2 Hz, 1H), 7.38-7.26 (m, 4H), 6.99 (d, J=8.3 Hz, 1H), 4.34 (dd, J=15.7, 8.6 Hz, 4H), 3.89 (s, 1H), 2.17-1.38 (m, 15H), 1.36 (t, J=7.1 Hz, 4H); MS (APCI+, M+1) 406.36.

Synthesis of ethyl 4-(1-adamantylamino)-3-(pyrimidin-5-ylmethylamino)-benzoate (SRS15-25, Scheme 8)

Following the above general procedure C or D, the crude reaction mixture was purified by column chromatography (dichloromethane:methanol=40:1) to provide the desired ethyl 4-(1-adamantylamino)-3-(pyrimidin-5-ylmethylamino)-benzoate (SRS15-25, Scheme 9) (23 mg, 0.056 mmol, 54%). ¹H NMR (400 MHz, CDCl₃) δ 9.24 (s, 1H), 8.71 (t, J=5.0 Hz, 1H), 7.53 (d, J=8.3 Hz, 1H), 7.37 (d, J=4.9 Hz, 1H), 7.31 (s, 1H), 7.00 (d, J=8.4 Hz, 1H), 4.47 (s, 2H), 4.33 (dd, J=9.6, 4.5 Hz, 2H), 2.17-1.40 (m, 15H), 1.36 (t, J=7.1 Hz, 3H); MS (APCI+, M+1) 406.36.

Scheme 9. Synthesis of Ferrostation analogs SRS15-17, SRS15-20, SRS15-21, SRS15-22. (a) alkylation reaction: arylhalide, DIPEA, THF, 60° C., 17 h. (b) reductive amination reaction: arylhaldehyde, NaBH(OAc)₃, molecular sieve (4 Å), DCE, r.t. to 80° C., 17 h.

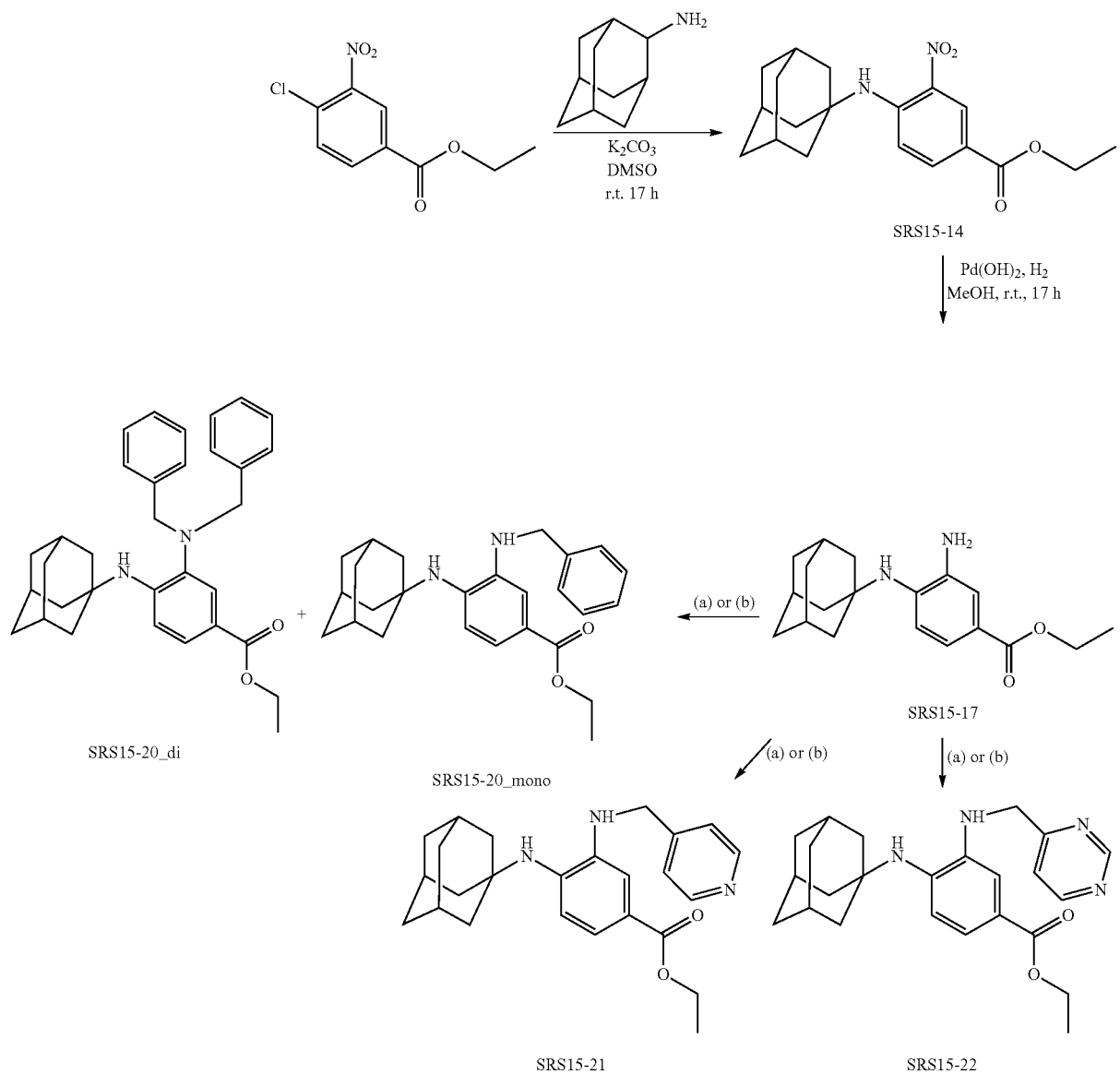

Synthesis of ethyl 3-amino-4-(2-adamantylamino)benzoate (SRS15-17, Scheme 9)

Following the above general procedure A and B and starting from the commercially available ethyl 4-chloro-3-nitrobenzoate (Scheme 9), the crude reaction mixture was purified by column chromatography (dichloromethane:methanol=40:1) to provide the desired ethyl 3-amino-4-(2-adamantylamino)-benzoate (SRS15-17, Scheme 10) (624 mg, 1.98 mmol, 91% (2 steps)). $^1$H NMR (500 MHz, CDCl$_3$) δ 7.60 (s, 1H), 7.45 (s, 1H), 6.57 (s, 1H), 4.86 (s, 1H), 4.34 (d, J=5.4 Hz, 2H), 3.83 (s, 1H), 3.65 (s, 1H), 3.29 (s, 1H), 2.04-1.60 (m, 14H), 1.38 (d, J=3.8 Hz, 3H); MS (APCI+, M+1) 315.36.

Synthesis of ethyl 3-(benzylamino)-4-(2-adamantylamino)benzoate (SRS15-20 Mono, Scheme 9)

Following the above general alkylation reaction (procedure C), the crude reaction mixture was purified by column chromatography (dichloromethane:methanol=100:1) to provide the desired ethyl 3-(benzylamino)-4-(2 adamantylamino)-benzoate (SRS15-20_mono, Scheme 9) (19 mg, 0.047 mmol, 50%) and the dialkylation compound, the ethyl 3-(dibenzylamino)-4-(2-adamantylamino)-benzoate, (SRS15-20_di, Scheme 9) (9 mg, 0.018 mmol, 19%). $^1$H NMR (400 MHz, CDCl$_3$) δ 7.68-7.61 (m, 1H), 7.52 (d, J=1.7 Hz, 1H), 7.49-7.25 (m, 5H), 6.69-6.52 (m, 1H), 4.53 (s, 1H), 4.40-4.29 (m, 4H), 3.67 (s, 1H), 3.23 (s, 1H), 2.09 (s, 2H), 1.99-1.86 (m, 8H), 1.80 (s, 2H), 1.66-1.58 (m, 2H), 1.41-1.36 (m, 3H); MS (APCI+, M+1) 405.36.

Synthesis of ethyl 3-(dibenzylamino)-4-(2-adamantylamino)benzoate (SRS15-20 di, Scheme 9)

$^1$H NMR (400 MHz, CDCl$_3$) δ 7.80 (s, 1H), 7.72 (d, J=8.5 Hz, 1H), 7.28 (dd, J=9.0, 1.4 Hz, 10H), 6.46 (d, J=8.6 Hz, 1H), 5.99 (d, J=7.0 Hz, 1H), 4.38-4.28 (m, 2H), 4.06 (s, 4H), 3.54 (s, 1H), 2.00-1.50 (m, 14H), 1.39 (t, J=7.1 Hz, 3H); MS (APCI+, M+1) 495.36.

Synthesis of ethyl 4-(2-adamantylamino)-3-((pyridin-4-ylmethyl)amino)-benzoate (SRS15-21, Scheme 9)

Following the above general procedure C or D, the crude reaction mixture was purified by column chromatography (dichloromethane:methanol=40:1) to provide the desired ethyl 4-(2-adamantylamino)-3-((pyridin-4-ylmethyl)amino)-benzoate (SRS15-21, Scheme 10) (25 mg, 0.061 mmol, 65%). $^1$H NMR (400 MHz, CDCl$_3$) δ 8.62 (s, 2H), 7.64 (d, J=8.2 Hz, 1H), 7.46-7.31 (m, 3H), 6.63 (d, J=8.4 Hz, 1H), 4.41 (s, 2H), 4.35-4.25 (m, 2H), 3.68 (s, 1H), 2.09 (s, 2H), 1.94 (d, J=15.1 Hz, 8H), 1.81 (s, 2H), 1.72-1.64 (m, 2H), 1.36 (t, J=7.1 Hz, 3H); MS (APCI+, M+1) 406.26.

Synthesis of ethyl 4-(2-adamantylamino)-3-(pyrimidin-5-ylmethylamino)-benzoate (SRS15-22, Scheme 9)

Following the above general procedure C or D, the crude reaction mixture was purified by column chromatography (dichloromethane:methanol=40:1) to provide the desired ethyl 4-(2-adamantylamino)-3-(pyrimidin-5-ylmethylamino)-benzoate (SRS15-22, Scheme 10) (26 mg, 0.064 mmol, 60%). $^1$H NMR (400 MHz, CDCl$_3$) δ 9.24 (s, 1H), 8.71 (d, J=5.1 Hz, 1H), 7.69-7.59 (m, 1H), 7.38 (d, J=2.0 Hz, 2H), 6.63 (d, J=8.4 Hz, 1H), 4.47 (d, J=21.3 Hz, 2H), 4.32 (dd, J=14.2, 7.1 Hz, 2H), 4.15 (s, 1H), 3.69 (s, 1H), 2.04-1.60 (m, 14H), 1.36 (d, J=7.1 Hz, 3H); MS (APCI+, M+1) 407.46.

Synthesis of ethyl 5-amino-4-(cyclohexylamino)-2-fluorobenzoate (SRS14-55, Scheme 10)

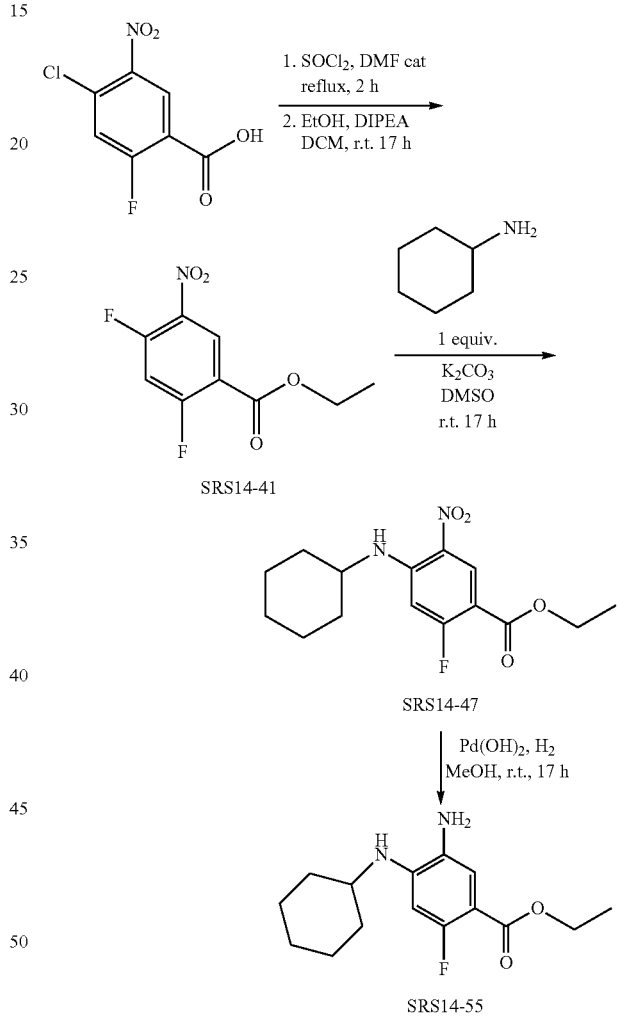

Scheme 10. Synthesis of Ferrostation analog SRS14-55.

Following the above general procedure A and B and starting from the ethyl ester (SRS14-41, Scheme 10), which was prepared from the corresponding acid, the crude reaction mixture was purified by column chromatography (dichloromethane:methanol=20:1) to provide the desired ethyl 5-amino-4-(cyclohexylamino)-2-fluorobenzoate (SRS14-55, Scheme 10) (109 mg, 0.389 mmol, 90% (2 steps)). $^1$H NMR (400 MHz, CDCl$_3$) δ 7.37-7.26 (m, 1H), 6.36-6.23 (m, 1H), 4.34 (dd, J=8.9, 6.2, 1.8 Hz, 2H), 3.27 (s, 1H), 3.01 (s, 1H), 2.07 (d, J=8.6 Hz, 2H), 1.81 (d, J=8.5 Hz, 2H), 1.69 (s, 1H), 1.38 (ddd, J=8.9, 6.3, 3.1 Hz, 5H), 1.27 (s, 3H); MS (APCI+, M+1) 281.36.

165
Synthesis of ethyl 5-amino-2-chloro-4-(cyclohexylamino)benzoate (SRS14-57, Scheme 11)

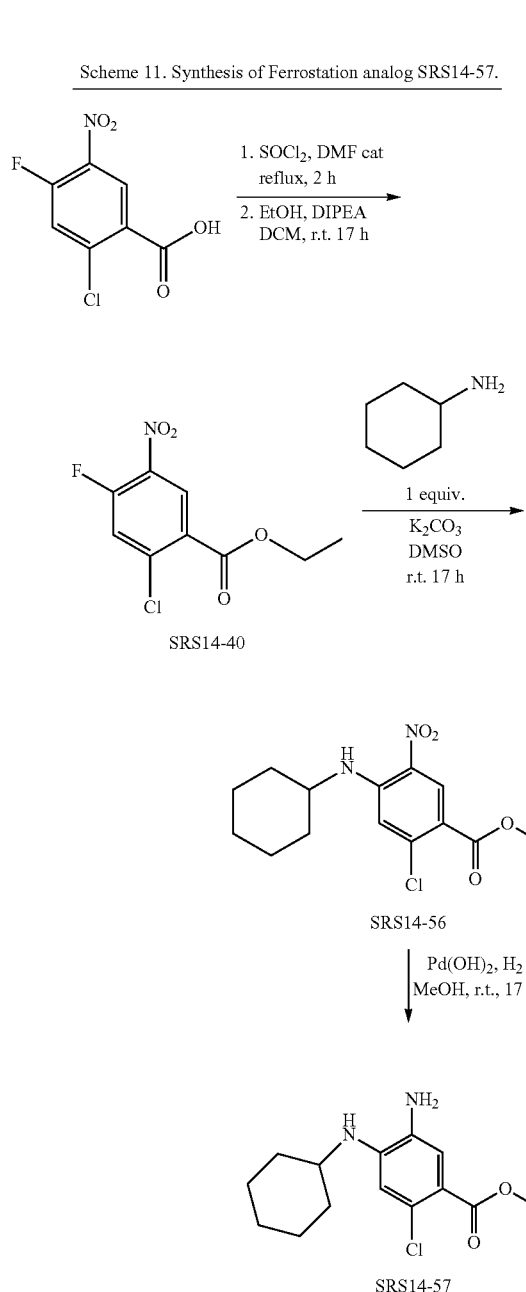

Following the above general procedure A and B and starting from the ethyl ester (SRS14-40, Scheme 11), which was prepared from the corresponding acid, the crude reaction mixture was purified by column chromatography (dichloromethane:methanol=20:1) to provide the desired ethyl 5-amino-2-chloro-4-(cyclohexylamino)benzoate (SRS14-57, Scheme 11) (136 mg, 0.459 mmol, 75% (2 steps)). $^1$H NMR (400 MHz, CDCl$_3$) δ 7.57 (d, J=8.4 Hz, 1H), 7.42 (s, 1H), 6.59 (d, J=8.4 Hz, 1H), 4.17-4.06 (m, 2H), 3.47 (s, 1H), 3.35-3.27 (m, 1H), 1.78 (d, J=13.0 Hz, 2H), 1.67 (d, J=12.0 Hz, 1H), 1.42-1.31 (m, 5H), 1.26 (td, J=7.1, 1.6 Hz, 5H); MS (APCI+, M+1) 297.47.

166
Synthesis of ethyl 5-amino-4-(cyclohexylamino)-2-methylbenzoate (SRS14-58, Scheme 12)

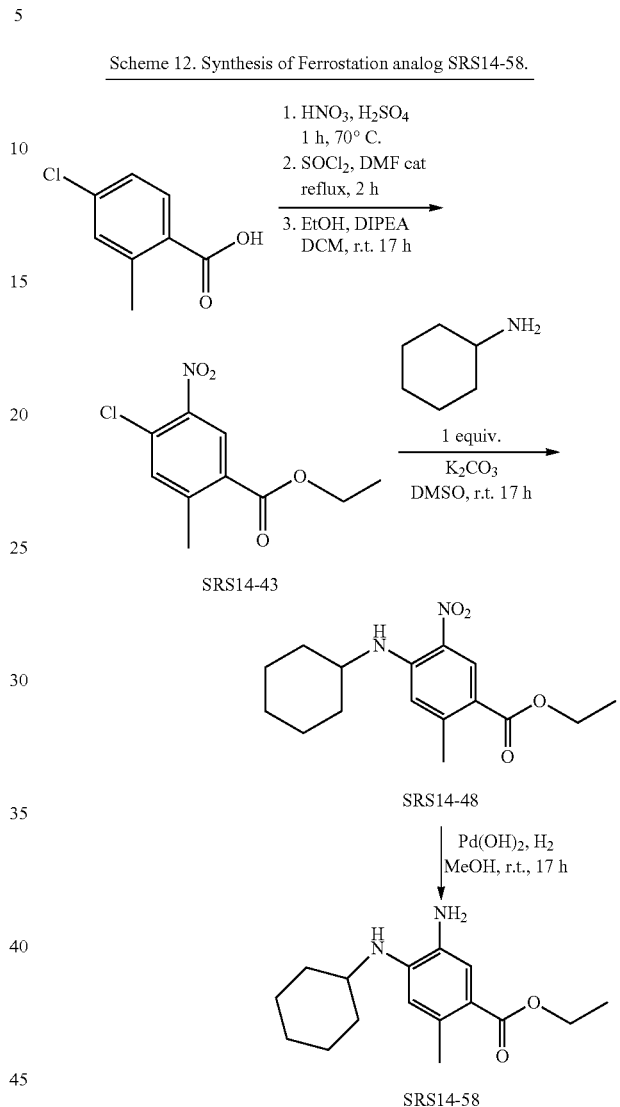

Following the above general procedure A and B, and starting from the ethyl ester (SRS14-43, Scheme 12), which was prepared from the corresponding acid, the crude reaction mixture was purified by column chromatography (dichloromethane:methanol=40:1) to provide the desired ethyl 5-amino-4-(cyclohexylamino)-2-methylbenzoate (SRS14-58, Scheme 12) (18 mg, 0.064 mmol, 83% (2 steps)). $^1$H NMR (400 MHz, CDCl$_3$) δ 7.43 (d, J=2.2 Hz, 1H), 6.41 (s, 1H), 4.30 (dd, J=9.5, 4.6 Hz, 2H), 3.40-3.28 (m, 2H), 2.56 (d, J=2.6 Hz, 3H), 2.09 (d, J=9.3 Hz, 2H), 1.81 (d, J=10.0 Hz, 2H), 1.70 (d, J=8.6 Hz, 1H), 1.39 (ddd, J=14.9, 9.3, 8.1 Hz, 5H), 1.29-1.16 (m, 3H); MS (APCI+, M+1) 277.16.

Example 3

Erastin Triggers Oxidative, Iron-Dependent Cell Death

RSL-induced cell death is a poorly characterized process involving the accumulation of ROS derived from an unknown source and the inhibition of cell death by iron chelation (Yagoda et al., 2007; Yang and Stockwell, 2008). It was observed that these two processes were linked. Treatment of NRAS-mutant HT-1080 fibrosarcoma cells with the RSL molecule erastin (10 μM) resulted in a time-dependent increase in cytosolic and lipid ROS beginning at 2 hours, as assayed by flow cytometry using the fluorescent probes $H_2DCFDA$ and C11-BODIPY, respectively (FIGS. 1B and 1C). This increase in ROS preceded cell detachment and overt death, which began at 6 hours (FIG. 1A). ROS accumulation and cell death were suppressed by co-treatment with the iron chelator deferoxamine (DFO, 100 μM) (FIGS. 1A-C), while incubation with three different exogenous sources of iron, but not by other divalent transition metal ions ($Cu^{2+}$, $Mn^{2+}$, $Ni^{2+}$, $Co^{2+}$), potentiated erastin-induced death (FIGS. 8A and 8B). Because cell death occurred in erastin-treated cells following a prolonged period of ROS accumulation and was suppressed by antioxidants (see below), the data suggest that the overwhelming, iron-dependent accumulation of ROS is what kills these cells.

Because two erastin targets, VDAC2 and VDAC3, reside in the mitochondria, it was hypothesized that erastin-induced death involved aberrant ROS production by the mitochondrial electron transport chain (ETC). However, in erastin-treated (10 μM, 6 hours) HT-1080 cells, no increase in MitoSOX-sensitive mitochondrial ROS production was observed (FIG. 1D, left). The ETC complex I inhibitor rotenone (250 nM, 6 hours) enhanced MitoSOX-sensitive ROS production, but in a manner that was insensitive to DFO (FIG. 1D, right). Furthermore, KRAS-mutant 143B osteosarcoma cells incapable of ETC-dependent ROS formation, due to the depletion of mitochondrial DNA (mtDNA)-encoded transcripts ($\rho^0$ cells), were as sensitive to erastin and RSL3 as matched mtDNA-wild-type ($\rho^+$) cells (FIGS. 1E, 1F, and 8C-E). Thus, erastin-induced cell death in human cancer cells involves DFO-sensitive ROS accumulation and can occur in cells lacking a functional ETC. This iron-dependent death phenotype was named ferroptosis.

Example 4

Ferroptosis is Distinct from Known Forms of Cell Death

Figure 2A:
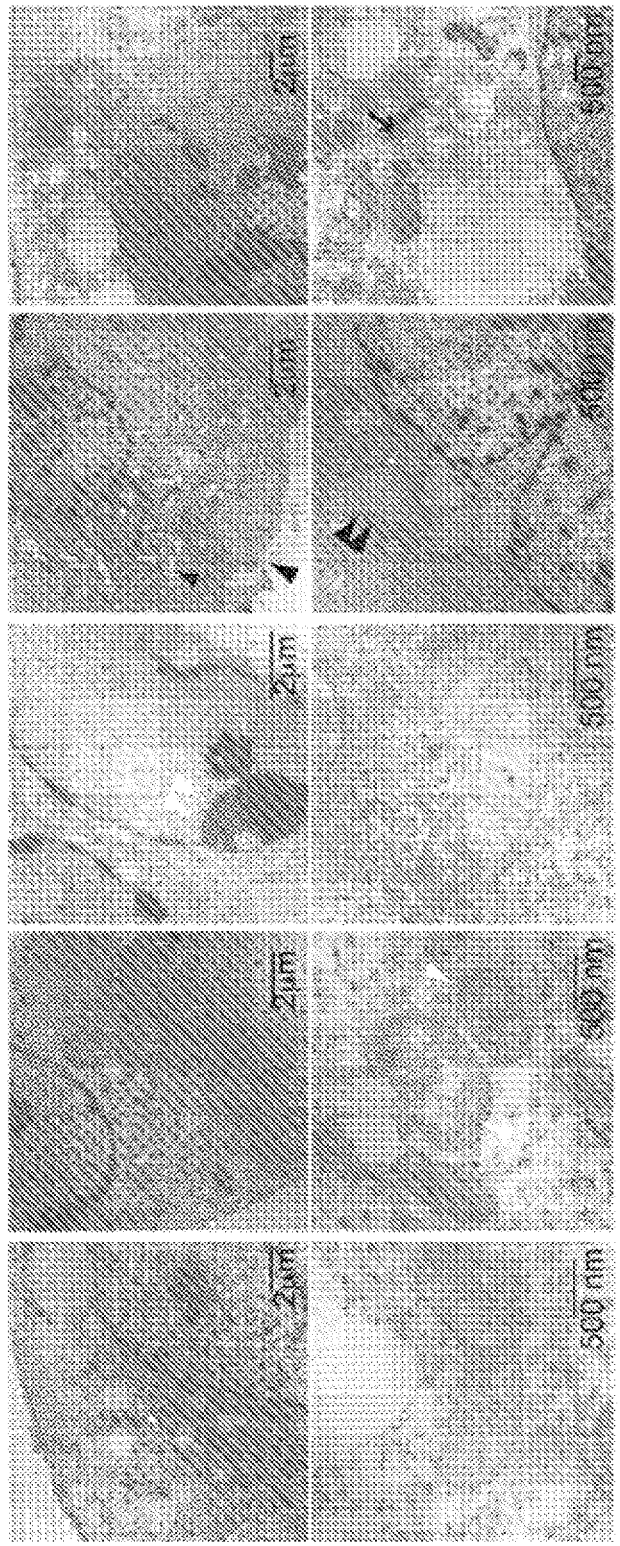
FIG. 2A to FIG. 2E shows that erastin-induced oxidative death is iron-dependent.
Figure 2B:
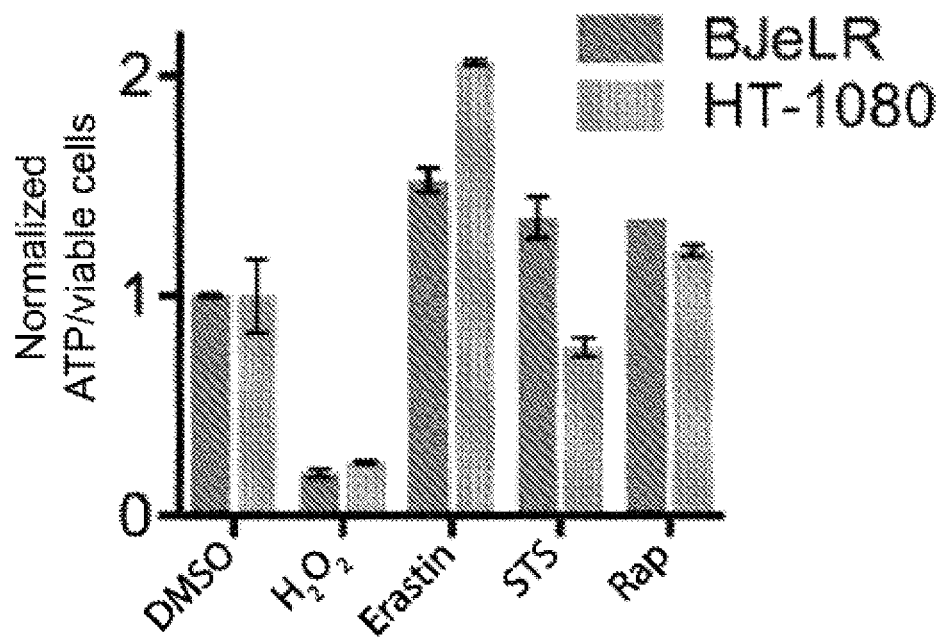

Whether ferroptosis shared morphological, bioenergetic or other similarities with apoptotic or necrotic death, or with autophagy was examined. Using transmission electron microscopy, it was observed that HRAS-mutant BJeLR engineered tumor cells treated with erastin exhibited none of the characteristic morphologic features associated with staurosporine (STS)-induced apoptosis (e.g. chromatin condensation and margination), hydrogen peroxide ($H_2O_2$)-induced necrosis (e.g. cytoplasmic and organelle swelling, plasma membrane rupture) or rapamycin-induced autophagy (e.g. formation of double-membrane enclosed vesicles) (FIG. 2A). The lone distinctive morphological feature of erastin-treated cells were mitochondria that appeared smaller than normal, with increased membrane density, consistent with the previous report (Yagoda et al., 2007) (FIG. 2A). With respect to bioenergetics, substantial depletion of intracellular ATP in BJeLR and HT-1080 cells treated with $H_2O_2$, but not erastin, STS or rapamycin, was observed (FIG. 2B), thus distinguishing ferroptosis from various forms of necrosis that involve bioenergetic failure.

Figure 2C:
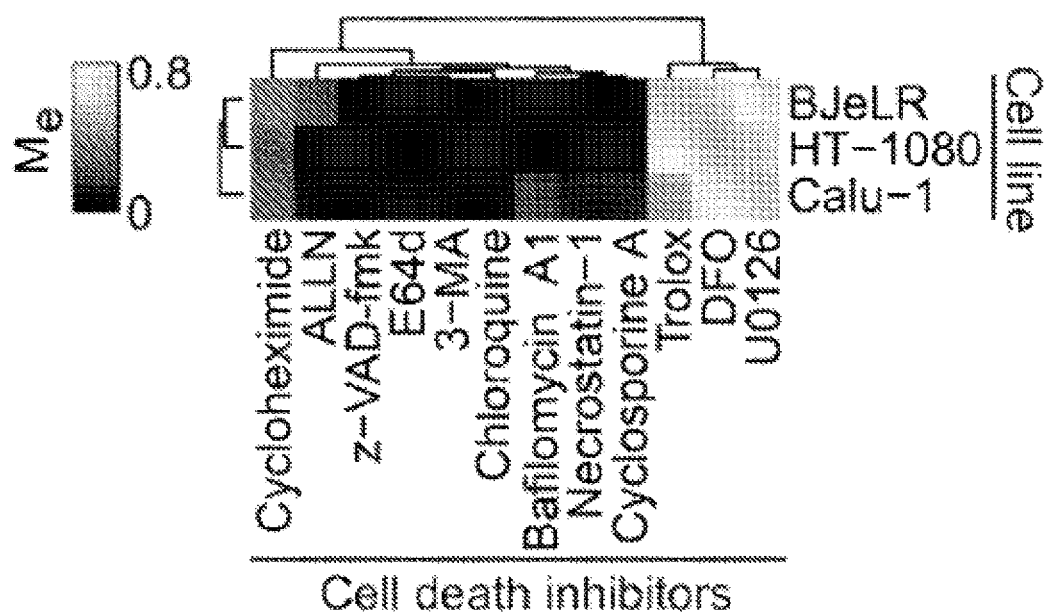

Using a variation of the modulatory profiling strategy (Wolpaw et al., 2011), the ability of twelve established small molecule cell death inhibitors to prevent ferroptosis in HT-1080, BJeLR and KRAS-mutant Calu-1 non-small cell lung cancer cells was tested. The modulatory effect ($M_e$) for each inhibitor (tested in a 10-point, 4-fold dilution series) on the normalized viability of cells treated with a lethal dose of erastin ($M_e$<0: death sensitization; $M_e$=0: no effect; $M_e$>0: death rescue) was computed. The resultant values were clustered hierarchically in an unsupervised fashion and displayed as a heatmap. Using this approach, it was observed that erastin-induced death was not consistently modulated by inhibitors of caspase, cathepsin or calpain proteases (z-VAD-fmk, E64d or ALLN), RIPK1 (necrostatin-1), cyclophilin D (cyclosporin A) or lysosomal function/autophagy (bafilomycin A1, 3-methyladenine, chloroquine), compounds known to inhibit various forms of apoptosis, necrosis and autophagic cell death (FIG. 2C).

Figure 2D:
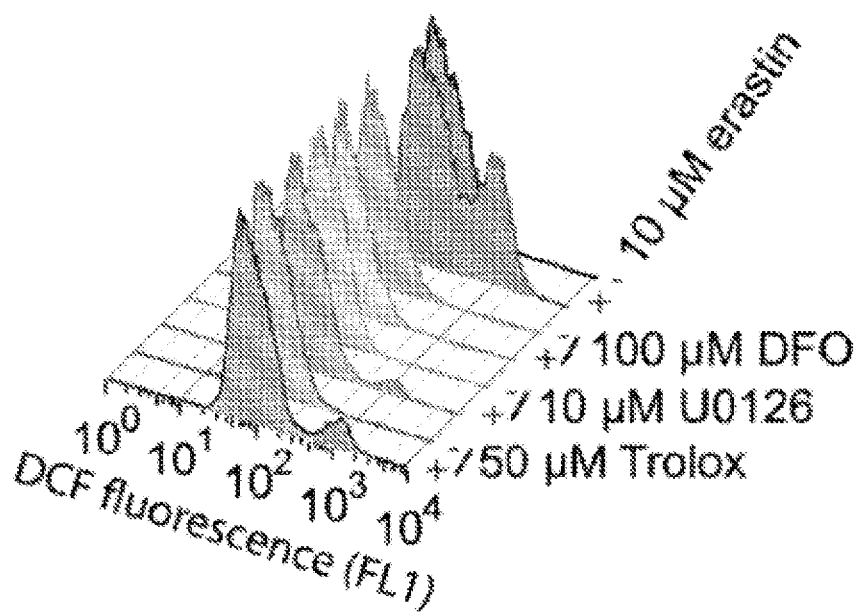

DFO, the anti-oxidant trolox, the MEK inhibitor U0126 and, to a weaker extent, the protein synthesis inhibitor cycloheximide (CHX), all rescued from erastin-induced death in HT-1080, BJeLR and Calu-1 cells (FIG. 2C) (Yagoda et al., 2007). These inhibitors were also effective at preventing erastin-induced ferroptosis in both wild-type and apoptosis-deficient Bax/Bak double knockout (DKO) mouse embryonic fibroblasts (FIGS. 9A and 9B), indicating that ferroptosis can be activated in human- and mouse-derived cells and is independent of the core apoptotic machinery regulated by Bax and Bak. DFO, trolox and U0126 all prevented the accumulation of $H_2DCFDA$-sensitive ROS in erastin-treated HT-1080 cells (FIG. 2D), demonstrating that these inhibitors act to prevent death upstream or at the level of ROS production. Because trolox, U0126 and the membrane permeable iron chelator 2,2-bipyridyl could be added to HT-1080 cells up to 6 hours after erastin and still confer substantial protection from death (FIG. 9C), ferroptosis likely requires continuous iron-dependent ROS formation over an extended period of time to trigger death.

Figure 2E:
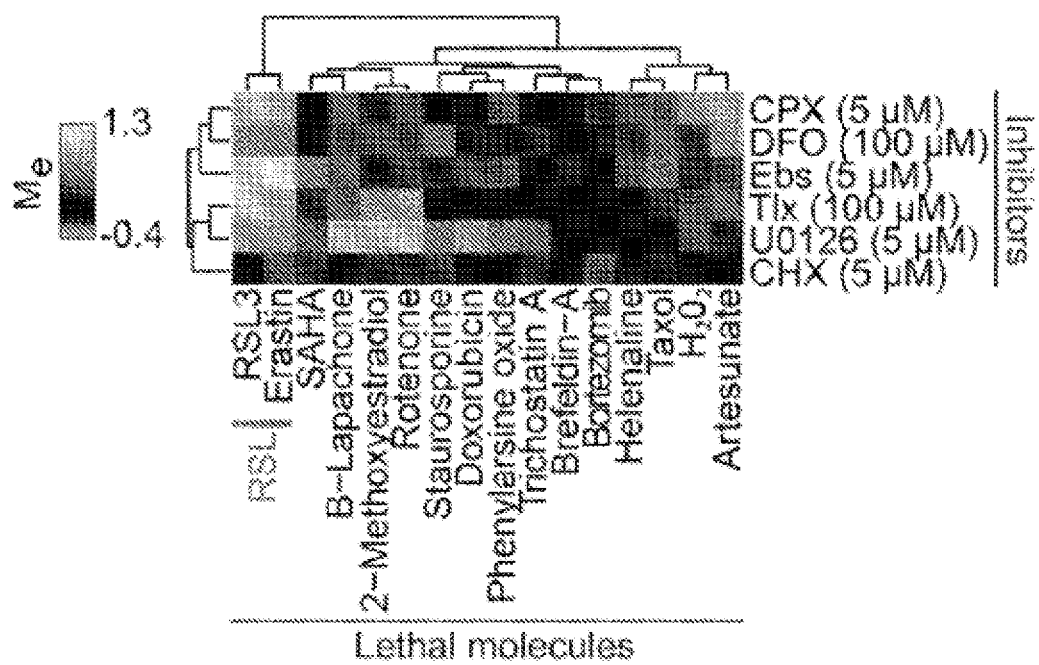

Finally, in a modulatory profiling experiment that tested the ability of DFO, trolox, U0126, CHX, the membrane permeable iron chelator ciclopirox olamine (CPX) and the glutathione peroxidase mimetic ebselen (Ebs) to modulate the lethality of erastin, RSL3 or sixteen other mechanistically distinct lethal compounds thought to kill cells through various ROS-dependent and -independent mechanisms, it was observed that erastin and RSL3 formed a distinct cluster, separate from all other inducers of cell death (FIG. 2E). Together, these data support the hypothesis that RSL-induced ferroptosis is a novel death phenotype distinct from apoptosis, various forms of necrosis and autophagy.

Example 5

Ferroptosis is Regulated by a Distinct Set of Genes

Figure 3A:
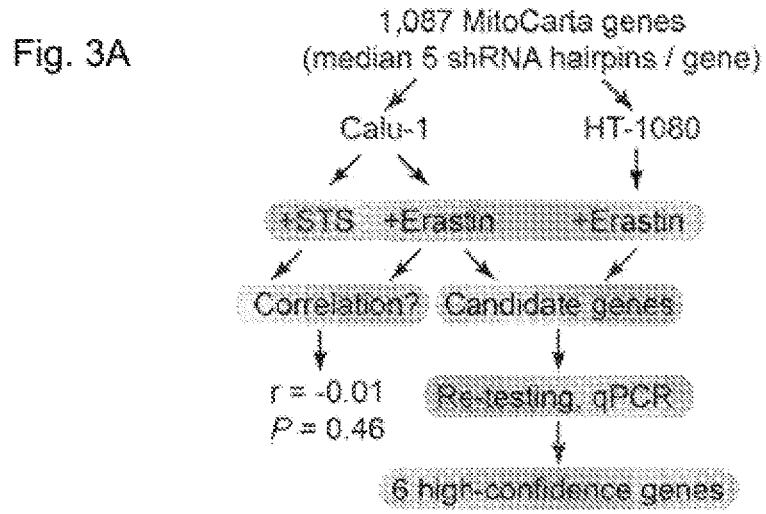
FIG. 3A to FIG. 3G shows that erastin-induced ferroptosis exhibits a unique genetic profile.

To explore the genetic basis of ferroptosis, genes uniquely required for this process were identify. The potential role of the mitochondria were focused on, because this organelle displayed an aberrant morphology in erastin-treated cells (FIG. 2A). Mitochondrial gene function was perturbed using a custom arrayed shRNA library targeting 1,087 genes (median 5 hairpins/gene), most of which (901, 88%) encode predicted mitochondrial proteins (Pagliarini et al., 2008) (FIG. 3A). Using this library, the genetic suppressibility of erastin (7.3 μM)-induced ferroptosis and STS (1 μM)-induced apoptosis in Calu-1 cells was compared (FIG. 3A). Across all 5,817 informative hairpins, no significant correlation between those shRNAs that rescued from erastin-induced ferroptosis and from STS-induced apoptosis (Spearman rank sum test, r=−0.01, P=0.46) was observed, thus confirming that distinct genetic networks govern erastin-induced ferroptosis and STS-induced apoptosis.

Figure 3B:
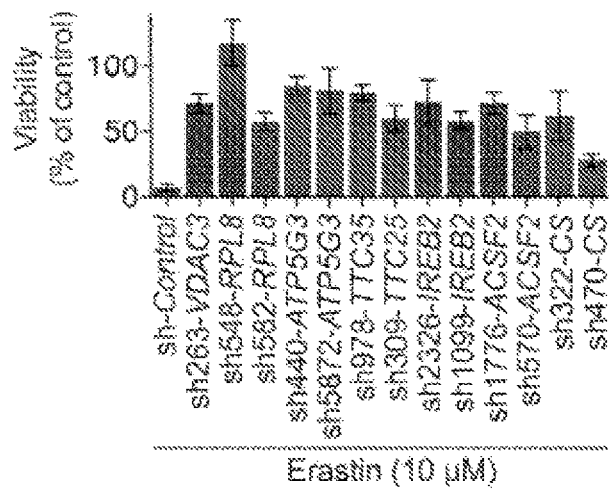
Figure 3C:
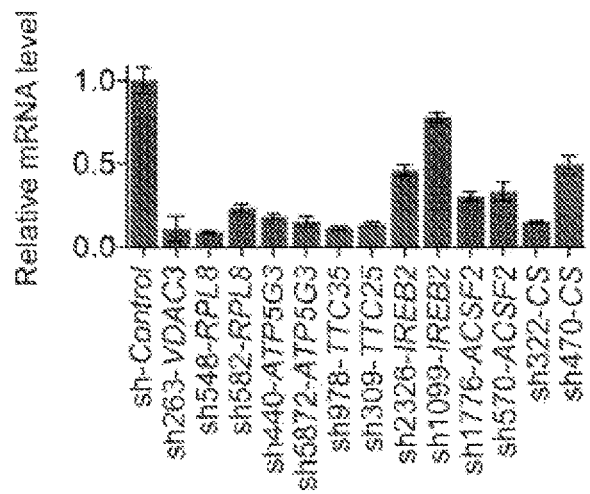
Figure 10A:
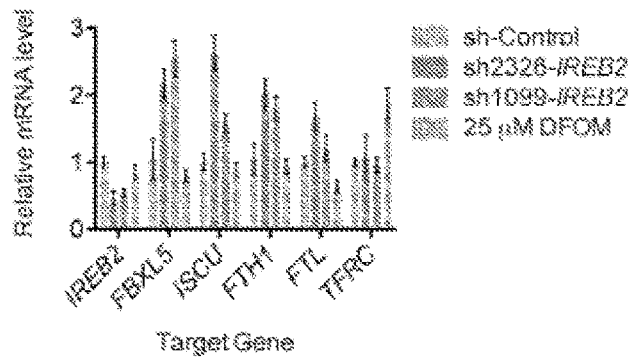
FIG. 10A to FIG. 10D shows various methods of validating the role of IREB2 in ferroptosis.
Figure 10B:
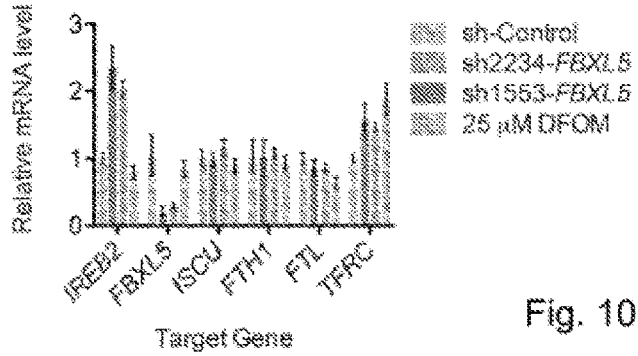
Figure 10C:
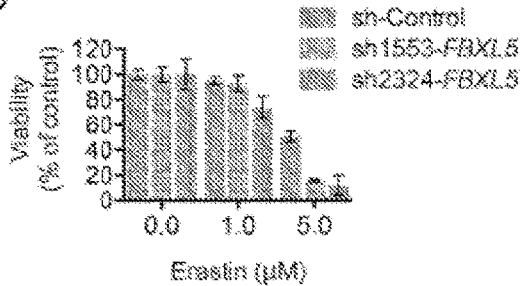

Next, a second erastin resistance screen in HT-1080 cells was performed and, using a rigorous confirmation pipeline, six high-confidence genes were identified. These six high-confidence genes were supported by at least two independent shRNAs per gene that are required for erastin-induced ferroptosis in both HT-1080 and Calu-1 cells-RPL8 (ribosomal protein L8), IREB2 (iron response element binding protein 2), ATP5G3 (ATP synthase $F_0$ complex subunit C3), CS (citrate synthase), TTC35 (tetratricopeptide repeat domain 35) and ACSF2 (acyl-CoA synthetase family member 2) (FIGS. 3B and 3C). Consistent with the established CHX- and DFO-sensitive nature of erastin-induced ferroptosis, RPL8 encodes a component of the 60S ribosomal subunit presumably required for translation and IREB2 encodes a master regulator of iron metabolism. These results were further validated. It was found that shRNA-mediated silencing of IREB2 and the IREB2 negative regulator FBXL5 (Salahudeen et al., 2009; Vashisht et al., 2009) resulted in reciprocal changes in the expression of the known iron uptake, metabolism and storage genes TFRC, ISCU, FTH1, FTL and in erastin sensitivity (FIG. 10A-C). These results provide confidence in the quality of the screening and confirmation procedures.

Figure 3D:
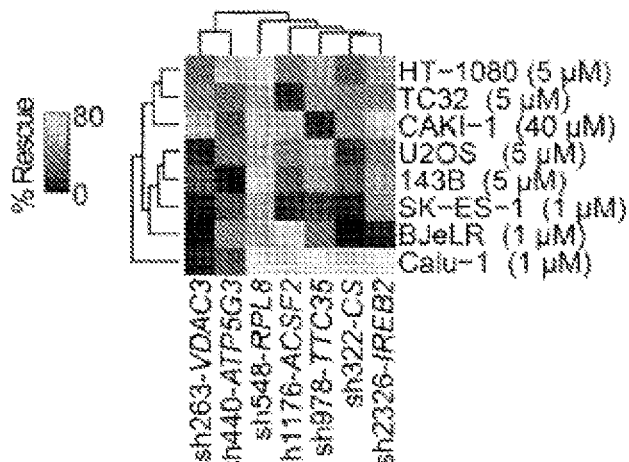
Figure 3E:
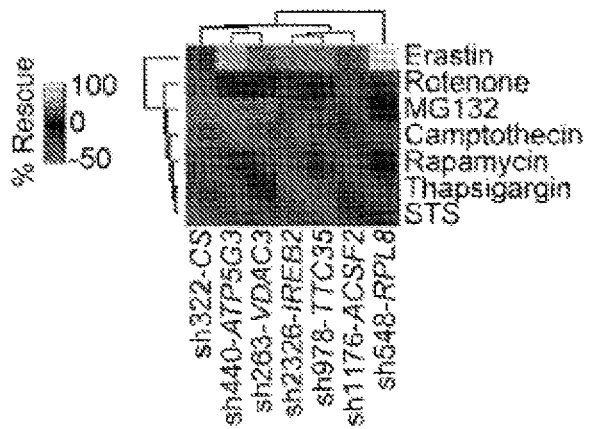

To establish the generalizability of the results obtained in HT-1080 and Calu-1 cells, the effects of silencing these genes in HT-1080, Calu-1 and six additional cell lines treated with erastin were tested. Silencing of these six high confidence genes using the most effective hairpin for each gene, defined by mRNA silencing levels in HT-1080 cells (FIG. 3C), conferred ≥20% rescue in 79% (38/48) of shRNA-cell line combinations (FIG. 3D). Thus, these genes appear to be broadly required for erastin-induced ferroptosis. Next, whether silencing of these genes specifically attenuated erastin-induced ferroptosis, or more broadly modulated a variety of lethal effects was tested. Silencing of these six genes conferred protection against erastin-induced ferroptosis (≥40% rescue for 6/6 hairpins), but not cell death/cytostasis induced by STS, rotenone, rapamycin, the proteasome inhibitor MG132, the DNA-damaging agent camptothecin or the $Ca^{2+}$-dependent ATPase inhibitor thapsigargin (≥40% rescue for 0/6 hairpins) (FIG. 3E). Together, these data support the hypothesis that a unique genetic network governs erastin-induced ferroptosis compared to other forms of cell death.

Figure 3F:
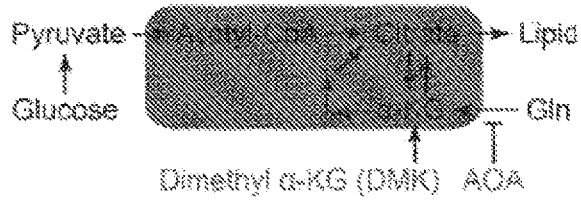
Figure 3G:
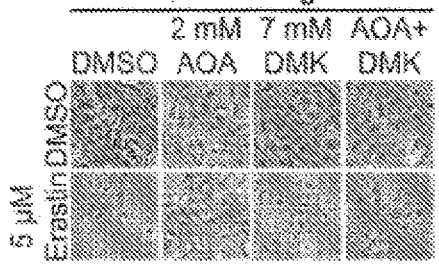
Figure 10D:
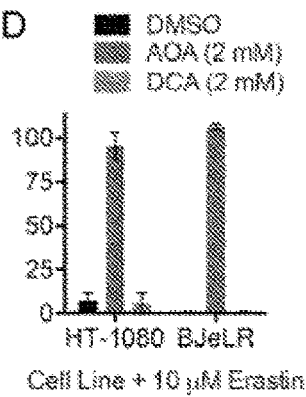

Both ACSF2 and CS are implicated in the regulation of mitochondrial fatty acid metabolism (Mullen et al., 2011; Watkins et al., 2007). Whether this process could contribute to ferroptosis was examined. In cancer cells, fatty acid synthesis is in part dependent upon the metabolism of glutamine (Gln) to alpha-ketoglutarate, a process that can be inhibited by the small molecule transaminase inhibitor aminooxyacetic acid (AOA) (Wise et al., 2008) (FIG. 3F). In cell culture media containing both glucose and Gln, AOA (2 mM) rescued both HT-1080 and BJeLR cells from erastin-induced ferroptosis (FIGS. 3F, 10D), mimicking the effects of silencing CS and ACSF2. In AOA-treated HT-1080 cells, the lethality of erastin was restored by co-incubation with dimethyl alpha ketoglutarate (DMK), which provides the downstream metabolite whose production from Gln is blocked by AOA (Wise et al., 2008) (FIGS. 3F and 3G). An unrelated modulator of mitochondrial function not predicted to directly affect Gln metabolism, dichloroacetic acid (DCA), had no effect on erastin-induced ferroptosis (FIG. 10D). These results suggest that a Gln- CS- and ACSF2-dependent lipid synthesis pathway could supply a specific lipid precursor required for ferroptosis.

Example 6

Identification of Ferrostatin-1 as a Small Molecule Inhibitor of Ferroptosis

Figure 4A:
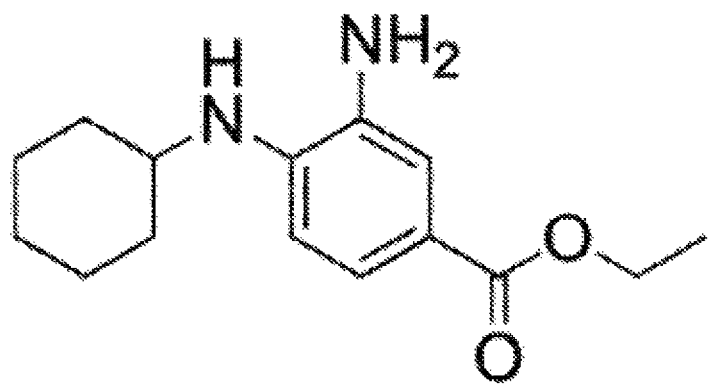
FIG. 4A to FIG. 4K shows the identification and characterization of Ferrostatin-1.
Figure 4B:
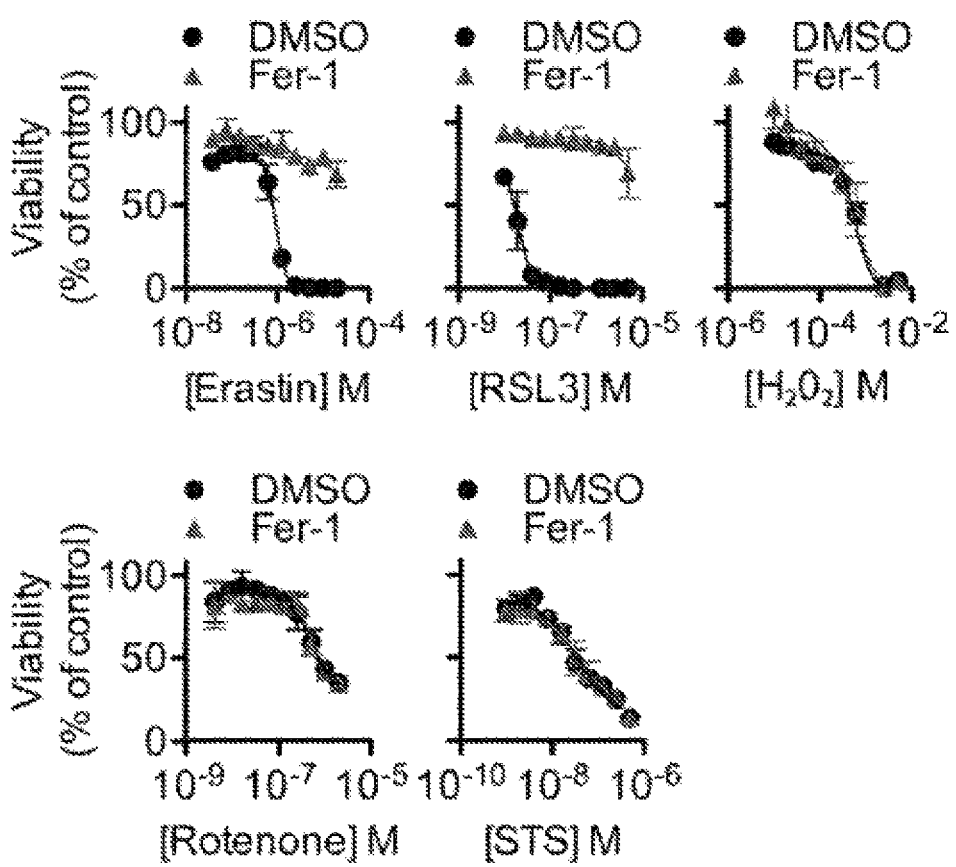
Figure 6A:
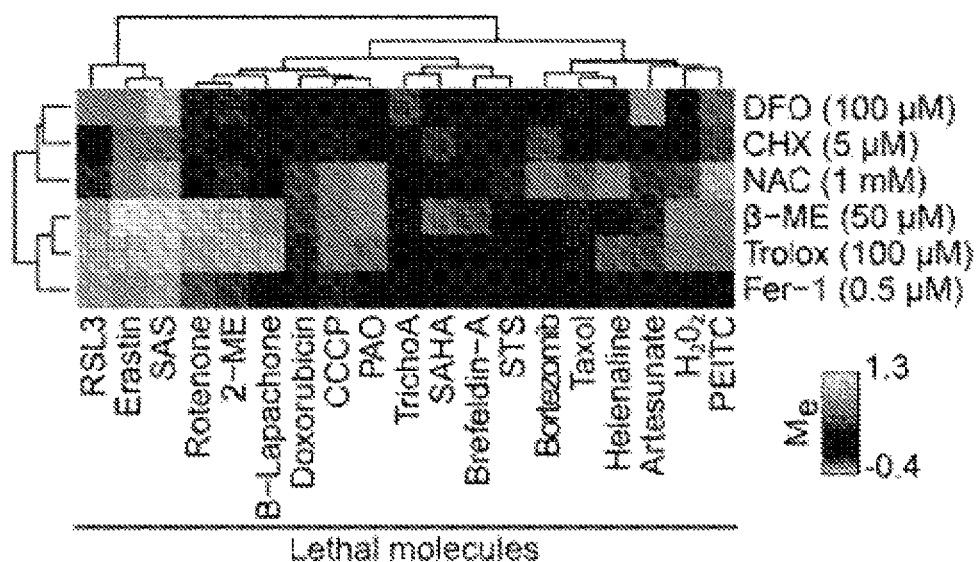

One ultimate aim is to investigate the potential role of ferroptosis in vivo. Therefore, a potent and specific drug-like small molecule inhibitor of this process was identified. As set forth above, to overcome the inherent limitations of many individual small molecule collections (Macarron et al., 2011), a custom screening library of 9,517 small molecules derived from a starting pool of 3,372,615 commercially available compounds that were filtered in silico on the basis of drug-likeness, solubility, scaffold diversity and other parameters was assembled. Screening of this 'lead-optimized compound' (LOC) library and subsequent confirmation studies identified a compound, which the inventors named ferrostatin-1 (Fer-1), as the most potent inhibitor of erastin-induced ferroptosis in HT-1080 cells ($EC_{50}$=60 nM) (FIGS. 4A, 10A, and 10B). To the inventors' knowledge, the activity for Fer-1 has not previously been reported in any biological system. A total synthesis of Fer-1 was performed as set forth above, and this material was used to confirm the activity of Fer-1 and to demonstrate that it specifically inhibited RSL-induced death, but not cell death induced by other oxidative lethal compounds and apoptosis-inducing agents (FIGS. 4B, 6A).

Figure 4C:
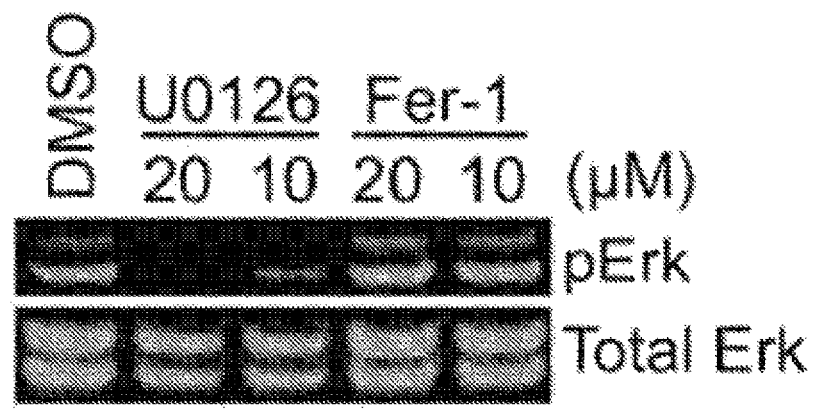
Figure 4D:
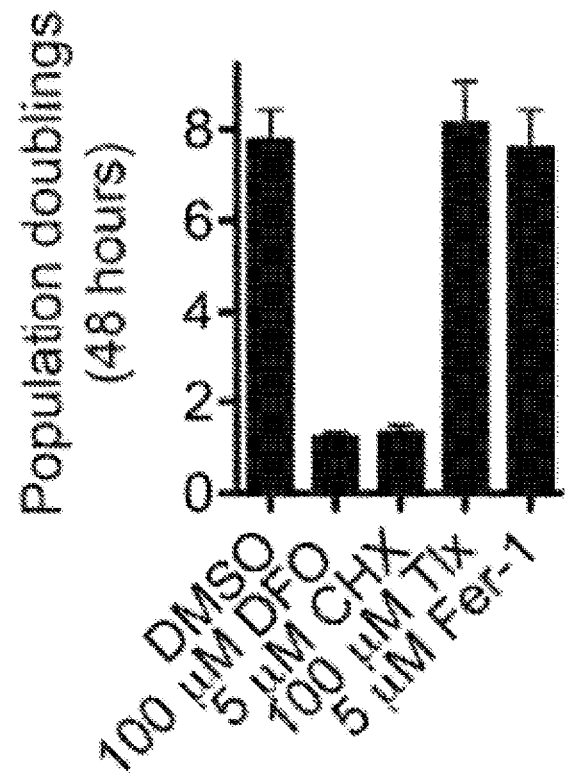
Figure 4E:
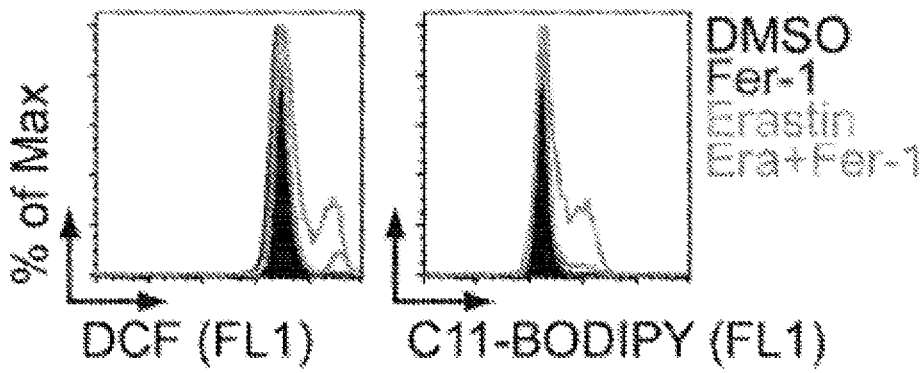
Figure 4F:
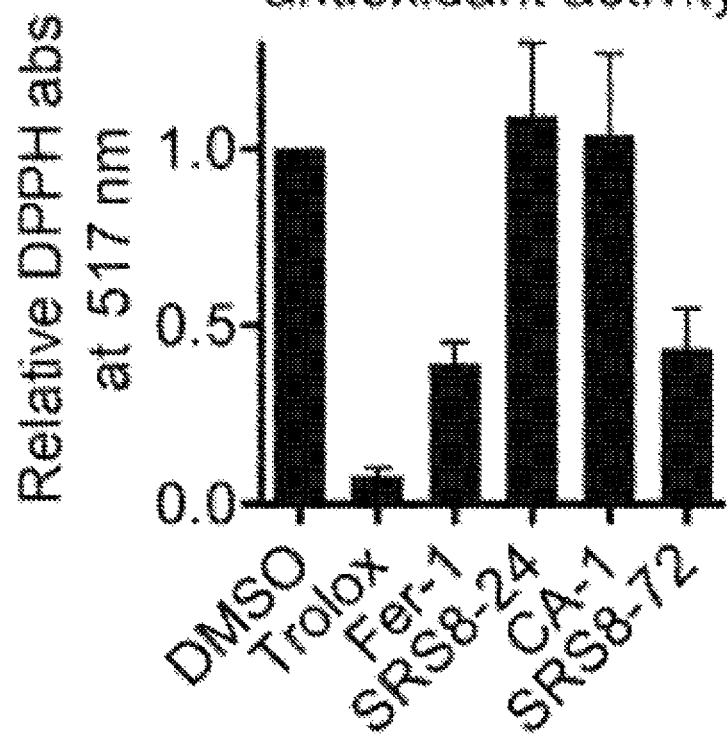
Figure 4G:
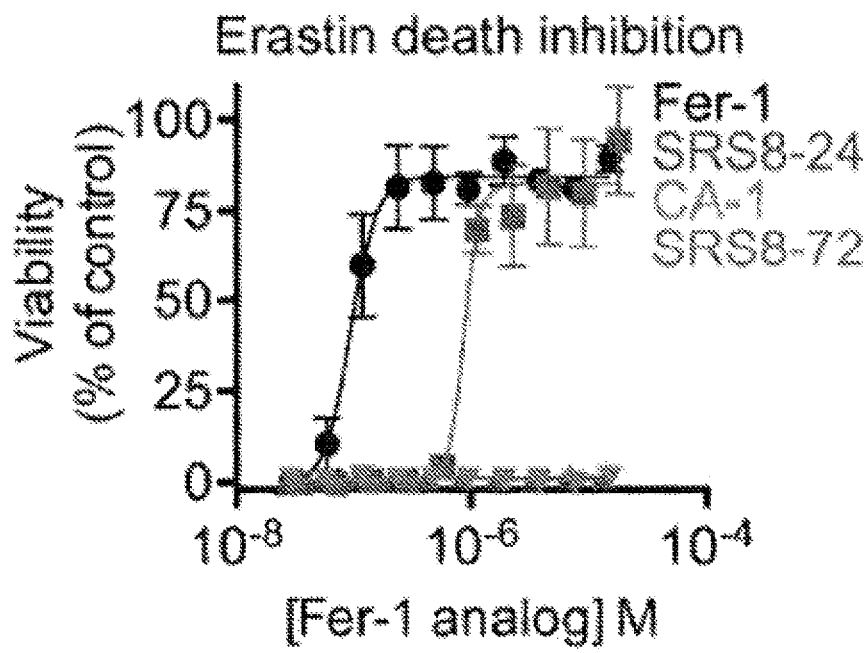
Figure 4H:
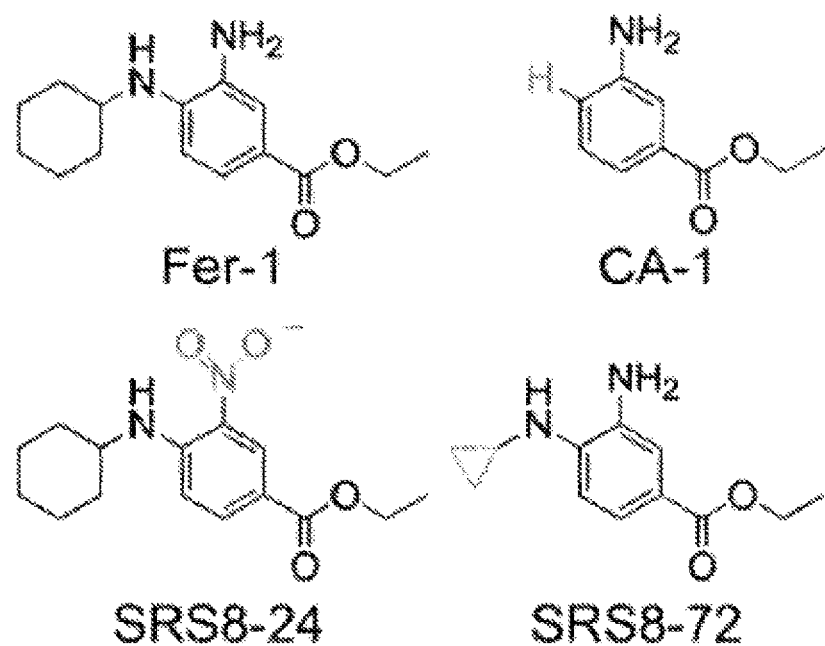

The Fer-1 mechanism of action was examined. Fer-1 did not inhibit ERK phosphorylation or arrest the proliferation of HT-1080 cells, suggesting that it does not inhibit the MEK/ERK pathway, chelate iron or inhibit protein synthesis (FIGS. 4C and 4D). Fer-1 did, however, prevent erastin-induced accumulation of cytosolic and lipid ROS (FIG. 4E). Moreover, similar to the positive control antioxidant trolox, Fer-1 readily oxidized the stable radical 2,2-diphenyl-1-picrylhydrazyl (DPPH) under cell free conditions, a test of intrinsic antioxidant potential (FIG. 4F). Substitution of the primary aromatic amine for a nitro group (SRS8-24), or elimination of the N-cyclohexyl moiety (CA-1), destroyed the antioxidant capability of Fer-1, as well as its ability to prevent erastin (10 µM)-induced death in HT-1080 cells (FIGS. 4F-H). Thus, both aromatic amines are required for Fer-1 to prevent RSL-induced death, a function plausibly linked to its ability to scavenge free radicals.

Figure 4I:
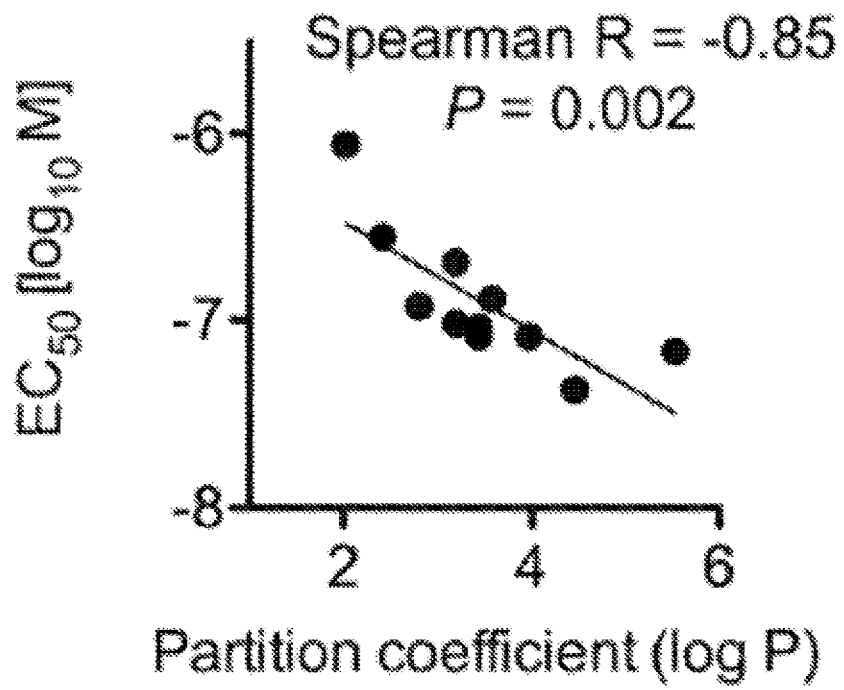
Figure 11C:
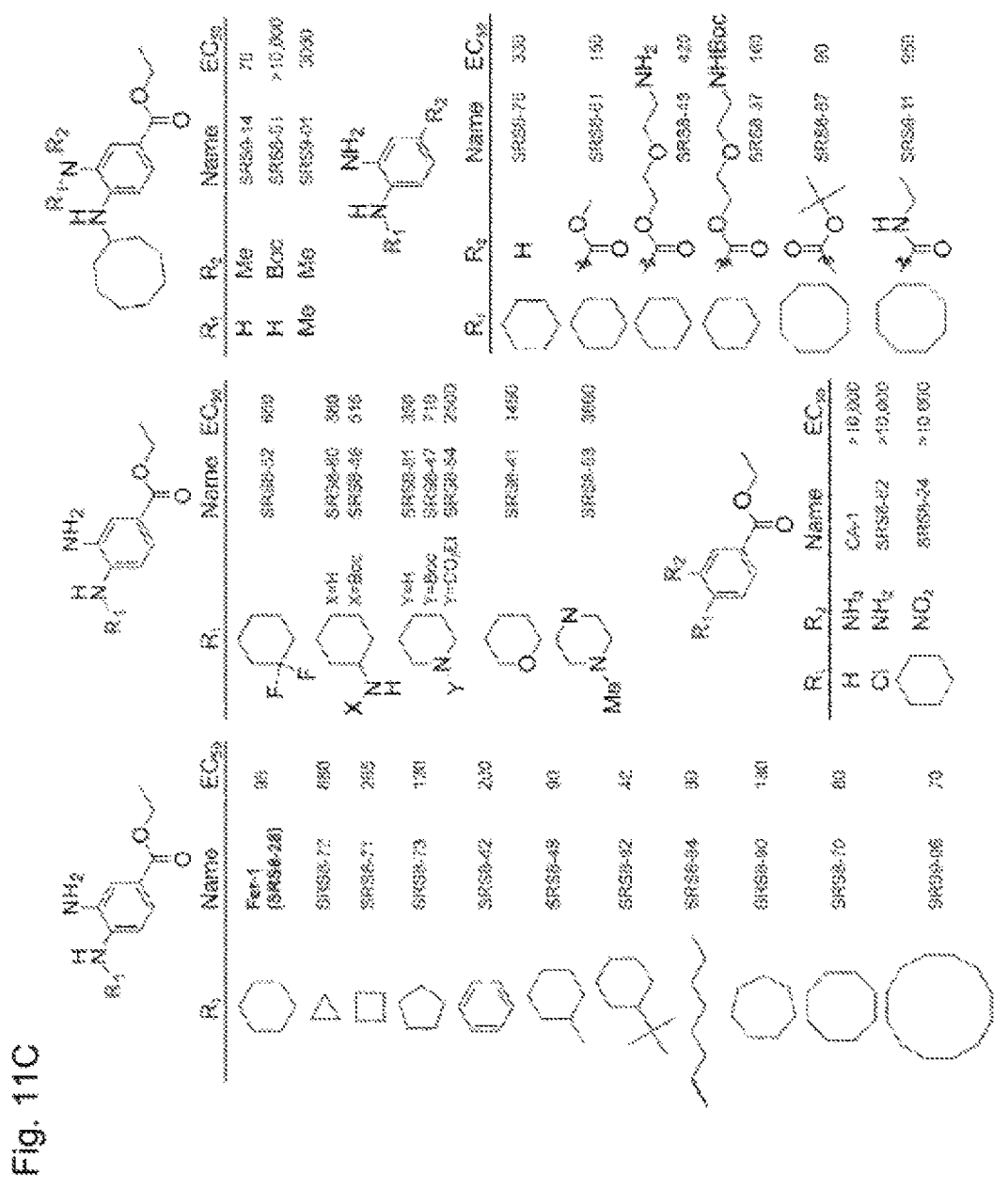

The results suggested that lipid ROS were crucial for erastin-induced death. The inventors therefore hypothesized that Fer-1 was a lipid ROS scavenger, with the N-cyclohexyl moiety serving as a lipophilic anchor within biological membranes. Consistent with this hypothesis, in a series of ten Fer-1 analogs, where the number of carbons in the N-substituted cyclic moiety was systematically varied, a significant correlation between the predicted lipophilicity (octanol-water partition coefficient, log P) and the erastin-death-suppressing ability of each molecule (Spearman R=−0.85, P=0.002) was observed (FIGS. 4I and 11C). Of note, SRS8-72, a Fer-1 analog with N-cyclopropyl in place of N-cyclohexyl, which was an order of magnitude less potent than Fer-1 at preventing death, nonetheless retained equivalent intrinsic antioxidant capability in the cell-free DPPH assay (FIGS. 4F-H and 10C). Thus, the N-cyclohexyl moiety likely enables Fer-1 to prevent ferroptosis by promoting the tethering of Fer-1 within lipid membranes, as opposed to influencing the intrinsic antioxidant potential of this molecule.

Figure 4J:
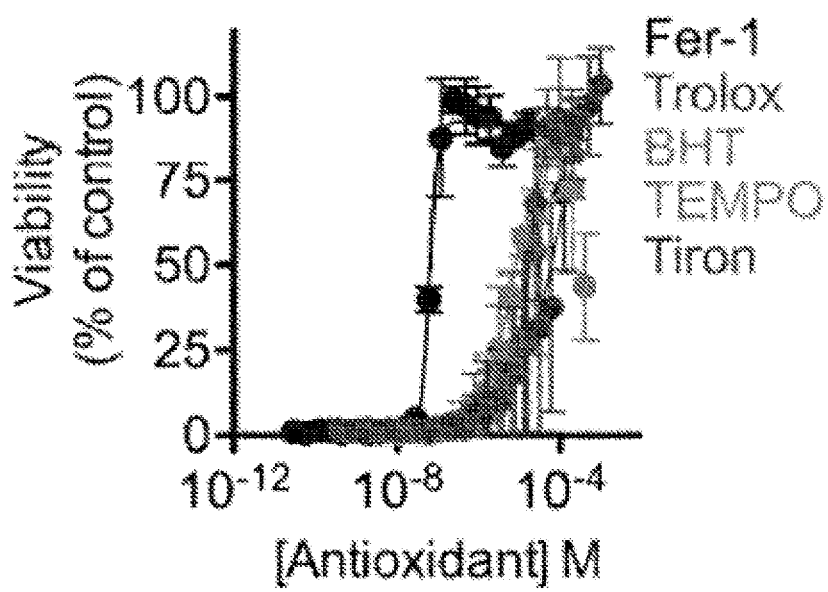
Figure 4K:
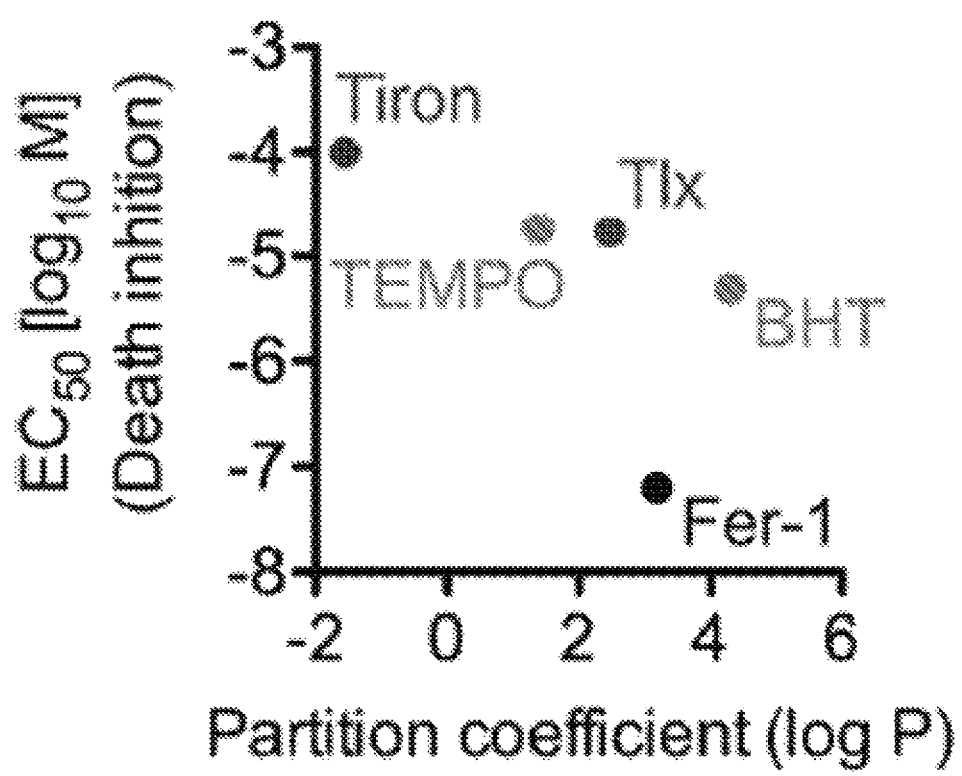

Intriguingly, lipid partitioning alone does not appear to be sufficient to account for the potency of Fer-1. Fer-1 has similar predicted lipophilicity, but much greater erastin-suppressing potency than two canonical lipophilic antioxidants (trolox and butylated hydroxyltoluene [BHT]), while being both considerably more lipophilic and more potent than two representative soluble antioxidants (Tiron, TEMPO) (FIGS. 4J and 4K). Both trolox and BHT are phenolic antioxidants, while Fer-1 contains an aromatic amine. It was hypothesized that this difference may confer a unique profile of radical reactivity upon Fer-1 that is better tuned to the RSL mechanism.

Example 7

Fer-1 Prevents Glutamate-Induced Neurotoxicity

Excitotoxic cell death that occurs in the nervous system in epilepsy, stroke and other trauma situations has also been described as an oxidative, iron-dependent process (Cheah et al., 2006; Choi, 1988; Murphy et al., 1989). It was hypothesized that excitotoxic death could be related to erastin-induced ferroptosis. This hypothesis was tested using a rat organotypic hippocampal slice culture (OHSC) model that closely resembles the hippocampus in vivo by preserving the integrity of neuronal connections, both inhibitory and excitatory, and their supporting cells, including astrocytes and microglia (Lossi et al., 2009). OHSCs have proven to be ideal complex preparations for lead-compound identification and validation (Noraberg et al., 2005; Sundstrom et al., 2005), capable of predicting in vivo efficacy (Cater et al., 2007; Morrison et al., 2002).

Figure 5A:
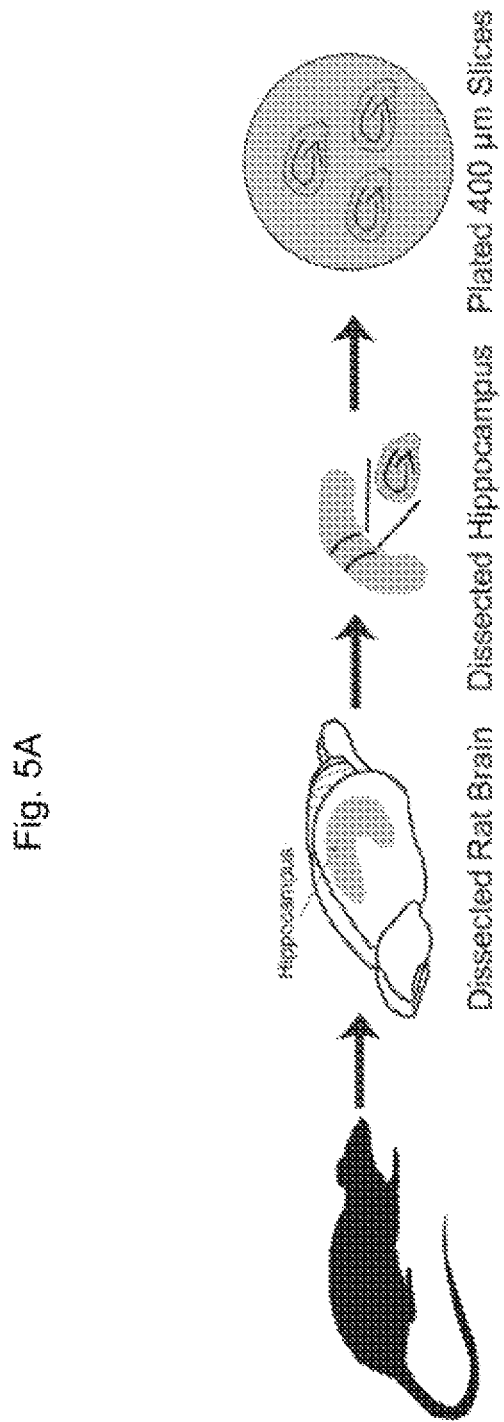
FIG. 5A to FIG. 5E shows the effects of Fer-1 on excitotoxic cell death in organotypic hippocampal slice cultures.
Figure 5B:
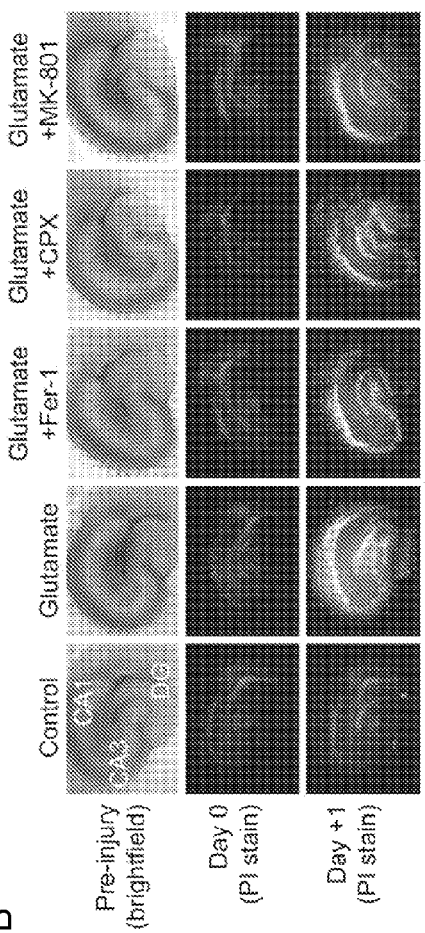
Figure 5C:
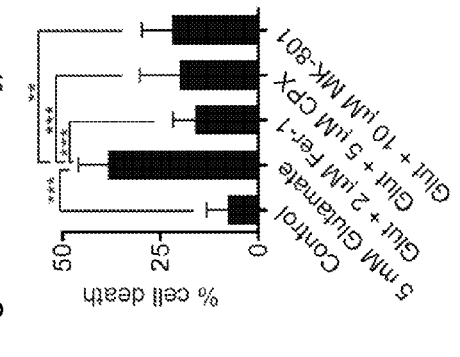
Figure 5D:
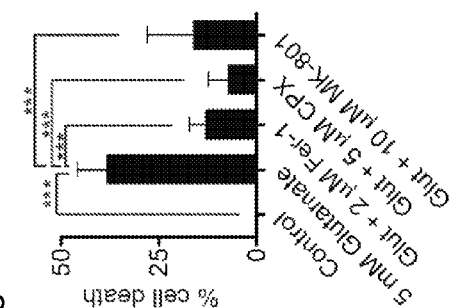
Figure 5E:
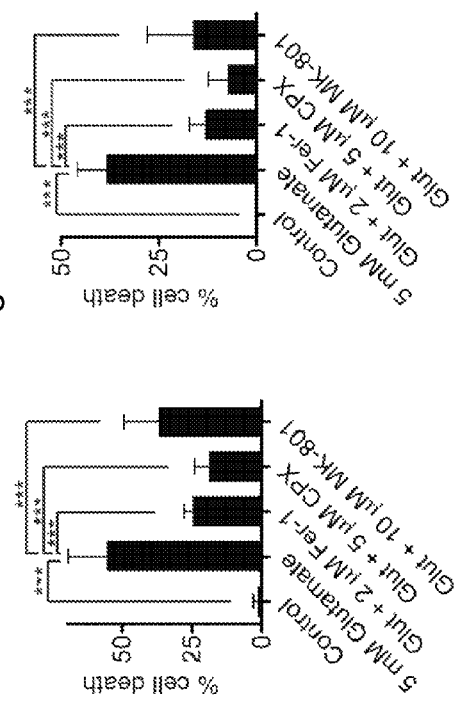

OHSCs were treated with a lethal excitotoxic stimulus (5 mM L-glutamate, 3 hours) that mimics the consequences of stroke and neurodegenerative disease (Morrison et al., 2002; Sundstrom et al., 2005) (FIG. 5A). These slices were co-incubated with glutamate and vehicle alone or with glutamate plus Fer-1 (2 μM), the iron chelator CPX (5 μM) or, as a positive control, the NMDA receptor antagonist MK-801 (10 μM). The effects of these compound treatments on propidium iodide (PI) uptake were analyzed, as an indicator of cell death, 24 hours following the end of glutamate treatment, in 3 defined regions of the OHSCs: the dentate gyrus (DG), the CA1 and the CA3 fields of the hippocampus. A two-way analysis of variance (ANOVA) suggested significant differences for both brain region ($F_{2,75}=19.23$, $P<0.0001$) and compound treatment ($F_{4,75}=67.8$, $P<0.0001$) factors. Focusing on the compound treatment effect, Bonferroni post-tests indicated that glutamate induced significant cell death in all three regions of the brain, and that this death was attenuated significantly and to an almost identical extent by co-treatment with Fer-1, CPX or MK-801 ($P<0.001$ for all interactions except glutamate+MK-801 within the DG, $P<0.01$) (FIG. 5B-E). These results suggest that glutamate-induced death in OHSCs and erastin-induced death in cancer cells share in common a core lethal mechanism that can be inhibited by iron chelation or Fer-1.

Example 8

Erastin Inhibits System $x_c^-$

CPX and Fer-1 suppressed erastin-induced death in cancer cells and glutamate-induced toxicity in OHSCs, consistent with a common iron- and ROS-dependent death execution mechanism. Whether any death-initiating mechanisms could also be shared between these two processes was investigated.

Glutamate-induced death in brain cells can be initiated by calcium influx through ionotropic glutamate receptors and through competitive inhibition of cystine uptake by the $Na^+$-independent cystine/glutamate antiporter, system $x_c^-$ (Choi, 1988; Murphy et al., 1989). The calcium chelators BAPTA-AM, Fura-2 and EGTA had no effect on erastin-induced death (FIG. 12A) (Wolpaw et al., 2011), arguing against a role for $Ca^{2+}$ influx in this process. However, striking clustering of erastin and sulfasalazine (SAS), a specific inhibitor of system $x_c^-$ (Gout et al., 2001), was observed in a modulatory profile of 19 oxidative and non-oxidative lethal molecules generated in HT-1080 cells (FIG. 6A). If blockade of system $x_c^-$-mediated cystine import can trigger ferroptosis, then providing this metabolite to cells through an alternative means should rescue from death. Indeed, β-mercaptoethanol (β-ME), which can circumvent the inhibition of system $x_c^-$ by promoting cystine uptake through an alternative pathway (Ishii et al., 1981), strongly inhibited cell death in HT-1080 cells induced by erastin, SAS and glutamate (FIGS. 6A and 12B). As predicted by these results, SAS, like erastin, behaved as an oncogenic RAS-selective lethal (RSL) compound, albeit with considerably lower potency than erastin (FIG. 12C). This is nonetheless noteworthy, as SAS is an FDA-approved drug not previously shown to demonstrate such activity.

Figure 6B:
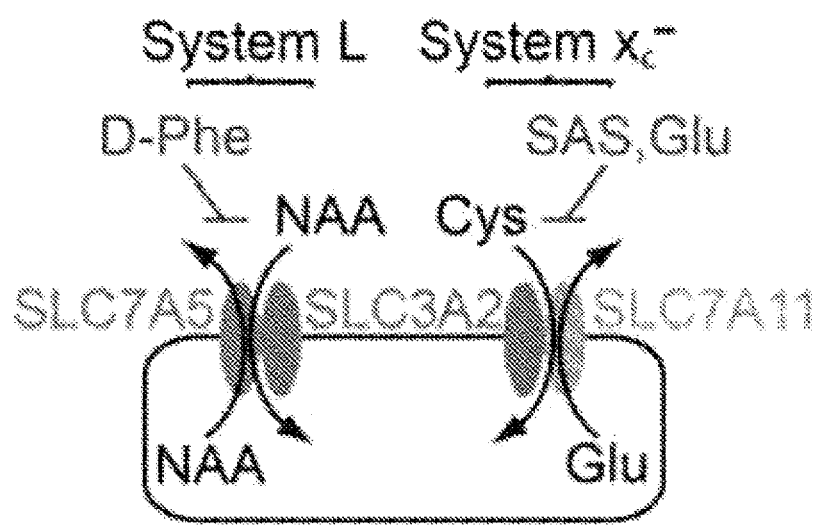
Figure 6C:
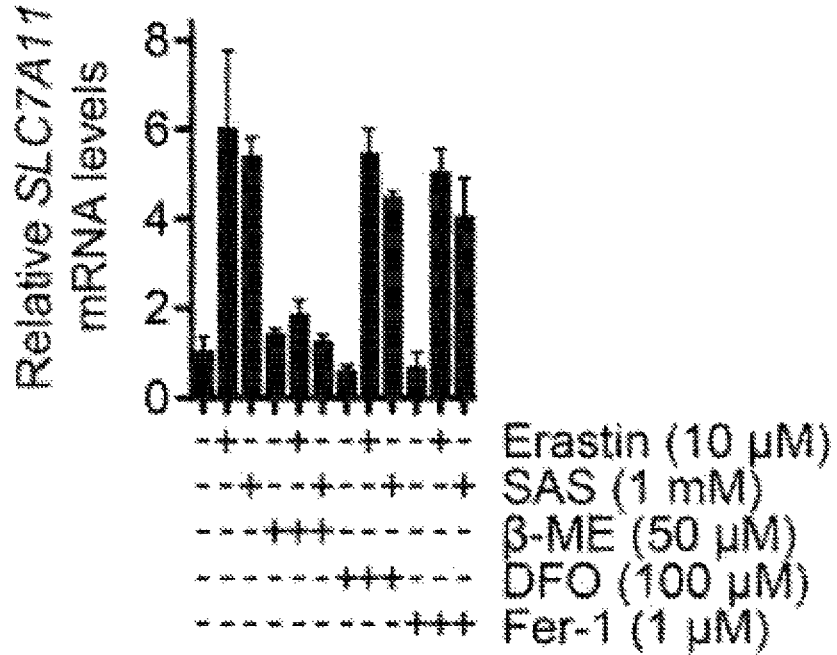
Figure 6D:
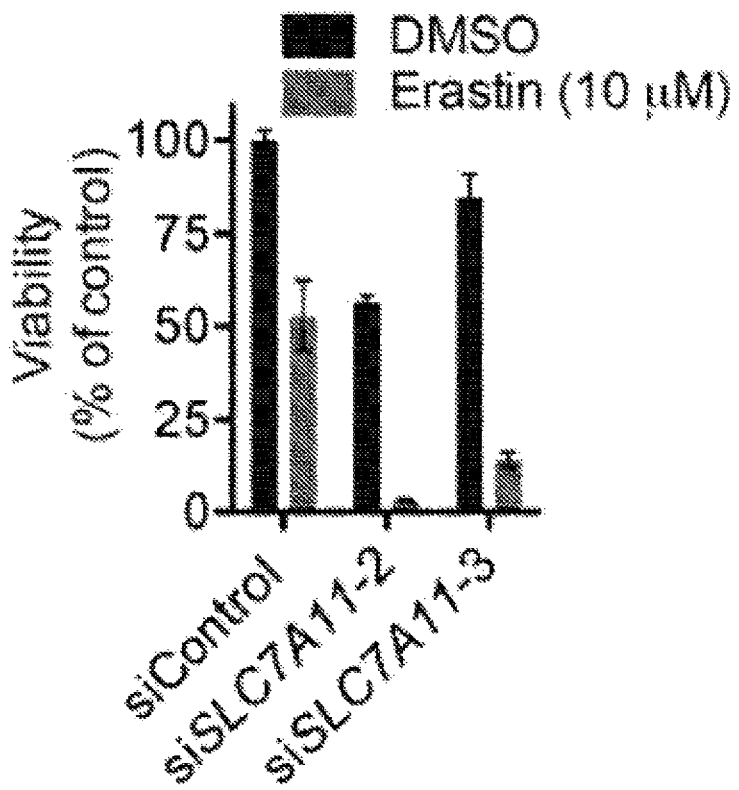
Figure 6E:
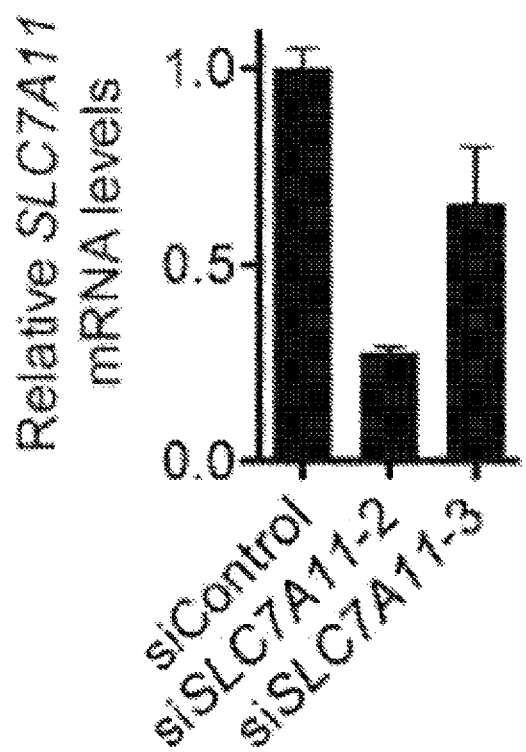
Figure 6F:
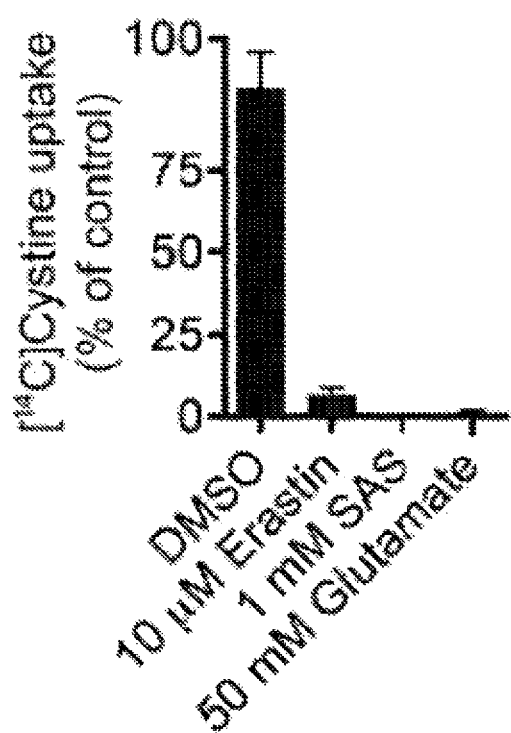

System $x_c^-$ is a disulfide-linked heterodimer composed of SLC7A11 (xCT) and SLC3A2 (4F2hc, CD98hc) (Sato et al., 1999) (FIG. 6B). Inhibition of system $x_c^-$ can lead to a compensatory transcriptional up-regulation of SLC7A11 (Lo et al., 2008). Consistent with this, substantial upregulation of SLC7A11 in HT-1080 cells treated with erastin or SAS was observed. This effect was suppressed by β-ME, but not DFO or Fer-1 (FIG. 6C). Further confirming the relevance of system $x_c^-$ to erastin-induced ferroptosis, siRNA-mediated silencing of SLC7A11 with two independent siRNAs sensitized HT-1080 cells to erastin-induced death (FIGS. 6D and 6E), while transfection of HT-1080 cells with a plasmid encoding DDK-tagged SLC7A11 conferred protection from erastin- and SAS-induced death (FIG. 12D). Given these results, the uptake of [$^{14}$C]cystine in HT-1080 cells was directly examined. Erastin (10 μM), glutamate (50 mM) and SAS (1 mM) abolished the $Na^+$-independent uptake of [$^{14}$C]cystine while RSL3 had no effect on this process (FIGS. 6F, 12E).

Figure 6I:
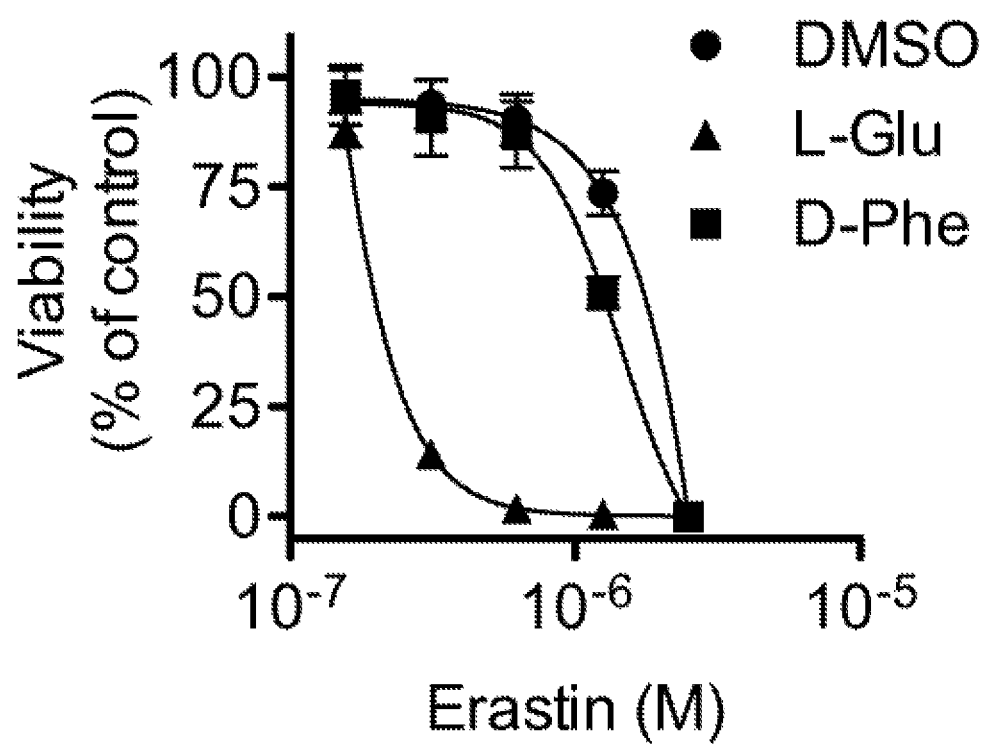

How erastin inhibits system $x_c^-$ was investigated. Analysis of affinity purification data (Yagoda et al., 2007) identified SLC7A5 (LAT1, 4F2lc, CD98lc) as the lone protein bound by an active erastin affinity analog in lysates from both HRAS-wildtype BJeH and HRAS-mutant BJeLR cells (FIG. 6G). SLC7A5 (like SLC7A11) is one of six light chains that bind SLC3A2 to form amino acid transporters of differing substrate selectivity. The SLC7A5/SLC3A2 complex (system L) transports large, neutral amino acids (Kanai and Endou, 2003) (FIG. 6B). In a profile of 123 metabolites from human Jurkat T lymphocytes treated with erastin (1 μM, 25 min) (Ramanathan and Schreiber, 2009), highly significant decreases were observed in the levels of system L substrates (Kanai and Endou, 2003), while the levels of non-system L substrates were unchanged or increased (FIG. 6H). However, unlike inhibition of system $x_c^-$ using excess glutamate (12.5 mM), inhibition of system L using excess D-phenylalanine (12.5 mM) (Kanai and Endou, 2003) did not strongly sensitize to erastin (FIG. 6I). Together, these results suggest that erastin inhibits system L-mediated amino acid uptake, but that this does not contribute directly to ferroptosis. Rather, erastin binding to SLC7A5 or the SLC7A5/SLC3A2 complex interferes with cystine uptake by the SLC3A2/SLC7A11 complex in trans.

Example 9

Figure 7A:
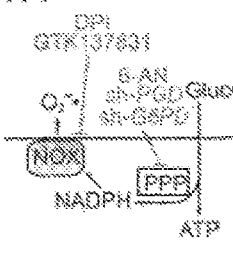
FIG. 7A to FIG. 7E shows the role of NOX in erastin-induced death.
Figure 7B:
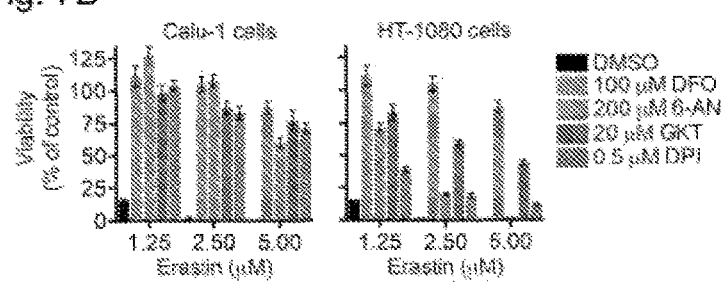
Figure 7C:
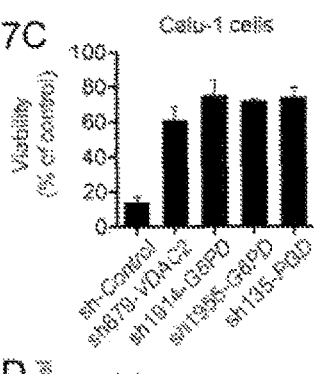

NAPDH Oxidases Provide One Source of Death-Inducing Ros in Erastin-Treated Cells Blocking system $x_c^-$ inhibits cysteine-dependent glutathione (GSH) synthesis and inhibits the trans-plasma membrane cysteine redox shuttle (Banjac et al., 2008; Ishii et al., 1981). Both effects impair cellular antioxidant defenses, thereby facilitating toxic ROS accumulation. Having ruled out the mitochondrial ETC as a source of death-inducing ROS in erastin-treated cells (FIGS. 1D-F), the role of the NADPH oxidase (NOX) family of superoxide-producing enzymes (NOX1-5, DUOX1,2), which are up-regulated in several RAS-mutant tumors (Kamata, 2009) was examined. Erastin-induced ferroptosis was strongly suppressed in Calu-1 cells by the canonical NOX inhibitor diphenylene iodonium (DPI), the NOX1/4 specific inhibitor GKT137831 (Laleu et al., 2010) and an inhibitor of the NADPH-generating pentose phosphate pathway (PPP), 6-aminonicotinamde (6-AN) (FIGS. 7A and 7B). Given that Calu-1 cells express NOX1 at much higher levels than NOX4 (FIG. 13A), NOX1 is the most likely candidate to mediate the observed NOX-dependent lethal effects in these cells. Additionally, shRNA-mediated silencing of two PPP enzymes, glucose-6-phosphate dehydrogenase (G6PD) and phosphoglycerate dehydrogenase (PGD), also prevented erastin-induced ferroptosis in Calu-1 cells to the same extent as silencing of VDAC2 (FIGS. 7C and 7D). 6-AN also prevented cell death as well as ROS production in BJeLR cells (FIGS. 13B and 13C), suggesting an important role for this pathway is these cell types. On the other hand, NOX and PPP inhibitors were only partially effective at preventing erastin-induced ferroptosis in HT-1080 cells (FIG. 7B), indicating that other pathways, in addition to the PPP/NOX pathway, can contribute to the onset of death in erastin-treated cells, once the appropriate conditions have been set by the inhibition of system $x_c^-$.

Figure 7E:
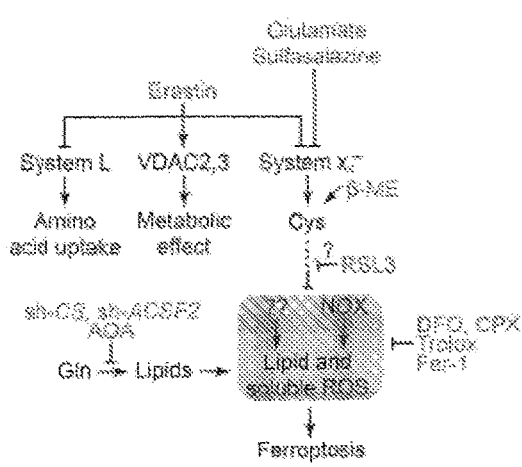
Figure 7D:
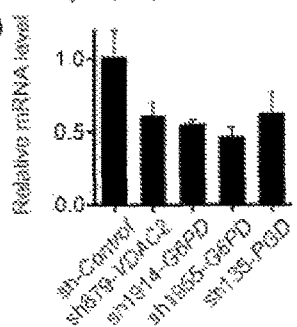

Ferroptotic death is morphologically, biochemically and genetically distinct from apoptosis, various forms of necrosis, and autophagy. This process is characterized by the overwhelming, iron-dependent accumulation of lethal lipid ROS (FIG. 7E, blue outline). Unlike other forms of apoptotic and non-apoptotic death (Christofferson and Yuan, 2010; Jacobson and Raff, 1995), this requirement for ROS accumulation appears to be universal. In at least some cells, NOX-family enzymes make important contributions to this process. Indeed, although the possibility of a death-inducing protein or protein complex activated downstream of ROS accumulation cannot be excluded, the inventors posit that the executioners of death in cancer cells undergoing ferroptosis are these ROS themselves. An important prediction of this model is that under anoxic conditions ferroptosis will be inactive. However, even here, agents such as erastin that prevent uptake of essential amino acids by system L are likely to be toxic to cells.

Using an shRNA library targeting most known genes encoding mitochondrial proteins (Pagliarini et al., 2008), specific roles for RPL8, IREB2, ATP5G3, TTC35, CS and ACSF2 in erastin-induced ferroptosis were identified. A plausible new hypothesis to emerge from these data is that CS and ACSF2 are required to synthesize a specific lipid precursor necessary for death (FIG. 7E). Just as important, the high-resolution of the arrayed approach (1 hairpin/well, minimum 5 hairpins/gene) provides confidence that the various mitochondrial genes not identified in the screen, including many implicated in apoptotic and non-apoptotic death (BID, BAK1, BAX, AIFM1, PP/F, HTRA2, ENDOG, PGAM5), are truly not required for erastin-induced ferroptosis. This screening collection will be a valuable resource for future studies of the role of the mitochondria in cell physiology.

In cancer cells, inhibition of system $x_c^-$-mediated cystine uptake by erastin, SAS or glutamate may be sufficient to initiate iron-dependent ferroptosis. Inhibition of system $x_c^-$ is, however, not necessary: RSL3 does not inhibit cystine uptake and yet triggers an otherwise similar iron and ROS-dependent ferroptototic death program. Thus, RSL3 likely modulates the activity of a target lying downstream of or in parallel to system $x_c^-$ (FIG. 7E). Importantly, this may enable RSL3 to activate ferroptosis in cells or conditions where cystine uptake via system $x_c^-$ is not limiting for survival. Lanperisone, another recently identified oncogenic RAS-selective lethal small molecule that causes non-apoptotic, iron-dependent death in mouse Kras-mutant tumor cells (Shaw et al., 2011), may also inhibit the function of system $x_c^-$ or another target in the ferroptotic pathway. Other compounds that behave as RSLs, such as PEITC, oncrasin and piperlongumine (Guo et al., 2008; Raj et al., 2011; Trachootham et al., 2006), trigger mitochondrial cytochrome C release, caspase activation and other features of apoptosis not observed in cancer cells undergoing ferroptosis. Certain tumor cells are highly resistant to apoptosis (Ni Chonghaile et al., 2011). Thus, agents such as erastin, RSL3 and lanperisone that can trigger non-apoptotic death may exhibit a unique spectrum of clinical activity.

In some brain cell populations, inhibition of system $x_c^-$ by glutamate triggers oxidative cell death dependent on iron and lipid ROS, but also $Ca^{2+}$ influx, mitochondrial damage, mitochondrial ROS production and chromatin fragmentation (Li et al., 1997; Murphy et al., 1989; Ratan et al., 1994; Tan et al., 1998; Yonezawa et al., 1996). These latter events are not required for RSL-induced ferroptosis in cancer cells, perhaps because heightened activity of NOX or other pro-oxidant enzymes, or basically altered membrane lipid composition, is sufficient to promote death in the absence of these additional features. Regardless, the oxidative death pathways triggered in cancer cells and brain cells by blockade of cystine uptake both appear to access a core iron- and ROS-dependent ferroptotic mechanism, accounting for the ability of Fer-1 and CPX to attenuate death in both cases (FIG. 7E).

The specific role of iron in ferroptosis remains unclear. Ferroptosis cannot be explained by a simple increase in $H_2O_2$-dependent, iron-catalyzed ROS production (i.e. Fenton chemistry), as $H_2O_2$-induced death is distinct from RSL-induced ferroptosis (FIGS. 1 and 2). Rather, the results are most consistent with one or more iron-dependent enzymes functioning as part of the core, oxidative lethal mechanism. The void created in the antioxidant defenses of the cell by the inhibition of cystine uptake by erastin may be required to unleash the activity of these enzymes. Thus, for better or worse, the aberrantly elevated levels of iron observed in some cancer cells (Pinnix et al., 2010) and pathological neuronal populations (Duce et al., 2010; Lei et al., 2012) may predispose to ferroptotic death in situations of cystine or cysteine limitation.

Example 10

Fer-1 and its Analogs are Able to Inhibit Death in Erastin Treated Cells

The ability of various compounds disclosed herein to inhibit death in erastin (10 µM)-treated HT-1080 cells were tested. The results are shown in Table 9 below. Cell viability was assessed by Alamar Blue. $EC_{50}$ values (nM) were computed from dose response curves.

TABLE 9

| Compound name | EC50 (nM) |
|---|---|
| SRS8-24 | >10,000 |
| SRS8-28 (Fer-1) | 95 |
| SRS8-37 | 160 |
| SRS8-41 | 1450 |
| SRS8-42 | 200 |
| SRS8-43 | 420 |
| SRS8-46 | 515 |
| SRS8-47 | 710 |
| SRS8-48 | 90 |
| SRS8-52 | 650 |
| SRS8-53 | 3600 |
| SRS8-54 | 2500 |
| SRS8-61 | 150 |
| SRS8-62 | >10,000 |
| SRS8-70 | 80 |
| SRS8-71 | 265 |
| SRS8-72 | 880 |
| SRS8-73 | 120 |
| SRS8-75 | 330 |
| SRS8-81 | 350 |
| SRS8-80 | 380 |
| SRS8-87 | 90 |
| SRS8-90 | 130 |
| SRS8-91 | >10,000 |
| SRS8-92 | 42 |
| SRS8-94 | 80 |
| SRS9-01 | 3460 |
| SRS9-06 | 70 |
| SRS9-11 | 950 |
| SRS9-14 | 70 |
| SRS11-89 | >10,000 |
| SRS11-92 | 6 |
| SRS11-97 | >10,000 |
| SRS11-98 | >10,000 |
| SRS12-12 | >10,000 |
| SRS12-29 | 76 |
| SRS12-33 | 50 |
| SRS12-34 | 40 |
| SRS12-35 | 44 |
| SRS12-36 | 35 |
| SRS12-43 | 69 |
| SRS12-45 | 25 |
| SRS12-46 | 32 |
| SRS12-47 | 660 |
| SRS12-48 | 46 |
| SRS12-49 | 371 |
| SRS12-50 | 100 |
| SRS12-51 | 56 |
| SRS12-52 | 105 |
| SRS12-53 | 41 |
| SRS12-54 | 158 |
| SRS12-57 | 100 |
| SRS12-58 | 41 |
| SRS12-59 | 95 |
| SRS12-69 | 58 |
| SRS12-71 | 126 |
| SRS12-80 | 33 |
| SRS12-84 | 52 |
| SRS13-12 | 48 |
| SRS13-29 | 83 |
| SRS13-30 | 114 |
| SRS13-35 | 27 |
| SRS13-37 | 15 |
| SRS14-55 | 104 |
| SRS14-57 | 54 |
| SRS14-58 | 28 |
| SRS14-86 | 544 |
| SRS14-91 | 48 |
| SRS14-92 | 194 |
| SRS14-93 | 1549 |
| SRS15-17 | 171 |
| SRS15-18 | 88 |
| SRS15-20-mono | 22 |
| SRS15-20-di | 914 |
| SRS15-21 | <5 nM |
| SRS15-22 | 21 |
| SRS15-23 | 23 |
| SRS15-24 | 9 |
| SRS15-25 | 54 |
| 4MO43 | 47 |

DOCUMENTS

Abdel-Magid, A. F.; Carson, K. G.; Harris, B. D.; Maryanoff, C. A.; Shah, R. D. J. Org. Chem. 1996, 61, 3849-3862

Banjac, A., Perisic, T., Sato, H., Seiler, A., Bannai, S., Weiss, N., Kolle, P., Tschoep, K., Issels, R. D., Daniel, P. T., et al. (2008). The cystine/cysteine cycle: a redox cycle regulating susceptibility versus resistance to cell death. Oncogene 27, 1618-1628.

Beaulieu, P. L.; Hache, B.; Von Moos, E. Synthesis, 2003, 11, 1683-1692.

Bergsbaken, T., Fink, S. L., and Cookson, B. T. (2009). Pyroptosis: host cell death and inflammation. Nat Rev Microbiol 7, 99-109.

Blois, M. S. (1958). Antioxidant determinations by the use of a stable free radical. Nature 181, 1199-1200.

Blois, M. S. (1958). Antioxidant determinations by the use of a stable free radical. Nature 181, 1199-1200.

Cater, H. L., Gitterman, D., Davis, S. M., Benham, C. D., Morrison, B., 3rd, and Sundstrom, L. E. (2007). Stretch-induced injury in organotypic hippocampal slice cultures reproduces in vivo post-traumatic neurodegeneration: role of glutamate receptors and voltage-dependent calcium channels. J Neurochem 101, 434-447.

Cater, H. L., Gitterman, D., Davis, S. M., Benham, C. D., Morrison, B., 3rd, and Sundstrom, L. E. (2007). Stretch-induced injury in organotypic hippocampal slice cultures reproduces in vivo post-traumatic neurodegeneration: role of glutamate receptors and voltage-dependent calcium channels. J Neurochem 101, 434-447.

Cater, H. L., Gitterman, D., Davis, S. M., Benham, C. D., Morrison, B., 3rd, and Sundstrom, L. E. (2007). Stretch-induced injury in organotypic hippocampal slice cultures reproduces in vivo post-traumatic neurodegeneration: role of glutamate receptors and voltage-dependent calcium channels. J Neurochem 101, 434-447.

Cheah, J. H., Kim, S. F., Hester, L. D., Clancy, K. W., Patterson, S. E., 3rd, Papadopoulos, V., and Snyder, S. H. (2006). NMDA receptor-nitric oxide transmission mediates neuronal iron homeostasis via the GTPase Dexrasl. Neuron 51, 431-440.

Choi, D. W. (1988). Glutamate neurotoxicity and diseases of the nervous system. Neuron 1, 623-634.

Christofferson, D. E., and Yuan, J. (2010). Necroptosis as an alternative form of programmed cell death. Current Opinion in Cell Biology 22, 263-268.

Chung, N., Zhang, X. D., Kreamer, A., Locco, L., Kuan, P. F., Bartz, S., Linsley, P. S., Ferrer, M., and Strulovici, B. (2008). Median absolute deviation to improve hit selection for genome-scale RNAi screens. J Biomol Screen 13, 149-158.

Chung, N., Zhang, X. D., Kreamer, A., Locco, L., Kuan, P. F., Bartz, S., Linsley, P. S., Ferrer, M., and Strulovici, B. (2008). Median absolute deviation to improve hit selection for genome-scale RNAi screens. J Biomol Screen 13, 149-158.

Dolma, S., Lessnick, S. L., Hahn, W. C., and Stockwell, B. R. (2003). Identification of genotype-selective antitumor agents using synthetic lethal chemical screening in engineered human tumor cells. Cancer Cell 3, 285-296.

Duce, J. A., Tsatsanis, A., Cater, M. A., James, S. A., Robb, E., Wikhe, K., Leong, S. L., Perez, K., Johanssen, T., Greenough, M. A., et al. (2010). Iron-export ferroxidase activity of beta-amyloid precursor protein is inhibited by zinc in Alzheimer's disease. Cell 142, 857-867.

Fuchs, Y., and Steller, H. (2011). Programmed cell death in animal development and disease. Cell 147, 742-758.

Gout, P. W., Buckley, A. R., Simms, C. R., and Bruchovsky, N. (2001). Sulfasalazine, a potent suppressor of lymphoma growth by inhibition of the x(c)– cystine transporter: a new action for an old drug. Leukemia 15, 1633-1640.

Guo, W., Wu, S., Liu, J., and Fang, B. (2008). Identification of a small molecule with synthetic lethality for K-ras and protein kinase C iota. Cancer Res 68, 7403-7408.

Ishida, T., Suzuki, T., Hirashima, S., Mizutani, K., Yoshida, A., Ando, I., Ikeda, S., Adachi, T., and Hashimoto, H. (2006). Benzimidazole inhibitors of hepatitis C virus NS5B polymerase: identification of 2-[(4-diarylmethoxy)phenyl]-benzimidazole. Bioorg Med Chem Lett 16, 1859-1863.

Ishida, T., Suzuki, T., Hirashima, S., Mizutani, K., Yoshida, A., Ando, I., Ikeda, S., Adachi, T., and Hashimoto, H. (2006). Benzimidazole inhibitors of hepatitis C virus NS5B polymerase: identification of 2-[(4-diarylmethoxy)phenyl]-benzimidazole. Bioorg Med Chem Lett 16, 1859-1863.

Ishii, T., Bannai, S., and Sugita, Y. (1981). Mechanism of growth stimulation of L1210 cells by 2-mercaptoethanol in vitro. Role of the mixed disulfide of 2-mercaptoethanol and cysteine. The Journal of biological chemistry 256, 12387-12392.

Jacobson, M. D., and Raff, M. C. (1995). Programmed cell death and Bcl-2 protection in very low oxygen. Nature 374, 814-816.

Kamata, T. (2009). Roles of Nox1 and other Nox isoforms in cancer development. Cancer Sci 100, 1382-1388.

Kanai, Y., and Endou, H. (2003). Functional properties of multispecific amino acid transporters and their implications to transporter-mediated toxicity. J Toxicol Sci 28, 1-17.

Kanai, Y., and Endou, H. (2003). Functional properties of multispecific amino acid transporters and their implications to transporter-mediated toxicity. J Toxicol Sci 28, 1-17.

Laleu, B., Gaggini, F., Orchard, M., Fioraso-Cartier, L., Cagnon, L., Houngninou-Molango, S., Gradia, A., Duboux, G., Merlot, C., Heitz, F., et al. (2010). First in class, potent, and orally bioavailable NADPH oxidase isoform 4 (Nox4) inhibitors for the treatment of idiopathic pulmonary fibrosis. Journal of medicinal chemistry 53, 7715-7730.

Lei, P., Ayton, S., Finkelstein, D. I., Spoerri, L., Ciccotosto, G. D., Wright, D. K., Wong, B. X., Adlard, P. A., Cherny, R. A., Lam, L. Q., et al. (2012). Tau deficiency induces parkinsonism with dementia by impairing APP-mediated iron export. Nature medicine 18, 291-295.

Li, Y., Maher, P., and Schubert, D. (1997). A role for 12-lipoxygenase in nerve cell death caused by glutathione depletion. Neuron 19, 453-463.

Lipinski, C. A., Lombardo, F., Dominy, B. W., and Feeney, P. J. (2001). Experimental and computational approaches to estimate solubility and permeability in drug discovery and development settings. Advanced drug delivery reviews 46, 3-26.

Lo, M., Ling, V., Wang, Y. Z., and Gout, P. W. (2008). The xc– cystine/glutamate antiporter: a mediator of pancreatic cancer growth with a role in drug resistance. British journal of cancer 99, 464-472.

Lossi, L., Alasia, S., Salio, C., and Merighi, A. (2009). Cell death and proliferation in acute slices and organotypic cultures of mammalian CNS. Prog Neurobiol 88, 221-245.

Macarron, R., Banks, M. N., Bojanic, D., Burns, D. J., Cirovic, D. A., Garyantes, T., Green, D. V., Hertzberg, R. P., Janzen, W. P., Paslay, J. W., et al. (2011). Impact of high-throughput screening in biomedical research. Nature reviews Drug discovery 10, 188-195.

Moffat, J., Grueneberg, D. A., Yang, X., Kim, S. Y., Kloepfer, A. M., Hinkle, G., Piqani, B., Eisenhaure, T. M., Luo, B., Grenier, J. K., et al. (2006). A lentiviral RNAi library for human and mouse genes applied to an arrayed viral high-content screen. Cell 124, 1283-1298.

Morrison, B., 3rd, Pringle, A. K., McManus, T., Ellard, J., Bradley, M., Signorelli, F., Iannotti, F., and Sundstrom, L. E. (2002). L-arginyl-3,4-spermidine is neuroprotective in several in vitro models of neurodegeneration and in vivo ischaemia without suppressing synaptic transmission. Br J Pharmacol 137, 1255-1268.

Morrison, B., 3rd, Pringle, A. K., McManus, T., Ellard, J., Bradley, M., Signorelli, F., Iannotti, F., and Sundstrom, L. E. (2002). L-arginyl-3,4-spermidine is neuroprotective in several in vitro models of neurodegeneration and in vivo ischaemia without suppressing synaptic transmission. Br J Pharmacol 137, 1255-1268.

Mullen, A. R., Wheaton, W. W., Jin, E. S., Chen, P. H., Sullivan, L. B., Cheng, T., Yang, Y., Linehan, W. M., Chandel, N. S., and Deberardinis, R. J. (2011). Reductive carboxylation supports growth in tumour cells with defective mitochondria. Nature.

Murphy, T. H., Miyamoto, M., Sastre, A., Schnaar, R. L., and Coyle, J. T. (1989). Glutamate toxicity in a neuronal cell line involves inhibition of cystine transport leading to oxidative stress. Neuron 2, 1547-1558.

Ni Chonghaile, T., Sarosiek, K. A., Vo, T. T., Ryan, J. A., Tammareddi, A., Moore Vdel, G., Deng, J., Anderson, K. C., Richardson, P., Tai, Y. T., et al. (2011). Pretreatment mitochondrial priming correlates with clinical response to cytotoxic chemotherapy. Science 334, 1129-1133.

Noraberg, J., Poulsen, F. R., Blaabjerg, M., Kristensen, B. W., Bonde, C., Montero, M., Meyer, M., Gramsbergen, J. B., and Zimmer, J. (2005). Organotypic hippocampal slice cultures for studies of brain damage, neuroprotection and neurorepair. Curr Drug Targets CNS Neurol Disord 4, 435-452.

Pagliarini, D. J., Calvo, S. E., Chang, B., Sheth, S. A., Vafai, S. B., Ong, S. E., Walford, G. A., Sugiana, C., Boneh, A., Chen, W. K., et al. (2008). A mitochondrial protein compendium elucidates complex I disease biology. Cell 134, 112-123.

Pinnix, Z. K., Miller, L. D., Wang, W., D'Agostino, R., Jr., Kute, T., Willingham, M. C., Hatcher, H., Tesfay, L., Sui, G., Di, X., et al. (2010). Ferroportin and iron regulation in breast cancer progression and prognosis. Sci Transl Med 2, 43ra56.

Raj, L., Ide, T., Gurkar, A. U., Foley, M., Schenone, M., Li, X., Tolliday, N. J., Golub, T. R., Carr, S. A., Shamji, A. F., et al. (2011). Selective killing of cancer cells by a small molecule targeting the stress response to ROS. Nature 475, 231-234.

Ramanathan, A., and Schreiber, S. L. (2009). Direct control of mitochondrial function by mTOR. Proc Natl Acad Sci USA 106, 22229-22232.

Ramanathan, A., and Schreiber, S. L. (2009). Direct control of mitochondrial function by mTOR. Proc Natl Acad Sci USA 106, 22229-22232.

Ratan, R. R., Murphy, T. H., and Baraban, J. M. (1994). Oxidative stress induces apoptosis in embryonic cortical neurons. J Neurochem 62, 376-379.

Salahudeen, A. A., Thompson, J. W., Ruiz, J. C., Ma, H. W., Kinch, L. N., Li, Q., Grishin, N. V., and Bruick, R. K. (2009). An E3 ligase possessing an iron-responsive hemerythrin domain is a regulator of iron homeostasis. Science 326, 722-726.

Sanchez, M., Galy, B., Schwanhaeusser, B., Blake, J., Bahrlvacevic, T., Benes, V., Selbach, M., Muckenthaler, M. U., and Hentze, M. W. (2011). Iron regulatory protein-1 and -2: transcriptome-wide definition of binding mRNAs and shaping of the cellular proteome by iron regulatory proteins. Blood 118, e168-179.

Sato, H., Tamba, M., Ishii, T., and Bannai, S. (1999). Cloning and expression of a plasma membrane cystine/glutamate exchange transporter composed of two distinct proteins. The Journal of biological chemistry 274, 11455-11458.

Shaw, A. T., Winslow, M. M., Magendantz, M., Ouyang, C., Dowdle, J., Subramanian, A., Lewis, T. A., Maglathin, R. L., Tolliday, N., and Jacks, T. (2011). Selective killing of K-ras mutant cancer cells by small molecule inducers of oxidative stress. Proc Natl Acad Sci USA.

Sundstrom, L., Morrison, B., 3rd, Bradley, M., and Pringle, A. (2005). Organotypic cultures as tools for functional screening in the CNS. Drug discovery today 10, 993-1000.

Tan, S., Sagara, Y., Liu, Y., Maher, P., and Schubert, D. (1998). The regulation of reactive oxygen species production during programmed cell death. The Journal of Cell Biology 141, 1423-1432.

Thompson, C. B. (1995). Apoptosis in the pathogenesis and treatment of disease. Science 267, 1456-1462.

Trachootham, D., Zhou, Y., Zhang, H., Demizu, Y., Chen, Z., Pelicano, H., Chiao, P. J., Achanta, G., Arlinghaus, R. B., Liu, J., et al. (2006). Selective killing of oncogenically transformed cells through a ROS-mediated mechanism by beta-phenylethyl isothiocyanate. Cancer Cell 10, 241-252.

Vashisht, A. A., Zumbrennen, K. B., Huang, X., Powers, D. N., Durazo, A., Sun, D., Bhaskaran, N., Persson, A., Uhlen, M., Sangfelt, O., et al. (2009). Control of iron homeostasis by an iron-regulated ubiquitin ligase. Science 326, 718-721.

Vigil, D., Cherfils, J., Rossman, K. L., and Der, C. J. (2010). Ras superfamily GEFs and GAPs: validated and tractable targets for cancer therapy? Nat Rev Cancer 10, 842-857.

Wang, Y., Dawson, V. L., and Dawson, T. M. (2009). Poly(ADP-ribose) signals to mitochondrial AIF: a key event in parthanatos. Exp Neurol 218, 193-202.

Watkins, P. A., Maiguel, D., Jia, Z., and Pevsner, J. (2007). Evidence for 26 distinct acyl-coenzyme A synthetase genes in the human genome. J Lipid Res 48, 2736-2750.

Wise, D. R., DeBerardinis, R. J., Mancuso, A., Sayed, N., Zhang, X. Y., Pfeiffer, H. K., Nissim, I., Daikhin, E., Yudkoff, M., McMahon, S. B., et al. (2008). Myc regulates a transcriptional program that stimulates mitochondrial glutaminolysis and leads to glutamine addiction. Proceedings of the National Academy of Sciences of the United States of America 105, 18782-18787.

Wolpaw, A. J., Shimada, K., Skouta, R., Welsch, M. E., Akavia, U. D., Pe'er, D., Shaik, F., Bulinski, J. C., and Stockwell, B. R. (2011). Modulatory profiling identifies mechanisms of small molecule-induced cell death. Proceedings of the National Academy of Sciences of the United States of America.

Yagoda, N., von Rechenberg, M., Zaganjor, E., Bauer, A. J., Yang, W. S., Fridman, D. J., Wolpaw, A. J., Smukste, I., Peltier, J. M., Boniface, J. J., et al. (2007). RAS-RAF-MEK-dependent oxidative cell death involving voltage-dependent anion channels. Nature 447, 864-868.

Yagoda, N., von Rechenberg, M., Zaganjor, E., Bauer, A. J., Yang, W. S., Fridman, D. J., Wolpaw, A. J., Smukste, I., Peltier, J. M., Boniface, J. J., et al. (2007). RAS-RAF-MEK-dependent oxidative cell death involving voltage-dependent anion channels. Nature 447, 864-868.

Yang, W. S., and Stockwell, B. R. (2008). Synthetic lethal screening identifies compounds activating iron-dependent, nonapoptotic cell death in oncogenic-RAS-harboring cancer cells. Chemistry & biology 15, 234-245.

Yang, W. S., and Stockwell, B. R. (2008). Synthetic lethal screening identifies compounds activating iron-dependent, nonapoptotic cell death in oncogenic-RAS-harboring cancer cells. Chemistry & biology 15, 234-245

Yonezawa, M., Back, S. A., Gan, X., Rosenberg, P. A., and Volpe, J. J. (1996). Cystine deprivation induces oligodendroglial death: rescue by free radical scavengers and by a diffusible glial factor. J Neurochem 67, 566-573.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

The invention claimed is:

1. A compound having the structure of formula (I):

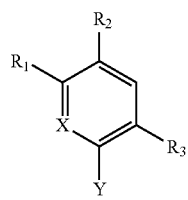

(I)

wherein
X is N;
Y is H, halo, or $C_{1-4}$alkyl;
$R_1$ is $NR_4R_5$, and at least one of $R_4$ and $R_5$ has a ring structure as defined below;
$R_2$ is $NR_6R_7$;
$R_3$ is selected from the group consisting of H,

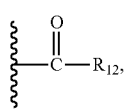

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;
$R_6$ and $R_7$ are independently selected from the group consisting of H, $C_{1-6}$alkyl, Boc, O, $COOR_{12}$,

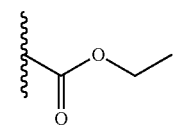

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;
$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, with the proviso that:

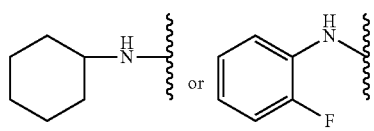

when $R_1$ is

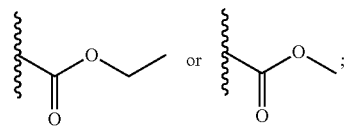

and $R_2$ is $NH_2$, $R_3$ cannot be

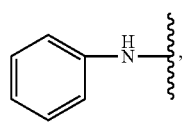 [SMILES: *Nc1ccccc1]

when $R_1$ is

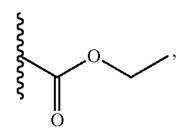 [SMILES: *C(=O)OCC]

$R_3$ cannot be

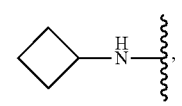 [SMILES: *NC1CCC1]

when $R_1$ is $R_3$ cannot be

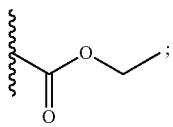 [SMILES: *C(=O)OCC]

or pharmaceutically acceptable salts thereof, or individual enantiomers or diastereomers thereof.

2. A compound according to claim 1 having the structure selected from the group consisting of:

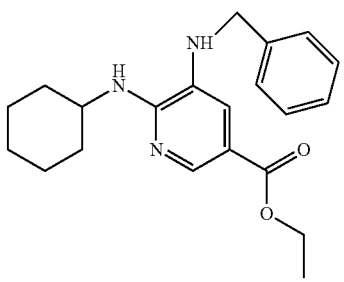

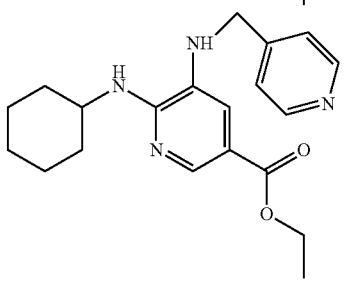

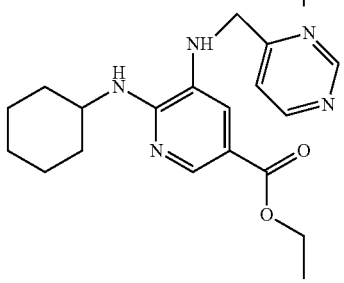

or pharmaceutically acceptable salts thereof, or individual enantiomers or diastereomers thereof.

3. A compound according to claim 1 having the structure of:

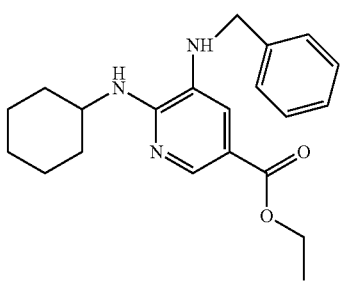 [SMILES: CCOC(=O)c1cnc(NC2CCCCC2)c(NCc2ccccc2)c1]

or pharmaceutically acceptable salts thereof, or individual enantiomers or diastereomers thereof.

4. A composition comprising a pharmaceutically acceptable carrier and a compound according to claim 1.

5. A method for treating or ameliorating the effects of an excitotoxic disorder in a subject in need thereof comprising administering to the subject an effective amount of a compound having the structure of formula (I):

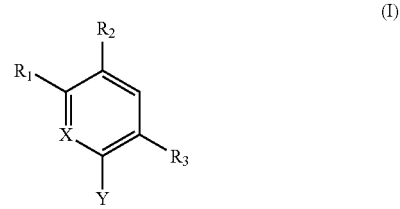

(I)

wherein
X is N;
Y is H, halo, or $C_{1-4}$alkyl;
$R_1$ is $NR_4R_5$, and at least one of $R_4$ and $R_5$ has a ring structure as defined below;
$R_2$ is $NR_6R_7$;
$R_3$ is selected from the group consisting of H,

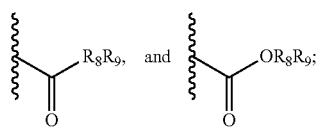

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

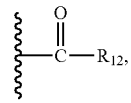

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, with the proviso that:
when R₁ is

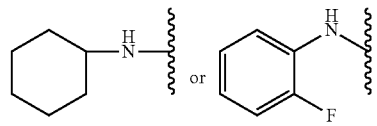

and R₂ is NH₂, R₃ cannot be

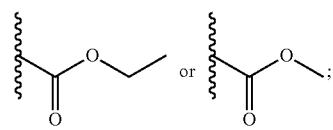

when R₁ is

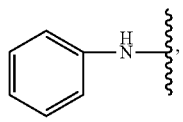

R₃ cannot be

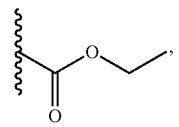

when R₁ is

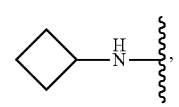

R₃ cannot be

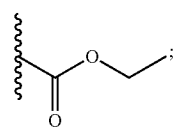

or pharmaceutically acceptable salts thereof, or individual enantiomers or diastereomers thereof.

6. The method according to claim 5, wherein the compound is selected from the group consisting of:

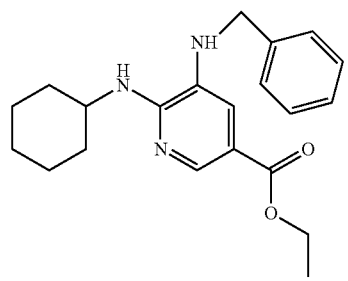 [SMILES: CCOC(=O)c1cnc(NC2CCCCC2)c(NCc2ccccc2)c1]

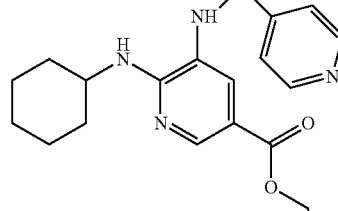

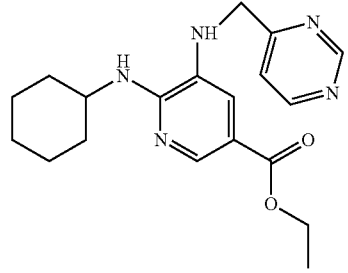

or pharmaceutically acceptable salts thereof, or individual enantiomers or diastereomers thereof.

7. The method according to claim 5, wherein the compound has the structure of:

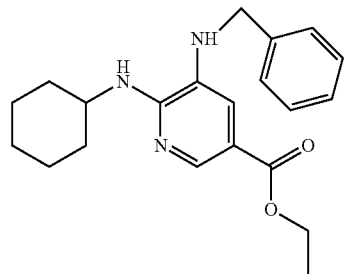

or pharmaceutically acceptable salts thereof, or individual enantiomers or diastereomers thereof.

8. The method according to claim 5, wherein the excitotoxic disorder is a disease involving oxidative cell death.

9. The method according to claim 5, wherein the excitotoxic disorder is selected from the group consisting of epilepsy, stroke, myocardial infarction, type I diabetes, and neurodegenerative disease.

10. The method according to claim 9, wherein the neurodegenerative disease is selected from the group consisting of Alzheimer's, Parkinson's, Amyotrophic lateral sclerosis, Friedreich's ataxia, Multiple sclerosis, Huntington's Disease, Transmissible spongiform encephalopathy, Charcot-Marie-Tooth disease, Dementia with Lewy bodies, Corticobasal degeneration, Progressive supranuclear palsy, and Hereditary spastic paraparesis.

11. The method according to claim 5 further comprising co-administering to the subject an effective amount of one or more compositions selected from the group consisting of: 5-hydroxytryptophan, Activase, AFQ056 (Novartis), Aggrastat, Albendazole, alpha-lipoic acid/L-acetyl carnitine, Alteplase, Amantadine (Symmetrel), amlodipine, Ancrod, Apomorphine (Apokyn), Arimoclomol, Arixtra, Armodafinil, Ascorbic acid, Ascriptin, Aspirin, atenolol, Avonex, baclofen (Lioresal), Banzel, Benztropine (Cogentin), Betaseron, BGG492 (Novartis Corp.), Botulinum toxin, Bufferin, Carbidopa/levodopa immediate-release (Sinemet), Carbidopa/levodopa oral disintegrating (Parcopa), Carbidopa/levodopa/Entacapone (Stalevo), CERE-110: Adeno-Associated Virus Delivery of NGF (Ceregene), cerebrolysin, CinnoVex, citalopram, citicoline, Clobazam, Clonazepam, Clopidogrel, clozapine (Clozaril), Coenzyme Q, Creatine, dabigatran, dalteparin, Dapsone, Davunetide, Deferiprone, Desmoteplase, Diastat, Diazepam, Digoxin, Dimebon, dipyridamole, divalproex (Depakote), Donepezil (Aricept), EGb 761, Eldepryl, ELND002 (Elan Pharmaceuticals), Enalapril, enoxaparin, Entacapone (Comtan), epoetin alfa, Eptifibatide, Erythropoietin, Escitalopram, Eslicarbazepine acetate, Esmolol, Ethosuximide, Ethyl-EPA, Exenatide, Extavia, Ezogabine, Felbamate, Fingolimod (Gilenya), fluoxetine (Prozac), fondaparinux, Fragmin, Frisium, Gabapentin, Galantamine, Glatiramer (Copaxone), haloperidol (Haldol), Heparin, human chorionic gonadotropin (hCG), Idebenone, insulin, Interferon beta 1a, Interferon beta 1b, ioflupane 123I, IPX066 (Impax Laboratories Inc.), JNJ-26489112 (Johnson and Johnson), Klonopin, Lacosamide, L-Alpha glycerylphosphorylcholine, Lamotrigine, Levetiracetam, liraglutide, Lisinopril, Lithium carbonate, Lopressor, Lorazepam, losartan, Lovenox, Lu AA24493, Luminal, LY450139 (Eli Lilly), Lyrica, Masitinib, Mecobalamin, Memantine, methylprednisolone, metoprolol tartrate, Minitran, Minocycline, mirtazapine, Mitoxantrone (Novantrone), Natalizumab (Tysabri), Niacinamide, Nitro-Bid, Nitro-Dur, nitroglycerin, Nitrolingual, Nitromist, Nitrostat, Nitro-Time, Norepinephrine (NOR), Carbamazepine, octreotide, Oxcarbazepine, Oxybutinin chloride, PF-04360365 (Pfizer), Phenobarbital, Phenytoin, piclozotan, Pioglitazone, Plavix, Potiga, Pramipexole (Mirapex), pramlintide, Prednisone, Primidone, Prinivil, probenecid, Propranolol, PRX-00023 (EPIX Pharmaceuticals Inc.), PXT3003, Quinacrine, Ramelteon, Rasagiline (Azilect), Rebif, ReciGen, remacemide, Resveratrol, Retavase, reteplase, riluzole (Rilutek), Rivastigmine (Exelon), Ropinirole (Requip), Rotigotine (Neupro), Rufinamide, Sabril, safinamide (EMD Serono), Salagen, Sarafem, Selegiline (I-deprenyl, Eldepryl), SEN0014196 (Siena Biotech), sertraline (Zoloft), Simvastatin, Sodium Nitroprussiate (NPS), sodium phenylbutyrate, Stanback Headache Powder, Tacrine (Cognex), Tamoxifen, tauroursodeoxycholic acid (TUDCA), Tenecteplase, Tenormin, Tetrabenazine (Xenazine), THR-18 (Thrombotech Ltd.), Tiagabine, Tideglusib, tirofiban, tissue plasminogen activator (tPA), tizanidine (Zanaflex), TNKase, Tolcapone (Tasmar), Tolterodine, Topiramate, Trihexyphenidyl (formerly Artane), ursodiol, Valproic Acid, valsartan, Varenicline (Pfizer), Vimpat, Vitamin E, Warfarin, Zestril, Zonisamide, Zydis selegiline HCL Oral disintegrating (Zelapar), and combinations thereof.

12. The method according to claim 5, wherein the subject is a mammal.

13. The method according to claim 12, wherein the mammal is selected from the group consisting of humans, veterinary animals, and agricultural animals.

14. The method according to claim 5, wherein the subject is a human.

15. A method for treating or ameliorating the effects of an excitotoxic disorder in a subject in need thereof comprising administering to the subject an effective amount of a composition comprising a pharmaceutically acceptable carrier and a compound having the structure (I):

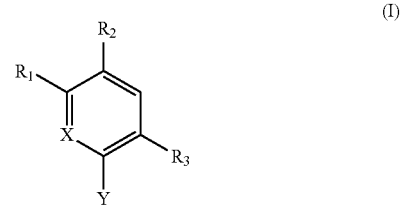

wherein
X is N;
Y is H, halo, or $C_{1-4}$alkyl;
$R_1$ is $NR_4R_5$, and at least one of $R_4$ and $R_5$ has a ring structure as defined below;
$R_2$ is $NR_6R_7$;
$R_3$ is selected from the group consisting of H,

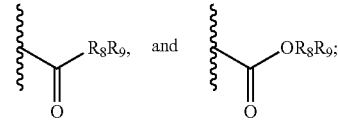

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

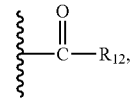

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and
$R_{12}$ is a $C_{1-4}$alkyl optionally substituted with aryl,
with the proviso that:
when $R_1$ is

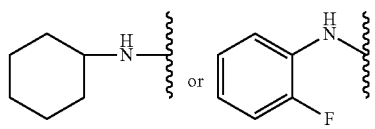

and $R_2$ is $NH_2$, $R_3$ cannot be

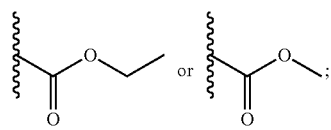

when $R_1$ is

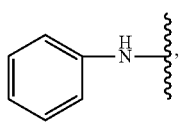

$R_3$ cannot be

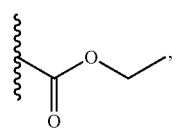

when $R_1$ is

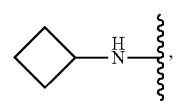

$R_3$ cannot be

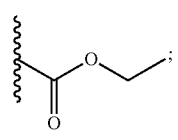

or pharmaceutically acceptable salts thereof, or individual enantiomers or diastereomers thereof.

16. The method according to claim 15, wherein the subject is a mammal.

17. The method according to claim 16, wherein the mammal is selected from the group consisting of humans, veterinary animals, and agricultural animals.

18. The method according to claim 15, wherein the subject is a human.

19. The method according to claim 15, wherein the compound is selected from the group consisting of:

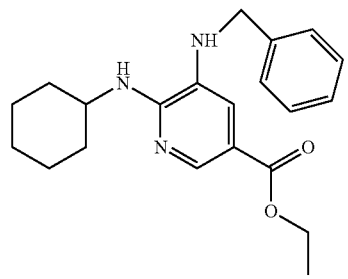 [SMILES: CCOC(=O)c1cnc(NC2CCCCC2)c(NCc2ccccc2)c1]

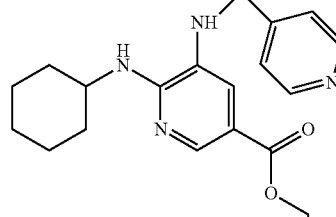

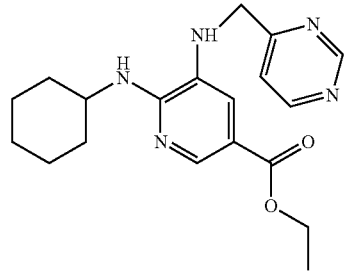

or pharmaceutically acceptable salts thereof, or individual enantiomers or diastereomers thereof.

20. The method according to claim 15, wherein the compound has the structure of:

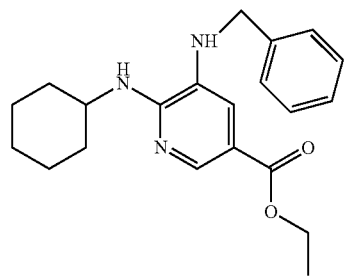

or pharmaceutically acceptable salts thereof, or individual enantiomers or diastereomers thereof.

21. The method according to claim 15, wherein the excitotoxic disorder is a disease involving oxidative cell death.

22. The method according to claim 21, wherein the excitotoxic disorder is selected from the group consisting of epilepsy, stroke, myocardial infarction, type I diabetes, and neurodegenerative disease.

23. The method according to claim 22, wherein the neurodegenerative disease is selected from the group consisting of Alzheimer's, Parkinson's, Amyotrophic lateral sclerosis, Friedreich's ataxia, Multiple sclerosis, Huntington's Disease, Transmissible spongiform encephalopathy, Charcot-Marie-Tooth disease, Dementia with Lewy bodies, Corticobasal degeneration, Progressive supranuclear palsy, and Hereditary spastic paraparesis.

24. The method according to claim 5 further comprising co-administering to the subject an effective amount of one or more compositions selected from the group consisting of: 5-hydroxytryptophan, Activase, AFQ056 (Novartis), Aggrastat, Albendazole, alpha-lipoic acid/L-acetyl carnitine, Alteplase, Amantadine (Symmetrel), amlodipine, Ancrod, Apomorphine (Apokyn), Arimoclomol, Arixtra, Armodafinil, Ascorbic acid, Ascriptin, Aspirin, atenolol, Avonex, baclofen (Lioresal), Banzel, Benztropine (Cogentin), Betaseron, BGG492 (Novartis Corp.), Botulinum toxin, Bufferin, Carbidopa/levodopa immediate-release (Sinemet), Carbidopa/levodopa oral disintegrating (Parcopa), Carbidopa/levodopa/Entacapone (Stalevo), CERE-110: Adeno-Associated Virus Delivery of NGF (Ceregene), cerebrolysin, CinnoVex, citalopram, citicoline, Clobazam, Clonazepam, Clopidogrel, clozapine (Clozaril), Coenzyme Q, Creatine, dabigatran, dalteparin, Dapsone, Davunetide, Deferiprone, Desmoteplase, Diastat, Diazepam, Digoxin, Dimebon, dipyridamole, divalproex (Depakote), Donepezil (Aricept), EGb 761, Eldepryl, ELND002 (Elan Pharmaceuticals), Enalapril, enoxaparin, Entacapone (Comtan), epoetin alfa, Eptifibatide, Erythropoietin, Escitalopram, Eslicarbazepine acetate, Esmolol, Ethosuximide, Ethyl-EPA, Exenatide, Extavia, Ezogabine, Felbamate, Fingolimod (Gilenya), fluoxetine (Prozac), fondaparinux, Fragmin, Frisium, Gabapentin, Galantamine, Glatiramer (Copaxone), haloperidol (Haldol), Heparin, human chorionic gonadotropin (hCG), Idebenone, insulin, Interferon beta 1a, Interferon beta 1b, ioflupane 123I, IPX066 (Impax Laboratories Inc.), JNJ-26489112 (Johnson and Johnson), Klonopin, Lacosamide, L-Alpha glycerylphosphorylcholine, Lamotrigine, Levetiracetam, liraglutide, Lisinopril, Lithium carbonate, Lopressor, Lorazepam, losartan, Lovenox, Lu AA24493, Luminal, LY450139 (Eli Lilly), Lyrica, Masitinib, Mecobalamin, Memantine, methylprednisolone, metoprolol tartrate, Minitran, Minocycline, mirtazapine, Mitoxantrone (Novantrone), Natalizumab (Tysabri), Niacinamide, Nitro-Bid, Nitro-Dur, nitroglycerin, Nitrolingual, Nitromist, Nitrostat, Nitro-Time, Norepinephrine (NOR), Carbamazepine, octreotide, Oxcarbazepine, Oxybutinin chloride, PF-04360365 (Pfizer), Phenobarbital, Phenytoin, piclozotan, Pioglitazone, Plavix, Potiga, Pram ipexole (Mirapex), pramlintide, Prednisone, Primidone, Prinivil, probenecid, Propranolol, PRX-00023 (EPIX Pharmaceuticals Inc.), PXT3003, Quinacrine, Ramelteon, Rasagiline (Azilect), Rebif, ReciGen, remacemide, Resveratrol, Retavase, reteplase, riluzole (Rilutek), Rivastigmine (Exelon), Ropinirole (Requip), Rotigotine (Neupro), Rufinamide, Sabril, safinamide (EMD Serono), Salagen, Sarafem, Selegiline (I-deprenyl, Eldepryl), SEN0014196 (Siena Biotech), sertraline (Zoloft), Simvastatin, Sodium Nitroprussiate (NPS), sodium phenylbutyrate, Stanback Headache Powder, Tacrine (Cognex), Tamoxifen, tauroursodeoxycholic acid (TUDCA), Tenecteplase, Tenormin, Tetrabenazine (Xenazine), THR-18 (Thrombotech Ltd.), Tiagabine, Tideglusib, tirofiban, tissue plasminogen activator (tPA), tizanidine (Zanaflex), TNKase, Tolcapone (Tasmar), Tolterodine, Topiramate, Trihexyphenidyl (formerly Artane), ursodiol, Valproic Acid, valsartan, Varenicline (Pfizer), Vimpat, Vitamin E, Warfarin, Zestril, Zonisamide, Zydis selegiline HCL Oral disintegrating (Zelapar), and combinations thereof.

25. A method of modulating ferroptosis in a subject in need thereof comprising administering to the subject an effective amount of a ferroptosis inhibitor, wherein the ferroptosis inhibitor comprises a compound having the structure of formula (I):

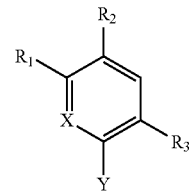

(I)

wherein

X is N;

Y is H, halo, or $C_{1-4}$alkyl;

$R_1$ is $NR_4R_5$, and at least one of $R_4$ and $R_5$ has a ring structure as defined below;

$R_2$ is $NR_6R_7$;

$R_3$ is selected from the group consisting of H,

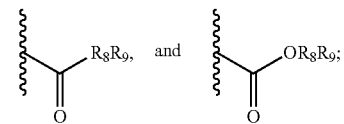

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

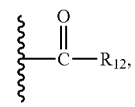

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, with the proviso that:
when $R_1$ is

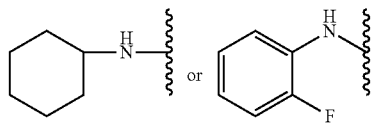

and $R_2$ is $NH_2$, $R_3$ cannot be

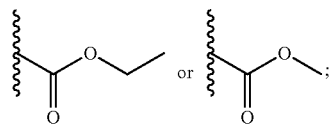

when $R_1$ is

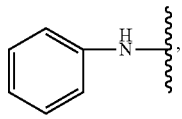

$R_3$ cannot be

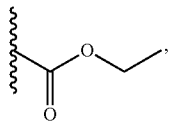

when $R_1$ is

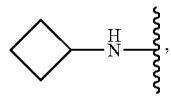

$R_3$ cannot be

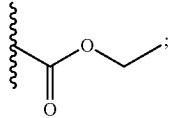

or pharmaceutically acceptable salts thereof, or individual enantiomers or diastereomers thereof.

26. A method of reducing reactive oxygen species (ROS) in a cell comprising contacting a cell with a ferroptosis modulator wherein the ferroptosis modulator is a ferroptosis inhibitor, which comprises a compound having the structure of formula (I):

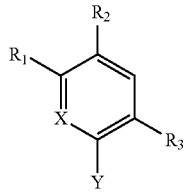

wherein
X is N;
Y is H, halo, or $C_{1-4}$alkyl;
$R_1$ is $NR_4R_5$, and at least one of $R_4$ and $R_5$ has a ring structure as defined below;
$R_2$ is $NR_6R_7$;
$R_3$ is selected from the group consisting of H,

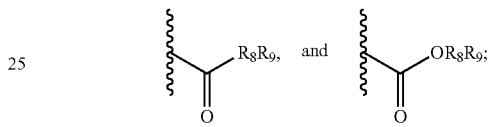

$R_4$ and $R_5$ are independently selected from the group consisting of H, $C_{1-12}$alkyl, $C_{3-12}$cycloalkyl, and aryl, wherein one or more of the ring carbons of the cycloalkyl are optionally substituted with one or more heteroatoms, and the cycloalkyl optionally comprises one or more pendant groups selected from the group consisting of H, F, $NR_{10}R_{11}$, Boc, $COOR_{12}$, and $C_{1-8}$alkyl;

$R_6$ and $R_7$ are independently selected from the group consisting of H, $C_{1-6}$alkyl, Boc, O, $COOR_{12}$,

and $C_{1-3}$alkyl-aryl, wherein one or more of the ring carbons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$alkyl, which $C_{1-8}$alkyl is optionally further substituted with one or more halo;

$R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$cycloalkyl, wherein one or more of the ring carbons of the cycloalkyl are optionally substituted with one or more heteroatoms;

$R_{10}$ and $R_{11}$ are independently selected from H and Boc; and $R_{12}$ is a $C_{1-4}$alkyl optionally substituted with aryl, with the proviso that:
 when $R_1$ is
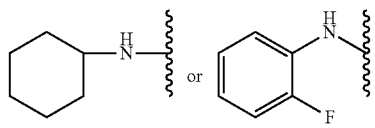 or
and $R_2$ is $NH_2$, $R_3$ cannot be
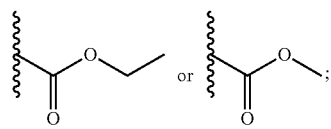 or ;
when $R_1$ is
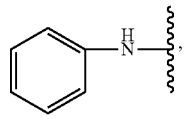 [SMILES: *Nc1ccccc1]
$R_3$ cannot be
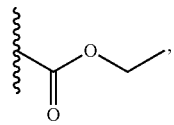 [SMILES: *C(=O)OCC]
when $R_1$ is
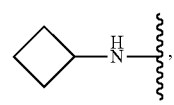
$R_3$ cannot be
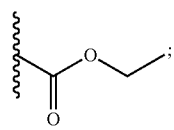 [SMILES: *C(=O)OCC]
or pharmaceutically acceptable salts thereof, or individual enantiomers or diastereomers thereof.
* * * * *

SEQUENCE LISTING

<160> NUMBER OF SEQ ID NOS: 7

<210> SEQ ID NO 1

-continued

```
<211> LENGTH: 21
<212> TYPE: DNA
<213> ORGANISM: Artificial
<220> FEATURE:
<223> OTHER INFORMATION: Synthetic construct

<400> SEQUENCE: 1
caggcaacct agaaaccaaa t                                              21

<210> SEQ ID NO 2
<211> LENGTH: 21
<212> TYPE: DNA
<213> ORGANISM: Artificial
<220> FEATURE:
<223> OTHER INFORMATION: Synthetic construct

<400> SEQUENCE: 2
ccgaattgac aaacccatct t                                              21

<210> SEQ ID NO 3
<211> LENGTH: 21
<212> TYPE: DNA
<213> ORGANISM: Artificial
<220> FEATURE:
<223> OTHER INFORMATION: Synthetic construct

<400> SEQUENCE: 3
cagtgcaatc agcagagaca t                                              21

<210> SEQ ID NO 4
<211> LENGTH: 21
<212> TYPE: DNA
<213> ORGANISM: Artificial
<220> FEATURE:
<223> OTHER INFORMATION: Synthetic construct

<400> SEQUENCE: 4
gaacttattg gcctgtaact t                                              21

<210> SEQ ID NO 5
<211> LENGTH: 21
<212> TYPE: DNA
<213> ORGANISM: Artificial
<220> FEATURE:
<223> OTHER INFORMATION: Synthetic construct

<400> SEQUENCE: 5
gcaggaagta tcgctaggaa t                                              21

<210> SEQ ID NO 6
<211> LENGTH: 21
<212> TYPE: DNA
<213> ORGANISM: Artificial
<220> FEATURE:
<223> OTHER INFORMATION: Synthetic construct

<400> SEQUENCE: 6
gattccgaag tacatcgtgt t                                              21

<210> SEQ ID NO 7
<211> LENGTH: 21
<212> TYPE: DNA
<213> ORGANISM: Artificial
<220> FEATURE:
<223> OTHER INFORMATION: Synthetic construct
```

```
<400> SEQUENCE: 7
gcaggccaga attaagactt t                                          21
```